US007244573B2

(12) United States Patent
Carman et al.

(10) Patent No.: US 7,244,573 B2

(45) Date of Patent: Jul. 17, 2007

(54) POLYNUCLEOTIDES AND POLYPEPTIDES ASSOCIATED WITH THE DEVELOPMENT OF RHEUMATOID ARTHRITIS

(75) Inventors: Julie Carman, Lawrenceville, NJ (US); Steven G. Nadler, Princeton, NJ (US); Michael Bowen, Rockville, MD (US); Michael G. Neubauer, Skillman, NJ (US); Pin Lu, Princeton Jct., NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 172 days.

(21) Appl. No.: 10/308,279

(22) Filed: Dec. 3, 2002

(65) Prior Publication Data

US 2003/0170742 A1 Sep. 11, 2003

Related U.S. Application Data

(60) Provisional application No. 60/337,429, filed on Dec. 3, 2001.

(51) Int. Cl.
*G01N 33/53* (2006.01)
*G01N 33/564* (2006.01)
*C07H 21/04* (2006.01)

(52) U.S. Cl. ...................... 435/7.1; 435/7.24; 536/23.5

(58) Field of Classification Search ................ 435/7.24
See application file for complete search history.

(56) References Cited

U.S. PATENT DOCUMENTS 5,876,923 A 3/1999 Leopardi et al.

OTHER PUBLICATIONS

Fridkis-Hareli et al, Human Immunology 61: 640-650, Jul. 2000.*

Ngo et al., 1994, The Protein Folding Problem and Tertiary Structure Prediction, pp. 491-495.*

Skolnick et al., From genes to protein structure and function: novel applications of computational approaches in the genomic era, Jan. 2000, Trends in Biotech. 18(1): 34-39.*

Singal et al, Ann Rheum Dis 49(3): 143-6, Mar. 1990.*

Tsukamoto et al, Immunogenetics 25(5): 343-346, 1987.*

Bathon, J.M. et al., "A Comparison of Etanercept and Methotrexate in Patients with Early Rheumatoid Arthritis", The New England Journal of Medicine, vol. 343, No. 22, pp. 1586-1593 (2000).

Bresnihan, B., "The Prospect of Treating Rheumatoid Arthritis with Recombinant Human Interleukin-1 Receptor Antagonist", BioDrugs, vol. 15, No. 2, pp. 87-97 (2001).

Heller, R.A. et al., "Discovery and analysis of inflammatory disease-related genes using cDNA microarrays", Proc. Natl. Acad. Sci. USA, vol. 94, pp. 2150-2155 (1997).

Jiang, Y. et al., "A Multicenter, Double-Blind, Dose-Ranging, Randomized, Placebo-Controlled Study of Recombinant Human Interleukin-1 Receptor Antagonist in Patients with Rheumatoid Arthritis", Arthritis & Rheumatism, vol. 43, No. 5, pp. 1001-1009 (2000).

Jootsen, L.A.B. et al., "IL-1αβ Blockade Prevents Cartilage and Bone Destruction in Murine Type II Collagen-Induced Arthritis, Whereas TNF-α Blockade Only Ameliorates Joint Inflammation", The Journal of Immunology, vol. 163, pp. 5049-5055 (1999).

Jüsten, H.-P. et al., "Differential Gene Expression in Synovium of Rheumatoid Arthritis and Osteoarthritis", Molecular Cell Biology Research Communications, vol. 3, pp. 165-172 (2000).

Lipsky, P.E. et al., "Infliximab and Methotrexate in the Treatment of Rheumatoid Arthritis", The New England Journal of Medicine, vol. 343, No. 22, pp. 1594-1602 (2000).

Mizel, S.B. et al., "Stimulation of rheumatoid synovial cell collagenase and prostaglandin production by partially purified lymphocyte-activating factor (interleukin 1)", Proc. Natl. Acad. Sci. USA, vol. 78, No. 4, pp. 2474-2477 (1981).

Niki, Y. et al., "Macrophage- and neutrophil-dominant arthritis in human IL-1α transgenic mice", The Journal of Clinical Investigation, vol. 107, No. 9, pp. 1127-1135 (2001).

Richard-Miceli, C. et al., "Tumour Necrosis Factor-α Blockers in Rheumatoid Arthritis—Review of the Clinical Experience", BioDrugs, vol. 15, No. 4, pp. 251-259 (2001).

Seki, T. et al., "Use of a Differential Subtraction Method to Identify Genes that Characterize the Phenotype of Cultured Rheumatoid Arthritis Synoviocytes", Arthritis & Rheumatism, vol. 41, No. 8, pp. 1356-1364 (1998).

Stuhlmüller, B. et al., "Identification of Known and Novel Genes in Activated Monocytes from Patients with Rheumatoid Arthritis", Arthritis & Rheumatism, vol. 43, No. 4, pp. 775-790 (2000).

Zanelli, E. et al., "HLA Class II Association with Rheumatoid Arthritis", Human Immunology, vol. 61, pp. 1254-1261 (2000).

Youssef et al., J. Rheumatol., 26:2523-2528 (1999).

Ng et al., Cancer Research 60:6581-6584 (2000).

Beyeler et al., J. Rheumatol. 27:15-19 (2000).

Yokota et al., J. Rheumatology 28:1952-1959 (2001).

Zhang et al., Nature 383:168-172 (1996).

Crystal, J. of Clinical Investigation 85:1343-1352 (1990).

Cheng et al., Molecular and Cellular Biology 4717-4725 (1991).

Marok et al., Arthritis & Rheumatism 39:583-591 (1996).

Weyand et al.. J. of Clinical Investigation 89:2033-2039 (1992).

Baeuerle et al., Science 242:540-546 (1988).

Bradley et al., J. of Rheumatology 21:1192-1196 (1994).

McInnes et al., Nature Medicine 2:175-182 (1996).

Plaksin et al., J. Exp. Med. 177:1651-1662 (1993).

(Continued)

*Primary Examiner*—Christina Chan
*Assistant Examiner*—Phuong Huynh
(74) *Attorney, Agent, or Firm*—Nickki L. Parlet

(57) ABSTRACT

The present invention is directed to polynucleotides encoding polypeptides associated with the development of rheumatoid arthritis and homologs thereof. The invention further relates to diagnostic and therapeutic methods for utilizing these polynucleotides and polypeptides in the diagnosis, treatment, and/or prevention of rheumatoid arthritis and related disease states. The invention further relates to screening methods for identifying agonists and antagonists of the polynucleotides and polypeptides of the present invention, and compounds identified thereby.

6 Claims, 111 Drawing Sheets

OTHER PUBLICATIONS

Nepom, Adv. Immunol. 68:315-332 (1998).
Tetlow et al., British J of Rheumatology 37:64-70 (1998).
Hessian et al., J of Leukocyte Biology 53:197-204 (1993).
Cheng et al., J of Biological Chemistry 258:7746-7750 (1983).
Guenzi et al., EMBO Journal 20:5568-5577 (2001).
Fujihara et al., J of Immunology 165:1004-1012 (2000).
Scheinman et al., Molecular and Cellular Biology 15:943-953 (1995).
Miagkov et al., Proc. Natl. Acad. Sci USA 95:13859-13864 (1998).
McKie et al., Science 291:1755-1759 (2001).
Marquet et al., Mammalian Genome 11:755-762 (2000).
Duchateau et al., J of Biological Chemistry 272:25576-25582 (1997).
Ahn et al., FEBS Letters 366:37-42 (1995).
DaSilva et al., Proc. Natl. Acad. Sci. USA 94:7493-7498 (1997).
Zeng et al., Molecular Biology of the Cell 9:2423-2437 (1998).
Bakker et al., Immunity 13:345-353 (2000).
Paloneva et al., Nature Genetics 25:357-361(2000).
Anderson et al., J of Biological Chemistry 270:29862-29869 (1995).
Aringer et al., Rheumatology 40:876-881 (2001).
Thurkow et al., J of Pathology 181:444-450 (1997).
Torsteinsdottir et al., Clin. Exp. Immunol. 115:554-560 (1999).
Kerkhoff et al., Biochimica et Biophysica Acta 1448:200-211 (1998).
Frosch et al., Arthritis & Rheumatism 43:628-637 (2000).
Cunnane et al., Rheumatology 38:34-42 (1999).
Kerlan-Candon et al., Arthritis & Rheumatism 44:1281-1292 (2001).
Yu et al., J of Biological Chemistry 273:21380-21385 (1998).
Gutierrez et al., J of Cell Biology 139:895-905 (1997).
Schindler et al., Proc. Natl. Acad. Sci. USA 89:7836-7839 (1992).
Ashcroft et al., Nature Cell Biology 1:260-266 (1999).
Knoell et al., Am. J. Respir. Crit. Care Med. 157:246-255(1998).
Dabbagh et al., J of Cellular Physiology 186:73-81 (2001).
Stuhlmuller et al., Arthritis & Rheumatism 43:775-790 (2000).
Zhang et al., J of Immunology 166:6-10 (2001).
Cheema et al., Arthritis & Rheumatism 44:1313-1319 (2001).
Wang et al., Nature Immunology 2:632-637 (2001).
Salmon et al., Arthritis & Rheumatism 44:739-750 (2001).
Yuan et al., Cancer Research 58:2196-2199 (1998).
Peterson et al., Science 293:2263-2265 (2001).
Ruchatz et al., J of Immunology 160:5654-5660 (1998).
Kleinau et al., J. Exp. Med. 191:1611-1616 (2000).

* cited by examiner

FIG. 2

CTGCAGGGGGGGGGGGGGCTGGGACAGTGAATCGACAATGCCGTCTTCTGTCT
CGTGGGGCATCCTCCTGCTGGCAGGCCTGTGCTGCCTGGTCCCTGTCTCCCTGGCT
GAGGATCCCCAGGGAGATGCTGCCCAGAAGACAGATACATCCCACCATGATCAG
GATCACCCAACCTTCAACAAGATCACCCCCAACCTGGCTGAGTTCGCCTTCAGCC
TATACCGCCAGCTGGCACACCAGTCCAACAGCACCAATATCTTCTTCTCCCCAGT
GAGCATCGCTACAGCCTTTGCAATGCTCTCCCTGGGGACCAAGGCTGACACTCAC
GATGAAATCCTGGAGGGCCTGAATTTCAACCTCACGGAGATTCCGGAGGCTCAG
ATCCATGAAGGCTTCCAGGAACTCCTCCGTACCCTCAACCAGCCAGACAGCCAGC
TCCAGCTGACCACCGGCAATGGCCTGTTCCTCAGCGAGGGCCTGAAGCTAGTGG
ATAAGTTTTTGGAGGATGTTAAAAAGTTGTACCACTCAGAAGCCTTCACTGTCAA
CTTCGGGGACACCGAAGAGGCCAAGAAACAGATCAACGATTACGTGGAGAAGG
GTACTCAAGGGAAAATTGTGGATTTGGTCAAGGAGCTTGACAGAGACACAGTTT
TTGCTCTGGTGAATTACATCTTCTTTAAAGGCAAATGGGAGAGACCCTTTGAAGT
CAAGGACACCGAGGAAGAGGACTTCCACGTGGACCAGGTGACCACCGTGAAGGT
GCCTATGATGAAGCGTTTAGGCATGTTTAACATCCAGCACTGTAAGAAGCTGTCC
AGCTGGGTGCTGCTGATGAAATACCTGGGCAATGCCACCGCCATCTTCTTCCTGC
CTGATGAGGGGAAACTACAGCACCTGGAAAATGAACTCACCCACGATATCATCA
CCAAGTTCCTGGAAAATGAAGACAGAAGGTCTGCCAGCTTACATTTACCCAAACT
GTCCATTACTGGAACCTATGATCTGAAGAGCGTCCTGGGTCAACTGGGCATCACT
AAGGTCTTCAGCAATGGGGCTGACCTCTCCGGGGTCACAGAGGAGGCACCCCTG
AAGCTCTCCAAGGCCGTGCATAAGGCTGTGCTGACCATCGACGAGAAAGGGACT
GAAGCTGCTGGGGCCATGTTTTTAGAGGCCATACCCATGTCTATCCCCCCCGAGG
TCAAGTTCAACAAACCCTTTGTCTTCTTAATGATTGAACAAAATACCAAGTCTCC
CCTCTTCATGGGAAAAGTGGTGAATCCCACCCAAAAATAACTGCCTCTCGCTCCT
CAACCCCTCCCCTCCATCCCTGGCCCCCTCCCTGGATGACATTAAAGAAGGGTTG
AGCTGG (SEQ ID NO:25)

FIG. 3

Alpha-1-antitrypsin Amino Acid Sequence (Accession No. Q13672)

MPSSVSWGILLAGLCCLVPVSLAEDPQGDAAQKTDTSHHDQDHPTFNKITPNLAEFA
FSLYRQLAHQSNSTNIFFSPVSIATAFAMLSLGTKADTHDEILEGLNFNLTEIPEAQIHE
GFQELLRTLNQPDSQLQLTTGNGLFLSEGLKLVDKFLEDVKKLYHSEAFTVNFGDHE
EAKKQINDYVEKGTQGKIVDLVKELDRDTVFALVNYIFFKGKWERPFEVKDTEDED
FHVDQVTTVKVPMMKRLGMFNIQHCKKLSSWVLLMKYLGNATAIFFLPDEGKLQH
LENELTHDIITKFLENEDRRSASLHLPKLSITGTYDLKSVLGQLGITKVFSNGADLSGV
TEEAPLKLSKAVHKAVLTIDEKGTEAAGAMFLEAIPMSIPPEVKFNKPFVFLMIEQNT
KSPLFMGKVVNPTQK (SEQ ID NO:26)

FIG. 5

B Lymphocyte Stimulator Nucleic Acid Sequence (GI:5730096)

ATGGATGACTCCACAGAAAGGGAGCAGTCACGCCTTACTTCTTGCCTTAAGAAA
AGAGAAGAAATGAAACTGAAGGAGTGTGTTTCCATCCTCCCACGGAAGGAAAGC
CCCTCTGTCCGATCCTCCAAAGACGGAAAGCTGCTGGCTGCAACCTTGCTGCTGG
CACTGCTGTCTTGCTGCCTCACGGTGGTGTCTTTCTACCAGGTGGCCGCCCTGCAA
GGGGACCTGGCCAGCCTCCGGGCAGAGCTGCAGGGCCACCACGCGGAGAAGCTG
CCAGCAGGAGCAGGAGCCCCCAAGGCCGGCTTGGAGGAAGCTCCAGCTGTCACC
GCGGGACTGAAAATCTTTGAACCACCAGCTCCAGGAGAAGGCAACTCCAGTCAG
AACAGCAGAAATAAGCGTGCCGTTCAGGGTCCAGAAGAAACAGTCACTCAAGAC
TGCTTGCAACTGATTGCAGACAGTGAAACACCAACTATACAAAAAGGATCTTAC
ACATTTGTTCCATGGCTTCTCAGCTTTAAAAGGGGAAGTGCCCTAGAAGAAAAAG
AGAATAAAATATTGGTCAAAGAAACTGGTTACTTTTTTATATATGGTCAGGTTTT
ATATACTGATAAGACCTACGCCATGGGACATCTAATTCAGAGGAAGAAGGTCCA
TGTCTTTGGGGATGAATTGAGTCTGGTGACTTTGTTTCGATGTATTCAAAATATGC
CTGAAACACTACCCAATAATTCCTGCTATTCAGCTGGCATTGCAAAACTGGAAGA
AGGAGATGAACTCCAACTTGCAATACCAAGAGAAAATGCACAAATATCACTGGA
TGGAGATGTCACATTTTTTGGTGCATTGAAACTGCTGTGA (SEQ ID NO:27)

FIG. 6

B Lymphocyte Stimulator Amino Acid Sequence (GI:5730097)

MDDSTEREQSRLTSCLKKREEMKLKECVSILPRKESPSVRSSKDGKLLAATLLLALLS
CCLTVVSFYQVAALQGDLASLRAELQGHHAEKLPAGAGAPKAGLEEAPAVTAGLKI
FEPPAPGEGNSSQNSRNKRAVQGPEETVTQDCLQLIADSETPTIQKGSYTFVPWLLSF
KRGSALEEKENKILVKETGYFFIYGQVLYTDKTYAMGHLIQRKKVHVFGDELSLVTL
FRCIQNMPETLPNNSCYSAGIAKLEEGDELQLAIPRENAQISLDGDVTFFGALKLL
(SEQ ID NO:28)

FIG. 8

Human Fc gamma RI Nucleic Acid Sequence (GI: 184840)

ATGTGGTTCTTGACAACTCTGCTCCTTTGGGTTCCAGTTGATGGGCAAGTGGACA
CCACAAAGGCAGTGATCACTTTGCAGCCTCCATGGGTCAGCGTGTTCCAAGAGG
AAACCGTAACCTTGCACTGTGAGGTGCTCCATCTGCCTGGGAGCAGCTCTACACA
GTGGTTTCTCAATGGCACAGCCACTCAGACCTCGACCCCCAGCTACAGAATCACC
TCTGCCAGTGTCAATGACAGTGGTGAATACAGGTGCCAGAGAGGTCTCTCAGGG
CGAAGTGACCCCATACAGCTGGAAATCCACAGAGGCTGGCTACTACTGCAGGTC
TCCAGCAGAGTCTTCACGGAAGGAGAACCTCTGGCCTTGAGGTGTCATGCGTGG
AAGGATAAGCTGGTGTACAATGTGCTTTACTATCGAAATGGCAAAGCCTTTAAGT
TTTTCCACTGGAATTCTAACCTCACCATTCTGAAAACCAACATAAGTCACAATGG
CACCTACCATTGCTCAGGCATGGGAAAGCATCGCTACACATCAGCAGGAATATCT
GTCACTGTGAAAGAGCTATTTCCAGCTCCAGTGCTGAATGCATCTGTGACATCCC
CACTCCTGGAGGGGAATCTGGTCACCCTGAGCTGTGAAACAAAGTTGCTCTTGCA
GAGGCCTGGTTTGCAGCTTTACTTCTCCTTCTACATGGGCAGCAAGACCCTGCGA
GGCAGGAACACATCCTCTGAATACCAAATACTAACTGCTAGAAGAGAAGACTCT
GGGTTATACTGGTGCGAGGCTGCCACAGAGGATGGAAATGTCCTTAAGCGCAGC
CCTGAGTTGGAGCTTCAAGTGCTTGGCCTCCAGTTACCAACTCCTGTCTGGTTTCA
TGTCCTTTTCTATCTGGCAGTGGGAATAATGTTTTTAGTGAACACTGTTCTCTGGG
TGACAATACGTAAAGAACTGAAAAGAAAGAAAAAGTGGGATTTAGAAATCTCTT
TGGATTCTGGTCATGAGAAGAAGGTAATTTCCAGCCTTCAAGAAGACAGACATTT
AGAAGAAGAGCTGAAATGTCAGGAACAAAAAGAAGAACAGCTGCAGGAAGGGG
TGCACCGGAAGGAGCCCCAGGGGGCCACGTAGCAG (SEQ ID NO:29)

FIG. 9

Human Fc gamma RI Amino Acid Sequence (GI: 292169)

MWFLTTLLLWVPVDGQVDTTKAVITLQPPWVSVFQEETVTLHCEVLHLPGSSSTQW
FLNGTATQTSTPSYRITSASVNDSGEYRCQRGLSGRSDPIQLEIHRGWLLLQVSSRVFT
EGEPLALRCHAWKDKLVYNVLYYRNGKAFKFFHWNSNLTILKTNISHNGTYHCSG
MGKHRYTSAGISVTVKELFPAPVLNASVTSPLLEGNLVTLSCETKLLLQRPGLQLYFS
FYMGSKTLRGRNTSSEYQILTARREDSGLYWCEAATEDGNVLKRSPELELQVLGLQL
PTPVWFHVLFYLAVGIMFLVNTVLWVTIRKELKRKKKWDLEISLDSGHEKKVISSLQ
EDRHLEEELKCQEQKEEQLQEGVHRKEPQGAT (SEQ ID NO:30)

FIG. 11

Migration Inhibitory Factor-Related Protein 14 Nucleic Acid Sequence (Accession No. X06233)

AAAACACTCTGTGTGGCTCCTCGGCTTTGACAGAGTGCAAGACGATGACTTGCAA
AATGTCGCAGCTGGAACGCAACATAGAGACCATCATCAACACCTTCCACCAATA
CTCTGTGAAGCTGGGGCACCCAGACACCCTGAACCAGGGGGAATTCAAAGAGCT
GGTGCGAAAAGATCTGCAAAATTTTCTCAAGAAGGAGAATAAGAATGAAAAGGT
CATAGAACACATCATGGAGGACCTGGACACAAATGCAGACAAGCAGCTGAGCTT
CGAGGAGTTCATCATGCTGATGGCGAGGCTAACCTGGGCCTCCCACGAGAAGAT
GCACGAGGGTGACGAGGGCCCTGGCCACCACCATAAGCCAGGCCTCGGGGAGGG
CACCCCCTAAGACCACAGTGGCCAAGATCACAGTGGCCACGGCCACGGCCACAG
TCATGGTGGCCACGGCCACAGCCACTAATCAGGAGGCCAGGCCACCCTGCCTCT
ACCCAACCAGGGCCCCGGGGCCTGTTATGTCAAACTGTCTTGGCTGTGGGGCTAG
GGGCTGGGGCCAAATAAAGTCTCTTCCTCCAAGTCAGTGCTCTG (SEQ ID NO:31)

FIG. 12

Migration Inhibitory Factor-Related Protein 14 Amino Acid Sequence (Accession No. P06702)

MTCKMSQLERNIETIINTFHQYSVKLGHPDTLNQGEFKELVRKDLQNFLKKENKNEK
VIEHIMEDLDTNADKQLSFEEFIMLMARLTWASHEKMHEGDEGPGHHHKPGLGEGT
P (SEQ ID NO:32)

FIG. 14

Human Skin Collagenase Nucleic Acid Sequence (GI:180664)

ATATTGGAGCAGCAAGAGGCTGGGAAGCCATCACTTACCTTGCACTGAGAAAGA
AGACAAAGGCCAGTATGCACAGCTTTCCTCCACTGCTGCTGCTGCTGTTCTGGGG
TGTGGTGTCTCACAGCTTCCCAGCGACTCTAGAAACACAAGAGCAAGATGTGGA
CTTAGTCCAGAAATACCTGGAAAAATACTACAACCTGAAGAATGATGGGAGGCA
AGTTGAAAAGCGGAGAAATAGTGGCCCAGTGGTTGAAAAATTGAAGCAAATGCA
GGAATTCTTTGGGCTGAAAGTGACTGGGAAACCAGATGCTGAAACCCTGAAGGT
GATGAAGCAGCCCAGATGTGGAGTGCCTGATGTGGCTCAGTTTGTCCTCACTGAG
GGAAACCCTCGCTGGGAGCAAACACATCTGAGGTACAGGATTGAAAATTACACG
CCAGATTTGCCAAGAGCAGATGTGGACCATGCCATTGAGAAAGCCTTCCAACTCT
GGAGTAATGTCACACCTCTGACATTCACCAAGGTCTCTGAGGGTCAAGCAGACAT
CATGATATCTTTTGTCAGGGGAGATCATCGGGACAACTCTCCTTTTGATGGACCT
GGAGGAAATCTTGCTCATGCTTTTCAACCAGGCCCAGGTATTGGAGGGGATGCTC
ATTTTGATGAAGATGAAAGGTGGACCAACAATTTCAGAGAGTACAACTTACATC
GTGTTGCGGCTCATGAACTCGGCCATTCTCTTGGACTCTCCCATTCTACTGATATC
GGGGCTTTGATGTACCCTAGCTACACCTTCAGTGGTGATGTTCAGCTAGCTCAGG
ATGACATTGATGGCATCCAAGCCATATATGGACGTTCCCAAAATCCTGTCCAGCC
CATCGGCCCACAAACCCCAAAAGCGTGTGACAGTAAGCTAACCTTTGATGCTATA
ACTACGATTCGGGGAGAAGTGATGTTCTTTAAAGACAGATTCTACATGCGCACAA
ATCCCTTCTACCCGGAAGTTGAGCTCAATTTCATTTCTGTTTTCTGGCCACAACTG
CCAAATGGGCTTGAAGCTGCTTACGAATTTGCCGACAGAGATGAAGTCCGGTTTT
TCAAAGGGAATAAGTACTGGGCTGTTCAGGGACAGAATGTGCTACACGGATACC
CCAAGGACATCTACAGCTCCTTTGGCTTCCCTAGAACTGTGAAGCATATCGATGC
TGCTCTTTCTGAGGAAAACACTGGAAAAACCTACTTCTTTGTTGCTAACAAATAC
TGGAGGTATGATGAATATAAACGATCTATGGATCCAAGTTATCCCAAAATGATA
GCACATGACTTTCCTGGAATTGGCCACAAAGTTGATGCAGTTTTCATGAAAGATG
GATTTTTCTATTTCTTTCATGGAACAAGACAATACAAATTTGATCCTAAAACGAA
GAGAATTTTGACTCTCCAGAAAGCTAATAGCTGGTTCAACTGCAGGAAAAATTG
AACATTACTAATTTGAATGGAAAACACATGGTGTGAGTCCAAAGAAGGTGTTTTC
CTGAAGAACTGTCTATTTTCTCAGTCATTTTTAACCTCTAGAGTCACTGATACACA
GAATATAATCTTATTTATACCTCAGTTTGCATATTTTTTTACTATTTAGAATGTAG
CCCTTTTTGTACTGATATAATTTAGTTCCACAAATGGTGGGTACAAAAAGTCAAG
TTTGTGGCTTATGGATTCATATAGGCCAGAGTTGCAAAGATCTTTTCCAGAGTAT
GCAACTCTGACGTTGATCCCAGAGAGCAGCTTCAGTGACAAACATATCCTTTCAA
GACAGAAAGAGACAGGAGACATGAGTCTTTGCCGGAGGAAAAGCAGCTCAAGA
ACACATGTGCAGTCACTGGTGTCACCCTAGATAGGCAAGGGATAACTCTTCTAAC
ACAAAATAAGTGTTTTATGTTTGGAATAAAGTCAACCTTGTTTCTACTGTTTT
(SEQ ID NO:33)

FIG. 15

Human Skin Collagenase Amino Acid Sequence (GI:180665)

MHSFPPLLLLLFWGVVSHSFPATLETQEQDVDLVQKYLEKYYNLKNDGRQVEKRRN
SGPVVEKLKQMQEFFGLKVTGKPDAETLKVMKQPRCGVPDVAQFVLTEGNPRWEQ
THLTYRIENYTPDLPRADVDHAIEKAFQLWSNVTPLTFTKVSEGQADIMISFVRGDHR
DNSPFDGPGGNLAHAFQPGPGIGGDAHFDEDERWTNNFREYNLHRVAAHELGHSLG
LSHSTDIGALMYPSYTFSGDVQLAQDDIDGIQAIYGRSQNPVQPIGPQTPKACDSKLT
FDAITTIRGEVMFFKDRFYMRTNPFYPEVELNFISVFWPQLPNGLEAAYEFADRDEVR
FFKGNKYWAVQGQNVLHGYPKDIYSSFGFPRTVKHIDAALSEENTGKTYFFVANKY
WRYDEYKRSMDPGYPKMIAHDFPGIGHKVDAVFMKDGFFYFFHGTRQYKFDPKTK
RILTLQKANSWFNCRKN (SEQ ID NO:34)

FIG. 17

Cysteine Dioxygenase Nucleic Acid Sequence (GI:2138109)

TCTTCCTCAGCATTTCCTGCCAACCCTTTTCTGGTTTCTGTTTCTTCAACCTCTTTT
TGTTTTATGGTCCCTTTTATGGTATTTTCTCTTATTTCTAGGAAAACATTAATGAT
AGGTTTTTGAACACTTCCCCTGAGTAGTCTCTGTTGCAGGTTGCTTTTTTGTTTGC
TCTGCCCTCTGTCTTTCATACTAGAGGCCTTGCTCAAATGTCTGGTGACCTTGGCA
ATGTGCTAATATTTAAAAACCAAGAACAAAAAAATTAATTGGTAACCCTGAACA
TGAGTGGAGCTTGTCAACTGGATTTCACTTTTTGATAGTCTGGCAGAGACTTTTTC
TTCAGGAACTTCCAGCGACAATATCTTTAAAGCTTTTTTCTTGAGCCAATCAGATT
CTCTGAGAAGTTGCTTCCTATCTTCTGCCCGGAAAGAAAAATCTTGTCTGGCAGC
ATTCTCGCAGCTAGGTGATGACTAAAGCAGGGATTTTTACCATTCAGTATGGAAG
CTTTTGTTTAATTCACCTGTTTTTCACCTGATTTCCATCAGTCCCAAGTTGATCTCT
TACACTCTTTCTAGAGACTAGACCTTACTCTGCTGCTGAAAAGAAAGAAGAGAG
AGAATTGGTAAAAGGGTTTTGAGACTCTACTTCATAAACAAGCTTTAAACCAGTT
CTTATATCTACAGCCTATCTTTACCCTCATTTCCAGAAGTACCTGGTGCTGTCAAT
TCCTGTGCTATTTGGAGTTTCAAGATATAAATCAGGTTATTTCTTGGTTTTCTCCA
TGGATAGCTTAGGATTTAGCTTTCTCTGCTCTGTAAAGCTATCCATCTTACTTTCT
AAGCTTTCAAATTTTTGGTAGGGTTTCTCTTTCCCTATTTGGCTTTGTATATTGAT
GTCTTTTTTATTTTTTTACTGCCATTGGAGAGGGTTTCAGGAAGGAGCAGAGGCT
AATGCATGCGTGTCACTTACTATCTTTAACTGCAAGTTCAATTCTAATTAATATCT
ATTCCATTTGCATCACAATTGATTCATGATCTCAGATGACTCACAGAGATTTTACC
TACAGCTGTTATCTAGGCTCCTTTATCTATTTTTCCTTCCCGGATATTGTTTAGATT
CCATTGGCTTACATCGAGTAGAGAACATCAGCCATACGGAACCTGCTGTGAGCCT
TCACTTGTACAGTCCACCTTTTGATACATGCCATGCCTTTGATCAAAGAACAGGA
CATAAAAACAAAGTCACAATGACATTCCATAGTAAATTTGGAATCAGAACTCCA
AATGTGAGTATAATTTCTTCTAGGTTTAAATGCTCTGTAGGTTGGCACTGTTACAC
TGCATGTATGCAAAGAATGAGATGAGTCTTAATTCATGGATAAGGCCCAATATAT
CTTGATTGTTTTATTTAACTTTAGCGACTATCTTTTCAATTTATTTTTAAAAACTTA
TTATGTTAGATCCAAACATTAGTTGAGAAATTTCAAAATGTATGCTTGTTTTTAAA
GAAAATGTTTTCATTTACTTGGGAAATGAGAGTGAAAACTATTATTTGATATAAC
TGTTACTGCCATGGCTTACTATGCATAGGTCTAATTTGCTGGGCCAACAGGGATA
AGTTGCATAATTAACCTTTGTAAAGGTTATTGGCTGATGATATAACTAAAGCAAA
TTGTCTGTTTTGTTTGCCAATGTTGCTTATTCTTAGAGTTGTTATGCCATTTATACC
ACAAATAAGAATAGACTATACTAACATGTTCCTCCTTGAGAAACAAGCATTTCCT
ACCAAAAATAAAAAGGCAACCAACACTAATATAGCAGGGCAGTCTTCTACCTCT
GAAATAAGTTTGTCATTTAGAGGAATAGTCTTTAATTATCAGAATATCCAGAAAT
AGACAATGTGTGAAAATGGAGACCCAAGCAATCCTTGAGTCTTAATGAAAGCGC
AGCCTCTGAGGGAAGCCAGGGCAGAATTTTCTCATTATCGCTCCGCTTCATCTTT
ATCTTCCACATTCCAAACCCTAAGAGATATTCTTATTGCGGGAAAAACAACAAGG
CTCCCTTGCCCTTGCTGAGTTTTCATACACTGCTACAAAAGCAGAACTATTTAGA
AGGAGTTAAAATGTCTTTTGTAAAGTTTCTTACACAGCTTTCTTTTTTTCCCTTTTT
TACAGGCAACTTCGGGCTCGCTGGAGAACAACTAAGGGGCACCAAAGCCCTCTG
AGGTTTTACTTTAAGGTTCGCTGTATGTTTGCCTTGGACAAAAAGGCTACCTACC

FIG. 17 (cont.)

ACGTGCTATCCAGTAATATACTTAAATAAGCCAATACTTAGATCTACTGTAAGGC
AGATGCTAATTATAAGGCATTAAGTAAGCAAATAGTGCCCTCAGCTACTGCAGA
AGAAAAGTCCCACTGAGGAAAAGAAAGTCTTGTGATTTTTAAAGGCAAGTTTTC
AAGTGCTCTCATAGTTCTATCCTCTAATTCCATTAAATCCATACTAGGAGCGTCA
GTGAGGGTTTTCATAGCTTTTGGAAATACTTTGGTCTCTGAACTGTAATTAGCGC
AAGAAGTAAAAACAGAAACGTCAAACGTCAAATGTTTGCTTTGTTACCTGGAGG
ACTAAATGTAGATGTCTTTAGTATACTTTGTATGTTCTTAAATATTGGAAGATAAT
TTTGTGAATCTGTAGATTTTATTTTTTCAGTCTTACCTTACAAATTTCTTTTCTATG
AATAATAGAGGAACTCACGGCACTCTGCCACTTGTTAATGAAAGGAAGTGCAGA
GGATTTAGAAAAGTACATGATCCCCAGACCACAACAAACCAAAACATAAACTCA
TGTCTGTGTCCCATGGTCATAGTCAAAGATTTTGTACTGCTAAAATTACCAAATA
ATTTAAATAAAGTGGATTTGAACACAATTTGAAGGTGTCTTTCTGATTAACATGA
TAGAAACTTCACATAAATCAGTTTCTTAGATCTAGATATACAAAAGCACTGTGAC
AAATGG (SEQ ID NO:35)

FIG. 18

Cysteine Dioxygenase Amino Acid Sequence (GI:2138111)

MEQTEVLKPRTLADLIRILHQLFAGDEVNVEEVQAIMEAYESDPIEWAMYAKFDQY
RYTRNLVDQGNGKFNLMILCWGEGHGSSIHDHTNSHCFLKMLQGNLKETLFAWPD
KKSNEMVKKSERVLRENQCAYINDSIGLHRVENISHTEPAVSLHLYSPPFDTCHAFDQ
RTGHKNKVTMTFHSKFGIRTPNATSGSLENN (SEQ ID NO:36)

FIG. 20

Human MHC Class II HLA-DR2/Dw12 Nucleic Acid Sequence (GI:188397)

GCACTGGACTGAGAACCTTCACCAAAAAAATGTCTGCCCAGAGACAGATGAGGT
CCTTCAGCTCCAGTGCTGATTGGTTCTTTTCCAAAGGCCCATCTAATCCTACCACG
CACGGAAATATCCACAGGTTTTATTCTTTCTGCCAGCTACATCAGATCCATCAG
GTCCGAGCTGAGTTGACTACCACTACTTTTCCCTTTGTCTCAATTATGTCTTGGAA
GAAGGCTTTGCGGATCCCCGGAGGCCTTCGGGCACCAACTGTGACCTTGATGCTG
GCGATGCTGAGCACCCCAGTGGCTGAGGGCAGAGACCCTCCCGAGGATTTCGTG
CTCCAGTTTAAGGCCATGTGCTACTTCACCAATGGGACGGAGCGCGTGCGTTATG
TGACCAGATACATCTATAACCGAGAGGAGGACGTGCGCTTCGACAGCGACGTGG
GGGTGTATCGGGCGGTGACGGCGCAGGGGCGGCCTGACGCCGAGTACTGGAACA
GCCAGAAGGACATCCTGGAGAGGACCCGAGCGGAGTTGGACACGGTGTGCAGAC
ACAACTACGAGGTGGCGTTCCGCGGGATCTTGCAGAGGAGAGTGGAGCCCACAG
TGACCATCTCCCCATCCAGGACAGAGGCCCTCAACCACCACAACCTGCTGGTCTG
CTCGGTGACAGATTTCTATCCAGGCCAGATCAAAGTCCGGTGGTTTCGGAATGAC
CAGGAGGAGACAGCTGGCGTTGTGTCCACCCCCCTTATTAGGAACGGTGACTGG
ACCTTCCAGATCCTGGTGATGCTGGAAATGACTCCCCAGCATGGAGACGTCTACA
CCTGCCACGTGGAGCACCCCAGCCTCCAGAGCCCCATCACCGTGGAGTGGCGGG
CTCAGTCTGAATCTGCCCAGAACAAGATGCTGAGTGGCATTGGAGGCTTCGTGCT
GGGGCTGATCTTCCTCGGGCTGGGCCTTATCATCCGTCAAAGGAGTCAGAAAGG
ACCTCAAGGGCCTCCACCAGCAGGGCTTCTGCACTGACTCCTGAGACTATTTTAA
CTAGGATTGGTTATCACTCTTCTGTGATGCCTGCTTGTGCCTGCCCAGAATTCCCA
GCTGCCTGTGTCAGCTTGTCCCCCGAGATCAAAGTCCTACAGTGGCTGTCACGCA
GCCACCAGGTCATCTCCTTTCATCCCCACCCCAAGGCGCTGGCTGTGACTCTGCTT
CCTGCACTGACCCAGAGCCTCTGCCTGTGCACGGCCAGCTGCGTCTACTCAGGTC
CCAAGGGGTTTCTGTTTCTATTCTCTCCTCAGACTGCTCAAGAGAAGCACATGAA
AAACATTACCTGACTTTAGAGCTTTTTACATAATTAAACATGATCCTGAGTTAA
AAAAAAAAAAGGAAATCGCTGCAGAATGAAGGAATATCCCTTGAGGTGACCCAG
CCAACCTGTGGCCAGAAGGAGGGTTGTACCTTGAAAAGACCACTGAAAGCATTT
TGGGGTGTCAAGTAAGGGTGGGCAGAGGAGGTAGAAAATCAATTCAATTGTCGC
ATCATTCATGGTTCTTTAATATTGATGCTCAGTGCATTGGCCTTAGAATATCCCAG
CCTCTCTTCTGGTTTGGTGAGTGCTGTGTAAGTAAGCATGGTAGAATTGTTTGGA
GACATATATAGTGATCCTTGGTCACTGGTGTTTCAAACATTCTGGAAAGTCACAT
CGATCAAGAATATTTTTTATTTTTAAGAAAGCATAACCAGCAATAAAAATACTAT
TTTTGAGTCT (SEQ ID NO:37)

FIG. 21

Human MHC Class II HLA-DR2/Dw12 Amino Acid Sequence (GI:307272)

MSWKKALRIPGGLRAPTVTLMLAMLSTPVAEGRDPPEDFVLQFKAMCYFTNGTERV
RYVTRYIYNREEDVRFDSDVGVYRAVTAQGRPDAEYWNSQKDILERTRAELDTVCR
HNYEVAFRGILQRRVEPTVTISPSRTEALNHHNLLVCSVTDFYPGQIKVRWFRNDQEE
TAGVVSTPLIRNGDWTFQILVMLEMTPQHGDVYTCHVEHPSLQSPITVEWRAQSESA
QNKMLSGIGGFVLGLIFLGLGLIIRQRSQKGPQGPPPAGLLH (SEQ ID NO:38)

FIG. 23

Stimulator of Iron Transport Nucleic Acid Sequence (GI: 2738924)

GAATTCGGCTGTCGCACTTACTGTTCAATAGTATATACTCTGTATTTGAAAAATA
GATGTATATATTCTAGGTGATAAATTAAAAATGAAAGAATTTAATCATTGGAAAG
TATTAAATATATATTGCTTATCTTCTCCAAGGAAGAGGAGTTCTCTCGTACCCATC
CAAACTGACCTAATTCTCAAGCTGCTTCATCTTGCTTGTACTGTAGGTTCATTTGC
AATTTGTAGATTATGCTCCTTCAGGATTGGCTTTTGTAAATTTCTGTTAGAAGCTG
GTTTCTGCATTTTTGATTTTTGTGTATTTGGATACATTTTCATATTGTGCAGAGAA
ATCCATGAGTTAAAAAATTATTTTTCCCTGTTTTATTTCTGCATGAACCTAAGTCA
CATTGACCCAGTAATTGATATATGTGTGATTATTGCAATTAAGTATAAGAAGGTA
GAATATATAGTTTTATTAGACAGATGCTTCCTGAAATATTATTTTGTATGTTTTTA
CTATATCCTTTTTGTGTATCTACAGATACAACAGACATGCAAGAGAATGGACTCA
GAAATATGCAATGTAAAAATCAAAAACATTTTCATATATAACCAGAGTACTGTA
AAATCTAGGTTTTTTTTCAACATTAGCAGTAAATTGAGCACTGTTTACCTGTTTCA
TTGTACCATGAAACCATTTGATTTTTACCATTTTAAATGTGTCTCAAGCAAGACA
AAACAAACTTCCAAAAATACCCTTAAGACTGTGATGAGAGCATTTATCATTTTGT
ATGCATTGAGAAAGACATTTATTATGGTTTTTAAGATACTTGGACATCTGCATCTT
CAGCTTACAAGATCTACAATGCAGCTGAAAAAGCAACCAAATTATTTTTTGCTGA
AAACTAGATGTTTTTTACATGAGAAAATACTGTATGTGTGTCTAAGATGTCAGTT
TTATAAATCTGTATTCAGATTTCATCCTTTGTTAGCTCACTTTATAATTTGTATTTT
TTTTCTGTATAGAACTAAATATATTCTATTTACATGTATGTCAACTCATTACTTTTT
TCCTGTGAACAGTATTGAAAACCCCAACCGGCTGATAATTAAGTGAATTAACTGT
GTCTCCCTTGTCTTAGGATATTCTGTAGATTGATTGCAGATTTCTTAAATCTGAAA
TGACTTTACACTGTAATTCTCAGCATACTGATTATGGAGAACACTTGTTTTGAATT
TTGTTATACTTGACTTAACTTTATTGCAATGTGAATTAATTGACTGCTAAGTAGGA
AGATGTGTAACTTTTATTTGTTGCTATTCACATTTGAATTTTTTCCTGTATAGGCA
ATATTATATTGACACCTTTTACAGATCTTACTGTAGCAAAAACCATATAAATAAA
ATGCTTTTTCTGCT (SEQ ID NO:39)

FIG. 24

Stimulator of Iron Transport Amino Acid Sequence (Accession No. O43465)

MKEFNHWKVLNIYCLSSPRKRSSLVPIQTDLILKLLHLACTVGSFAICRLCSFRIGFCK
FLLEAGFCIFDFCVFGYIFILCREIHELKNYFSLFYFCMNLSHIDPVIDICVIIAIKYKKVE
YIVLLDRCFLKYYFVCFYYILFVYLQIQQTCKRMDSEICNVKIKNIFIYNQSTVKSRFF
FNISSKLSTVYLFHCTMKPFDFYHFKCVSSKTKQTSKNTLKTVMRAFIILYALRKTFI
MVFKILGHLHLQLTRSTMQLKKQPNYFLLKTRCFLHEKILYVCLRCQFYKSVFRFHP
LLAHFIICIFFLYRTKYILFTCMSTHYFFPVNSIENPNRLIIK (SEQ ID NO:40)

FIG. 26

Guanylate Binding Protein Isoform 1 Nucleic Acid Sequence (GI:183001)

ACAGAAGTGCTAGAAGCCAGTGCTCGTGAACTAAGGAGAAAAAGAACAGACAA
GGGAACAGCCTGGACATGGCATCAGAGATCCACATGACAGGCCCAATGTGCCTC
ATTGAGAACACTAATGGGCGACTGATGGCGAATCCAGAAGCTCTGAAGATCCTT
TCTGCCATTACACAGCCTATGGTGGTGGTGGCAATTGTGGGCCTCTACCGCACAG
GCAAATCCTACCTGATGAACAAGCTGGCTGGAAAGAAAAAGGGCTTCTCTCTGG
GCTCCACGGTGCAGTCTCACACTAAAGGAATCTGGATGTGGTGTGTGCCCCACCC
CAAGAAGCCAGGCCACATCCTAGTTCTGCTGGACACCGAGGGTCTGGGAGATGT
AGAGAAGGGTGACAACCAGAATGACTCCTGGATCTTCGCCCTGGCCGTCCTCCTG
AGCAGCACCTTCGTGTACAATAGCATAGGAACCATCAACCAGCAGGCTATGGAC
CAACTGTACTATGTGACAGAGCTGACACATAGAATCCGATCAAAATCCTCACCTG
ATGAGAATGAGAATGAGGTTGAGGATTCAGCTGACTTTGTGAGCTTCTTCCCAGA
CTTTGTGTGGACACTGAGAGATTTCTCCCTGGACTTGGAAGCAGATGGACAACCC
CTCACACCAGATGAGTACCTGACATACTCCCTGAAGCTGAAGAAAGGTACCAGT
CAAAAAGATGAAACTTTTAACCTGCCCAGACTCTGTATCCGGAAATTCTTCCCAA
AGAAAAAATGCTTTGTCTTTGATCGGCCCGTTCACCGCAGGAAGCTTGCCCAGCT
CGAGAAACTACAAGATGAAGAGCTGGACCCCGAATTTGTGCAACAAGTAGCAGA
CTTCTGTTCCTACATCTTTAGTAATTCCAAAACTAAAACTCTTTCAGGAGGCATCC
AGGTCAACGGGCCTCGTCTAGAGAGCCTGGTGCTGACCTACGTCAATGCCATCAG
CAGTGGGGATCTGCCGTGCATGGAGAACGCAGTCCTGGCCTTGGCCCAGATAGA
GAACTCAGCTGCAGTGCAAAAGGCTATTGCCCACTATGAACAGCAGATGGGCCA
GAAGGTGCAGCTGCCCACAGAAAGCCTCCAGGAGCTGCTGGACCTGCACAGGGA
CAGTGAGAGAGAGGCCATTGAAGTCTTCATCAGGAGTTCCTTCAAAGATGTGGA
CCATCTATTTCAAAAGGAGTTAGCGGCCCAGCTAGAAAAAAAGCGGGATGACTT
TTGTAAACAGAATCAGGAAGCATCATCAGATCGTTGCTCAGGTTTACTTCAGGTC
ATTTTCAGTCCTCTAGAAGAAGAAGTGAAGGCGGGAATTTATTCGAAACCAGGG
GGCTATCGTCTCTTTGTTCAGAAGCTACAAGACCTGAAGAAAAAGTACTATGAGG
AACCGAGGAAGGGGATACAGGCTGAAGAGATTCTGCAGACATACTTGAAATCCA
AGGAGTCTATGACTGATGCAATTCTCCAGACAGACCAGACTCTCACAGAAAAAG
AAAAGGAGATTGAAGTGGAACGTGTGAAAGCTGAGTCTGCACAGGCTTCAGCAA
AAATGTTGCAGGAAATGCAAAGAAAGAATGAGCAGATGATGGAACAGAAGGAG
AGGAGTTATCAGGAACACTTGAAACAACTGACTGAGAAGATGGAGAACGACAG
GGTCCAGTTGCTGAAAGAGCAAGAGAGGACCCTCGCTCTTAAACTTCAGGAACA
GGAGCAACTACTAAAAGAGGGATTTCAAAAAGAAAGCAGAATAATGAAAAATG
AGATACAGGATCTCCAGACGAAAATGAGACGACGAAAGGCATGTACCATAAGCT
AAAGACCAGAGCCTTCCTGTCACCCCTAACCAAGGCATAATTGAAACAATTTTAG
AATTTGGAACAAGCGTCACTACATTTGATAATAATTAGATCTTGCATCATAACAC
CAAAAGTTTATAAAGGCATGTGGTACAATGATCAAAATCATGTTTTTTCTTAAAA
AAAAAAAAAAGACTGTAAATTGTGCAACAAAGATGCATTTACCTCTGTATCAAC
TCAGGAAATCTCATAAGCTGGTACCACTCAGGAGAAGTTTATTCTTCCAGATGAC
CAGCAGTAGACAAATGGATACTGAGCAGAGTCTTAGGTAAAAGTCTTGGGAAAT
ATTTGGGCATTGGTCTGGCCAAGTCTACAATGTCCCAATATCAAGGACAACCACC

FIG. 26 (cont.)

CTAGCTTCTTAGTGAAGACAATGTACAGTTATCCATTAGATCAAGACTACACGGT
CTATGAGCAATAATGTGATTTCTGGACATTGCCCATGTATAATCCTCACTGATGA
TTTCAAGCTAAAGCAAACCACCTTATACAGAGATCTAGAATCTCTTTATGTTCTC
CAGAGGAAGGTGGAAGAAACCATGGGCAGGAGTAGGAATTGAGTGATAAACAA
TTGGGCTAATGAAGAAAACTTCTCTTATTGTTCAGTTCATCCAGATTATAACTTCA
ATGGGACACTTTAGACCATTAGACAATTGACACTGGATTAAACAAATTCACATAA
TGCCAAATACACAATGTATTTATAGCAACGTATAATTTGCAAAGATGGACTTTAA
AAGATGCTGTGTAACTAAACTGAAATAATTCAATTACTTATTATTTAGAATGTTA
AAGCTTATGATAGTCTTTTCTAATTCTTAACACTCATACTTGAAATCTTTCCGAGT
TTCCCCAGAAGAGAATATGGGATTTTTTTTGACATTTTTGACCCATTTAATAATGC
TCTTGTGTTTACCTAGTATATGTAGACTTTGTCTTATGTGTCAAAAGTCCTAGGAA
AGTGGTTGATGTTTCTTATAGCAATTAAAAATTATTTTTGAACTGA (SEQ ID NO:41)

FIG. 27

Guanylate Binding Protein Isoform 1 Amino Acid Sequence (GI:183002)

MASEIHMTGPMCLIENTNGRLMANPEALKILSAITQPMVVVAIVGLYRTGKSYLMNK
LAGKKKGFSLGSTVQSHTKGIWMWCVPHPKKPGHILVLLDTEGLGDVEKGDNQND
SWIFALAVLLSSTFVYNSIGTINQQAMDQLYYVTELTHRIRSKSSPDENENEVEDSAD
FVSFFPDFVWTLRDFSLDLEADGQPLTPDEYLTYSLKLKKGTSQKDETFNLPRLCIRK
FFPKKKCFVFDRPVHRRKLAQLEKLQDEELDPEFVQQVADFCSYIFSNSKTKTLSGGI
QVNGPRLESLVLTYVNAISSGDLPCMENAVLALAQIENSAAVQKAIAHYEQQMGQK
VQLPTESLQELLDLHRDSEREAIEVFIRSSFKDVDHLFQKELAAQLEKKRDDFCKQNQ
EASSDRCSGLLQVIFSPLEEEVKAGIYSKPGGYRLFVQKLQDLKKKYYEEPRKGIQAE
EILQTYLKSKESMTDAILQTDQTLTEKEKEIEVERVKAESAQASAKMLQEMQRKNEQ
MMEQKERSYQEHLKQLTEKMENDRVQLLKEQERTLALKLQEQEQLLKEGFQKESRI
MKNEIQDLQTKMRRRKACTIS (SEQ ID NO:42)

FIG. 29

Homo Sapiens Transcription Factor ISGF-3 Nucleic Acid Sequence (GI:2281070)

ATTAAACCTCTCGCCGAGCCCCTCCGCAGACTCTGCGCCGGAAAGTTTCATTTGC
TGTATGCCATCCTCGAGAGCTGTCTAGGTTAACGTTCGCACTCTGTGTATATAAC
CTCGACAGTCTTGGCACCTAACGTGCTGTGCGTAGCTGCTCCTTTGGTTGAATCCC
CAGGCCCTTGTTGGGGCACAAGGTGGCAGGATGTCTCAGTGGTACGAACTTCAG
CAGCTTGACTCAAAATTCCTGGAGCAGGTTCACCAGCTTTATGATGACAGTTTTC
CCATGGAAATCAGACAGTACCTGGCACAGTGGTTAGAAAAGCAAGACTGGGAGC
ACGCTGCCAATGATGTTTCATTTGCCACCATCCGTTTTCATGACCTCCTGTCACAG
CTGGATGATCAATATAGTCGCTTTTCTTTGGAGAATAACTTCTTGCTACAGCATA
ACATAAGGAAAAGCAAGCGTAATCTTCAGGATAATTTTCAGGAAGACCCAATCC
AGATGTCTATGATCATTTACAGCTGTCTGAAGGAAGAAAGGAAAATTCTGGAAA
ACGCCCAGAGATTTAATCAGGCTCAGTCGGGGAATATTCAGAGCACAGTGATGT
TAGACAAACAGAAAGAGCTTGACAGTAAAGTCAGAAATGTGAAGGACAAGGTT
ATGTGTATAGAGCATGAAATCAAGAGCCTGGAAGATTTACAAGATGAATATGAC
TTCAAATGCAAAACCTTGCAGAACAGAGAACACGAGACCAATGGTGTGGCAAAG
AGTGATCAGAAACAAGAACAGCTGTTACTCAAGAAGATGTATTTAATGCTTGAC
AATAAGAGAAAGGAAGTAGTTCACAAAATAATAGAGTTGCTGAATGTCACTGAA
CTTACCCAGAATGCCCTGATTAATGATGAACTAGTGGAGTGGAAGCGGAGACAG
CAGAGCGCCTGTATTGGGGGGCCGCCCAATGCTTGCTTGGATCAGCTGCAGAACT
GGTTCACTATAGTTGCGGAGAGTCTGCAGCAAGTTCGGCAGCAGCTTAAAAAGTT
GGAGGAATTGGAACAGAAATACACCTACGAACATGACCCTATCACAAAAAACAA
ACAAGTGTTATGGGACCGCACCTTCAGTCTTTTCCAGCAGCTCATTCAGAGCTCG
TTTGTGGTGGAAAGACAGCCCTGCATGCCAACGCACCCTCAGAGGCCGCTGGTCT
TGAAGACAGGGGTCCAGTTCACTGTGAAGTTGAGACTGTTGGTGAAATTGCAAG
AGCTGAATTATAATTTGAAAGTCAAAGTCTTATTTGATAAAGATGTGAATGAGAG
AAATACAGTAAAAGGATTTAGGAAGTTCAACATTTTGGGCACGCACACAAAAGT
GATGAACATGGAGGAGTCCACCAATGGCAGTCTGGCGGCTGAATTTCGGCACCT
GCAATTGAAAGAACAGAAAAATGCTGGCACCAGAACGAATGAGGGTCCTCTCAT
CGTTACTGAAGAGCTTCACTCCCTTAGTTTTGAAACCCAATTGTGCCAGCCTGGTT
TGGTAATTGACCTCGAGACGACCTCTCTGCCCGTTGTGGTGATCTCCAACGTCAG
CCAGCTCCCGAGCGGTTGGGCCTCCATCCTTTGGTACAACATGCTGGTGGCGGAA
CCCAGGAATCTGTCCTTCTTCCTGACTCCACCATGTGCACGATGGGCTCAGCTTTC
AGAAGTGCTGAGTTGGCAGTTTTCTTCTGTCACCAAAAGAGGTCTCAATGTGGAC
CAGCTGAACATGTTGGGAGAGAAGCTTCTTGGTCCTAACGCCAGCCCCGATGGTC
TCATTCCGTGGACGAGGTTTTGTAAGGAAAATATAAATGATAAAAATTTTCCCTT
CTGGCTTTGGATTGAAAGCATCCTAGAACTCATTAAAAAACACCTGCTCCCTCTC
TGGAATGATGGGTGCATCATGGGCTTCATCAGCAAGGAGCGAGAGCGTGCCCTG
TTGAAGGACCAGCAGCCGGGGACCTTCCTGCTGCGGTTCAGTGAGAGCTCCCGG
GAAGGGGCCATCACATTCACATGGGTGGAGCGGTCCCAGAACGGAGGCGAACCT
GACTTCCATGCGGTTGAACCCTACACGAAGAAAGAACTTTCTGCTGTTACTTTCC
CTGACATCATTCGCAATTACAAAGTCATGGCTGCTGAGAATATTCCTGAGAATCC
CCTGAAGTATCTGTATCCAAATATTGACAAAGACCATGCCTTTGGAAAGTATTAC

FIG. 29 (cont.)

TCCAGGCCAAAGGAAGCACCAGAGCCAATGGAACTTGATGGCCCTAAAGGAACT
GGATATATCAAGACTGAGTTGATTTCTGTGTCTGAAGTTCACCCTTCTAGACTTCA
GACCACAGACAACCTGCTCCCCATGTCTCCTGAGGAGTTTGACGAGGTGTCTCGG
ATAGTGGGCTCTGTAGAATTCGACAGTATGATGAACACAGTATAGAGCATGAAT
TTTTTTCATCTTCTCTGGCGACAGTTTTCCTTCTCATCTGTGATTCCCTCCTGCTAC
TCTGTTCCTTCACATCCTGTGTTTCTAGGGAAATGAAAGAAAGGCCAGCAAATTC
GCTGCAACCTGTTGATAGCAAGTGAATTTTTCTCTAACTCAGAAACATCAGTTAC
TCTGAAGGGCATCATGCATCTTACTGAAGGTAAAATTGAAAGGCATTCTCTGAAG
AGTGGGTTTCACAAGTGAAAAACATCCAGATACACCCAAAGTATCAGGACGAGA
ATGAGGGTCCTTTGGGAAAGGAGAAGTTAAGCAACATCTAGCAAATGTTATGCA
TAAAGTCAGTGCCCAACTGTTATAGGTTGTTGGATAAATCAGTGGTTATTTAGGG
AACTGCTTGACGTAGGAACGGTAAATTTCTGTGGGAGAATTCTTACATGTTTTCT
TTGCTTTAAGTGTAACTGGCAGTTTTCCATTGGTTTACCTGTGAAATAGTTCAAAG
CCAAGTTTATATACAATTATATCAGTCCTCTTTCAAAGGTAGCCATCATGGATCT
GGTAGGGGGAAAATGTGTATTTTATTACATCTTTCACATTGGCTATTTAAAGACA
AAGACAAATTCTGTTTCTTGAGAAGAGAATATTAGCTTTACTGTTTGTTATGGCTT
AATGACACTAGCTAATATCAATAGAAGGATGTACATTTCCAAATTCACAAGTTGT
GTTTGATATCCAAAGCTGAATACATTCTGCTTTCATCTTGGTCACATACAATTATT
TTTACAGTTCTCCCAAGGGAGTTAGGCTATTCACAACCACTCATTCAAAAGTTGA
AATTAACCATAGATGTAGATAAACTCAGAAATTTAATTCATGTTTCTTAAATGGG
CTACTTTGTCCTTTTTGTTATTAGGGTGGTATTTAGTCTATTAGCCACAAAATTGG
GAAAGGAGTAGAAAAAGCAGTAACTGACAACTTGAATAATACACCAGAGATAAT
ATGAGAATCAGATCATTTCAAAACTCATTTCCTATGTAACTGCATTGAGAACTGC
ATATGTTTCGCTGATATATGTGTTTTTCACATTTGCGAATGGTTCCATTCTCTCTCC
TGTACTTTTTCCAGACACTTTTTTGAGTGGATGATGTTTCGTGAAGTATACTGTAT
TTTTACCTTTTTCCTTCCTTATCACTGACACAAAAAGTAGATTAAGAGATGGGTTT
GACAAGGTTCTTCCCTTTTACATACTGCTGTCTATGTGGCTGTATCTTGTTTTTCC
ACTACTGCTACCACAACTATATTATCATGCAAATGCTGTATTCTTCTTTGGTGGAG
ATAAAGATTTCTTGAGTTTTGTTTTAAAATTAAAGCTAAAGTATCTGTATTGCATT
AAATATAATATCGACACAGTGCTTTCCGTGGCACTGCATACAATCTGAGGCCTCC
TCTCTCAGTTTTTATATAGATGGCGAGAACCTAAGTTTCAGTTGATTTTACAATTG
AAATGACTAAAAAACAAAGAAGACAACATTAAAAACAATATTGTTTCTA (SEQ ID NO:43)

FIG. 30

Homo Sapiens Transcription Factor ISGF-3 Amino Acid Sequence (GI:2281071)

MSQWYELQQLDSKFLEQVHQLYDDSFPMEIRQYLAQWLEKQDWEHAANDVSFATI
RFHDLLSQLDDQYSRFSLENNFLLQHNIRKSKRNLQDNFQEDPIQMSMIIYSCLKEER
KILENAQRFNQAQSGNIQSTVMLDKQKELDSKVRNVKDKVMCIEHEIKSLEDLQDEY
DFKCKTLQNREHETNGVAKSDQKQEQLLLKKMYLMLDNKRKEVVHKIIELLNVTEL
TQNALINDELVEWKRRQQSACIGGPPNACLDQLQNWFTIVAESLQQVRQQLKKLEE
LEQKYTYEHDPITKNKQVLWDRTFSLFQQLIQSSFVVERQPCMPTHPQRPLVLKTGV
QFTVKLRLLVKLQELNYNLKVKVLFDKDVNERNTVKGFRKFNILGTHTKVMNMEES
TNGSLAAEFRHLQLKEQKNAGTRTNEGPLIVTEELHSLSFETQLCQPGLVIDLETTSLP
VVVISNVSQLPSGWASILWYNMLVAEPRNLSFFLTPPCARWAQLSEVLSWQFSSVTK
RGLNVDQLNMLGEKLLGPNASPDGLIPWTRFCKENINDKNFPFWLWIESILELIKKHL
LPLWNDGCIMGFISKERERALLKDQQPGTFLLRFSESSREGAITFTWVERSQNGGEPD
FHAVEPYTKKELSAVTFPDIIRNYKVMAAENIPENPLKYLYPNIDKDHAFGKYYSRPK
EAPEPMELDGPKGTGYIKTELISVSEVHPSRLQTTDNLLPMSPEEFDEVSRIVGSVEFD
SMMNTV (SEQ ID NO:44)

FIG. 32

Mad Protein Homolog Nucleic Acid Sequence (Accession No. U68019)

CCCGGCGTCCCGTCGAGCCCAGCCCCGCCGGGGGCGCTCCTCGCCGCCCGCACGC
CCTCCCCAGCCATGTCGTCCATCCTGCCTTTCACTCCCCCGATCGTGAAGCGCCTG
CTGGGCTGGAAGAAGGGCGAGCAGAACGGGCAGGAGGAGAAATGGTGCGAGAA
GGCGGTCAAGAGCCTGGTCAAGAAACTCAAGAAGACGGGGCAGCTGGACGAGC
TGGAGAAGGCCATCACCACGCAGAACGTCAACACCAAGTGCATCACCATCCCCA
GGTCCCTGGATGGCCGGTTGCAGGTGTCCCATCGGAAGGGGCTCCCTCATGTCAT
CTACTGCCGCCTGTGGCGATGGCCAGACCTGCACAGCCACCACGAGCTGCGGGC
CATGGAGCTGTGTGAGTTCGCCTTCAATATGAAGAAGGACGAGGTCTGCGTGAA
TCCCTACCACTACCAGAGAGTAGAGACACCAGTTCTACCTCCTGTGTTGGTGCCA
CGCCACACAGAGATCCCGGCCGAGTTCCCCCCACTGGACGACTACAGCCATTCCA
TCCCCGAAAACACTAACTTCCCCGCAGGCATCGAGCCCCAGAGCAATATTCCAG
AGACCCCACCCCCTGGCTACCTGAGTGAAGATGGAGAAACCAGTGACCACCAGA
TGAACCACAGCATGGACGCAGGTTCTCCAAACCTATCCCCGAATCCGATGTCCCC
AGCACATAATAACTTGGACCTGCAGCCAGTTACCTACTGCGAGCCGGCCTTCTGG
TGCTCCATCTCCTACTACGAGCTGAACCAGCGCGTCGGGGAGACATTCCACGCCT
CGCAGCCATCCATGACTGTGGATGGCTTCACCGACCCCTCCAATTCGGAGCGCTT
CTGCCTAGGGCTGCTCTCCAATGTCAACAGGAATGCAGCAGTGGAGCTGACACG
GAGACACATCGGAAGAGGCGTGCGGCTCTACTACATCGGAGGGGAGGTCTTCGC
AGAGTGCCTCAGTGACAGCGCTATTTTTGTCCAGTCTCCCAACTGTAACCAGCGC
TATGGCTGGCACCCGGCCACCGTCTGCAAGATCCCACCAGGATGCAACCTGAAG
ATCTTCAACAACCAGGAGTTCGCTGCCCTCCTGGCCCAGTCGGTCAACCAGGGCT
TTGAGGCTGTCTACCAGTTGACCCGAATGTGCACCATCCGCATGAGCTTCGTCAA
AGGCTGGGGAGCGGAGTACAGGAGACAGACTGTGACCAGTACCCCCTGCTGGAT
TGAGCTGCACCTGAATGGGCCTTTGCAGTGGCTTGACAAGGTCCTCACCCAGATG
GGCTCCCCAAGCATCCGCTGTTCCAGTGTGTCTTAGAGACATCAAGTATGGTAGG
GGAGGGCAGGCTTGGGGAAAATGGCCATACAGGAGGTGGAGAAAATTGGAACT
CTACTCAACCCATTGTTGTCAAGGAAGAAGAAATCTTTCTCCCTCAACTGAAGGG
GTGCACCCACCTGTTTTCTGAAACACACGAGCAAACCCAGAGGTGGATGTTATGA
ACAGCTGTGTCTGCCAAACACATTTACCCTTTGGCCCCACTTTGAAGGGCAAGAA
ATGGCGTCTGCTCTGGTGGCTTAAGTGAGCAGAACAGGTAGTATTACACCACCGG
CACCCTCCCCCCAGACTCTTTTTTGAGTGACAGCTTTCTGGGATGTCACAGTCCA
ACCAGAAACGCCCCTCTGTCTAGGACTGCAGTGTGGAGTTCACCTTGGAAGGGC
GTTCTAGGTAGGAAGAGCCCGCACGATGCAGACCTCATGCCCAGCTCTCTGACGC
TTGTGACAGTGCCTCTTCCAGTGAACATTCCCAGCCCAGCCCCGCCCCGTTGTGA
GCTGGATAGACTTGGGATGGGGAGGGAGGGAGTTTTGTCTGTCTCCCTCCCCTCT
CAGAACATACTGATTGGGAGGTGCGTGTTCAGCAGAACCTGCACACAGGACAGC
GGGAAAAATCGATGAGCGCCACCTCTTTAAAAACTCACTTACGTTGTCCTTTTTC
ACTTTGAAAAGTTGGAAGGACTGCTGAGGCCCAGTGCATATGCAATGTATAGTGT
CTATTATCACATTAATCTCAAAGAGATTCGAATGACGGTAAGTGTTCTCATGAAG
CAGGAGGCCCTTGTCGTGGGATGGCATTTGGTCTCAGGCAGCACCACACTGGGTG
CGTCTCCAGTCATCTGTAAGAGCTTGCTCCAGATTCTGATGCATACGGCTATATT
GGTTTATGTAGTCAGTTGCATTCATTAAATCAACTTTATCATATGCTCAAAAAAA
AAAAAAAG (SEQ ID NO:45)

FIG. 33

Mad Protein Homolog Amino Acid Sequence (GI:13633920)

MSSILPFTPPIVKRLLGWKKGEQNGQEEKWCEKAVKSLVKKLKKTGQLDELEKAITT
QNVNTKCITIPRSLDGRLQVSHRKGLPHVIYCRLWRWPDLHSHHELRAMELCEFAFN
MKKDEVCVNPYHYQRVETPVLPPVLVPRHTEIPAEFPPLDDYSHSIPENTNFPAGIEPQ
SNIPETPPPGYLSEDGETSDHQMNHSMDAGSPNLSPNPMSPAHNNLDLQPVTYCEPA
FWCSISYYELNQRVGETFHASQPSMTVDGFTDPSNSERFCLGLLSNVNRNAAVELTR
RHIGRGVRLYYIGGEVFAECLSDSAIFVQSPNCNQRYGWHPATVCKIPPGCNLKIFNN
QEFAALLAQSVNQGFEAVYQLTRMCTIRMSFVKGWGAEYRRQTVTSTPCWIELHLN
GPLQWLDKVLTQMGSPSIRCSSVS (SEQ ID NO:46)

FIG. 35

Human Transforming Growth Factor-Beta Type III Receptor Nucleic Acid Sequence (Accession No. L07594)

TCTTTAAGATTTGTAGCTACTAAGAAAGAAAGGAGCTTTTTTCCTTGGGCCTTCA
AACTGAAAGAACCGCATGAGCCTGACGGCGCATGGTCTTAACATCAGGCTGTGC
AGGAAGAAGCTATCTGCAGATGGATGCCAGCACACACAAGGAAGCAGAGCTCTG
GCAACATTGAGTCAAAGCAAGGACACAACATCAGAGGGACGGCAGAGAATCCTT
GTGTGTAGTCTTTGGTGGCAGTTTGAAAATTGCAAGGAGGGACTTTAAGACTACT
TCTGATTTGCAAAGATGGTCTGTGCTCCGAGCAGGCTAAAGTGACTGGACGAGA
CGCACTGTTGGAGAAATAAAAATGACTTCCCATTATGTGATTGCCATCTTTGCCC
TGATGAGCTTCTGTTTAGCCACTGCAGGTCCAGAGCCTGGTGCACTGTGTGAACT
GTCACCTGTCAGTGCCTCCCATCCTGTCCAGGCCTTGATGGAGAGCTTCACTGTTT
TGTCAGGCTGTGCCAGCAGAGGCACAACTGGGCTGCCACAGGAGGTGCATGTCC
TGAATCTCGCACTGCGCCAGGGGCCTGGCCAGCTACAGAGAGAGGTCACACTTC
ACCTGAATCCCATCTCCTCAGTCCACATCCACCACAAGTCTGTTGTGTTCCTGCTC
AACTCCCCACACCCCCTGGTGTGGCATCTGAAGACAGAGAGACTTGCCACTGGG
GTCTCCAGACTGTTTTTGGTGTCTGAGGGTTCTGTGGTCCAGTTTTCATCAGCAAA
CTTCTCCTTGACAGCAGAAACAGAAGAAAGGAACTTCCCCCATGGAAATGAACA
TCTGTTAAATTGGGCCCGAAAAGAGTATGGAGCAGTTACTTCATTCACCGAACTC
AAGATAGCAAGAAACATTTATATTAAAGTGGGGGAAGATCAAGTGTTCCCTCCA
AAGTGCAACATAGGGAAGAATTTTCTCTCACTCAATTACCTTGCTGAGTACCTTC
AACCCAAAGCAGCAGAAGGGTGTGTGATGTCCAGCCAGCCCCAGAATGAGGAAG
TACACATCATCGAGCTAATCACCCCCAACTCTAACCCCTACAGTGCTTTCCAGGT
GGATATAACAATTGATATAAGACCTTCTCAAGAGGATCTTGAAGTGGTCAAAAA
TCTCATCCTGATCTTGAAGTGCAAAAAGTCTGTCAACTGGGTGATCAAATCTTTT
GATGTTAAGGGAAGCCTGAAAATTATTGCTCCTAACAGTATTGGCTTTGGAAAAG
AGAGTGAAAGATCTATGACAATGACCAAATCAATAAGAGATGACATTCCTTCAA
CCCAAGGGAATCTGGTGAAGTGGGCTTTGGACAATGGCTATAGTCCAATAACTTC
ATACACAATGGCTCCTGTGGCAATAGTATTTCATCTTCGGCTTGAAAATAATGAG
GAGATGGGAGATGAGGAAGTCCACACTATTCCTCCTGAGCTACGGATCCTGCTG
GACCCTGGTGCCCTGCCTGCCCTGCAGAACCCGCCCATCCGGGGAGGGGAAGGC
CAAAATGGAGGCCTTCCGTTTCCTTTCCCAGATATTTCCAGGAGAGTCTGGAATG
AAGAGGGAGAAGATGGGCTCCCTCGGCCAAAGGACCCTGTCATTCCCAGCATAC
AACTGTTTCCTGGTCTCAGAGAGCCAGAAGAGGTGCAAGGGAGCGTGGATATTG
CCCTGTCTGTCAAATGTGACAATGAGAAGATGATCGTGGCTGTAGAAAAAGATT
CTTTTCAGGCCAGTGGCTACTCGGGGATGGACGTCACCCTGTTGGATCCTACCTG
CAAGGCCAAGATGAATGGCACACACTTTGTTTTGGAGTCTCCTCTGAATGGCTGC
GGTACTCGGCCCCGGTGGTCAGCCCTTGATGGTGTGGTCTACTATAACTCCATTG
TGATACAGGTTCCAGCCCTTGGGGACAGTAGTGGTTGGCCAGATGGTTATGAAG
ATCTGGAGTCAGGTGATAATGGATTTCCGGGAGATATGGATGAAGGAGATGCTT
CCCTGTTCACCCGACCTGAAATCGTGGTGTTTAATTGCAGCCTTCAGCAGGTGAG
GAACCCCAGCAGCTTCCAGGAACAGCCCCACGGAAACATCACCTTCAACATGGA
GCTATACAACACTGACCTCTTTTTGGTGCCCTCCCAGGGCGTCTTCTCTGTGCCAG

FIG. 35 (cont.)

AGAATGGACACGTTTATGTTGAGGTATCTGTTACTAAGGCTGAACAAGAACTGG
GATTTGCCATCCAAACGTGCTTTATCTCTCCATATTCGAACCCTGATAGGATGTCT
CATTACACCATTATTGAGAATATTTGTCCTAAAGATGAATCTGTGAAATTCTACA
GTCCCAAGAGAGTGCACTTCCCTATCCCGCAAGCTGACATGGATAAGAAGCGAT
TCAGCTTTGTCTTCAAGCCTGTCTTCAACACCTCACTGCTCTTTCTACAGTGTGAG
CTGACGCTGTGTACGAAGATGGAGAAGCACCCCCAGAAGTTGCCTAAGTGTGTG
CCTCCTGACGAAGCCTGCACCTCGCTGGACGCCTCGATAATCTGGGCCATGATGC
AGAATAAGAAGACGTTCACCAAGCCCCTTGCTGTGATCCACCATGAAGCAGAAT
CTAAAGAAAAAGGTCCAAGCATGAAGGAACCAAATCCAATTTCTCCACCAATTT
TCCATGGTCTGGACACCCTAACCGTGATGGGCATTGCGTTTGCAGCCTTTGTGAT
CGGAGCACTCCTGACGGGGGCCTTGTGGTACATCTATTCTCACACAGGGGAGAC
AGCAGGAAGGCAGCAAGTCCCCACCTCCCCGCCAGCCTCGGAAAACAGCAGTGC
TGCCCACAGCATCGGCAGCACGCAGAGCACGCCTTGCTCCAGCAGCAGCACGGC
CTAGCCCAACCCAGGCCCAACCCGGCCCAACCCAGCCCAGCCCAGCTCAGCTCA
GCTACTCCAAGGGCAGGACCAATGGCTGAGCCTCGTGTCCAGACTCAGAGGGCT
GGATTTTGGTTCCCTTGTAAAGACAGAGTGAATTTCAGTATAAAGATCACCCGTT
GTATTCACCCCACACCCAGGGCTAGTATAAACATGACCCTGGGCTTCTGTACCAC
ACTAGAATTCATGTGAGAAAGCTAAAATGGTGGTCTTCTCCACCAGCCCCTCACA
GGCTTGGGGGTTTTCTATGTGAAACACATGCCAGTTTTTAAAATGCTGCTTTGTCC
AGGTGAGAACATCCATAATTTGGGGCCCTGAGTTTTACCCAGACTCAAGGAGTTG
GTAAAGGGTTAATAGCCAGATAGTAGAACCAGTGAGGAGATGCGGCCAAAGATT
CTTTATATCTGAACCAAGATGTAAAACAAGAAATGCTTTGAGGCTTTCTAAGCGA
TCCTCCTGTCTAATTTGCACCTTTGTCTGGATGCACTCTTCTGACCTTGCTGCCAC
AACCTGTGGGGTCTGATGTGTCCCAAGATGGGTGCTGCCCTCAGGGACTGCACCC
TGACAAGTGTTAAGGCAACATTCCTTGCTTGTGCCCTGGGCCAAAACCAATGCTG
ATGACCTTATCAGCTTCCTGTTTCTTCCCATACTGCATACACCACTGCAAAATGTC
TTAATGCAAATTTTGTATTTCTTACAGGCCTACAGAAATTGAAAATGACCAAAAT
CAGGAACCACAGATTTGTGCCCATTCCTAATATTTTGTTCTGCAAATTAATGTATA
ATTTGAGGTGAAATTCAGTTATAAAGTCAAGGACGAATTTGCACAGTGATATATT
TCTATGTGTATGCAAGTACAAGTATATAATATGTCACCTGGCACATTCATTTTCTC
AGTTGAAGAAGAGAAAATTTGAAAATGTCCTTATGCTTTTAGAGTTGCAACTTAA
GTATATTTGGTAGGGTGAGTGTTTCCACTCAAAATATGTCAACTTAAAAAAAAAT
AGGCCCTTTCATAAAAACCAAACTGTAGCAAGATGCAAATGCATGGCAAATCTG
TCGGTCTCCAGTTGGTTATCTGAATAGTGTCACCAATTCCACCAAGACAGTGCTG
AGATTGGAAAGGGCACTCATTTGGATTGCCTTACTTCTCTTGCCTTAAATATATCC
CATATATTTAATATGTCAAAAAGGGCTTGAGGTGAATTTCATTAAATGGAATAAT
ATGATGCCACTTTGCAGCTAAAATAAGCTCAGTGATACCTCCTTGTT (SEQ ID NO:47)

FIG. 36

Human Transforming Growth Factor-Beta Type III Receptor Amino Acid Sequence (Accession No. Q03167)

MTSHYVIAIFALMSFCLATAGPEPGALCELSPVSASHPVQALMESFTVLSGCASRGTT
GLPQEVHVLNLALRQGPGQLQREVTLHLNPISSVHIHHKSVVFLLNSPHPLVWHLKT
ERLATGVSRLFLVSEGSVVQFSSANFSLTAETEERNFPHGNEHLLNWARKEYGAVTS
FTELKIARNIYIKVGEDQVFPPKCNIGKNFLSLNYLAEYLQPKAAEGCVMSSQPQNEE
VHIIELITPNSNPYSAFQVDITIDIRPSQEDLEVVKNLILILKCKKSVNWVIKSFDVKGSL
KIIAPNSIGFGKESERSMTMTKSIRDDIPSTQGNLVKWALDNGYSPITSYTMAPVAIVF
HLRLENNEEMGDEEVHTIPPELRILLDPGALPALQNPPIRGGEGQNGGLPFPFPDISRR
VWNEEGEDGLPRPKDPVIPSIQLFPGLREPEEVQGSVDIALSVKCDNEKMIVAVEKDS
FQASGYSGMDVTLLDPTCKAKMNGTHFVLESPLNGCGTRPRWSALDGVVYYNSIVI
QVPALGDSSGWPDGYEDLESGDNGFPGDMDEGDASLFTRPEIVVFNCSLQQVRNPSS
FQEQPHGNITFNMELYNTDLFLVPSQGVFSVPENGHVYVEVSVTKAEQELGFAIQTC
FISPYSNPDRMSHYTIIENICPKDESVKFYSPKRVHFPIPQADMDKKRFSFVFKPVFNTS
LLFLQCELTLCTKMEKHPQKLPKCVPPDEACTSLDASIIWAMMQNKKTFTKPLAVIH
HEAESKEKGPSMKEPNPISPPIFHGLDTLTVMGIAFAAFVIGALLTGALWYIYSHTGET
AGRQQVPTSPPASENSSAAHSIGSTQSTPCSSSSTA (SEQ ID NO:48)

FIG. 38

Early B Cell Factor Nucleic Acid Sequence (GI:6630993)

GGAAAGCATCCAACGGAGTGGAAGCAGCATGAAGGAAGAGCCGCTGGGCAGCG
GCATGAACGCGGTGCGGACGTGGATGCAGGGCGCCGGGGTGCTGGACGCCAACA
CGGCGGCGCAGAGCGGGGTGGGTCTGGCCCGGGCTCACTTTGAGAAGCAGCCGC
CTTCCAATCTGCGGAAATCCAACTTCTTCCACTTCGTCCTGGCCCTCTACGACAGA
CAGGGCCAGCCCGTGGAGATCGAGAGGACAGCGTTTGTGGGGTTCGTGGAGAAG
GAAAAAGAAGCCAACAGCGAAAAGACCAATAACGGAATTCACTACCGGATTCA
GCTTCTCTACAGCAATGGGATAAGGACGGAGCAGGATTTCTACGTGCGCCTCATT
GACTCCATGACAAAACAAGCCATAGTGTATGAAGGCCAAGACAAGAGCCCAGAA
ATGTGCCGAGTCTTGCTCACACATGAGATCATGTGCAGCCGCTGTTGTGACAAGA
AAAGCTGTGGCAACCGAAATGAGACTCCCTCAGATCCAGTGATAATTGACAGAT
TCTTCTTGAAATTTTTCCTCAAATGTAACCAAAATTGCCTAAAGAATGCGGGAAA
CCCACGTGACATGCGGAGATTCCAGGTCGTGGTGTCTACGACAGTCAATGTGGAT
GGCCATGTCCTGGCAGCTCCTGATAACATGTTTGTCCATAATAATTCCAAGCATG
GGCGGAGGGCTCGGAGGCTTGACCCCTCGGAAGGTACGCCCTCTTATCTGGAAC
ATGCTACTCCCTGTATCAAAGCCATCAGCCCGAGTGAAGGATGGACGACCGGAG
GTGCGACTGTCATCATCATAGGGGACAATTTCTTTGATGGGTTACAGGTCATATT
CGGTACCATGCTGGTCTGGAGTGAGTTGACAGGTCCTCATTCCATCCGTGTGCAG
ACCCCTCCTCGGCACATCCCTGGTGTTGTGGAAGTCACACTGTCCTACAAATCTA
AGCAGTTCTGCAAAGGAACACCAGGCAGATTCATTTATACAGCGCGCAACGAAC
CCACCATCGATTATGGTTTCCAGAGGTTACAGAAGGTCATTCCTCGGCACCCTGG
TGACCCTGAGCGTTTGCCAAAGGAAGTAATACTGAAAAGGGCTGCGGATCTGGT
AGAAGCACTGTATGGGATGCCACACAACAACCAGGAAATCATTCTGAAGAGAGC
GGCCGACATTGCCGAGGCCCTGTACAGTGTCCCCCGCAACCACAACCAACTCCCG
GCCCTTGCTAACACCTCGGTCCACGCAGGGATGATGGGCGTGAATTCGTTCAGTG
GACAACTGGCCGTGAATGTCTCCGAGGCATCACAAGCCACCAATCAGGGTTTCA
CCCGCAACTCAAGCAGCGTATCACCACACGGGTACGTGCCGAGCACCACTCCCC
AGCAGACCAACTATAACTCCGTCACCACGAGCATGAACGGATACGGCTCTGCCG
CAATGTCCAATTTGGGTGGCTCCCCCACCTTCCTCAACGGCTCAGCTGCCAACTC
CCCCTATGCCATAGTGCCATCCAGCCCCACCATGGCCTCCTCCACAAGCCTCCCC
TCCAACTGCAGCAGCTCCTCGGGCATCTTCTCCTTCTCACCAGCCAACATGGTCTC
AGCCGTGAAACAGAAGAGTGCTTTCGCACCAGTCGTCAGACCCCAGACCTCCCC
ACCTCCCACCTGCACCAGCACCAACGGGAACAGCCTGCAAGCGATATCTGGCAT
GATTGTTCCTCCTATGTGAAAGAATTGCCTTGAAGAATTGTATTAATGAAGAGGT
TGGATTCTGCTACAGAGAGTAATCTGATACAAGTCCCAGAGTGGAACTTTTAACT
CAGGCCTTTATAAGAGGAATCACACAATAACTGCAGATTTTTAAACAAAATCACC
GACCTTGCAAATACTGAAATTGGAAGAGGAATCTGAAAGTGCAGGGTGTTGGTT
AAAGTTGTACCTCCCAAGTATTTTGGGGATATATTTATTCTGTATTGACAAAAGC
AAATCCACTTTTTCTTTTTCTTTTTTTTTTTTAAGCTTAATTCTGCAATCATTTGAC
TTTTATATACCGTAATGCTCTATACAAGGGACACTATAAATAAGACTCCATGTTT
TAATTTATGTTTTTAAAGCTGTGTAAAGGAAGAATGAAGTGGTGATATTTAC
(SEQ ID NO:49)

FIG. 39

Early B Cell Factor Amino Acid Sequence (GI:6630994)

ESIQRSGSSMKEEPLGSGMNAVRTWMQGAGVLDANTAAQSGVGLARAHFEKQPPS
NLRKSNFFHFVLALYDRQGQPVEIERTAFVGFVEKEKEANSEKTNNGIHYRIQLLYSN
GIRTEQDFYVRLIDSMTKQAIVYEGQDKSPEMCRVLLTHEIMCSRCCDKKSCGNRNE
TPSDPVIIDRFFLKFFLKCNQNCLKNAGNPRDMRRFQVVVSTTVNVDGHVLAAPDN
MFVHNNSKHGRRARRLDPSEGTPSYLEHATPCIKAISPSEGWTTGGATVIIIGDNFFD
GLQVIFGTMLVWSELTGPHSIRVQTPPRHIPGVVEVTLSYKSKQFCKGTPGRFIYTAR
NEPTIDYGFQRLQKVIPRHPGDPERLPKEVILKRAADLVEALYGMPHNNQEIILKRAA
DIAEALYSVPRNHNQLPALANTSVHAGMMGVNSFSGQLAVNVSEASQATNQGFTRN
SSSVSPHGYVPSTTPQQTNYNSVTTSMNGYGSAAMSNLGGSPTFLNGSAANSPYAIV
PSSPTMASSTSLPSNCSSSSGIFSFSPANMVSAVKQKSAFAPVVRPQTSPPPTCTSTNG
NSLQAISGMIVPPM (SEQ ID NO:50)

FIG. 41

Duodenal Cytochrome b Nucleic Acid Sequence (GI:13637447)

GTGGCCCCCGCGGTGCGGAGTATGGGGCGCTGATGGCCATGGAGGGCTACTGGC
GCTTCCTGGCGCTGCTGGGGTCGGCACTGCTCGTCGGCTTCCTGTCGGTGATCTTC
GCCCTCGTCTGGGTCCTCCACTACCGAGAGGGGCTTGGCTGGGATGGGAGCGCA
CTAGAGTTTAACTGGCACCCAGTGCTCATGGTCACCGGCTTCGTCTTCATCCAGG
GCATCGCCATCATCGTCTACAGACTGCCGTGGACCTGGAAATGCAGCAAGCTCCT
GATGAAATCCATCCATGCAGGGTTAAATGCAGTTGCTGCCATTCTTGCAATTATC
TCTGTGGTGGCCGTGTTTGAGAACCACAATGTTAACAATATAGCCAATATGTACA
GTCTGCACAGCTGGGTTGGACTGATAGCTGTCATATGCTATTTGTTACAGCTTCTT
TCAGGTTTTTCAGTCTTTCTGCTTCCATGGGCTCCGCTTTCTCTCCGAGCATTTCTC
ATGCCCATACATGTTTATTCTGGAATTGTCATCTTTGGAACAGTGATTGCAACAG
CACTTATGGGATTGACAGAGAAACTGATTTTTTCCCTGAGAGATCCTGCATACAG
TACATTCCCGCCAGAAGGTGTTTTCGTAAATACGCTTGGCCTTCTGATCCTGGTGT
TCGGGGCCCTCATTTTTTGGATAGTCACCAGACCGCAATGGAAACGTCCTAAGGA
GCCAAATTCTACCATTCTTCATCCAAATGGAGGCACTGAACAGGGAGCAAGAGG
TTCCATGCCAGCCTACTCTGGCAACAACATGGACAAATCAGATTCAGAGTTAAAC
AGTGAAGTAGCAGCAAGGAAAAGAAACTTAGCTCTGGATGAGGCTGGGCAGAG
ATCTACCATGTAAAATGTTGTAGAGATAGAGCCATATAACGTCACGTTTCAAAAC
TAGCTCTACAGTTTTGCTTCTCCTATTAGCCATATGATAATTGGGCTATGTAGTAT
CAATATTTACTTTAATCACAAAGGATGGTTTCTTGAAATAATTTGTATTGATTGAG
GCCTATGAACTGACCTGAATTGGAAAGGATGTGATTAATATAAATAATAGCAGA
TATAAATTAAAAAAAAAAAAAAAGAAAA (SEQ ID NO:51)

FIG. 42

Duodenal Cytochrome b Amino Acid Sequence (GI:13637448)

MAMEGYWRFLALLGSALLVGFLSVIFALVWVLHYREGLGWDGSALEFNWHPVLM
VTGFVFIQGIAIIVYRLPWTWKCSKLLMKSIHAGLNAVAAILAIISVVAVFENHNVNNI
ANMYSLHSWVGLIAVICYLLQLLSGFSVFLLPWAPLSLRAFLMPIHVYSGIVIFGTVIA
TALMGLTEKLIFSLRDPAYSTFPPEGVFVNTLGLLILVFGALIFWIVTRPQWKRPKEPN
STILHPNGGTEQGARGSMPAYSGNNMDKSDSELNSEVAARKRNLALDEAGQRSTM
(SEQ ID NO:52)

FIG. 44

Nuclear LIM Interactor-Interacting Factor Nucleic Acid Sequence (GI:10864008)

CGCCTAGCCGCGCCGGTCCCAGAAGTGGCGAAAGCCGCAGCCGAGTCCAGGTCA
CGCCGAAGCCGTTGCCCTTTTAAGGGGGAGCCTTGAAACGGCGCCTGGGTTCCAT
GTTTGCATCCGCCTCGCGGGAAGGAAACTCCATGTTGTAACAAAGTTTCCTCCGC
GCCCCCTCCCTCCCCCTCCCCCCTAGAACCTGGCTCCCCTCCCCTCCGGAGCTCGC
GGGGATCCCTCCCTCCCACCCCTCCCCTCCCCCCCGCGCCCCGATTCCGGCCCCA
GCCGGGGGGGAGGCCGGGCGCCCGGGCCAGAGTCCGGCCGGAGCGGAGCGCGC
CCGGCCCCATGGACAGCTCGGCCGTCATTACTCAGATCAGCAAGGAGGAGGCTC
GGGGCCCGCTGCGGGGCAAAGGTGACCAGAAGTCAGCAGCTTCCCAGAAGCCCC
GAAGCCGGGGCATCCTCCACTCACTCTTCTGCTGTGTCTGCCGGGATGATGGGGA
GGCCCTGCCTGCTCACAGCGGGGCGCCCCTGCTTGTGGAGGAGAATGGAGCCAT
CCCTAAGCAGACCCCAGTCCAATACCTGCTCCCTGAGGCCAAGGCCCAGGACTC
AGACAAGATCTGCGTGGTCATCGACCTGGACGAGACCCTGGTGCACAGCTCCTTC
AAGCCAGTGAACAACGCGGACTTCATCATCCCTGTGGAGATTGATGGGGTGGTC
CACCAGGTCTACGTGTTGAAGCGTCCTCACGTGGATGAGTTCCTGCAGCGAATGG
GCGAGCTCTTTGAATGTGTGCTGTTCACTGCTAGCCTCGCCAAGTACGCAGACCC
AGTAGCTGACCTGCTGGACAAATGGGGGGCCTTCCGGGCCCGGCTGTTTCGAGA
GTCCTGCGTCTTCCACCGGGGGAACTACGTGAAGGACCTGAGCCGGTTGGGTCG
AGACCTGCGGCGGGTGCTCATCCTGGACAATTCACCTGCCTCCTATGTCTTCCAT
CCAGACAATGCTGTACCGGTGGCCTCGTGGTTTGACAACATGAGTGACACAGAG
CTCCACGACCTCCTCCCCTTCTTCGAGCAACTCAGCCGTGTGGACGACGTGTACT
CAGTGCTCAGGCAGCCACGGCCAGGGAGCTAGTGAGGGTGATGGGGCCAGGACC
TGCCCCTGACCAATGATACCCACACCTCCTCCCAGGAAGACTGCCCAGGCCTTTG
TTAGGAAAACCCATGGGCCGCCGCCACACTCAGTGCCATGGGGAAGCGGGCGTC
TCCCCCACCAGCCCCACCAGGCGGTGTAGGGGCAGCAGGCTGCACTGAGGACCG
TGAGCTCCAGGCCCCGTGTCAGTGCCTTCAAACCTCCTCCCCTATTCTCAGGGGA
CCTGGGGGGCCCTGCCTGCTGCTCCCTTTTTCTGTCTCTGTCCATGCTGCCATGTT
TCTCTGCTGCCAAATTGGGCCCCTTGGCCCCTTCCGGTTCTGCTTCCTGGGGGCAG
GGTTCCTGCCTTGGACCCCCAGTCTGGGAACGGTGGACATCAAGTGCCTTGCATA
GAGCCCCCTCTTCCCCGCCCAGCTTTCCCAGGGGCACAGCTCTAGGCTGGGAGGG
GAGAACCAGCCCCTCCCCCTGCCCCACCTCCTCCCTTGGGACTGAGAGGGCCCCT
ACCAACCTTTGCCTCTGCCTTGGAGGGAGGGGAGGTCTGTTACCACTGGGGAAG
GCAGCAGGAGTCTGTCCTTCAGGCCCCACAGTGCAGCTTCTCCAGGGCCGACAGC
TGAGGGCTGCTCCCTGCATCATCCAAGCAATGACCTCAGACTTCTGCCTTAACCA
GCCCCGGGGCTTGGCTCCCCCAGCTCTGAGCGTGGGGGCATAGGCAGGACCCCC
CTTGTGGTGCCATATAAATATGTACATGTGTATATAGATTTTTAGGGGAAGGAGA
GAGGGAAGGGTCAGGGTAGAGACACCCCTCCCTTGCCCCTTTCCTGGGCCCAGA
AGTTGGGGGGAGGGAGGGAAAGGATTTTTACATTTTTTAAACTGCTATTTTCTGA
ATGGAACAAGCTGGGCCAAGGGGCCCAGGCCCTGTCCTCTGTCCCTCACACCCCT
TTGCTCCGTTCATTCATTCAAAAAAACATTTCTTGAGCACCTTCTGTGCCCAGCAT
ATGCTAGGCCCACCAGCTAAGTGTGTGTGGGGGGTCTCTACGCCAGCTCATCAGT
GCCTCCTTGCCCATCCTTCACCGGTGCCTTTGGGGGATCTGTAGGAGGTGGGACC

FIG. 44 (cont.)

TTCTGTGGGGTTTGGGGATCTCCAGGAAGCCCGACCAAGCTGTCCCCTTCCCCTG
TGCCAACCCATCTCCTACAGCCCCCTGCCTGATCCCCTGCTGGCTGGGGGCAGCT
CCCAGGATATCCTGCCTTCCAACTGTTTCTGAAGCCCCTCCTCCTAACATGGCGAT
TCCGGAGGTCAAGGCCTTGGGCTCTCCCCAGGGTCTAACGGTTAAGGGGACCCA
CATACCAGTGCCAAGGGGGATGTCAAGTGGTGATGTCGTTGTGCTCCCCTCCCCC
AGAGCGGGTGGGCGGGGGGTGAATATGGTTGGCCTGCATCAGGTGGCCTTCCCA
TTTAAGTGCCTTCTCTGTGACTGAGAGCCCTAGTGTGATGAGAACTAAAGAGAAA
GCCAGACCCCTAAAAAAAAAAAAAAAAAA (SEQ ID NO:53)

FIG. 45

Nuclear LIM Interactor-Interacting Factor Amino Acid Sequence (GI:10864009)

MDSSAVITQISKEEARGPLRGKGDQKSAASQKPRSRGILHSLFCCVCRDDGEALPAHS
GAPLLVEENGAIPKQTPVQYLLPEAKAQDSDKICVVIDLDETLVHSSFKPVNNADFIIP
VEIDGVVHQVYVLKRPHVDEFLQRMGELFECVLFTASLAKYADPVADLLDKWGAF
RARLFRESCVFHRGNYVKDLSRLGRDLRRVLILDNSPASYVFHPDNAVPVASWFDN
MSDTELHDLLPFFEQLSRVDDVYSVLRQPRPGS (SEQ ID NO:54)

FIG. 47

Deleted In Liver Cancer 1 Nucleic Acid Sequence (GI:13644952)

GCCCGAGCGAGGGCGCTTCGCTCCCAGCCAGGACATGGCCGCACCTCTCCGCATC
AGGAGCGCCGGCTCACGGACTTCTCGCCCAACTCCCTGAGCGCTCCCTCGTTTCG
ATCTTTAGAAAACCCCGCTTTCTTTCTGGGGCCGTGACGAGGGGCAGGGAGCGGC
GAGCAAGGATGCGTTGAGGACCGCGAGGGCGCGCGTCTCGGGTGCCGCCGTGGG
TCCCGACGCGGAAGCCGAGCCGCCTCCGCCTGCCTCGACTTCCCCACAGCGCTTC
CGCCGCCGCCTGCCGTGCTTGTATGTGCAGAAAGAAGCCGGACACCATGATCCTA
ACACAAATTGAAGCCAAGGAAGCTTGTGATTGGCTACGGGCAACTGGTTTCCCCC
AGTATGCACAGCTTTATGAAGATTTCCTGTTCCCCATCGATATTTCCTTGGTCAAG
AGAGAGCATGATTTTTTGGACAGAGATGCCATTGAGGCTCTATAGGCGTCTAAAT
ACTTTAAACAAATGTGCGGTGATGAAGCTAGAAATTAGTCCTCATCGGAAACGA
GTGACGATTCAGACGAGGATGAGCCTTGTGCCATCAGTGGCAAATGGACTTTCCA
AAGGGACAGCAAGAGGTGGTCCCGGCTTGAAGAGTTTGATGTCTTTTCTCCAAAA
CAAGACCTGGTCCCTGGGTCCCCAGACGACTCCCACCCGAAGGACGGCCCCAGC
CCCGGAGGCACGCTGATGGACCTCAGCGAGCGCCAGGAGGTGTCTTCCGTCCGC
AGCCTCAGCAGCACTGGCAGCCTCCCCAGCCACGCGCCCCCCAGCGAGGATGCT
GCCACCCCCCGGACTAACTCCGTCATCAGCGTTTGCTCCTCCAGCAACTTGGCAG
GCAATGACGACTCTTTCGGCAGCCTGCCCTCTCCCAAGGAACTGTCCAGCTTCAG
CTTCAGCATGAAAGGCCACGAAAAAACTGCCAAGTCCAAGACGCGCAGTCTGCT
GAAACGGATGGAGAGCCTGAAGCTCAAGAGCTCCCATCACAGCAAGCACAAAGC
GCCCTCAAAGCTGGGGTTGATCATCAGCGGGCCCATCTTGCAAGAGGGGATGGA
TGAGGAGAAGCTGAAGCAGCTCAACTGCGTGGAGATCTCCGCCCTCAATGGCAA
CCGCATCAACGTCCCCATGGTACGAAAGAGGAGCGTTTCCAACTCCACGCAGAC
CAGCAGCAGCAGCAGCCAGTCGGAGACCAGCAGCGCGGTCAGCACGCCCAGCCC
TGTTACGAGGACCCGGAGCCTCAGTGCGTGCAACAAGCGGGTGGGCATGTACTT
AGAGGGCTTCGATCCTTTCAATCAGTCAACATTTAACAACGTGATGGAGCAGAAC
TTTAAGAACCGCGAGAGCTACCCAGAGGACACGGTGTTCTACATCCCTGAAGAT
CACAAGCCTGGCACTTTCCCCAAAGCTCTCACCAATGGCAGTTTCTCCCCCTCGG
GGAATAACGGCTCTGTGAACTGGAGGACGGGAAGCTTCCACGGCCCTGGCCACA
TCAGCCTCAGGAGGGAAAACAGTAGCGACAGCCCCAAGGAACTGAAGAGACGC
AATTCTTCCAGCTCCATGAGCAGCCGCCTGAGCATCTACGACAACGTGCCGGGCT
CCATCCTCTACTCCAGTTCAGGGGACCTGGCGGATCTGGAGAACGAGGACATCTT
CCCCGAGCTGGACGACATCCTCTACCACGTGAAGGGGATGCAGCGGATAGTCAA
TCAGTGGTCGGAGAAGTTTTCTGATGAGGGAGATTCGGACTCAGCCCTGGACTCG
GTCTCTCCCTGCCCGTCCTCTCCAAAACAGATACACCTGGATGTGGACAACGACC
GAACCACACCCAGCGACCTGGACAGCACAGGCAACTCCCTGAATGAACCGGAAG
AGCCCTCCGAGATCCCGGAAAGAAGGGATTCTGGGGTTGGGGCTTCCCTAACCA
GGTCCAACAGGCACCGACTGAGATGGCACAGTTTCCAGAGCTCACATCGGCCAA
GCCTCAACTCTGTATCACTACAGATTAACTGCCAGTCTGTGGCCCAGATGAACCT
GCTGCAGAAATACTCACTCCTAAAGCTAACGGCCCTGCTGGAGAAATACACACC
TTCTAACAAGCATGGTTTTAGCTGGGCCGTGCCCAAGTTCATGAAGAGGATCAAG
GTTCCAGACTACAAGGACCGGAGTGTGTTTGGGGTCCCACTGACGGTCAACGTGC

FIG. 47 (cont.)

AGCGCACAGGACAACCGTTGCCTCAGAGCATCCAGCAGGCCATGCGATACCTCC
GGAACCATTGTTTGGATCAGGTTGGGCTCTTCAGAAAATCGGGGGTCAAGTCCCG
GATTCAGGCTCTGCGCCAGATGAATGAAGGTGCCATAGACTGTGTCAACTACGA
AGGACAGTCTGCTTATGACGTGGCAGACATGCTGAAGCAGTATTTTCGAGATCTT
CCTGAGCCACTAATGACGAACAAACTCTCAGAAACCTTTCTACAGATCTACCAAT
ATGTGCCCAAGGACCAGCGACTGCAGGCCATCAAGGCTGCCATCATGCTGCTGC
CTGACGAGAACCGGGAGGTTCTGCAGACCCTGCTTTATTTCCTGAGCGATGTCAC
AGCAGCCGTAAAAGAAAACCAGATGACCCCAACCAACCTGGCCGTGTGCTTAGC
GCCTTCCCTCTTCCATCTCAACACCCTGAAGAGAGAGAATTCCTCTCCCAGGGGT
AATGCAAAGAAAACAAAGTTTGGGCAAACCAGATCAGAAAGATTTGAATGAAA
ACCTAGCTGCCACTCAAGGGCTGGCCCATATGATCGCCGAGTGCAAGAAGCTTTT
CCAGGTTCCCGAGGAAATGAGCCGATGTCGTAATTCCTATACCGAACAAGAGCT
GAAGCCCCTCACTCTGGAAGCACTCGGGCACCTGGGTAATGATGACTCAGCTGA
CTACCAACACTTCCTCCAGGACTGTGTGGATGGCCTGTTTAAAGAAGTCAAAGAG
AAGTTTAAAGGCTGGGTCAGCTACTCCACTTCGGAGCAGGCTGAGCTGTCCTATA
AGAAGGTGAGCGAAGGACCCCCTCTGAGGCTTTGGAGGTCAGTCATTGAAGTCC
CTGCTGTGCCAGAGGAAATCTTAAAGCGCCTACTTAAAGAACAGCACCTCTGGG
ATGTAGACCTGTTGGATTCAAAAGTGATCGAAATTCTGGACAGCCAAACTGAAA
TTTACCAGTATGTCCAAAACAGTATGGCACCTCATCCTGCTCGAGACTACGTTGT
TTTAAGAACCTGGAGGACTAATTTACCCAAAGGAGCCTGTGCCCTTTTACTAACC
TCTGTGGATCACGATCGCGCACCTGTGGTGGGTGTGAGGGTTAATGTGCTCTTGT
CCAGGTATTTGATTGAACCCTGTGGGCCAGGAAAATCCAAACTCACCTACATGTG
CAGAGTTGACTTAAGGGGCCACATGCCAGAATGGTACACAAAATCTTTTGGACA
TTTGTGTGCAGCTGAAGTTGTAAAGATCCGGGATTCCTTCAGTAACCAGAACACT
GAAACCAAAGACACCAAATCTAGGTGATCACTGAAGCAACGCAACCGCTTCCAC
CACCATGGTGTTTGTTTCTAGAACTTTTGCCAGTCCTTGAAGAATGGGTTCTGTGT
CTAATCCTGAAACAAAGAAAACTACAAGCTGGAGTGTAGGAATTGACTATAGCA
ATTTGATACATTTTTAAAGCTGCTTCCTGTTTGTTGAGGGTCTGTATTCATAGACC
TTGACTGGAATATGTAAGACTGTGCAAAAAAAAAAAAAAAA (SEQ ID NO:55)

FIG. 48

Deleted In Liver Cancer 1 Amino Acid Sequence (GI:13644953)

MCRKKPDTMILTQIEAKEACDWLRATGFPQYAQLYEDFLFPIDISLVKREHDFLDRD
AIEALCRRLNTLNKCAVMKLEISPHRKRSDDSDEDEPCAISGKWTFQRDSKRWSRLE
EFDVFSPKQDLVPGSPDDSHPKDGPSPGGTLMDLSERQEVSSVRSLSSTGSLPSHAPPS
EDAATPRTNSVISVCSSSNLAGNDDSFGSLPSPKELSSFSFSMKGHEKTAKSKTRSLLK
RMESLKLKSSHHSKHKAPSKLGLIISGPILQEGMDEEKLKQLSCVEISALNGNRINVP
MVRKRSVSNSTQTSSSSSQSETSSAVSTPSPVTRTRSLSACNKRVGMYLEGFDPFNQS
TFNNVVEQNFKNRESYPEDTVFYIPEDHKPGTFPKALTNGSFSPSGNNGSVNWRTGS
FHGPGHISLRRENSSDSPKELKRRNSSSSMSSRLSIYDNVPGSILYSSSGDLADLENEDI
FPELDDILYHVKGMQRIVNQWSEKFSDEGDSDSALDSVSPCPSSPKQIHLDVDNDRTT
PSDLDSTGNSLNEPEEPSEIPERRDSGVGASLTRSNRHRLRWHSFQSSHRPSLNSVSLQ
INCQSVAQMNLLQKYSLLKLTALLEKYTPSNKHGFSWAVPKFMKRIKVPDYKDRSV
FGVPLTVNVQRTGQPLPQSIQQAMRYLRNHCLDQVGLFKKSGVKSRIQALRQMNEG
AIDCVNYEGQSAYDVADMLKQYFRDLPEPLMTNKLSETFLQIYQYVPKDQRLQAIK
AAIMLLPDENRVVLQTLLYFLCDVTAAVKENQMTPTNLAVCLAPSLFHLNTLKRENS
SPRVMQRKQSLGKPDQKDLNENLAATQGLAHMIAECKKLFQVPEEMSRCRNSYTEQ
ELKPLTLEALGHLGNDDSADYQHFLQDCVDGLFKEVKEKFKGWVSYSTSEQAELSY
KKVSEGPRLRLWRSVIEVPAVPEEILKRLLKEQHLWDVDLLDSKVIEILDSQTEIYQY
VQNSMAPHPARDYVVLRTWRTNLPKGACALLLTSVDHDRAPVVGVRVNVLLSRYL
IEPCGPGKSKLTYMCRVDLRGHMPEWYTKSFGHLCAAEVVKIRDSFSNQNTETKDT
KSR (SEQ ID NO:56)

FIG. 50

GI:12005907 Nucleic Acid Sequence

CTGGCCCCGAGCAGCTGAAGCCTGGGGTCAGCAGGCGCTGCGGGCGCAGCTCCG
GTGCAAGCGAGGACACGACACATGCAGTGGCTTCTGGACTGCGCGATGACTGGA
CGCAAGTAACTTCTAGGTCTGCAGACAAGAGGAAGAGAAGATGAAGGAAGACT
GTCTGCCGAGTTCTCACGTGCCCATCAGTGACAGCAAGTCCATTCAGAAGTCGGA
GCTCTTAGGCCTGCTGAAAACCTACAACTGCTACCATGAGGGCAAGAGCTTCCAG
CTGAGACACCGTGAGGAAGAAGGGACTCTGATCATCGAGGGGCTCCTCAACATT
GCCTGGGGGCTGAGGCGGCCCATCCGGCTGCAGATGCAGGATGACCGGGAG:CA
GGTGCACCTCCCCTCCACCTCATGGATGCCCAGACGGCCTAGCTGCCCTCTAAAG
GAGCCATCGCCCCAGAACGGGAACATCACAGCCCAGGGGCCAAGCATTCAGCCA
GTGCACAAGGCTGAGAGTTCCACAGACAGCTCGGGGCCCCTGGAGGAGGCAGAG
GAGGCCCCCCAGCTGATGCGGACCAAGAGCGACGCCAGTTGCATGAGCCAGAGG
AGGCCCAAGTGCCGCGCCCCCGGTGAGGCCCAGCGCATCCGGCGACACCGGTTC
TCTATCAACGGCCACTTCTACAATCATAAGACCTCCGTGTTTACTCCAGCCTATG
GATCCGTGACCAATGTGAGGGTCAACAGCACCATGACAACCCTGCAGGTGCTCA
CCCTGCTGCTGAACAAATTTAGGGTGGAAGATGGCCCCAGTGAGTTCGCACTCTA
CATCGTTCACGAGTCTGGGGAGCGGACAAAATTAAAAGACTGCGAGTACCCGCT
GATTTCCAGAATCCTGCATGGGCCATGTGAGAAGATCGCCAGGATCTTCCTGATG
GAAGCTGACTTGGGCGTGGAAGTCCCCCATGAAGTCGCTCAGTACATTAAGTTTG
AAATGCCGGTGCTGGACAGTTTTGTTGAAAAATTAAAAGAAGAGGAAGAAAGAG
AAATAATCAAACTGACCATGAAGTTCCAAGCCCTGCGTCTGACGATGCTGCAGC
GCCTGGAGCAGCTGGTGGAGGCCAAGTAACTGGCCAACACCTGCCTCTTCCAAA
GTCCCCAGCAGTGGCAGGTGTACACTGAGCCCTGGTTGCTGGCCCCGGCCGGTCA
CATTGACTGATGGCCACCGCCTGACGAATCGAGTGCCTGTGTGTCTACCTCTCTG
AAGCCTGAGCACCATGATTCCCACAGCCAGCTCTTGGCTCCAAGATGAGCACCCA
CAGGAAGCCGACCCAGGCCTGAGGGGCCAGGAACTTGCTGGGTCAGATCTGTGT
GGCCAGCCCTGTCCACACCATGCCTCTCCTGCACTGGAGAGCAGTGCTGGCCCAG
CCCCTGCGGCTTAGGCTTCATCTGCTTGCACATTGCCTGTCCCAGAGCCCCTGTGG
GTCCACAAGCCCCTGTCCTCTTCCTTCATATGAGATTCTTGTCTGCCCTCATATCA
CGCTGCCCCACAGGAATGCTGCTGGGAAAAGCAGGGCCTGCCAGCAGGTATGAG
ATCTAGCCTGCTTTCAGCCATCACCTTGCCACAGTGTCCCCGGCTTCTAAGCCTCC
AATATCACCCTGTGAGCCTCGCACAGCTCAGCCCCAACACAGAGGTGAGACCAG
GAATAAGGCCACAAGTATCTCACTTTCTCGCAGGGAATCAATCTTAGCTTCAGCA
GAGAGACTTAAAGCGATTCTGACAAGGAGCTGCTGCAAGAAACGCGGTCATTCA
ATCGCATTGAGGAGGGTCCACATGGCATTGAGAGGGTGCTGCCCGCTCAATGCC
CAGCAGCAGCTCTGGAAGGCAGTGCTCAGCCCCATCACCACTGTCCCGTGGATGC
CTGTGTACCTCTTGCCTTTTCTGGGCTTGCGTTTCTCTCCTCTAGTGGGTGGGGAT
GACTTTCAATGACTTTCAATACTTCCCCTGAAGGAAGAATGATAAGGAGAAATGT
CTGTTTTGAGGAAAGGGCTTTGAATTCCCCAGATACTGAACAATTTGTGTTTGTG
ACTGATGGAGAATTTCAGGAATGAATGAGAAAGCCTTTGCGAAACTATGCAACA
GTTTACATCAGTCATGTGAAGTATTTGTCTAAAACAGAGCAAACTGAAGACCAA
ATTATTCTCCTGTTGAGGTCCGTGGATGGCAGATTTAAAGGGAAGAACCACAAA

FIG. 50 (cont.)

GGCTTGCAAAGATAGGAGAGGCTCCATCTCTAATGCATGTAGAAGCTCCTTACGG
GTGCCCATCAAGAGCATAGCTTGGAAGCCACCATGCTGTGCGGAACTGCGTCAG
GGCAAATGTCACAGCAGGATTTCCCCAACCCAGCTCCATCATCACAGACACAGA
GAGCTGCAGGGGAGGCCTGCCCACTGTTTTGTCGACTCTGCCCTCCTCTGGCAGC
ATAGATCCTTAGGTGCTCAATAAAGGTGTGCTGTATTGAACTGAAGAA (SEQ ID NO:57)

FIG. 51

GI:12005908 Amino Acid Sequence

MKEDCLPSSHVPISDSKSIQKSELLGLLKTYNCYHEGKSFQLRHREEEGTLIIEGLLNI
AWGLRRPIRLQMQDDREQVHLPSTSWMPRRPSCPLKEPSPQNGNITAKGPSIQPVHK
AESSTDSSGPLEEAEEAPQLMRTKSDASCMSQRRPKCRAPGEAQRIRRHRFSINGHFY
NHKTSVFTPAYGSVTNVRVNSTMTTLQVLTLLLNKFRVEDGPSEFALYIVHESGERT
KLKDCEYPLISRILHGPCEKIARIFLMEADLGVEVPHEVAQYIKFEMPVLDSFVEKLKE
EEEREIIKLTMKFQALRLTMLQRLEQLVEAK (SEQ ID NO:58)

FIG. 53

Apolipoprotein L Nucleic Acid Sequence (Accession No. NM_003661)

ATGAGTGCACTTTTCCTTGGTGTGGGAGTGAGGGCAGAGGAAGCTGGAGCGAGG
GTGCAACAAAACGTTCCAAGTGGGACAGATACTGGAGATCCTCAAAGTAAGCCC
CTCGGTGACTGGGCTGCTGGCACCATGGACCCAGAGAGCAGTATCTTTATTGAGG
ATGCCATTAAGTATTTCAAGGAAAAAGTGAGCACACAGAATCTGCTACTCCTGCT
GACTGATAATGAGGCCTGGAACGGATTCGTGGCTGCTGCTGAACTGCCCAGGAA
TGAGGCAGATGAGCTCCGTAAAGCTCTGGACAACCTTGCAAGACAAATGATCAT
GAAAGACAAAAACTGGCACGATAAAGGCCAGCAGTACAGAAACTGGTTTCTGAA
AGAGTTTCCTCGGTTGAAAAGTGAGCTTGAGGATAACATAAGAAGGCTCCGTGC
CCTTGCAGATGGGGTTCAGAAGGTCCACAAAGGCACCACCATCGCCAATGTGGT
GTCTGGCTCTCTCAGCATTTCCTCTGGCATCCTGACCCTCGTCGGCATGGGTCTGG
CACCCTTCACAGAGGGAGGCAGCCTTGTACTCTTGGAACCTGGGATGGAGTTGG
GAATCACAGCCGCTTTGACCGGGATTACCAGCAGTACCATGGACTACGGAAAGA
AGTGGTGGACACAAGCCCAAGCCCACGACCTGGTCATCAAAAGCCTTGACAAAT
TGAAGGAGGTGAGGGAGTTTTTGGGTGAGAACATATCCAACTTTCTTTCCTTAGC
TGGCAATACTTACCAACTCACACGAGGCATTGGGAAGGACATCCGTGCCCTCAG
ACGAGCCAGAGCCAATCTTCAGTCAGTACCGCATGCCTCAGCCTCACGCCCCCGG
GTCACTGAGCCAATCTCAGCTGAAAGCGGTGAACAGGTGGAGAGGGTTAATGAA
CCCAGCATCCTGGAAATGAGCAGAGGAGTCAAGCTCACGGATGTGGCCCCTGTA
AGCTTCTTTCTTGTGCTGGATGTAGTCTACCTCGTGTACGAATCAAAGCACTTACA
TGAGGGGGCAAAGTCAGAGACAGCTGAGGAGCTGAAGAAGGTGGCTCAGGAGC
TGGAGGAGAAGCTAAACATTCTCAACAATAATTATAAGATTCTGCAGGCGGACC
AAGAACTGTGA (SEQ ID NO:59)

FIG. 54

Apolipoprotein L Amino Acid Sequence

MSALFLGVGVRAEEAGARVQQNVPSGTDTGDPQSKPLGDWAAGTMDPESSIFIEDAI
KYFKEKVSTQNLLLLLTDNEAWNGFVAAAELPRNEADELRKALDNLARQMIMKDK
NWHDKGQQYRNWFLKEFPRLKSELEDNIRRLRALADGVQKVHKGTTIANVVSGSLS
ISSGILTLVGMGLAPFTEGGSLVLLEPGMELGITAALTGITSSTMDYGKKWWTQAQA
HDLVIKSLDKLKEVREFLGENISNFLSLAGNTYQLTRGIGKDIRALRRARANLQSVPH
ASASRPRVTEPISAESGEQVERVNEPSILEMSRGVKLTDVAPVSFFLVLDVVYLVYES
KHLHEGAKSETAEELKKVAQELEEKLNILNNNYKILQADQEL (SEQ ID NO:60)

FIG. 56

Homo Sapiens Guanylate Binding Protein 5 Nucleic Acid Sequence (Accession No. AF288815)

ATGGCTTTAGAGATCCACATGTCAGACCCCATGTGCCTCATCGAGAACTTTAATG
AGCAGCTGAAGGTTAATCAGGAAGCTTTGGAGATCCTGTCTGCCATTACGCAACC
TGTAGTTGTGGTAGCGATTGTGGGCCTCTATCGCACTGGCAAATCCTACCTGATG
AACAAGCTGGCTGGGAAGAACAAGGGCTTCTCTGTTGCATCTACGGTGCAGTCTC
ACACCAAGGGAATTTGGATATGGTGTGTGCCTCATCCCAACTGGCCAAATCACAC
ATTAGTTCTGCTTGACACCGAGGGCCTGGGAGATGTAGAGAAGGCTGACAACAA
GAATGATATCCAGATCTTTGCACTGGCACTCTTACTGAGCAGCACCTTTGTGTAC
AATACTGTGAACAAAATTGATCAGGGTGCTATCGACCTACTGCACAATGTGACA
GAACTGACAGATCTGCTCAAGGCAAGAAACTCACCCGACCTTGACAGGGTTGAA
GATCCTGCTGACTCTGCGAGCTTCTTCCCAGACTTAGTGTGGACTCTGAGAGATT
TCTGCTTAGGCCTGGAAATAGATGGGCAACTTGTCACACCAGATGAATACCTGGA
GAATTCCCTAAGGCCAAAGCAAGGTAGTGATCAAAGAGTTCAAAATTTCAATTT
GCCTCGTCTGTGTATACAGAAGTTCTTTCCAAAAAAGAAATGCTTTATCTTTGACT
TACCTGCTCACCAAAAAAAGCTTGCCCAACTTGAAACACTGCCTGATGATGAGCT
AGAGCCTGAATTTGTGCAACAAGTGACAGAATTCTGTTCCTACATCTTTAGCCAT
TCTATGACCAAGACTCTTCCAGGTGGCATCATGGTCAATGGATCTCGTCTAAAGA
ACCTGGTGCTGACCTATGTCAATGCCATCAGCAGTGGGGATCTGCCTTGCATAGA
GAATGCAGTCCTGGCCTTGGCTCAGAGAGAGAACTCAGCTGCAGTGCAAAAGGC
CATTGCCCACTATGACCAGCAAATGGGCCAGAAAGTGCAGCTGCCCATGGAAAC
CCTCCAGGAGCTGCTGGACCTGCACAGGACCAGTGAGAGGGAGGCCATTGAAGT
CTTCATGAAAAACTCTTTCAAGGATGTAGACCAAAGTTTCCAGAAAGAATTGGA
GACTCTACTAGATGCAAAACAGAATGACATTTGTAAACGGAACCTGGAAGCATC
CTCGGATTATTGCTCGGCTTTACTTAAGGATATTTTTGGTCCTCTAGAAGAAGCA
GTGAAGCAGGGAATTTATTCTAAGCCAGGAGGCCATAATCTCTTCATTCAGAAAA
CAGAAGAACTGAAGGCAAAGTACTATCGGGAGCCTCGGAAAGGAATACAGGCT
GAAGAAGTTCTGCAGAAATATTTAAAGTCCAAGGAGTCTGTGAGTCATGCAATA
TTACAGACTGACCAGGCTCTCACAGAGACGGAAAAAAAGAAGAAAGAGGCACA
AGTGAAAGCAGAAGCTGAAAAGGCTGAAGCGCAAAGGTTGGCGGCGATTCAAA
GGCAGAACGAGCAAATGATGCAGGAGAGGGAGAGACTCCATCAGGAACAAGTG
AGACAAATGGAGATAGCCAAACAAAATTGGCTGGCAGAGCAACAGAAAATGCA
GGAACAACAGATGCAGGAACAGGCTGCACAGCTCAGCACAACATTCCAAGCTCA
AAATAGAAGCCTTCTCAGTGAGCTCCAGCACGCCCAGAGGACTGTTAATAACGA
TGATCCATGTGTTTTACTCTAA (SEQ ID NO:61)

FIG. 57

Homo Sapiens Guanylate Binding Protein 5 Amino Acid Sequence

MALEIHMSDPMCLIENFNEQLKVNQEALEILSAITQPVVVVAIVGLYRTGKSYLMNK
LAGKNKGFSVASTVQSHTKGIWIWCVPHPNWPNHTLVLLDTEGLGDVEKADNKNDI
QIFALALLLSSTFVYNTVNKIDQGAIDLLHNVTELTDLLKARNSPDLDRVEDPADSAS
FFPDLVWTLRDFCLGLEIDGQLVTPDEYLENSLRPKQGSDQRVQNFNLPRLCIQKFFP
KKKCFIFDLPAHQKKLAQLETLPDDELEPEFVQQVTEFCSYIFSHSMTKTLPGGIMVN
GSRLKNLVLTYVNAISSGDLPCIENAVLALAQRENSAAVQKAIAHYDQQMGQKVQL
PMETLQELLDLHRTSEREAIEVFMKNSFKDVDQSFQKELETLLDAKQNDICKRNLEA
SSDYCSALLKDIFGPLEEAVKQGIYSKPGGHNLFIQKTEELKAKYYREPRKGIQAEEV
LQKYLKSKESVSHAILQTDQALTETEKKKKEAQVKAEAEKAEAQRLAAIQRQNEQM
MQERERLHQEQVRQMEIAKQNWLAEQQKMQEQQMQEQAAQLSTTFQAQNRSLLS
ELQHAQRTVNNDDPCVLL (SEQ ID NO:62)

FIG. 59

Human Proteasome Activator hPA28 Subunit Beta Nucleic Acid Sequence (D45248)

GGGGGAGTGAAAGCGAAAGCCCGGGCGACTAGCCGGGAGACCAGAGATCTAGC
GACTGAAGCAGCATGGCCAAGCCGTGTGGGGTGCGCCTGAGCGGGGAAGCCCGC
AAACAGGTGGAGGTCTTCAGGCAGAATCTTTTCCAGGAGGCTGAGGAATTCCTCT
ACAGATTCTTGCCACAGAAAATCATATACCTGAATCAGCTCTTGCAAGAGGACTC
CCTCAATGTGGCTGACTTGACTTCCCTCCGGGCCCCACTGGACATCCCCATCCCA
GACCCTCCACCCAAGGATGATGAGATGGAAACAGATAAGCAGGAGAAGAAAGA
AGTCCCTAAGTGTGGATTTCTCCCTGGGAATGAGAAAGTCCTGTCCCTGCTTGCC
CTGGTTAAGCCAGAAGTCTGGACTCTCAAAGAGAAATGCATTCTGGTGATTACAT
GGATCCAACACCTGATCCCCAAGATTGAAGATGGAAATGATTTTGGGGTAGCAA
TCCAGGAGAAGGTGCTGGAGAGGGTGAATGCCGTCAAGACCAAAGTGGAAGCTT
TCCAGACAACCATTTCCAAGTACTTCTCAGAACGTGGGGATGCTGTGGCCAAGGC
CTCCAAGGAGACTCATGTAATGGATTACCGGGCCTTGGTGCATGAGCGAGATGA
GGCAGCCTATGGGGAGCTCAGGGCCATGGTGCTGGACCTGAGGGCCTTCTATGCT
GAGCTTTATCATATCATCAGCAGCAACCTGGAGAAAATTGTCACCCCAAAGGGT
GAAGAAAAGCCATCTATGTACTGAACCCGGGACTAGAAGGAAAATAAATGATCT
ATATGTTGTGTGG (SEQ ID NO:63)

FIG. 60

Human Proteasome Activator hPA28 Subunit Beta Amino Acid Sequence

MAKPCGVRLSGEARKQVEVFRQNLFQEAEEFLYRFLPQKIIYLNQLLQEDSLNVADL
TSLRAPLDIPIPDPPPKDDEMETDKQEKKEVPKCGFLPGNEKVLSLLALVKPEVWTLK
EKCILVITWIQHLIPKIEDGNDFGVAIQEKVLERVNAVKTKVEAFQTTISKYFSERGDA
VAKASKETHVMDYRALVHERDEAAYGELRAMVLDLRAFYAELYHIISSNLEKIVTP
KGEEKPSMY (SEQ ID NO:64)

FIG. 62

Homo Sapiens FYN Binding Protein Nucleic Acid Sequence (Accession No. AF001862; GI: 2232149)

CTTTTGTCTCTCAGCTATTTTTTGTTCCCTATGTTTGTAGGATGGAAAGGCAGATG
TAAAGTCCCTCATGGCGAAATATAACACGGGGGGCAACCCGACAGAGGATGTCT
CAGTCAATAGCCGACCCTTCAGAGTCACAGGGCCAAACTCATCTTCAGGAATAC
AAGCAAGAAAGAACTTATTCAACAACCAAGGAAATGCCAGCCCTCCTGCAGGAC
CCAGCAATGTACCTAAGTTTGGGTCCCCAAAGCCACCTGTGGCAGTCAAACCTTC
TTCTGAGGAAAAGCCTGACAAGGAACCCAAGCCCCCGTTTCTAAAGCCCACTGG
AGCAGGCCAAAGATTCGGAACACCAGCCAGCTTGACCACCAGAGACCCCGAGGC
GAAAGTGGGATTTCTGAAACCTGTAGGCCCCAAGCCCATCAACTTGCCCAAAGA
AGATTCCAAACCTACATTTCCCTGGCCTCCTGGAAACAAGCCATCTCTTCACAGT
GTAAACCAAGACCATGACTTAAAGCCACTAGGCCCGAAATCTGGGCCTACTCCTC
CAACCTCAGAAAATGAACAGAAGCAAGCGTTTCCCAAATTGACTGGGGTTAAAG
GGAAATTTATGTCAGCATCACAAGATCTTGAACCCAAGCCCCTCTTCCCCAAACC
CGCCTTTGGCCAGAAGCCGCCCCTAAGTACCGAGAACTCCCATGAAGACGAAAG
CCCCATGAAGAATGTGTCTTCATCAAAAGGGTCCCCAGCTCCCCTGGGAGTCAGG
TCCAAAAGCGGCCCTTTAAAACCAGCAAGGGAAGACTCAGAAAATAAAGACCAT
GCAGGGGAGATTTCAAGTTTGCCCTTTCCTGGAGTGGTTTTGAAACCTGCTGCGA
GCAGGGGAGGCCCAGGTGTCTCCAAAAATGGTGAAGAAAAAAAGGAAGATAGG
AAGATAGATGCTGCTAAGAACACCTTCCAGAGCAAAATAAATCAGGAAGAGTTG
GCCTCAGGGACTCCTCCTGCCAGGTTCCCTAAGGCCCCTTCTAAGCTGACAGTGG
GGGGGCCATGGGGCCAAAGTCAGGAAAAGGAAAAGGGAGACAAGAATTCAGCC
ACCCCGAAACAGAAGCCATTGCCTCCCTTGTTTACCTTGGGTCCACCTCCACCAA
AACCCAACAGACCACCAAATGTTGACCTGACGAAATTCCACAAAACCTCTTCTGG
AAACAGTACTAGCAAAGGCCAGACGTCTTACTCAACAACTTCCCTGCCACCACCT
CCACCATCCCATCCGGCCAGCCAACCACCATTGCCAGCATCTCACCCATCACAAC
CACCAGTCCCAAGCCTACCTCCCAGAAACATTAAACCTCCGTTTGACCTAAAAAG
CCCTGTCAATGAAGACAATCAAGATGGTGTCACGCACTCTGATGGTGCTGGAAAT
CTAGATGAGGAACAAGACAGTGAAGGAGAAACATATGAAGACATAGAAGCATC
CAAAGAAAGAGAGAAGAAAAGGGAAAAGGAAGAAAAGAAGAGGTTAGAGCTG
GAGAAAAAGGAACAGAAAGAGAAAGAAAAGAAAGAACAAGAAATAAAGAAGA
AATTTAAACTAACAGGCCCTATTCAAGTCATCCATCTTGCAAAAGCTTGTTGTGA
TGTCAAAGGAGGAAAGAATGAACTGAGCTTCAAGCAAGGAGAGCAAATTGAAA
TCATCCGCATCACAGACAACCCAGAAGGAAAATGGTTGGGCAGAACAGCAAGGG
GTTCATATGGCTATATTAAAACAACTGCTGTAGAGATTGACTATGATTCTTTGAA
ACTGAAAAAAGACTCTCTTGGTGCCCCTTCAAGACCTATTGAAGATGACCAAGA
AGTATATGATGATGTTGCAGAGCAGGATGATATTAGCAGCCACAGTCAGAGTGG
AAGTGGAGGGATATTCCCTCCACCACCAGATGATGACATTTATGATGGGATTGAA
GAGGAAGATGCTGATGATGGTTTCCCTGCTCCTCCTAAACAATTGGACATGGGAG
ATGAAGTTTACGATGATGTGGATACCTCTGATTTCCCTGTTTCATCAGCAGAGAT
GAGTCAAGGAACTAATTTTGGAAAAGCTAAGACAGAAGAAAAGGACCTTAAGA
AGCTAAAAAAGCAGGAAAAAGAAGAAAAAGACTTCAGGAAAAAATTTAAATAT

FIG. 62 (cont.)

GATGGTGAAATTAGAGTCCTATATTCAACTAAAGTTACAACTTCCATAACTTCTA
AAAAGTGGGGAACCAGAGATCTACAGGTAAAACCTGGTGAATCTCTAGAAGTTA
TACAAACCACAGATGACACAAAAGTTCTCTGCAGAAATGAAGAAGGGAAATATG
GTTATGTCCTTCGGAGTTACCTAGCGGACAATGATGGAGAGATCTATGATGATAT
TGCTGATGGCTGCATCTATGACAATGACTAGCACTCAACTTTGGTCATTCTGCTGT
GTTCATTAGGTGCCAATGTGAAGTCTGGATTTTAATTGGCATGTTATTGGGTATC
AAGAAAATTAATGCACAAAACCACTTATTATCATTTGTTATGAAATCCCAATTAT
CTTTACAAAGTGTTTAAAGTTTGA (SEQ ID NO:65)

FIG. 63

Homo Sapiens FYN Binding Protein Amino Acid Sequence (Accession No. AF001862; GI: 2232149)

MAKYNTGGNPTEDVSVNSRPFRVTGPNSSSGIQARKNLFNNQGNASPPAGPSNVPKF
GSPKPPVAVKPSSEEKPDKEPKPPFLKPTGAGQRFGTPASLTTRDPEAKVGFLKPVGP
KPINLPKEDSKPTFPWPPGNKPSLHSVNQDHDLKPLGPKSGPTPPTSENEQKQAFPKL
TGVKGKFMSASQDLEPKPLFPKPAFGQKPPLSTENSHEDESPMKNVSSSKGSPAPLGV
RSKSGPLKPAREDSENKDHAGEISSLPFPGVVLKPAASRGGPGVSKNGEEKKEDRKID
AAKNTFQSKINQEELASGTPPARFPKAPSKLTVGGPWGQSQEKEKGDKNSATPKQKP
LPPLFTLGPPPPKPNRPPNVDLTKFHKTSSGNSTSKGQTSYSTTSLPPPPPSHPASQPPL
PASHPSQPPVPSLPPRNIKPPFDLKSPVNEDNQDGVTHSDGAGNLDEEQDSEGETYED
IEASKEREKKREKEEKKRLELEKKEQKEKEKKEQEIKKKFKLTGPIQVIHLAKACCDV
KGGKNELSFKQGEQIEIIRITDNPEGKWLGRTARGSYGYIKTTAVEIDYDSLKLKKDS
LGAPSRPIEDDQEVYDDVAEQDDISSHSQSGSGGIFPPPPDDDIYDGIEEEDADDGFPA
PPKQLDMGDEVYDDVDTSDFPVSSAEMSQGTNFGKAKTEEKDLKKLKKQEKEEKD
FRKKFKYDGEIRVLYSTKVTTSITSKKWGTRDLQVKPGESLEVIQTTDDTKVLCRNEE
GKYGYVLRSYLADNDGEIYDDIADGCIYDND (SEQ ID NO:66)

FIG. 65

VAMP5 Nucleic Acid Sequence (GI:4027902)

GCGGCCGCTCCGCAGGCAGAGAAGCCGGGAGCGTTTGAGGCGGCGGCGGCACG
AGCGATGGCAGGAATAGAGTTGGAGCGGTGCCAGCAGCAGGCGAACGAGGTGA
CGGAAATTATGCGTAACAACTTCGGCAAGGTCCTGGAGCGTGGTGTGAAGCTGG
CCGAACTGCAGCAGCGTTCAGACCAACTCCTGGATATGAGCTCAACCTTCAACAA
GACTACACAGAACCTGGCCCAGAAGAAGTGCTGGGAGAACATCCGTTACCGGAT
CTGCGTGGGGCTGGTGGTGGTTGGTGTCCTGCTCATCATCCTGATTGTGCTGCTG
GTCGTCTTTCTCCCTCAGAGCAGTGACAGCAGTAGTGCCCCACGGACCCAGGATG
CAGGCATTGCCTCAGGGCCTGGGAACTGACCCAGCTGGTCCTGAAGGAGAAGCC
CAATGGCTGCACTGGCCGATTCTGGTCTCCAAGGACCTTGGTGTTTGCTCTCCCTG
ACCCAGCCCAGTGAGTGCCAAAGGGCAGCCCCAACATGTGCACCCCTGCATTCC
CGTCATGCACAGACTTGCCCTTGAGCAGGCCGCTGTACTGGCCAGCTGGGCAACC
CCCCTGGAGCTCATAAAAAT (SEQ ID NO:67)

FIG. 66

VAMP5 Amino Acid Sequence

MAGIELERCQQQANEVTEIMRNNFGKVLERGVKLAELQQRSDQLLDMSSTFNKTTQ
NLAQKKCWENIRYRICVGLVVVGVLLIILIVLLVVFLPQSSDSSSAPRTQDAGIASGPG
N (SEQ ID NO:68)

FIG. 68

GI:2466183 Nucleic Acid Sequence

GGGTTTGGGGTAGAAGGGAGGGAGGGGGCAGGACAGTGTGGAATCTCTAGGGT
GTATGGGTAGGTAGGGGGCACAGTTAGTTCTAAGTGGGCTTTTATGCTAAAAGCC
TCTGGGGATATCTGTTTTGAAAATAAAGATAGGTGTCCCCTCCTTGCTGTCATCTA
GCCCAGACACTCTGCTTGCTCTCTGGCTGTCTGCTCCCTGGGAAGGCTTTAGGAG
GACCACCCAGGACAGGATGACCATGCTGCCATCTGCTCTGGAGCTGGGTCTCAGT
GCAGAGGGACAGTGACTGTGGATGGTTGCAGTCTCTGGTGGGAGGTGAGGATAG
AAGTGATAAAGAGCTAAGAGGAGCTTCTGGGAGCCTTGGAGGAGGTCAGTCTTG
CAGTGGTGAAGCCAGGACATAGGAGATGGAGCAGGGCTGTGAGAGGAGGAGAT
TCTGAGGAGGATGCAGGGGAAATCTTGTCTGTTAATGAAATAGGAGTGGGGTGG
GGTTTGGGGTGGGGTGGTCATTGCCGTTTGAGCTGCTGATTTCATGAGTCGCCTT
CAAAACTCTCGTGTAGGGTTGACAATGTGGGGGGGTGGGGGATCCAGCTTATTCT
TTTATTTTCAAGTCCATTCTTGGGGCTGGTGGGGAGGCAGGAGAATACCCCTCCC
TAAGCCCTTAGTGTGTGCCGAGCTTGCTTTGTGATGTTGGCAGGGGAGGGGAGAC
CTGGGTGGTGACTGAGTTCCCTTTATCAAACCCTTCAGTGGGCACAAAATTGAGT
GCTTGATTTTAGGTTTTATTTTTTTATGAATGTCCAAATCTGTGTTTCCCCCTGCCC
TCCCAGACTGTGTGGCCAGTTGAAAGTGTCTGGTTTGTGTTCATCTCTCCCTCATT
TCTGGAGCAGGGCCTGAGACCCTGCCACATCTCCTATGCTCTGCATCCACGCCTC
TTTTGGACATTAAAGGTTGATTGATGCACCTCTGCACTGTTTGGGTCTCTTTGGGG
ATGAGGGGTTGGCATGGTGGCAGTGGTGCCACACAGTGGGTGAGGGTGGAGAGT
CTCCAGGGTGGAATAGAATGGGGACTGAAGGGAAGACCAGCCACTAGATACTGA
TTGGCCTGTAGCAGCACTTATTTGTGCCTAGGCTTATGCCCCTTAAGTAGAGGAA
AACTAACCAGCAGCACTCACCCTTAAGGGCTCCTGGGTTCTGCCTTCCTTGGTGG
TGATGGCCAGGTGAATCATATTTTGTGTCTTTGGGATAGTAACTGCTACCTTCCCA
GCTGCCGTCATGGACCTGCCTGAGCTTTGCTGCTTCAACTTTTGCCCAAAGCT
(SEQ ID NO:69)

FIG. 70

GI:2219283 Nucleic Acid Sequence

CCGTAAAGCGGTGGAGAATCTCAAGCATGTGCATTTAATTGAGGAATAGCAGAA
GGGCTAAAGCAACCAAGAAAAGAAGTGTGGGTATTTTTGTTAAGTAAAACAGCC
CAAGTGCTTCTGGAGGTGGGTTTCTACCAAGATAGAGGAAAAGGGCTGAATTCC
CTCTAAGTGGGACAGCCGAGCTCAGGATGTGCTTCCCAGCTTCACTGGTTAATTT
GACCTGAACCTATTTAAAGATCCCTTCTGCCCCTGAAGACCTATCCGCACTCAAA
TTCTAACATGAAGAAATCTACTCGAATGCATCCTTTACTTTGAATGAGCTCTATTC
GGTTGCATGTTATATGTGATTTCCTTCCTCCCAACTGTTTCCACTGAGCGCACCCA
GTCTCCCCTAGTCTTCCTCTGTGGGTGTGATTTTTGTGATTTTTACAAACAAAACC
CTTGAAGTTCTTGGCAGATGTGTTTGTTTCTGTTTGCATGTACTGCAGATACCCCA
GGACAAGCGGGGGATTCATTTTCAGCCATTCAGTTGTTTCCTCAATAATCCGCA
GCAAAGTGAAAATATTCTTAGCACTCAGACTGTACTTAGAGTGTTTTCTCAGTCC
AGTCTGTACAGTCTGTAGGCAGAAGGCCTCAGAAGAAAGTCATGGCCACTCAGT
GCCCACTGTGGGCTTTGTAAGTCCTGGCTCTCCCGTCAAGGTTACCCAGAGGTAA
AAGCTTCCTGGGAGTGGGGCCAGGTGTGTTTGGCACTCCAGATAGAAGGCAAAA
TGCTCAGATTCGGGCCTGTGCACTTGTATGCAACCTGTCGGTCGATACCTAGCAT
TTATTTTTCCCTGACAATGAACGACCTTTCCCTCACCCACCCTAAGCTCAAAGAGT
TTAGCAAAATTCTCTTTTAAATAAACAGAATGCCAGTAAGAGGTTGACCCCTACC
ATGGAACTTCTGGGATGCTAAATACTTCCTCATGAACAAAATAAGTTCCTTATTA
TAAGTTCCTTATACTAGCAGCTTCACCTAAAGAATTTTCTCTCCAGCAATATTGAC
TTCACTGGGGAAAAGCCAAGAGTGTGTGGTGAGTGATTTGTTCTCACTCGACCTG
GCTAGGACTGGCTAGGAGCTGTTTTTTGTACATGAGGGAATTTGGGCTTTCCTCA
GTTATCTGAATGTTTTACCCAAGTGCCTTCCTGCTATTGTAGCAAAGTAGCTCAGC
TTCCTTGTCCACAGGGTGAAAAAGGACTAATGCATTTTCCATCAGTTTTCTAACT
ATGTTAGCAAAAACGGCCTCCTGGTAGCTCAACCTCCTGTACGCGTGTGTGTGTG
TAATACACACACAAATAAACCCCTCTGTTTTTCTAAGACATCTTAGCTGGATATT
ATAGGAAGCACTTTCATAAACAACTGTAACAAATCGCAAAGGAAAGAGAAACAA
AAGCATTAGATTTGAGACATAAACAGGCAAGAGAAAGTGTATTAGGAACTGACA
GCTATCAAGGAAGTTTTGTCAGTTACAAATGCTAGGAGGAAATTTTGCCAAGAA
GGATGGCTCATGAAATATTTCCAGTACGGGAAGAGGCAATAAGATCCTCTAAGA
GAATGAGAAAGTAGGGGTGTCTAAATGGTAAAGATGGGTGTGTTGCACGTGTGT
TAGAAGGATCTCAGTTGAGTGAAGGTTTGCACTGCTACATCTAAGTTAATGTAAA
TATGTAGCACTCTGACAGGTCTACCGTGTTGCTGAATGTAGTATATTTCCAAAGT
TTGCAAGTCTTCCTGTATTGTACAAAGATGCTGCTGCTTGATAATATGTATAGCA
ATCCAGATTAGTATGTTATTAAATTTTATTTCTTACCTGTATTTTTATGCTTTTTA
CCTGTCCTCAAAATATTACACCCCTGTTGGAATTAGATTTATATTTATAAATGGTC
AGAAATCTTTTTAAGTGTCTCTTTTTACACATAGGTTGATTTTTTTTTCTTAAGAG
AAATGATGTATTCTTGAAACATTTGTTACTCATTCCAGGAAACAAAAACCCATAT
AATAAAACCCCCACTCAGAGCCTGTTAGTCACCTCTCTAGAAGATGGCATCTCAG
GAGAAGGAATGGCTTTGTGGAAGAAGGAATCACCTTTTTCTTGCTCAAGAATTAT
GCTGACTTCAGCCCTGAGCCTGGATCTGGTCACTGAGAATCATCAAGTGTCTAGA
TCCTCCCCCCAAAATAACTAATTTAGTAGGTGATTTTGATTTTAAAAAATTGACA

FIG. 70 (cont.)

CCAAAACCCTGCCTGCATTGTAATGGAATTCGAAAAGAATTCATGTTCACAGAAC
TCAACGTTCAGGCTAATATTTACAGAAGGGACCAAATCTAAATCCTGGTAGATAA
CTCCTGTATGCTTTATCCAAAGGACACCCACAGTTTTCCAGCATAGATATAACCA
AGGATGAATTGATTCCTTCAAAGAACTGGGAGGCACGGATATTGCATTTTTTGTT
TACATCCAGTAGCCAAGACGCCTCAGTGAGCCAGTCTTGGGCAGAGGCTGTCAC
ATTTAGGCAGATTGGAAGTTGGTATGTTCTAATTCTCACTCTGGACTACAGTGAG
GCTGAATTTATCATGTCAAAAAAAAAAAAAAAAAAAGACCTTTCCAAGTGCTTT
CTATTGCTCAGAATTGAAAGAATGTTTTCATTTCAAGTTTACAAGAGGCATGGAT
GGAGTTGTGACGTTCTTGACAAGCTGGGCTAACCTTTCCCGAACTTGTTTCCCGG
AGGCAAGGTGCTCGGTGACCCAGCGCATCTTAACCTTGGGTCTCCTAGGCTCGAG
GCTAGGGCATTACGTTTCGTGGAACCAAAGCAGCCAATTGCATAGCAAGTATTTT
CCTGCATTCCAATTAAATGCTTAAGAAAAAGCAGCATCCTATAAAATTGTGATCA
TAAACATCCATTTCCCTCAGCTTTTGTGAGTGCCTTGACTTACAGCCAACATCACT
GTTTAACTCAGTCTGTTTAAAAACAAACTTTTCTGGTGGTTGATAACAGAGAGTT
GCTCCCTGAGCCATCAGGGTCCTGGGAGCTGGAAGTGAAAGGGTTATTAACATTC
TACCTTTATGCAGCTGTTGGCTGACCAGAATAAACTCCCTGCTGAGTTCAAGCTT
TGAATGGAATGGATGCAAATGATGTTGTTTCCATTAGAGCAGGTGCTCACAGCAT
TCTGATTGGCCTGAGCAGACCGAGGCTATGGCTGTTGGGACAAGCTTAGCATCCT
GGACATCTTGTCAAAGAACCTCACTCACCCCTCTGGCCTCTACAGCCCTCAGAGG
AGAGAAAACCAATTCTCCAACAAACAGGTCTCTCCAACATGGTGGTGCTGGCAG
GCTTAGGTTTAGAAAATCCTGACTGTTAAAGGCGTTTGAATACATCACATTCCTA
TGCAAATGTTTTTAATCTCCAGTTTAATGTAGTTTATTTTTCCTATATGTAAAGTA
TTTTTATACGGCTTGTATCATGATAGTTTAGCAATAAAACAGTTGGAAGCAA
(SEQ ID NO:70)

FIG. 72

Hypothetical Protein FLJ20152 Nucleic Acid Sequence (GI:9506660)

ACACCTTCTCACAGGACTGGAGAGAGAATGCGGGGCAGCTGGGCAGGGCTCACT
TCCAGCCGCCTGTCACAGTACTGGGAGTAAGAGGTGACCTATTTATTTTTAGAAG
GGGGCAGTGATAATAACCCAGCTCCTAGCTTCATTCAAGGGAGGCAGGCGCTTT
GGAAGTTTGTAAACACCAACTTTCTGAGTAAGGGAGGAGCACTTTTTTTCCAAAA
AGGAAAGAACGTCTCTACTGGGTTTTTTCCTCCTGATATTCAGCATTAGAGTAG
AAAAGAAACTATTGTTTGGCCACATTAGCCGTGGTTAGCAGGTGCTGCAGCCTTT
GCCACTGTTATTATTTTTAAAGGGCAGAAATGCCTGAAGGTGAAGACTTTGGACC
AGGCAAAAGCTGGGAAGTTATCAATTCCAAACCAGATGAAAGACCCAGGCTCAG
CCACTGTATTGCAGAATCATGGATGAATTTCAGCATATTTCTTCAAGAAATGTCT
CTTTTTAAACAGCAGAGCCCTGGCAAGTTTTGTCTCCTGGTCTGTAGTGTGTGCAC
ATTTTTTACGATCTTGGGAAGTTACATTCCTGGGGTTATACTCAGCTATCTACTGT
TACTGTGTGCATTTTTGTGTCCATTGTTTAAATGTAATGATATTGGACAAAAAATT
TACAGCAAAATTAAGTCAGTTCTGCTGAAACTGGATTTTGGAATTGGAGAATATA
TTAATCAGAAGAAACGTGAGAGATCTGAAGCAGACAAAGAAAAAAGTCACAAA
GATGACAGTGAATTAGACTTTTCAGCTCTTTGTCCTAAGATTAGCCTCACGGTTG
CTGCCAAAGAGTTATCTGTGTCTGACACAGACGTCTCAGAGGTATCCTGGACTGA
TAATGGGACCTTCAACCTTTCAGAAGGATACACTCCACAGACAGACACTTCTGAT
GATCTTGACCGACCCAGTGAGGAAGTTTTCTCTAGAGATCTTTCAGATTTTCCATC
TCTAGAAAATGGCATGGGAACAAATGATGAAGATGAATTAAGCCTTGGTTTGCC
CACTGAGCTCAAGAGAAAGAAGGAACAGTTGGACAGTGGTCACAGACCAAGCA
AAGAGACGCAATCAGCAGCTGGTCTCACCCTTCCTCTGAACAGTGACCAAACCTT
TCACCTGATGAGCAACCTGGCTGGGGATGTTATCACAGCTGCAGTGACTGCAGCT
ATCAAAGACCAGTTAGAGGGTGTGCAGCAAGCACTTTCTCAGGCTGCCCCCATCC
CAGAAGAGGACACAGACACTGAAGAAGGTGATGACTTTGAACTACTTGACCAGT
CAGAGCTGGATCAAATTGAGAGTGAATTGGGACTTACACAAGACCAGGAAGCAG
AAGCACAGCAAAATAAGAAGTCTTCAGGTTTCCTTTCAAATCTGCTGGGAGGCCA
TTAATCTAGGAATCAGCTTGCAACAGAGCACAAAAAACACCAAAAAAATTTCAA
ACAAGAAAAAAAAAAAAAAAAGGAAAAGAAAAAAATTGAACTGTAAGCTTTAA
TGATTACTTTAGATTTGTTTTATTTTCCCTCCTGCAGTGAATTAATTGGATATATA
TCAGCTGACACTGATAGATTGATATTTCTGATCGTTATTTTTGTGTCATAAGCATG
GAAATGAACTTTATACACACCACTGTGTTGTCAGAGATAAATATTAGGGGTTGTT
TTTAAAGCAAAAAGAAAAAAACAAAAACCAAACTATTAAAATCCTCCTATAAAT
ATTCTTTTTCTTTACAGTTTTTCAAGCATGCAAAACAGTTTATTGTAACTTACTGA
AAAATATTAACAATTAATTGTGAATACATGCTGTTACCAGCTTCCTTATTCCTAAT
ACCTGGAAAATTTTTTTTTCAACGGATAGATTTTGATGTAAAAAAGACCGAAATT
ATCAAGGTATCTTAGTTGAAGGACTTGGGAAATACTATCAAAATTAATTTCTTAG
GAAAAAATTTAAAAGTATATTTAAGTACTCTGGATAGACTGAAACGTTTCCATGT
TATTTCTGCAGTTGTAGACTTAGGCTTATTTGTAAAGAAGCATGCTCCATTGACTG
CCATCTCTAGTCTTGCAGTGGGTGGTATTAACCCATAGAAAGCAAGCAGTTGTGT
ATCACATAGACAATGGTTATGATGTAAACAGATTCAGTTGTTTTGTTGTTCATTCG
TCATATGTTTGTGATAGGGATGTTGGGAGCACAGCTCTATTCTGCCTGCTCAGAC

FIG. 72 (cont.)

TTAAGTTAGACCCTTATCTTTTATATTATGTCATGAAAAAAGTCTCCTAAAATTGT
GAAACTAGTTCTTGATGAGTGATGTGATCATCAGCAATAAAGATATAATAACTCT
GTTTTCTTAGCCTGTATAGAGGAGAGGAACTTGCTTGGCTTTAAAATATATTTATT
TGCCATTTAAGTATAAATATGAAATCTGTTTCTTATTGGGAAGATAGAATATATA
TATTTTCCTTTAAACTTTTTAAGGTCACTTTTAAATAACCAAATTTGATTTATGGT
TTTTAACAAAGGACTAAAGAGCTGAAACCAACCTAGTTTTGTTTTTGTGATATAA
ACTTTAAGTGTCGAGGGACCATGCCAGCAACTACCAAAAATCTCTTAAATCTTCA
GGTACAGCTGGCATTTTGGCAGATGCATAGAGACATCTGAGACCCTCAGAAAGG
AAGGATAATCCAAGAATATAGGAAATCTGTGTTCTCTTCCTTTCATTTTATCCCTT
ATATTTCTAAAGACTAATTATAAGTAATCTGACATTTTAATGTAGCTACTCTTATT
TATTTTTTCTTTCTGAGGTATTAAAATATCTGGACTGAGTTTTGCCAAATGTTAAA
GGGAGAAGAGTTACTGAAGACTTTGAACACTTGCTTTTTGTGATTGCTTATGTCA
TTAGTGCCTCATGACTGTGTTTGATGTCCTTTATTGATACAAAGTGAGCCTGTGCC
TTCATTATCTTGCCCATTTTAATACAAATGGAAACCTGGTGTTTGAAAATCTCTGA
ACTGTGTGGGTTTTGGAGGAATATACCTGAATTTTATTCAATAACAGTTTCTGGA
CAGGAAGAAAAATACAGTTACATATTTATAAAATAGTCGTTATCAGTATTTTTTT
ATGTGTATGTTTCTTTCTTTAAAACAATATTCTTGGATATAAAGTAGAAAAGTTTA
AAGGTCATTTCCATTTCTTCACTAAGGAGAAAAAAAGTTAAATAATCCAAGTAAT
TAAAGAATATAAGTCACTAGATGACCTTACAGGAAGACGAACTCAAGGGCTGAT
AATCTGTGGTGGTATGAACAATAAATCTAGAATAAAATGTTAATAACTACAAATT
AAAAGGGGTGTGAGGATGGGAGGAAGTTGGTAGGGTAGAAAAATGTGCTATTAC
CACTATTGAGGAGACATGCCAGCTCTCTAGGGACAGCAGCATTATAACTATGTAT
GAATTTTAATATTATTTGTATATGACTGTATGACTACAAATTTACACAATACAAT
AATGGGACTTTCTCACAACTATTAATTCAAACAAACACAAGGATGTTGAAGGTTC
TTGTTTGTGTATATGTGTGTTTTGGTGGTGGGGGGTCACTGTTTCTGGTTTTAAAA
GATGAAGGAGCAGATACATTTCATATGATTGATCCAGTGTAGTAGAGGACTACA
TGTCCTTTACTATGAGAATATAAATAGCAATAT (SEQ ID NO:71)

FIG. 73

Hypothetical Protein FLJ20152 Amino Acid Sequence (GI:10437336)

MPEGEDFGPGKSWEVINSKPDERPRLSHCIAESWMNFSIFLQEMSLFKQQSPGKFCLL
VCSVCTFFTILGSYIPGVILSYLLLLCAFLCPLFKCNDIGQKIYSKIKSVLLKLDFGIGEY
INQKKRERSEADKEKSHKDDSELDFSALCPKISLTVAAKELSVSDTDVSEVSWTDNG
TFNLSEGYTPQTDTSDDLDRPSEEVFSRDLSDFPSLENGMGTNDEDELSLGLPTELKR
KKEQLDSGHRPSKETQSAAGLTLPLNSDQTFHLMSNLAGDVITAAVTAAIKDQLEGV
QQALSQAAPIPEEDTDTEEGDDFELLDQSELDQIESELGLTQDQEAEAQQNKKSSGFL
SNLLGGH (SEQ ID NO:72)

FIG. 75

GI:5876137 Nucleic Acid Sequence

GTAAGTATTTAAATACAATTATTTTTTCTCTCAATGGTATAGCATATTCCTATGC
TTGAGAAGTATAGGTCTACTGAAAAACCATTGTAAATGGACGTTACAGGTATGCT
GTATTTTTGAAGGTATTTTGTTGTATTAAGTTTGATGAAGCTAAAATTAGGGAAC
TCTGAACAGATTTGCAGGAAAAAATGTTTTAAAGGCTTTAAAACATTAGGGAGG
CAGTCTAGGGTGATAACGAACAGGGGTTAAGTATTAAATACACGAAGTTACATT
TTTGTTCATGTTTCATTGTCCAGAAAGCAGCAGGAAACTATTCAGTTGTGATCAA
GCAGGAAAAAAGAAACACCAACAGTTGCCAGTGTTTTTGCTTTTTAGCTTAAAAG
CATAGTGAAGATGCTTGAGGAAGACTTTGCTACCTGGGGTGTGTAGACAGACAG
ACTGAGAGCTATCAGCATTTGAAGGCCCAGCCCTTGACTCTGAGACACATTTGAA
TTTTTTCTTTCCCATCAAATGGCATTAACAAGATTGGGCAAAGATGAGTCCCTCA
AATTTCTGTGTTTTTTGTTTGTTTGTTTGTTTGTTTTTTCTTTGGGAACTGAAGTCA
GAGGCACGAACACTAACTCTTAGCATTTTTCTGTAGACTTTTTCTTCTGGCCCTTG
TCCCTGCCAGCAAAACGCCCCTTTTCTGATCATTCGTGCGCAGAGGGCCTCCCAG
TAATGCCACGCTCTCCATGCTAGAGAGCCTTCTCTTTCCTCTGAGGTTTGAACTGA
TGTTCTGTGTCTTCACACCCTGGCATGACAGTTACGTGTGGTCAGCCCGCTCCCCA
GGCCCGTCCCTGCCGCCGCCAGGTGTGGGCTCTAGGCAGGCCGACAAGGTTACA
CCTCCCAGAGCTTGTGATCTTCATTTTCTGACAGTCAAAGTGTGAAGGAACCCAG
ACTTCCCCGAGCCACGGTGTTCAGTCAGCCCACAGGAATATGCAAGACCCATCTC
CAAAAGTTTGTCTTTGATTTTTTCCAAGCCCTTAGCCCCATAAGCTTTGAATCCTG
TAGTTACAGTGGCATAAAGGACTGACAAAACCTGGATAAGGAAAAACCTTTTTTT
TCTATGAATTTTTTTTGTTTTTTAGGGGAAAGGGATTCTAAGAATGTCATTTAATG
TACTTTGCATCATGTCTCTAGAAATATCTTTGTCCATAGTGGTGGTGGAGTCTCTC
TCTCTCTCTCTCTTTTTGTTTGCTTCTGTTTTCTTTCTTGTCTTCATTCTTTCTTTTCT
TTTTTATTTCTGGTAGCAGGCCTCCATAGAACAAATCTAAAACACAACCACCATA
GTAATGTAAGGAGAGCTTCAGTGGCACCTCAAAACCCACCCTTCGAGATCTGTCC
AAAGACAGTCTCAGAAAGCTGCACTGCCCACCGGCTCAGCTTTCATTCAAAAAG
GCTTCCAAGGCCAATTCTGTCTTGAAGTCAATGCATGTATTTACTGTTTGACAGTA
AACCCGCTCTGCCTTCTCCACGTCCAAGGCTGTGCATTCGTCTAATTAGCGTCGTG
TATGTTTTCCTTTTATTTTTTCCAATAAAAAAGCAGTGGGATGAAAATTGCTTTGA
TATATAGCAGGTAACATTGAAGCTATTCCATAGCACTTAACTGTAGTGAATACTG
TGTCACCAATTTTGAAATCAATTTAATGTTTAATGCAAATCCATTACATGGTGCTA
TTATAGGCTGACAAAATGATTTACACAAATGTGACAACTTGGGCTCAATTCACTC
TGCTTTCCAACAGTGTAAATGCATAGCAGTGTTTATCTGCATGAGAACTATGCAC
TAATCTATCTGAAGAAAAAAACTATATCAACTTTGGTATCTACTTTCCGTTTACTT
CAATCCTTGCCTTTTTGGTCATTGTTATAATGCCAGCTTTAGGACAGAAAGAATT
ATAAGAAAACCAGCATAATACCTGATATATTAAAATGTAGTGCCTGTGAAATCTG
TATTATATTGCTCTTCTGAAGTAAGATTTTTCTACACCGGTAGCCTTCGCTGTCTG
TCAGTCAGGACCTTCTGGTATAGGTGATGTAAAATAACCGTACAATATTAATGCA
TGCGATTCCATAATGCTTAGTGAACTGTATGAATATTACTCAAAGTTATGTTAGT
CTTTTTTTCCGACTTGGTTCTTGTCAGCTAGGTTTAAAGGTATTTCACTGAGAACG
CAAATTCTGTCTTTTCTTGATTTCGGCTGTTTTCAGTATTTTGGAGGTATACATTTA

FIG. 75 (cont.)

CTTAAATTCAGTATTACTCGTGTTTTGTTTTGTTTTGTTTTTGTTTTCTTTTTCC
TAGGGGACAAGCATGGGTGTTTGATTTCAGAAATCAGTACCTGGCGAGATTTTTG
TCTCAAAACGACTATTTGAATTTCAAGAACTGTGCTGCGAAGACACTCTGAGAAC
ATTTGCAAGTCAGGGGCATTTTCCTTGACCCTTGACTGATGCTATGCGGAGACTG
ATACATTTTCTTAATGGACAATGTTCAAGCCAGGTACCCATGCTTGATCTGTCTTC
ACACCAGACCTCCTCATATTAAAAGGAAAAATAAGAAAAAAAATGTAAGAAATC
ACATGGCTATTTAGTTTCATGCACAGTTGCAATATTTTCTTCAAAAATAAAACTCT
GTACAAACTTTGGGCCCGATTCATAAGAAAAAGAAGTTTGCTATTAACACGGGA
TTTTTTTAATATACTTTTTTTGGTCTAAATTTGAAATTACTTGCTTCCCAAATTAAA
TAAATTTCATCTCATTTTTTTCCCTAAACCAGCACCCATCTGCCTTTTATTCCCCA
AAGAGTTACCTTTCCCAGATTAGGGGGATGGTATGTGGGGAGCAGATAGCGGAA
ATGCTTAGAAAGATAAGGGGGACCACCCACAGCTGGTCGTGAGAACAGGGAGAC
AGTGTGTGGGGGTGGGACCTCATCTGTGTGCCTGGTATCCTGAGTTTTACATGTA
GATGCATTCGCCTATTTGATTCAGAAAAATAAACTTTCCCAAAATGTGTCTGAAC
CACAAGAGCATACAGTGGAAGTGCTACCTCTAATCTAACCAGAGCACCTTCATG
GTGGAAGACACCCACCAGGTCATACAATGTGAACTTTTGTATCTCTGCAGTGGTT
TCAAGGACAAATAGTGTCCAATGTATTGGGCCATTTTTCCTGCTGTTTTTATACTC
AACTTCTCAAAATGAAAAAAGCTTTTATTTTTCCTTTGACTTATTTGTGTTGTTCTT
ATTTTTTAAATTTTTATTTTTTGATAATAGTCTGTAAGTTAGCCTTTTTGGGTTTTT
TTTTTTTTTTTTTGGCTTTTTTTTTTTGTTTGTTTTTTTTTCTTTTGACATTGCAACCG
AAGGTCATAAGGCCGCTAGCTCCGCTGGGACAGAGGCTTGAGAGAACTAACGGC
TCGGTGCCTTCTCCCTGGTCTCAGACCATCGTCTCTGCACTGCGAAGGCATTTGGT
AGCCTCGCCACTGAGATACTAACTAGACCTAGACTAGGAGCTTTATCAGGTTCTA
GGAGGTCCTTTAGGAAGACTCTCAAAGGCAAATCCCTGATCCCCCGCCCCACCCT
TAGCCCTGCCCTCTCACCAGAGCAAAATTCACTGGGGACTTTTCCCACCACACAT
GGAAATCTGTCCACTCGGAATACCTCTGTTTTCCATTTCAAATTGTAGGGGGAGG
GGATGGAACACTTCCAGTGATGGTAAGAGATCTGTTATGAAACGAAACACCCCC
CGTGTTAATAACTTGGTCTGAAATCTGTTTTTATGAGCCGGGCCCCCTGTGCCTCT
AGTATACTTGTATTGACTCTCATAGTTACCCTTTTAGTTTTACTGTGTTCTGTGAA
AATTTGTAATTGGTTGAGAATCACTGTGGGCGTCCATTCTTATTCAACTAAATCTC
CACAGGTTTTTTGAGCTGGTGTGGATTAGTTTAACTCTTGTATTCAACCATTAGTG
CTACCACCTTCTCACATTACAATACAATTACTGGAAGCAAGTACTGCATTTCCTA
TGCAAC (SEQ ID NO:73)

FIG. 77

GI:2185828 Nucleic Acid Sequence

CCGCTTTCTCCGCGCGGTGCCTGCAGGGCTCCCAGCGAGTGGCAGCTTGGGAGGG
GCCGCCCGGGCGGTCAGACTGGCACCTGAGCGGCCACCGCGTCCCGGCCAGGCG
GGCAGACCGACCCCCTCCTCACCTCGCGCGCGGCTGACGCAGGCAGGGCGCCCG
GCCCCTCCTGGGGACCATCAGGTGCCGGCTGGGGGCTGTAGGCACCGGACGGAA
GCAGGCGGTGTGAGGACCGACGACGCGGGCATGGCGGGGGCGGCCTGCGAGCC
GGTGGCCAGGCCGAGCCTGACCTCCATCTCGTCTGGGGAGCTTCGCAGCCTGTGG
ACCTGCGACTGCGAGCTGGCCCTGCTGCCGCTGGCTCAGCTGCTGCGCCTGCAGC
CCGGTGCCTTCCAGCTGAGCGGCGACCAGCTCGTGGTGGCCAGGCCCGGGGAGC
CGGCGGCGGCGCGGGGGGGCTTCAACGTCTTCGGTGACGGCCTCGTGCGCCTCG
ACGGGCAGCTCTACCGCCTCAGCAGCTACATCAAGAGGTATGTGGAACTGACCA
ACTACTGTGATTATAAAGACTACAGGGAAACTATATTGAGCAAACCAATGTTGTT
CTTTATTAATGTACAGACCAAAAAAGACACCTCAAAAGAAAGGACGTACGCGTT
TCTTGTAAACACGAGGCACCCCAAGATAAGAAGACAGATAGAGCAAGGGATGG
ACATGGTCATCTCCTCAGTGATTGGAGAAAGTTACCGGCTTCAGTCAATGCAATG
TTCCTCTCTCTTTCAGTTTGATTTTCAAGAGGCAGTGAAGAATTTCTTCCCCCCAG
GAAATGAAGTGGTTAATGGAGAAAATTTAAGCTTTGCATATGAATTCAAAGCTG
ATGCATTATTTGATTTCTTCTATTGGTTTGGGCTCAGTAATTCCGTTGTAAAAGTA
AATGGAAAAGTTCTGAATTTGTCAAGTACAAGTCCAGAAAAGAAGGAGACGATT
AAGTTATTTCTGGAAAAAATGAGTGAGCCTTTAATCCGAAGGAGCAGTTTCTCTG
ACCGAAAGTTCAGTGTAACTTCCAGAGGTTCAATAGATGATGTTTTTAACTGCAA
TCTGTCACCCAGATCATCTCTGACAGAGCCTCTTTTGGCAGAATTACCATTTCCAA
GTGTTCTGGAATCTGAAGAGACACCCAACCAATTTATCTGATTGAACTGAACATT
GTAGCAGTTGCTCCCGCACTCCAGGCCTGTGCTAGACTATAGGCTGGGGGGAGG
GTAGGAGGTGGGAGGCAGATACTTCCACCTGCGTGTCAATCTCCGGCTCCTCCAT
GGCTTCTATGGAGGACTCCTCTCTTCTGCTTCTGTGGATGTGATGCCCTGGCAGGC
CCAGGGCAGCTGATTCCCCTAAAACTTATGATTACCAGGATGGAAAGGCCTTGGT
CCCATGGCACTGGGTGGGGCTGGGGGATATTCTCTACTTTGAACACTTCTCCAAA
GAGGCAGAAGGGCCACAGAGTTCTGCCACCCTGAACATTTTTCTCAGTTCCCTGG
GAGTTTTTGTGGCAGCCTTTGTGGGAGTGGTCTGACTGGCTGTTGACCTAGCATG
CTTCATAAATCAGGGTTTGGCCCTCTGCTTGGAGCATCCAACCCCTTGAACTCAA
ACCTGTCGAGCAAGGGGTTAAGAGTTCTGTTCTCTTGCCAACCTGGCTGGGCAAA
AGCCTGTGCCATCTTTCACTGGGAGGCAAATATGTTTTTCATCCTGCCATATGAC
ACCTATGAGAAACGTTCACAGTGAGGAGTAGCCAGGTTGCTAGGACAGTAACCC
TGCCACACACTGCCTGAAATCGGAACTCCCTTGGCCTCCCTCTTAACTAAGTGAC
CCATGTAGAAGGAAGCCAGGAGATATGGTACCGAACAATGACAGGGGAAGGGT
ATTGGACACGGCAGCGTCCTCCTTATTGAAAACACATTATGTCAGTTGGGAATTT
TAAATAAGCTTTTAGCAAACCTAACACTAAAAGCAAAATAGAAGAAAGCTATAC
CATTACCATAATACATTTTTCATCTCATGGCTACAATGGAATTCTTGAAAAGGAA
AAAAAAATCCTATCTACATATAAAAACCTGCATGAATGAATCACTACATATGCTT
ATAATGAGGAAGAGTTATGGGTCCTGAGTGTAATTTTTTATCCTTTCTTAAAAAG
TTTCTGTATTATGCATTTTGATAACACTACTGATGATCCTTCCACTTATATTTGAA

FIG. 77 (cont.)

ATGTTATGTACCACATTTGCACAATTAAAACTTTTCTTAGCATTCAACCTAGAATT
GATTAAATTTATGACTGAGGCTTCATGTGAGCTTTCCATTGTGGTTTGTGGGTGTT
GTATTTGCCTTGTAACTTACTGAATTACAATAAGAATTGTGGGTTTTCATAGCCAC
TTTCTCAAGAAGCGCCTTTTGAAGAACAAGGCTATGAAGTATTTGAAGAAAGGA
AATAAAATTTGATACTGATCTTTCAGAAAAGAGAAGGGGAATGCTACTTAATAA
CAGAAGATGTTAAACATTTATTATTACACTCAATAAAAAATGAAGAGTATTAAC
(SEQ ID NO:74)

FIG. 78

GI:2185828 Translated Amino Acid Sequence

MAGAACEPVARPSLTSISSGELRSLWTCDCELALLPLAQLLRLQPGAFQLSGDQLVV
ARPGEPAAARGGFNVFGDGLVRLDGQLYRLSSYIKRYVELTNYCDYKDYRETILSKP
MLFFINVQTKKDTSKERTYAFLVNTRHPKIRRQIEQGMDMVISSVIGESYRLQSMQCS
SLFQFDFQEAVKNFFPPGNEVVNGENLSFAYEFKADALFDFFYWFGLSNSVVKVNG
KVLNLSSTSPEKKETIKLFLEKMSEPLIRRSSFSDRKFSVTSRGSIDDVFNCNLSPRSSL
TEPLLAELPFPSVLESEETPNQFI (SEQ ID NO:75)

FIG. 80

Homo sapiens proteasome (prosome, macropain) subunit, beta type, 9 Polynucleotide Sequence (XM_016877 ;GI:14754802)

CAGGCGGCGAGGAGAGCGGTGCCTTGCAGGGATGCTGCGGGCGGGAGCACCAA
CCGGGGACTTACCCCGGGCGGGAGAAGTCCACACCGGGACCACCATCATGGCAG
TGGAGTTTGACGGGGGCATTGTGATGGGTTCTGATTCCCGAGTGTCTGCAGGCGA
GGCGGTGGTGAACCGAGTGTTTGACAAGCTGTCCCCGCTGCACGAGCGCATCTAC
TGTGCACTCTCTGGTTCAGCTGCTGATGCCCAAGCCGTGGCCGACATGGCCGCCT
ACCAGCTGGAGCTCCATGGGATAGAACTGGAGGAACCTCCACTTGTTTTGGCTGC
TGCAAATGTGGTGAGAAATATCAGCTATAAATATCGAGAGGACTTGTCTGCACAT
CTCATGGTAGCTGGCTGGGACCAACGTGAAGGAGGTCAGGTATATGGAACCCTG
GGAGGAATGCTGACTCGACAGCCTTTTGCCATTGGTGGCTCCGGCAGCACCTTTA
TCTATGGTTATGTGGATGCAGCATATAAGCCAGGCATGTCTCCCGAGGAGTGCAG
GCGCTTCACCACAGACGCTATTGCTCTGGCCATGAGCCGGGATGGCTCAAGCGG
GGGTGTCATCTACCTGGTCACTATTACAGCTGCCGGTGTGGACCATCGAGTCATC
TTGGGCAATGAACTGCCAAAATTCTATGATGAGTGAACCTTCCCCAGACTTCTCT
TTCTTATTTTGTAATAAACTCTCTAGGACCAAAACCTGGTATGGTCATTGGGAAA
TGAGTGCTCAGGGAGATGGAGCTTAGGGGAGGTGGGTGCTTCCCTCCTAGATGTC
AGCATACACTCTTTCTTCTTTTGTCCCAGGTCTAAAACATCTTTCCTAGAGAAAAC
AAAAGGGACTAAACTAGAAATATAAAGAGCCCTATACATGACAGGTGATCACGT
ACTGAATGATTTTGAAGTAGTACAAACAATAAAAATTCTCATTCCGCATCATCAT
GCGGTCCATGATGATGAGGCCGCAA (SEQ ID NO:76)

FIG. 81

Homo sapiens proteasome (prosome, macropain) subunit, beta type, 9
Amino Acid Sequence

MLRAGAPTGDLPRAGEVHTGTTIMAVEFDGGVVMGSDSRVSAGEAVVNRVFDKLS
PLHEHIYCALSGSAADAQAVADMAAYQLELHGIELEEPPLVLAAANVVRNISYKYRE
DLSAHLMVAGWDQREGGQVYGTLGGMLTRQPFAIGGSGSTFIYGYVDAAYKPGMS
PEECRRFTTDAIALAMSRDGSSGGVIYLVTITAAGVDHRVILGNELPKFYDE (SEQ ID NO:77)

FIG. 83

TYRO Protein Tyrosine Kinase Binding Protein
Polynucleotide Sequence (GI:4507754)

CCACGCGTCCGCGCTGCGCCACATCCCACCGGCCCTTACACTGTGGTGTCCAGCA
GCATCCGGCTTCATGGGGGGACTTGAACCCTGCAGCAGGCTCCTGCTCCTGCCTC
TCCTGCTGGCTGTAAGTGGTCTCCGTCCTGTCCAGGCCCAGGCCCAGAGCGATTG
CAGTTGCTCTACGGTGAGCCCGGGCGTGCTGGCAGGGATCGTGATGGGAGACCT
GGTGCTGACAGTGCTCATTGCCCTGGCCGTGTACTTCCTGGGCCGGCTGGTCCCT
CGGGGGCGAGGGGCTGCGGAGGCAGCGACCCGGAAACAGCGTATCACTGAGAC
CGAGTCGCCTTATCAGGAGCTCCAGGGTCAGAGGTCGGATGTCTACAGCGACCTC
AACACACAGAGGCCGTATTACAAATGAGCCCGAATCATGACAGTCAGCAACATG
ATACCTGGATCCAGCCATTCCTGAAGCCCACCCTGCACCTCATTCCAACTCCTAC
CGCGATACAGACCCACAGAGTGCCATCCCTGAGAGACCAGACCGCTCCCCAATA
CTCTCCTAAAATAAACATGAAGCACAAAAAAAAAAAAAAAAAAAAAAAAAAA
AAAAAA (SEQ ID NO:78)

FIG. 84

TYRO Protein Tyrosine Kinase Binding Protein
Amino Acid Sequence

MGGLEPCSRLLLLPLLLAVSGLRPVQAQAQSDCSCSTVSPGVLAGIVMGD
LVLTVLIALAVYFLGRLVPRGRGAAEAATRKQRITETESPYQELQGQRSD
VYSDLNTQRPYYK (SEQ ID NO:79)

FIG. 86

Interleukin 15 Receptor, alpha Polynucleotide Sequence (GI:4504648)

CCCAGAGCAGCGCTCGCCACCTCCCCCCGGCCTGGGCAGCGCTCGCCCGGGGAG
TCCAGCGGTGTCCTGTGGAGCTGCCGCCATGGCCCCGCGGCGGGCGCGCGGCTG
CCGGACCCTCGGTCTCCCGGCGCTGCTACTGCTGCTGCTGCTCCGGCCGCCGGCG
ACGCGGGGCATCACGTGCCCTCCCCCCATGTCCGTGGAACACGCAGACATCTGG
GTCAAGAGCTACAGCTTGTACTCCAGGGAGCGGTACATTTGTAACTCTGGTTTCA
AGCGTAAAGCCGGCACGTCCAGCCTGACGGAGTGCGTGTTGAACAAGGCCACGA
ATGTCGCCCACTGGACAACCCCCAGTCTCAAATGCATTAGAGACCCTGCCCTGGT
TCACCAAAGGCCAGCGCCACCCTCCACAGTAACGACGGCAGGGGTGACCCCACA
GCCAGAGAGCCTCTCCCCTTCTGGAAAAGAGCCCGCAGCTTCATCTCCCAGCTCA
AACAACACAGCGGCCACAACAGCAGCTATTGTCCCGGGCTCCCAGCTGATGCCTT
CAAAATCACCTTCCACAGGAACCACAGAGATAAGCAGTCATGAGTCCTCCCACG
GCACCCCCTCTCAGACAACAGCCAAGAACTGGGAACTCACAGCATCCGCCTCCC
ACCAGCCGCCAGGTGTGTATCCACAGGGCCACAGCGACACCACTGTGGCTATCTC
CACGTCCACTGTCCTGCTGTGTGGGCTGAGCGCTGTGTCTCTCCTGGCATGCTACC
TCAAGTCAAGGCAAACTCCCCCGCTGGCCAGCGTTGAAATGGAAGCCATGGAGG
CTCTGCCGGTGACTTGGGGGACCAGCAGCAGAGATGAAGACTTGGAAAACTGCT
CTCACCACCTATGAAACTCGGGGAAACCAGCCCAGCTAAGTCCGGAGTGAAGGA
GCCTCTCTGCTTTAGCTAAAGACGACTGAGAAGAGGTGCAAGGAAGCGGGCTCC
AGGAGCAAGCTCACCAGGCCTCTCAGAAGTCCCAGCAGGATCTCACGGACTGCC
GGGTCGGCGCCTCCTGCGCGAGGGAGCAGGTTCTCCGCATTCCCATGGGCACCAC
CTGCCTGCCTGTCGTGCCTTGGACCCAGGGCCCAGCTTCCCAGGAGAGACCAAAG
GCTTCTGAGCAGGATTTTTATTTCATTACAGTGTGAGCTGCCTGGAATACATGTG
GTAATGAAATAAAAACCCTGCCCCGAATCTTCCGTCCCTCATCCTAACTTGCAGT
TCACAGAGAAAAGTGACATACCCAAAGCTCTCTGTCAATTACAAGGCTTCTCCTG
GCGTGGGAGACGTCTACAGGGAAGACACCAGCGTTTGGGCTTCTAACCACCCTG
TCTCCAGCTGCTCTGCACACATGGACAGGGACCTGGGAAAGGTGGGAGAGATGC
TGAGCCCAGCGAATCCTCTCCATTGAAGGATTCAGGAAGAAGAAAACTCAACTC
AGTGCCATTTTACGAATATATGCGTTTATATTTATACTTCCTTGTCTATTATATCT
ATACATTATATATTATTTGTATTTTGACATTGTACCTTGTATAAACAAAATAAAAC
ATCTATTTTCAATATTTTTAAAATGCA (SEQ ID NO:80)

FIG. 87

Interleukin 15 Receptor, alpha Amino Acid Sequence

MAPRRARGCRTLGLPALLLLLLLRPPATRGITCPPPMSVEHADIWVKSYSLYSRERYI
CNSGFKRKAGTSSLTECVLNKATNVAHWTTPSLKCIRDPALVHQRPAPPSTVTTAGV
TPQPESLSPSGKEPAASSPSSNNTAATTAAIVPGSQLMPSKSPSTGTTEISSHESSHGTP
SQTTAKNWELTASASHQPPGVYPQGHSDTTVAISTSTVLLCGLSAVSLLACYLKSRQ
TPPLASVEMEAMEALPVTWGTSSRDEDLENCSHHL (SEQ ID NO:81)

POLYNUCLEOTIDES AND POLYPEPTIDES ASSOCIATED WITH THE DEVELOPMENT OF RHEUMATOID ARTHRITIS

CROSS-REFERENCE TO RELATED APPLICATIONS

This application claims priority to U.S. Provisional Patent Application No. 60/337,429, filed Dec. 3, 2001, and hereby expressly incorporated by reference in its entirety.

FIELD OF THE INVENTION

The present invention provides polynucleotides encoding polypeptides associated with the development and progression of rheumatoid arthritis and homologs thereof. Also provided are vectors, host cells, antibodies, and recombinant and synthetic methods for producing said polypeptides. The invention further relates to diagnostic and therapeutic methods for utilizing these polypeptides in the diagnosis, treatment, and/or prevention of rheumatoid arthritis and related disease states. The invention further relates to screening methods for identifying agonists and antagonists of the polynucleotides and polypeptides of the present invention.

BACKGROUND OF RELATED TECHNOLOGY

Rheumatoid arthritis (RA) is a chronic inflammatory disease characterized by progressive joint destruction. Initial destruction of cartilage and bone is associated with the formation of a pannus, consisting of a hypertrophic synovial membrane containing hyperplastic synoviocytes and an infiltrate of inflammatory cells including T cells, B cells, CD68+ macrophages, mast cells, and endothelial cells. The causes of RA are not well understood. Genetic studies have linked expression of specific major histocompatibility complex class II antigens to the development of RA, suggesting the involvement of antigen-specific mechanisms in disease progression (Zanelli et al., *Hum. Immunol.* 61:1254-1261 (2000)).

CD4+ T cells are thought to play a key role in initiation and progression of disease. Although many putative self antigens have been proposed, none have been definitively associated with the initiation of disease. Antigen-activated T cells stimulate monocytes, macrophages, and synovial fibroblasts to secrete pro-inflammatory cytokines including interleukin-1 (IL-1), interleukin-6 (IL-6), and TNF-α. These cytokines stimulate synovial fibroblasts, osteoclasts, and chondrocytes to release matrix metalloproteinases (MMPs) that destroy surrounding tissue. Activated CD4+ T cells stimulate osteoclastogenesis that can also contribute to joint damage. The activated T cells also stimulate B cells present in the synovium via the CD40 pathway to differentiate into antibody secreting cells producing rheumatoid factor, which may also contribute to disease pathology.

Many of the cytokines found in rheumatoid synovium have been directly linked to disease pathology. For example, TNF-α promotes inflammation by inducing secretion of other inflammatory cytokines including IL-1, IL-6, IL-8, GM-CSF, as well as by upregulating adhesion molecule expression on endothelial cells and synovial fibroblasts. These two events promote increased migration of lymphocytes including neutrophils, monocytes, and T cells into the synovium. Neutrophils release elastase and proteases that degrade proteoglycan and contribute to joint destruction. Therapies targeting TNF-α include the use of soluble TNF-α receptor (Etanercept) and neutralizing antibodies specific for TNF-α (Infliximab), and result in a significant decrease in the number of swollen joints, as well as the numbers of T cells and plasma cells in the synovium of RA patients. Such therapies also result in a decrease in the expression of VCAM-1 and IL-1 in the synovium of treated patients (Bathon, et al., *New Engl. J. Med.* 343:1586-1593 (2000); Lipsky, et al., *New Engl. J. Med.* 343:1594-1602 (2000); Richard-Miceli, et al., *Biodrugs* 15:251-259 (2001)).

IL-1 has also been closely linked to the pathophysiology of RA. IL-1 induces synovial cell proliferation and activates MMP and prostaglandin production in vitro (Mizel et al., *Proc. Natl. Acad. Sci. USA* 78:2474-2477 (1981)). In several mouse models of arthritis, IL-1 is believed to play a dominant role in cartilage destruction, whereas TNF-α is primarily proinflammatory (Joosten et al., *J. Immunol.* 163:5049-5055 (1999)). Transgenic mice constitutively expressing human IL-1α in various organs develop a severe polyarthritic phenotype with a predominance of neutrophils and macrophages in the diseased joints (Niki et al., *J. Clin. Invest.* 107:1127-1135 (2001)). Synovitis developed within two weeks of birth, followed by pannus formation and cartilage destruction within 8 weeks after birth. Treatment of RA patients with a natural inhibitor of IL-1, recombinant human IL-1 receptor antagonist (IL-1Ra), significantly reduced clinical symptoms and the rate of progressive joint damage (Jiang et al., *Arthritis Rheum.* 43:1001-1009 (2000); Bresnihan et al., *Biodrugs* 15:87-97 (2001)).

A number of studies have sought to identify genes whose expression is associated with the development of RA. cDNA microarrays have been used to compare expression profiles between tissue samples derived from RA and inflammatory bowel disease patients. Such studies have found that prominently upregulated genes in RA samples include: IL-6; the MMPs stromelysin-1, collagenase-1, gelatinase A, and human matrix metalloelastase; tissue inhibitors of metalloproteinases, including TIMP-1 and TIMP-3; the adhesion molecule VCAM-1; and chemokines including MCP-1, MIF, and RANTES (Heller et al. *Proc. Natl. Acad. Sci. USA* 94: 2150-2155 (1997)). Further, a cDNA library has been generated from monocytes obtained from a RA patient with active disease (Stuhlmuller et al., *Arthritis Rheum.* 43:775-790 (2000)). Genes found to be upregulated in these cells include IL-1α, IL-1β, IL-6, TNF-α, growth-related oncogene α, macrophage inflammatory protein 2, ferritin, α1-antitrypsin, lysozyme, transaldolase, Epstein-Barr virus-encoded RNA 1-associated protein, thrombospondin 1, angiotensin receptor II C-terminal homologue, and RNA polymerase II elongation factor.

In one study, a cDNA library was generated by subtracting cDNA derived from noninflammatory osteoarthritis (OA) synoviocytes from cDNA derived from cultured RA fibroblastoid synoviocytes (Seki et al., *Arthritis Rheum.* 41:1356-1364 (1998)). Genes found to be constitutively overexpressed in the rheumatoid synoviocyte line include: chemokine stromal cell-derived factor 1α; adhesion molecule VCAM-1; interferon-inducible 56-kD protein; 2'-5'-oligoadenylate synthetase; Mac-2 binding protein; extracellular matrix components biglycan, lumican, and IGFBP5; and semaphorin VI.

Studies have also been conducted using suppression subtractive hybridization to identify genes that are highly expressed in RA synovium relative to OA synovium (Justen et al., *Mol. Cell Biol. Res. Comm.* 3:165-172 (2000)). Genes found to be specifically upregulated in RA synovium include: cytoskeletal γ-actin; the extracellular matrix components fibronectin and collagen IIIα1; superficial zone protein; elongation factor α1; granulin precursor; interferon-γ inducible lysosomal thiol reductase; the protease cathepsin B; phospholipase A2 group IIA; and annexin II.

Accordingly, there is a continuing need to identify genes whose expression is associated with the development and progression of RA. The identification of such genes permits the development of clones expressing such genes, thereby permitting the identification of compounds capable of modulating the activity of such genes and/or their expression products. Such compounds may have therapeutic utility in the diagnosis and/or treatment of RA and related disease states. The present invention is directed to meeting these and other needs.

BRIEF DESCRIPTION OF THE DRAWINGS

FIGS. 2, 5, 8, 11, 14, 17, 20, 23, 26, 29, 32, 35, 38, 41, 44, 47, 50, 53, 56, 59, 62, 65, 68, 70, 72, 75, 77, 80, 83 and 86 show polynucleotide sequences for genes of the present invention shown to be upregulated and downregulated in rheumatoid arthritis synovial fluid.

FIGS. 3, 6, 9, 12, 15, 18, 21, 24, 27, 30, 33, 36, 39, 42, 45, 48, 51, 54, 57, 60, 63, 66, 73, 78, 81, 84 and 87 show amino acid sequences for the expression product of genes of the present invention shown to be upregulated and downregulated in rheumatoid arthritis synovial fluid.

SUMMARY OF THE INVENTION

Figure 1:
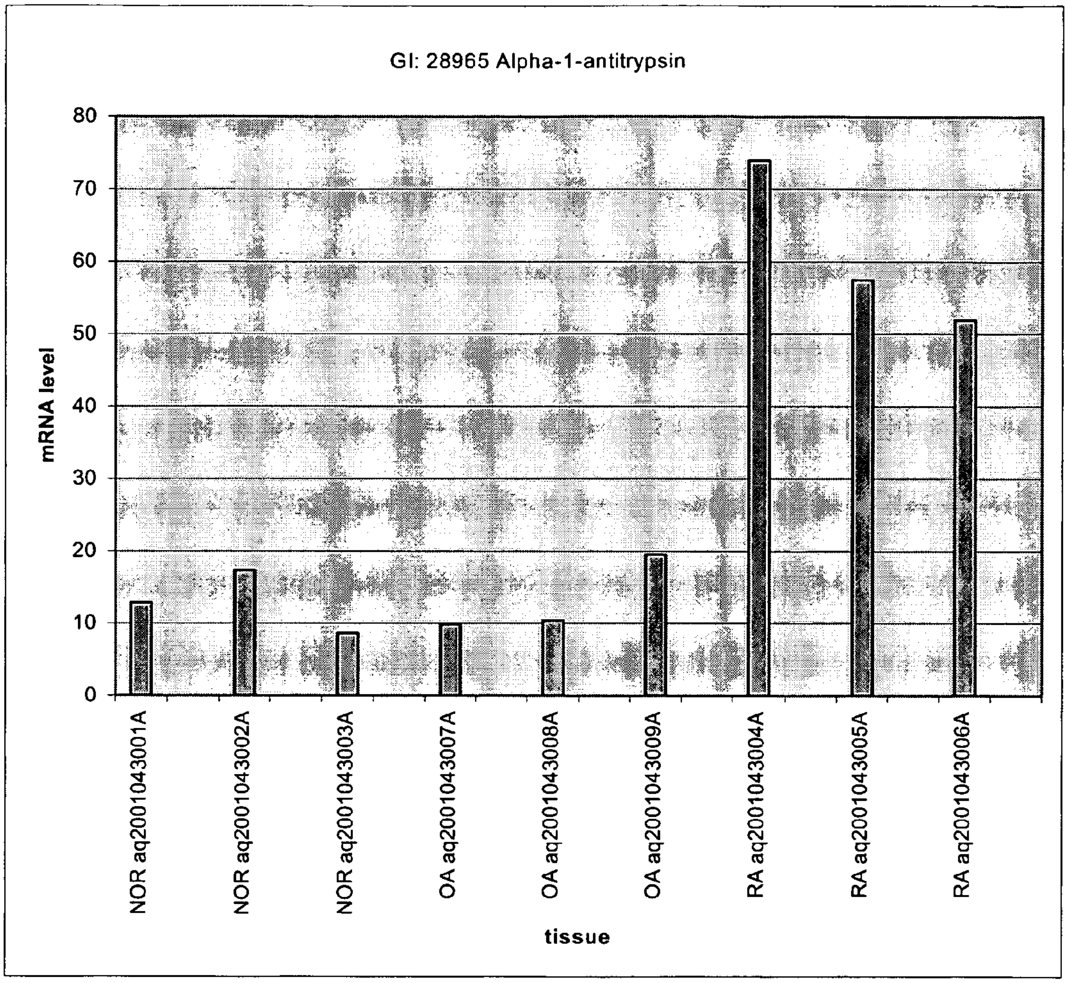
FIGS. 1, 4, 7, 10, 13, 16, 19, 22, 25, 28, 31, 34, 37, 40, 43, 46, 49, 52, 55, 58, 61, 64, 67, 69, 71, 74, 76, 79, 82 and 85 show microarray data for genes of the present invention shown to be upregulated and downregulated in rheumatoid arthritis synovial fluid.

In one aspect, the present invention is directed to an assay for identifying a compound that modulates the activity of a gene associated with rheumatoid arthritis, including the steps of: (1) providing a cell expressing a gene associated with rheumatoid arthritis, wherein the nucleic acid sequence of the gene associated with rheumatoid arthritis is at least 95% identical to a nucleic acid sequence selected from the group consisting of SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:70, SEQ ID NO:71, SEQ ID NO:73, and SEQ ID NO:74; (2) contacting the cell expressing the gene associated with rheumatoid arthritis with a test compound; and (3) determining whether the test compound modulates the activity of the gene associated with rheumatoid arthritis. The assay may be cell-based assay or may be a cell-free assay, such as a ligand-binding assay. The test compound desirably modulates the activity of the gene associated with rheumatoid arthritis, may be an antagonist or an agonist of the gene associated with rheumatoid arthritis, and may bind to the gene associated with rheumatoid arthritis. The assay is desirably useful for identifying compounds which are useful for the treatment of rheumatoid arthritis.

In another aspect, the present invention is directed to an assay for identifying a compound that modulates the activity of a protein associated with rheumatoid arthritis, including the steps of: (1) providing a cell expressing a gene associated with rheumatoid arthritis, wherein the gene encodes a polypeptide having an amino acid sequence which is at least 95% identical to an amino acid sequence selected from the group consisting of SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:72, and SEQ ID NO:75; (2) contacting the cell expressing the gene associated with rheumatoid arthritis with a test compound; and (3) determining whether the test compound modulates the activity of the protein associated with rheumatoid arthritis. The test compound desirably modulates the activity of the protein associated with rheumatoid arthritis, may be an antagonist or an agonist of the protein associated with rheumatoid arthritis, and may bind to the protein associated with rheumatoid arthritis. The assay is desirably useful for identifying compounds which are useful for the treatment of rheumatoid arthritis.

In another aspect, the present invention is directed to a method for the treatment of rheumatoid arthritis, including the steps of: (1) identifying a patient suffering from rheumatoid arthritis; and (2) administering to the patient a therapeutically effective amount of a modulator of a gene associated with rheumatoid arthritis, wherein the gene associated with rheumatoid arthritis has a nucleic acid sequence which is at least 95% identical to a nucleic acid sequence selected from the group consisting of SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:70, SEQ ID NO:71, SEQ ID NO:73, and SEQ ID NO:74. The patient is desirably identified as suffering from rheumatoid arthritis by measuring the expression level of the gene associated with rheumatoid arthritis in the patient. The modulator is desirably an antagonist of a gene associated with rheumatoid arthritis.

In another aspect, the present invention is directed to a method for the treatment of rheumatoid arthritis, including the steps of: (1) identifying a patient suffering from rheumatoid arthritis; and (2) administering to the patient suffering from rheumatoid arthritis a therapeutically effective amount of a modulator of a polypeptide associated with rheumatoid arthritis, wherein the polypeptide associated with rheumatoid arthritis has an amino acid sequence which is at least 95% identical to an amino acid sequence selected from the group consisting of SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:72, and SEQ ID NO:75. The patient is desirably identified as suffering from rheumatoid arthritis by measuring the expression level of the polypeptide associated with rheumatoid arthritis. The modulator is desirably an antagonist of a polypeptide associated with rheumatoid arthritis.

In another aspect, the present invention is directed to a method for the prevention of rheumatoid arthritis, including the steps of: (1) identifying a patient at risk for rheumatoid arthritis; and (2) administering to the patient at risk for rheumatoid arthritis a therapeutically effective amount of a modulator of a gene associated with rheumatoid arthritis, wherein the gene associated with rheumatoid arthritis has a nucleic acid sequence which is at least 95% identical to a nucleic acid sequence selected from the group consisting of SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:70, SEQ ID NO:71, SEQ ID NO:73, and SEQ ID NO:74. The patient is desirably identified as being at risk for rheumatoid arthritis by measuring the expression level of the gene associated with rheumatoid arthritis in the patient.

In another aspect, the present invention is directed to a method for the prevention of rheumatoid arthritis, including the steps of: (1) identifying a patient at risk for rheumatoid arthritis; and (2) administering to the patient at risk for rheumatoid arthritis a therapeutically effective amount of a modulator of a polypeptide associated with rheumatoid arthritis, wherein the polypeptide associated with rheumatoid arthritis has an amino acid sequence which is at least 95% identical to an amino acid sequence selected from the group consisting of SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:72, and SEQ ID NO:75. The patient is desirably identified as being at risk for rheumatoid arthritis by measuring the expression level of the polypeptide associated with rheumatoid arthritis in the patient.

In another aspect, the present invention is directed to a compound useful for the treatment of rheumatoid arthritis, wherein the compound is identified by: (1) providing a cell expressing a gene associated with rheumatoid arthritis, wherein the gene associated with rheumatoid arthritis has a nucleic acid sequence which is at least 95% identical to a nucleic acid sequence selected from the group consisting of SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:70, SEQ ID NO:71, SEQ ID NO:73, and SEQ ID NO:74; (2) contacting the cell expressing the gene associated with rheumatoid arthritis with the compound; and (3) determining whether the compound modulates the activity of the gene associated with rheumatoid arthritis.

In another aspect, the present invention is directed to a compound useful for the treatment of rheumatoid arthritis, wherein the compound is identified by: (1) providing a cell expressing a polypeptide associated with rheumatoid arthritis, wherein the polypeptide associated with rheumatoid arthritis has an amino acid sequence which is at least 95% identical to an amino acid sequence selected from the group consisting of SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:72, and SEQ ID NO:75; (2) contacting the cell expressing the polypeptide associated with rheumatoid arthritis with the compound; and (3) determining whether the compound modulates the activity of the polypeptide associated with rheumatoid arthritis.

DETAILED DESCRIPTION OF THE INVENTION

The present invention is directed to the identification of genes associated with Rheumatoid Arthritis (RA). Such genes and their polypeptide expression products are hereinafter referred to as "RA-associated genes and polypeptides". In the present invention, RA-associated genes and polypeptides have been identified by probing Affymetrix chips (describe) with mRNA derived from the synovia of RA patients, as set forth in Section A of "Materials and Methods", hereinbelow. Gene expression patterns were compared to those obtained using mRNA derived from synovia of control joint trauma patients. Several genes were identified as having significantly increased expression in the RA synovium relative to the controls, as further described hereinbelow. Several genes have also been identified as having significantly decreased expression in the RA synovium relative to the controls, as further described hereinbelow.

The present invention provides synthetic methods for producing RA-associated genes and polypeptides. Also provided are diagnostic methods for detecting diseases, disorders, and/or conditions related to RA-associated genes and polypeptides, and therapeutic methods for treating such diseases, disorders, and/or conditions. The invention further relates to screening methods for identifying binding partners of RA-associated genes and polypeptides.

Examples of functional assays useful in the present invention include LPS-induced TNFα and TNFα-induced IL-1β secretion by THP-1 monocytes, anti-CD3/anti-CD28-induced IL-2 secretion by Jurkat T cells, TNFα-induced IL-1β secretion by synovial fibroblasts, TNFα-induced E-selectin expression by endothelial cells, and anti-CD40-induced homotypic aggregation of Raji B cells.

One of skill in the art will recognize that RA-associated genes and polypeptides of the present invention are desirably murine or human, but may be from any suitable organism. The genomic and protein sequences of RA-associated genes and polypeptides from these organisms are readily accessed via Genbank or The National Center for Biotechnology Information.

Further, derivatives and homologues of RA-associated genes and polypeptides may be used in the present invention. For example, nucleic acid sequences of RA-associated genes of the present invention may be altered by substitutions, additions, or deletions that provide for functionally equivalent-conservative variants of such genes. Further, one or more amino acid residues within the amino acid sequence of RA-associated polypeptides can be substituted by another amino acid of similar properties, such as, for example, positively charged amino acids (arginine, lysine, and histidine); negatively charged amino acids (aspartate and glutamate); polar neutral amino acids; and non-polar amino acids.

Other conservative amino acid substitutions can be taken from the Table 1, below.

TABLE 1

Conservative Amino Acid Replacements

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the present invention are those with modifications which increase protein stability; such analogs may contain, for example, one or more non-peptide bonds (which replace the peptide bonds) in the protein sequence. Also included are analogs that include residues other than naturally occurring L-amino acids, e.g., D-amino acids or non-naturally occurring or synthetic amino acids, e.g., β or γ amino acids.

RA-associated polypeptides of the present invention may be modified by, for example, phosphorylation, sulfation, acylation, or other protein modifications. They may also be modified with a label capable of providing a detectable signal, either directly or indirectly, including, but not limited to, radioisotopes and fluorescent compounds.

It will be apparent to one of skill in the art that conventional screening assays may be used in methods of the present invention for the identification of modulators of RA-associated genes and polypeptides.

In the present invention, techniques for screening large gene libraries may include cloning the gene library into replicable expression vectors, transforming appropriate cells with the resulting library of vectors, and expressing the genes under conditions for detection of a desired activity. Techniques known in the art are amenable to high throughput analysis for screening large numbers of sequences created, e.g., by random mutagenesis techniques. High throughput assays can be followed by secondary screens in order to identify further biological activities which will, e.g., allow one skilled in the art to differentiate agonists from antagonists. The type of a secondary screen used will depend on the desired activity that needs to be tested.

Drug screening assays are also provided in the present invention. By producing purified and recombinant forms of RA-associated genes and polypeptides of the present invention, or fragments thereof, one skilled in the art can use these to screen for drugs which are either agonists or antagonists of the normal cellular function or their role in cellular signaling. In one aspect, the assay evaluates the ability of a compound to modulate binding between RA-associated genes and polypeptides of the present invention and a naturally occurring ligand. The term "modulating" encompasses enhancement, diminishment, activation or inactivation of activity of RA-associated genes and polypeptides. Assays useful for identifying ligands to RA-associated genes and polypeptides of the present invention are encompassed herein. Such ligands include peptides, proteins, small molecules, and antibodies, which are capable of binding to RA-associated genes and polypeptides of the present invention and modulating their activity. A variety of assay formats may be used in the present invention and are known by those skilled in the art.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as primary screens in that they can be generated to permit rapid development and relatively easy detection of an alteration in a molecular target which is mediated by a test compound.

Compounds identified using assays, as discussed hereinabove, may be antagonists or agonists of RA-associated genes and polypeptides. These compounds are useful in modulating the activity of RA-associated genes and polypeptides and in treating disorders associated with RA-associated genes and polypeptides.

"Disorders associated with RA-associated genes and polypeptides" refers to any disorder or disease state in which RA-associated genes and polypeptides play a regulatory role in the metabolic pathway of that disorder or disease. As used herein, the term "treating" refers to the alleviation of symptoms of a particular disorder in a patient, the improvement of an ascertainable measurement associated with a particular disorder, or the prevention of a particular immune, inflammatory or cellular response.

A compound which acts as a modulator of RA-associated genes and polypeptides may be administered for therapeutic use as a raw chemical or may be the active ingredient in a pharmaceutical formulation. Such formulations of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Compounds of the present invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

Such compounds may, for example, be administered in a form suitable for immediate release or extended release. Immediate release or extended release may be achieved by the use of suitable pharmaceutical compositions comprising compounds of the present invention, or, particularly in the case of extended release, by the use of devices such as subcutaneous implants or osmotic pumps. Compounds of the present invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art.

Compounds of the present invention may also be delivered through the oral cavity by sublingual and/or buccal administration. Molded tablets, compressed tablets or freeze-dried tablets are exemplary forms which may be used. Exemplary compositions include those formulating the compound(s) of the present invention with fast dissolving diluents such as mannitol, lactose, sucrose and/or cyclodextrins.

Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to disorders associated with RA-associated genes and polypeptides.

The compounds of the present invention may be employed alone or in combination with each other and/or other suitable therapeutic agents useful in the treatment of disorders associated with RA-associated genes and polypeptides.

In another aspect, the present invention relates to the use of an isolated nucleic acid in "antisense" therapy. As used herein, "antisense" therapy refers to administration or in situ generation of oligonucleotides or their derivatives which specifically hybridize under cellular conditions with the cellular mRNA and/or genomic DNA of RA-associated genes so as to inhibit expression of the proteins encoded by such genes, e.g., by inhibiting transcription and/or translation. In general, "antisense" therapy refers to the range of techniques generally employed in the art, and includes any therapy which relies on specific binding to oligonucleotide sequences.

Gene constructs useful in antisense therapy may be administered may be administered in any biologically effective carrier, e.g., any formulation or composition capable of effectively delivering a nucleic acid sequence to cells in vivo. Approaches include insertion of the subject gene in viral vectors including recombinant retroviruses, adenoviruses, adeno-associated viruses, and herpes simplex virus-1, or recombinant bacterial or eukaryotic plasmids. Viral vectors transfect cells directly; an advantage of infection of cells with a viral vector is that a large proportion of the targeted cells can receive the nucleic acid. Several viral delivery systems are known in the art and can be utilized by one practicing the present invention.

In addition to viral transfer methods, non-viral methods may also be employed. Most non-viral methods of gene transfer rely on normal mechanisms used by mammalian cells for the uptake and intracellular transport of macromolecules. Exemplary gene delivery systems of this type include liposomal derived systems, poly-lysine conjugates, and artificial viral envelopes. Nucleic acid sequences may also be introduced to cell(s) by direct injection of the gene construct or by electroporation.

In clinical settings, the gene delivery systems can be introduced into a patient by any of a number of methods, each of which is known in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

The following sections sets forth the materials and methods utilized in the present invention.

Materials and Methods

A. Microarray Experimentation

1. RNA Isolation

Human knee biopsy samples were homogenized in 3 ml TRIZOL® Reagent (Life Technologies, Rockville, Md.) and frozen in liquid nitrogen. The samples were thawed, one-third (1 ml) of the sample was removed and mixed with 1 ml TRIZOL®. The mixture was then homogenized and snap frozen in liquid nitrogen. Following a thaw, the samples were spun at 14,000 rpm for 10 minutes at 4° C. The supernatants were transferred to new microfuge tubes, extracted with chloroform, and precipitated with isopropanol overnight at −20° C. The RNA was pelleted by centrifugation at 14,000 rpm for 30 minutes. The supernatant was aspirated, and the samples washed two times with 75% ethanol. Following the last spin, the pellets were air-dried, and resuspended in 20 ul of ultra-pure RNase-free water. The RNA samples were further purified using Qiagen RNease mini columns (Qiagen Inc., Valencia Calif.), according to manufacturer's instructions. The RNA was eluted with 50 ul of RNase-free water.

2. Probe Preparation

The RNA was treated in a total reaction volume of 100 ul with RNase Inhibitor (Invitrogen Corp., Carlsbad, Calif.), DNase I (Ambion, Houston, Tex.) for 30 minutes at 37° C. The treated RNA was purified using Qiagen RNease mini columns, according to the manufacturer's instructions.

For the first strand cDNA synthesis, the RNA was incubated with T7-(dT)24 primer, having the sequence: 5'GGCCAGTGAATTGTAATACGACTCACTATAGGGAGGCGGTTTTTTTT TTTTTTTTTTTTTTTT3' (SEQ ID NO:1) for 10 minutes at 70° C., followed by one minute on ice. First strand buffer, DTT, dNTP and RNase were added, and the samples incubated for 2 minutes at 45° C. Superscript II reverse transcriptase (Invitrogen Corp, Carlsbad, Calif.) was added, and the samples incubated for an additional 60 minutes at 45° C.

For the second strand synthesis, the first strand cDNA was incubated with second strand buffer, dNTPs, *E. coli* ligase, *E. coli* RNase H, *E. coli* Polymerase I in a total volume of 150 ul for two hours at 16° C. T4 polymerase was added, and the incubation continued for an additional 5 minutes. Following this incubation, EDTA was added, and the samples placed on ice. The cDNA samples were extracted with phenol:chloroform:isoamyl alcohol and precipitated by addition of 0.5 volumes of 7.5 M ammonium acetate and 2.5 volumes of 100% ethanol. The samples were pelleted by a 30 minute room temperature spin at 12,000×g. The pelleted samples were washed with 0.5 ml 80% ethanol, spun for 10 minutes at 12,000×g, and air dried. The samples were resuspended in 12 ul RNase free water.

The cDNA was labeled using the Enzo Bio Array High Yield RNA transcript labeling kit (Enzo Therapeutics, Farmingdale, N.Y.). The cDNA was incubated with HY reaction buffer, biotin labeled NTP, DTT, RNase mix, and T7 DNA polymerase for six hours at 37° C. Unincorporated nucleotides were removed using Qiagen RNeasy columns according to manufacturer's instructions. The cRNA was fragmented by addition of fragmentation buffer, and incubated for 35 minutes at 95° C. The fragmented cRNA (0.05 mg/ml) was added to a hybridization solution master mix that included 0.1 mg/ml herring sperm DNA, 5 nM oligo B2, 1× standard curve pool, 0.5 mg/ml acetylated BSA, 1×MES hybridization buffer.

The Affymetrix human U95v2 A, B, and C GeneChips® were probed with the hybridization master mix. The hybridization, washing, and Phycoerythrin streptavidin staining were performed using the Affymetrix hybridization oven and fluidics workstation according to manufacturer's instructions. Stained chips were scanned on the Affymetrix GeneChip scanner, and data was analyzed using the Affymetrix GeneChip software to determine the specifically hybridizing signal for each gene. The differentially expressed genes demonstrated at least a three-fold change in signal when comparing between tissue samples. The differences were all statistically significant ($p<0.001$) when compared to controls using a T-test.

3. Real Time PCR Analysis

Reverse transcription reactions were performed using up to 3.6 ug mRNA. The RNA was incubated for five minutes at 70° C. and then chilled on ice. A master mix was added containing dNTPs, RT buffer (259 mM Tris-HCl pH 8.3, 375 mM KCl, 15 mM $MgCl_2$), dithiothreitol, random hexamers, RNasin, and reverse transcriptase (Life Technologies, Rockville, Md.). The reactions were incubated for 60 minutes at 37° C., denatured for 5 minutes at 90° C., then chilled on ice for 5 minutes. PCR reactions were performed on ABI Prism® 5700 Sequence Detection System with SYBR green core reagents (PE Applied Biosystem, Foster City, Calif.). All PCR was done at 40 cycles with a pre-incubation period of 50° C. for 2 minutes followed by 95° C. for 10 minutes. Cycling conditions were 95° C. for 15 seconds, 55° C. for 20 seconds, and 75° C. for one minute. Some reactions were done with cycling conditions of 95° C. for 15 seconds and 60° C. for 60 seconds. All data was normalized relative to the signal for the housekeeping gene human hypoxanthine phosphoribosyltransferase I ("HPRT") (Accession No. BC000578; GI: 12653602) (SEQ ID NO:2), the nucleotide sequence of which is set forth in Table 2, below.

TABLE 2

Human Hypoxanthine Phosphoribosyltransferase I: Nucleotide Sequence Accession No. BC000578: GI: 12653602

(SEQ ID NO:2)

| | |
|---|---|
| 1 | ggcacgaggc ctcctgagca gtcagcccgc gcgccggccg gctccgttat ggcgacccgc |
| 61 | agccctggcg tcgtgattag tgatgatgaa ccaggttatg accttgattt attttgcata |
| 121 | cctaatcatt atgctgagga tttggaaagg gtgtttattc ctcatggact aattatggac |
| 181 | aggactgaac gtcttgctcg agatgtgatg aaggagatgg gaggccatca cattgtagcc |
| 241 | ctctgtgtgc tcaagggggg ctataaattc tttgctgacc tgctggatta catcaaagca |

TABLE 2-continued

| Human Hypoxanthine Phosphoribosyltransferase I: Nucleotide Sequence Accession No. BC000578: GI: 12653602 |
|---|
| 301 ctgaatagaa atagtgatag atccattcct atgactgtag attttatcag actgaagagc |
| 361 tattgtaatg accagtcaac aggggacata aaagtaattg gtggagatga tctctcaact |
| 421 ttaactggaa agaatgtctt gattgtggaa gatataattg acactggcaa aacaatgcag |
| 481 actttgcttt ccttggtcag gcagtataat ccaaagatgg tcaaggtcgc aagcttgctg |
| 541 gtgaaaagga ccccacgaag tgttggatat aagccagact ttgttggatt tgaaattcca |
| 601 gacaagtttg ttgtaggata tgcccttgac tataatgaat acttcaggga tttgaatcat |
| 661 gtttgtgtca ttagtgaaac tggaaaagca aaatacaaag cctaagatga gagttcaagt |
| 721 tgagtttgga aacatctgga gtcctattga catcgccagt aaaattatca atgttctagt |
| 781 tctgtggcca tctgcttagt agagcttttt gcatgtatct tctaagaatt ttatctgttt |
| 841 tgtactttag aaatgtcagt tgctgcattc ctaaactgtt tatttgcact atgagcctat |
| 901 agactatcag ttccctttgg gcggattgtt gtttaacttg taaatgaaaa aattctctta |
| 961 aaccacagca ctattgagtg aaacattgaa ctcatatctg taagaaataa agagaagata |
| 1021 tattagtttt ttaattggta ttttaatttt tatatatgca ggaaagaata gaagtgattg |
| 1081 aatattgtta attataccac cgtgtgttag aaaagtaaga agcagtcaat tttcacatca |
| 1141 aagacagcat ctaagaagtt ttgttctgtc ctggaattat tttagtagtg tttcagtaat |
| 1201 gttgactgta ttttccaact tgttcaaatt attaccagtg aatctttgtc agcagttccc |
| 1261 ttttaaatgc aaatcaataa attcccaaaa atttaaaaaa aaaaaaaaaa aaaaaa |

Primer sets were as follows:

| | | |
|---|---|---|
| HPRT: | | |
| Forward: | GGTATACTGCCTGACCAAGG | (SEQ ID NO:3) |
| Reverse: | CGAGATGTGATGAAGGAGATGG | (SEQ ID NO:4) |
| Name: | gi475254 homo sapiens transcription factor ISGF-3 mRNA | |
| Forward exon 3 | CCCCATGGAAATCAGACAGT | (SEQ ID NO:5) |
| Reverse exon 4 | TTGCTTTTCCGTATGTTGTG | (SEQ ID NO:6) |
| Name: | gi28965 human alpha-1-antitrypsin gene (S variant) | |
| Forward | TGAAGAGCGTCCTGGGTC | (SEQ ID NO:7) |
| Reverse | CGTCGATGGTCAGCACAG | (SEQ ID NO:8) |
| Name: | gi5595355 human ADO37 protein | |
| Forward | GCCCATCAGTGACAGCAAG | (SEQ ID NO:9) |
| Reverse | CCCAGGCAATGTTGAGGAG | (SEQ ID NO:10) |
| Name: | gi2185828 human hypothetical protein FLI14834 | |
| Forward 417–436 | CCTTCCCCTGTCATTGTTC Tm = 58 | (SEQ ID NO:11) |
| Reverse 515–534 | GACAGTAACCCTGCCACAC Tm = 60 | (SEQ ID NO:12) |
| Name: | gi183001 human guanylate binding protein isoform I | |
| Forward 124–132 | GGCGACTGATGGCGAATC Tm = 58 | (SEQ ID NO:13) |
| Reverse 264–282 | CACCGTGGAGCCCAGAGA Tm = 60 | (SEQ ID NO:14) |
| Name: | gi2138110 human cysteine dioxygenease | |
| Forward 321–341 exon 1 | GGCGATGAGGTCAATGTAGA Tm = 60 | (SEQ ID NO:15) |
| Reverse 473–493 exon 2 | CTGTGTCCTTCACCCCAACA Tm = 62 | (SEQ ID NO:16) |
| Name: | gi180278 IgG Fc Receptor I | |
| Forward | GGACACCACAAAGGCAGTGAT | (SEQ ID NO:17) |
| Reverse | GCAGATGGAGCACCTCACAGT | (SEQ ID NO:18) |
| Name: | gi1382379 MRP-14 | |
| Forward | AGCTCAGCTGCTTGTCTGCAT | (SEQ ID NO:19) |
| Reverse | TTCAAAGAGCTGGTGCGAAA | (SEQ ID NO:20) |

-continued

```
Name:               gi1382285 Early B Cell Factor
Forward             GGCCAGGGCAATGTTATGC                 (SEQ ID NO:21)
Reverse             ACATTCTGGCCCTCTGATCCT               (SEQ ID NO:22)

Name:               gi2185828 human hypothetical protein FLI14834
Forward 417–436     CCTTCCCCTGTCATTGTTC                 (SEQ ID NO:23)
Reverse 515–534     GACAGTAACCCTGCCACAC                 (SEQ ID NO:24)
```

B. Further Characterization of GBP-1 (SEQ ID NOS. 41 and 42): and GBP-5 (SEQ ID NOS. 61 and 62)

1. Cell Culture

For real time PCR analyses, THP-1 cells ($10^7$/group) were cultured at $10^6$/ml in RPMI containing 10% heat inactivated fetal calf serum, 2 mM L-glutamine with either medium, BMS-205820 (2 uM), or dexamethasone (100 nM) for 30 minutes at 37° C. in 5% $CO_2$. LPS was added to each group (100 ng/ml), and the incubation continued for 0.5-8 hr. At the end of each time point, cells were pelleted, washed one time with 10 ml PBS, and stored at −80° C.

Wild type 3T3 fibroblasts and immortalized fibroblast lines derived from p65 and IkBα germline knockouts were cultured in DMEM with 10% calf serum, glutamax and penicillin/streptomycin. Primary embryonic fibroblasts derived from germline knockouts of relB and p50 were cultured in DMEM with 10% fetal calf serum, glutamax and penicillin/streptomycin. The fibroblasts were plated at $5\times10^5$/well of a 6 well plate and cultured overnight at 37° C. in 5% $CO_2$. Cells were stimulated for 2 or 8 hours with either medium, human TNFα (10 ng/ml) or PMA (10 ng/ml). At each time point, cells were harvested using trypsin/EDTA, washed one time with PBS, and stored at −80° C.

For the microarray analyses, THP-1 cells ($10^7$/group) were cultured at $10^6$/ml as above for 1, 6, 24, or 48 hours with either medium, TNFα (10 ng/ml), IFN-γ (100 U/ml), or LPS (100 ng/ml). At each time point, mRNA was isolated, labeled, and used to probe Affymetrix HG_U95Av2, HG_U95B, and HG_U95C chips.

Human microvascular endothelial cells from three different donors were obtained from Clonetics (Walkersville, Md.), and cultured in EGM-2 medium (Clonetics). Cells were cultured in 100 mm dishes coated with mouse type IV collagen and allowed to grow to approximately 80% confluency. The cells were then stimulated for 1, 6, or 24 hours with either medium, TNFα (10 ng/ml), or IL-1β (10 ng/ml). At each time point, mRNA was isolated, labeled and used to probe Affymetrix HG_U95Av2 and HG_U95B chips.

For VEGF and bFGF stimulations, microvascular endothelial cells from three independent donors were obtained, cultured in 100 mm dishes coated with mouse type IV collagen and allowed to grow to 30% confluency. At this time, the media was replaced with DMEM containing 2% fetal calf serum, and the cells were cultured an additional day. The cells were stimulated for 1, 6, or 24 hours with either medium, VEGF (30 ng/ml) or bFGF (10 ng/ml). At each time point, mRNA was isolated, labeled, and used to probe Affymetrix chips as described above.

Synovial fibroblasts were obtained from Cell Applications, Inc. (San Diego, Calif.), and cultured for 1, 6, or 24 hours with either medium, TNFα (10 ng/ml), IL-1α (10 ng/ml, Peprotech), IL-17 (10 ng/ml, R&D Systems, Minneapolis, Minn.), or IL-17b-Ig fusion protein (5 ng/ml). The IL-17b protein was produced by fusing the full length IL-17b sequence (Shi et al., *J. Biol. Chem.* 275:19167-19176 (2000)) to the human IgG1 Fc region. At each time point, mRNA was isolated, labeled, and used to probe Affymetrix HG_U95Av2, HG_U95B, HG_U95C, HG_U95D, and HG_U95E chips.

T cells were isolated from the blood of 4 donors. Lymphocytes were isolated by centrifugation over Accu-prep lymphocyte separation medium (Accurate Chemical and Scientific Corporation, Westbury, N.Y.). The T cells were isolated by rosetting with sheep red blood cells. The isolated T cells were cultured for 6 hours with either medium, or immobilized anti-CD3 (1 ug/ml) plus soluble anti-CD28 (1 ug/ml) antibodies. After 6 hours, mRNA was isolated, labeled, and used to probe Affymetrix HG_U133A and HG_U133B chips.

2. cDNA Synthesis for Real Time PCR Analysis

Total RNA was isolated from cells using the RNeasy® Kit from Qiagen (Valencia, Calif.), including the on-the-column DNase digestion procedure. RNA quality and quantity were evaluated using UV spectrometry. Total RNA was used for first-strand cDNA synthesis using the SuperScript™ First-Strand Synthesis System for RT-PCR (Invitrogen, Carlsbad, Calif.) following the manufacturer's instructions with 50 ng of random hexamers.

For tissue expression analyses, Human Multiple Tissue cDNA Panel I and Human Immune System MTC Panels were obtained from Clontech (Palo Alto, Calif.). PCR reactions were performed using 2 microliters of cDNA sample (diluted with six microliters of water).

3. Primers

Gene specific primers were designed using the Primer Express software and synthesized by Sigma Genosys (The Woodlands, Tex.).

Primer sets were as follows:

```
Name:      mGBP-1              (SEQ ID NO:82)
Forward    GGAACAGGAAAGACTTCTCAAGCA

                               (SEQ ID NO:83)
Reverse    CTTGACGTAGTTGCAAGCTCTCA

Name:      mGBP-5              (SEQ ID NO:84)
Forward    GCTGAAGCAAGGTAGCGATGA

                               (SEQ ID NO:85)
Reverse    CCTCGTTGCTGAGTGTTGGA

Name:      mHPRT               (SEQ ID NO:86)
Forward    TCAGACTGAAGAGCTACTGTAATGATCA

                               (SEQ ID NO:87)
Reverse    CAACAATCAAGACATTCTTTCCAGTT

Name:      hGBP-5              (SEQ ID NO:88)
Forward    TGCTTTCACTTGTGCCTCTTTC

                               (SEQ ID NO:89)
Reverse    CAGGCTCTCACAGAGACGGAA
```

-continued

| | | |
|---|---|---|
| Name: | hGAPDH | (SEQ ID NO:90) |
| Forward | AGCCGAGCCACATCGCT | |
| | | (SEQ ID NO:91) |
| Reverse | GTGACCAGGCGCCCAATAC | |

3. PCR Assay Conditions

Reactions were performed in a total volume of 40 μl. The master mix contained SYBR Green I Dye, 50 mM Tris-HCl pH 8.3, 75 mM KCl, DMSO, Rox reference dye, 5 mM $MgCl_2$, 2 mM dNTP, Platinum Taq High Fidelity (1U/reaction), and 0.5 μM of each primer. Eight microliters of diluted cDNA was used in each PCR reaction. The amplification program consisted of a 10 minute incubation at 95° C. followed by forty cycles of incubations at 95° C. for 15 seconds and 60° C. for 1 minute. Amplification was followed by melting curve analysis at 60° C. to demonstrate that the amplification was specific to a single amplicon. A negative control without cDNA template was run to assess the overall specificity.

4. Data Analysis

A relative value for the initial target concentration in each reaction was determined using the TaqMan 5700 software. The threshold value was set to 0.5 to obtain cycle threshold values that were used to assign relative message levels for each target. The message levels of hGAPDH were used to normalize all other genes tested from the same cDNA. Message levels from the mouse fibroblast experiment were normalized using mouse HPRT values.

EXAMPLE 1

Upregulated Genes and Downregulated Genes in RA

1. α-1 Antitrypsin Expression

Using the materials and methods described hereinabove (Materials and Methods, Section A), increases in expression of α-1 antitrypsin were detected in the RA synovium. This increased expression is shown in the microarray data in FIG. 1. The polynucleotide sequence (SEQ ID NO:25) and amino acid sequence (SEQ ID NO:26) of α-1 antitrypsin are shown in FIGS. 2 and 3, respectively.

Using the materials and methods described hereinabove (Materials and Methods, Section A), Real Time PCR was conducted to quantify the expression of α-1 antitrypsin in the RA synovium, the results of which are set forth in Table 3, below. As used in Table 3 and hereinafter, "OA" stands for "Osteoarthritis".

TABLE 3

α-1 antitrypsin: Real Time PCR Results

| | Expression Level | T test |
|---|---|---|
| Normal | 1 | |
| OA | 1.02 | 0.9574 |
| RA | 5.94 | 0.0034 |

α-1 Antitrypsin is the major endogenous inhibitor of the serine protease elastase. It also inhibits other circulating proteases including cathepsin G, thrombin, trypsin, and chymotrypsin. α-1 Antitrypsin is primarily synthesized by the liver. However, neutrophils, monocytes, and alveolar macrophages also increase expression of α-1 antitrypsin in response to proinflammatory stimuli including TNF-α, IL-6 and endotoxin (Knoell, et al., *Am. J. Respir. Crit. Care Med.* 157:246-255 (1998)). The deficiency of α-1 antitrypsin is associated with connective tissue destruction and the development of emphysema (Crystal, *J. Clin. Invest.* 85:1343-1352 (1990)).

At physiological concentrations, (α-1 antitrypsin is a potent stimulator of fibroblast proliferation and collagen production (Dabbagh et al., *J. Cell Physiol.* 186:73-81 (2001)). High levels of the elastase-α-1 antitrypsin complex have been measured in the serum and synovial fluid of RA patients (Beyeler, et al., *J. Rheumatol.* 27:15-19 (2000)). α-1 Antitrypsin has also been isolated in a subtraction library examining genes upregulated in monocytes from RA patients (Stuhlmuller, et al., *Arthritis Rheum.* 43:775-790 (2000)).

2. B Lymphocyte Stimulator Expression

Figure 4:
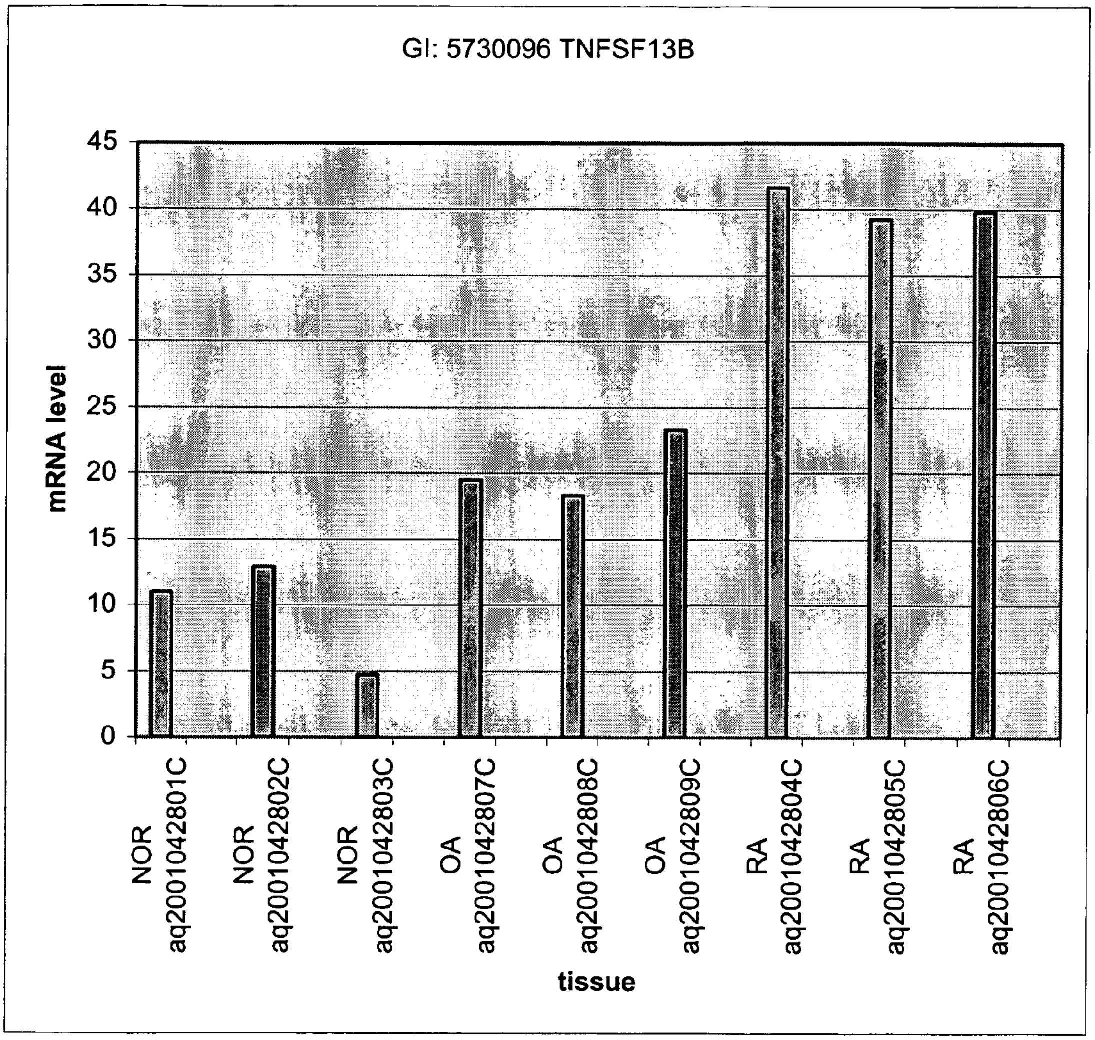

Using the materials and methods described hereinabove (Materials and Methods, Section A), increases in expression of B Lymphocyte Stimulator (BLyS, TNSF13B) were detected in the RA synovium. This increased expression is shown in the microarray data in FIG. 4. The polynucleotide sequence (SEQ ID NO:27) and amino acid sequence (SEQ ID NO:28) of BLyS are shown in FIGS. 5 and 6, respectively.

BLyS is a member of the TNF family produced by activated T cells, monocytes, and dendritic cells that stimulates B cell expansion and function. Serum BLyS levels have been shown to be elevated in patients with systemic autoimmune diseases, including lupus erythematosus (Zhang, et al., *J. Immunol.* 166:6-10 (2001)) and RA (Cheema, et al., *Arthritis Rheum.* 44:1313-1319 (2001)). Mice deficient for the BLyS receptor are resistant to collagen-induced arthritis (Wang, et al., *Nature Immunol.* 2:632-637 (2001)).

3. Fc Gamma RI Expression

Figure 7:
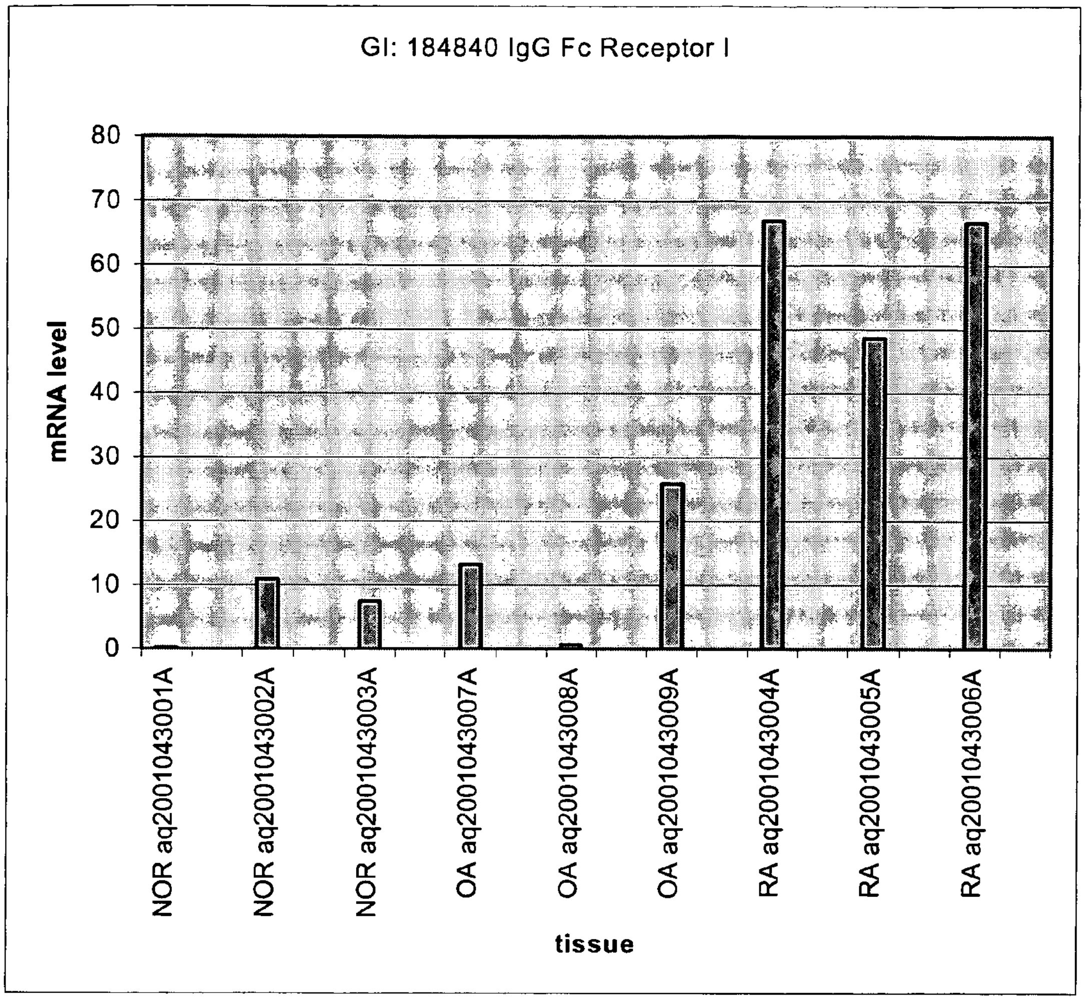

Using the materials and methods described hereinabove (Materials and Methods, Section A), increases in expression of Fc gamma RI were detected in the RA synovium. This increased expression is shown in the microarray data in FIG. 7. The polynucleotide sequence (SEQ ID NO:29) and amino acid sequence (SEQ ID NO:30) of Fc gamma RI are shown in FIGS. 8 and 9, respectively.

Using the materials and methods described hereinabove (Materials and Methods, Section A), Real Time PCR was conducted to quantify the expression of Fc gamma RI in the RA synovium, the results of which are set forth in Table 4, below.

TABLE 4

Fc gamma RI: Real Time PCR Results

| | Expression Level | T test |
|---|---|---|
| Normal | 1 | 1 |
| OA | 1.89 | 0.35 |
| RA | 6.57 | 0.02 |

Fc gamma RI receptors bind IgG immune complexes and trigger cell activation and IL-8 secretion (Salmon, et al., *Arthritis Rheum.* 44:739-750 (2001)). The expression of Fc gamma RI was increased on monocytes derived from RA patients as compared to healthy controls. A significant correlation between Fc gamma RI, C-reactive protein, and blood platelet count was found in the RA patients. Further-more, treatment with the steroid prednisolone induced down-regulation of Fc gamma RI expression suggesting that increased expression is associated with disease activity (Torsteinsdottir et al. (1999) *Clin. Exp. Immunol.* 115:554-560). Mice lacking functional Fc gamma RI and RIII receptors are resistant to collagen-induced arthritis (Kleinau et al. (2000) *J. Exp. Med.* 191:1611-1616).

4. Migration Inhibitory Factor-related Protein 14 Expression

Figure 10:
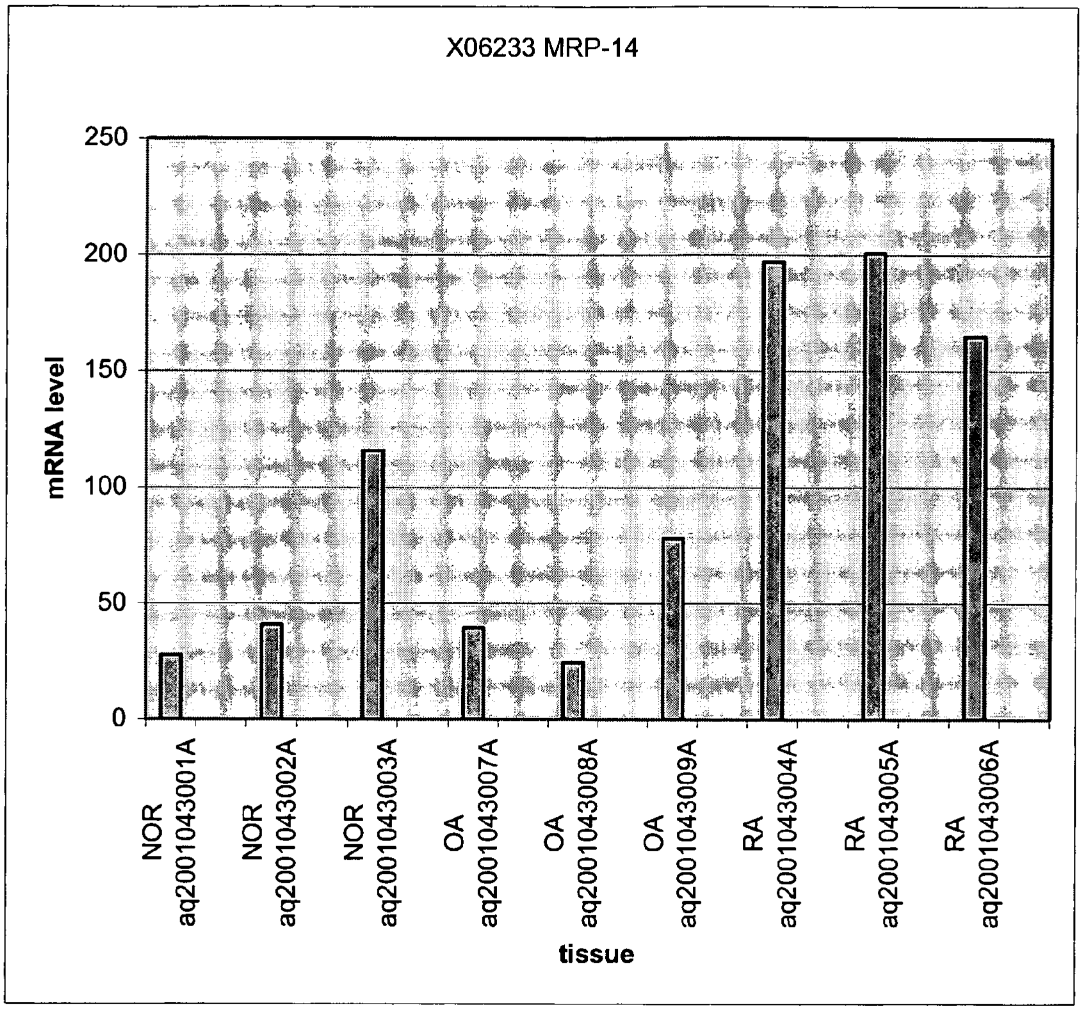

Using the materials and methods described hereinabove (Materials and Methods, Section A), increases in expression of Migration inhibitory factor-related protein 14 (MRP-14) were detected in the RA synovium. This increased expression is shown in the microarray data in FIG. 10. The polynucleotide sequence (SEQ ID NO:31) and amino acid sequence (SEQ ID NO:32) of MRP-14 are shown in FIGS. 11 and 12, respectively.

Using the materials and methods described hereinabove (Materials and Methods, Section A), Real Time PCR was conducted to quantify the expression of MRP-14 in the RA synovium, the results of which are set forth in Table 5, below.

TABLE 5

MRP-14: Real Time PCR Results

| | Expression Level | T test |
|---|---|---|
| Normal | 1 | 1 |
| OA | 0.64 | 0.49 |
| RA | 4.37 | 0.07 |

MRP-14 is a calcium binding protein expressed primarily by circulating neutrophils and monocytes that belongs to the S100 family of proteins (Kerkhoff, et al., *Biochim. Biophys. Acta* 1448:200-211 (1998); Hessian, et al., *J. Leuk. Biol.* 53:197-204 (1993)). MRP-14 is strongly expressed by infiltrating neutrophils and monocytes within the inflamed joints of juvenile RA patients (Youssef, et al., *J. Rheumatol.* 26:2523-2528 (1999)). MRP14 is specifically released during the interaction of monocytes with inflammatory activated endothelium, and is found in high concentrations in the synovial fluid of juvenile RA patients (Frosch, et al., *Arthritis Rheum.* 43:628-637 (2000)).

5. Skin Collagenase Expression

Figure 13:
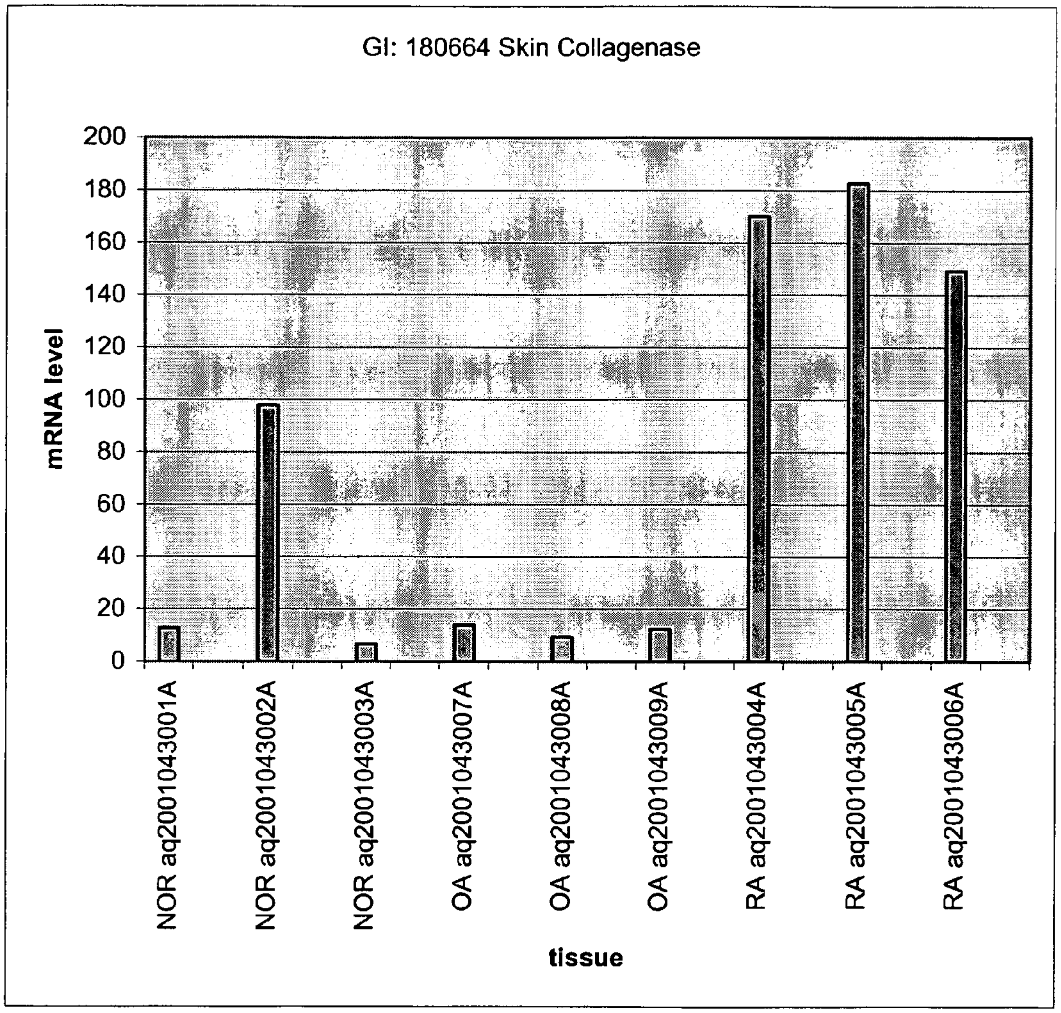

Using the materials and methods described hereinabove (Materials and Methods, Section A), increases in expression of Skin Collagenase (MMP-1) were detected in the RA synovium. This increased expression is shown in the microarray data in FIG. 13. The polynucleotide sequence (SEQ ID NO:33) and amino acid sequence (SEQ ID NO:34) of MRP-14 are shown in FIGS. 14 and 15, respectively.

MMP-1 is an enzyme that degrades interstitial collagens types I, II, and III. Elevated expression of MMP-1 was detected in synovium from patients with early inflammatory arthritis and with established erosive arthritis. Little expression was detected in normal synovium (Cunnane, et al., *Rheumatology* 38:34-42 (1999)). Primary cultures of rheumatoid synoviocytes produced MMP-1 as detected using immunohistochemistry. Expression has also been detected in the rheumatoid lesion (Tetlow, et al., *Br. J. Rheum.* 37:64-70 (1998)).

6. Cysteine Dioxygenase Expression

Figure 16:
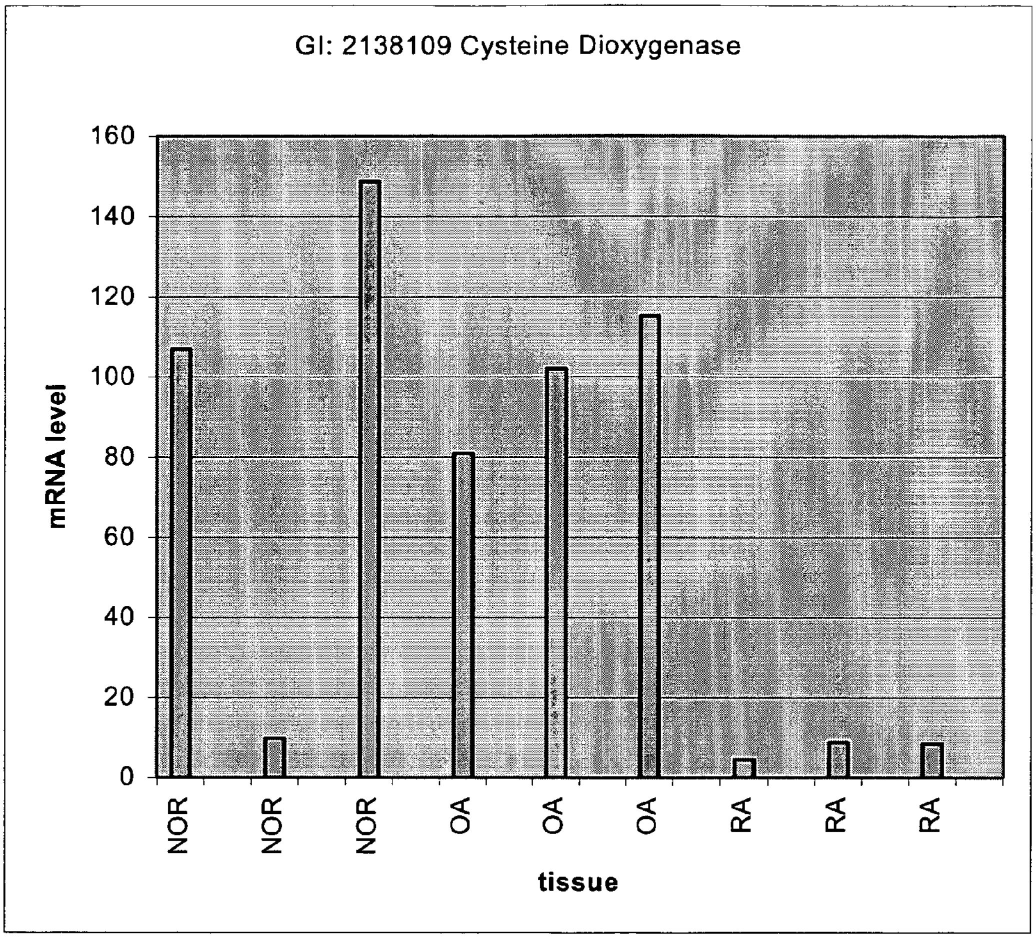

Using the materials and methods described hereinabove (Materials and Methods, Section A), decreases in expression of cysteine dioxygenase were detected in the RA synovium. This decreased expression is shown in the microarray data in FIG. 16. The polynucleotide sequence (SEQ ID NO:35) and amino acid sequence (SEQ ID NO:36) of cysteine dioxygenase are shown in FIGS. 17 and 18, respectively.

Using the materials and methods described hereinabove (Materials and Methods, Section A), Real Time PCR was conducted to quantify the expression of Cysteine Dioxygenase in the RA synovium, the results of which are set forth in Table 6, below.

TABLE 6

Cysteine Dioxygenase: Real Time PCR Results

| | Expression Level | T test |
|---|---|---|
| Normal | 1 | |
| OA | 1.21 | 0.77 |
| RA | 0.19 | 0.06 |

Cysteine dioxygenase is an enzyme involved in sulphate metabolism whose activity has been shown to be decreased in RA patients (Bradley, et al., *J. Rheumatol.* 21:1192-1196 (1994)).

EXAMPLE 2

Upregulated Genes and Downregulated Genes in RA

1. HLA-DR2/Dw12 Expression

Figure 19:
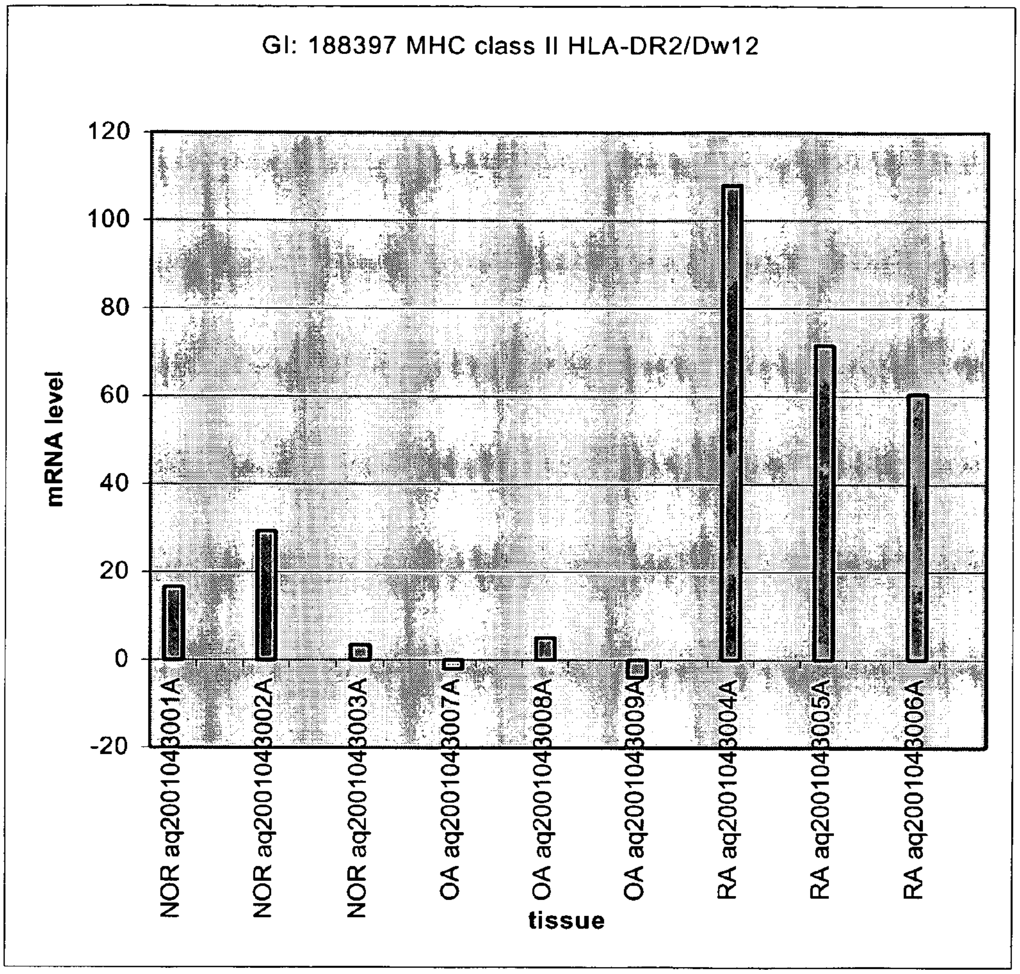

Using the materials and methods described hereinabove (Materials and Methods, Section A), significant increases in expression of HLA-DR2/Dw12 were detected in the RA synovium. This increased expression is shown in the microarray data in FIG. 19. The polynucleotide sequence (SEQ ID NO:37) and amino acid sequence (SEQ ID NO:38) of HLA-DR2/Dw12 are shown in FIGS. 20 and 21, respectively.

Upregulation of MHC class II alleles, specifically HLA-DRB1 and HLA-DR4 subtypes, has previously been associated with development of RA (Kerlan-Candon, et al., *Arthritis Rheum.* 44:1281-1292 (2001)). Evidence suggests that expression of the DRB1*0401 and related haplotypes predisposes individuals to RA (Nepom, *Adv. Immunol.* 68:315-332 (1998)). This allele is also associated with the most severe form of RA leading to extraarticular manifestations (Weyand, et al., *J. Clin. Invest.* 89:2033-2039 (1992)). Specific associations of HLA-DR2 expression with RA, shown in the present invention, have not been previously demonstrated.

2. Stimulator of Iron Transport Expression

Figure 22:
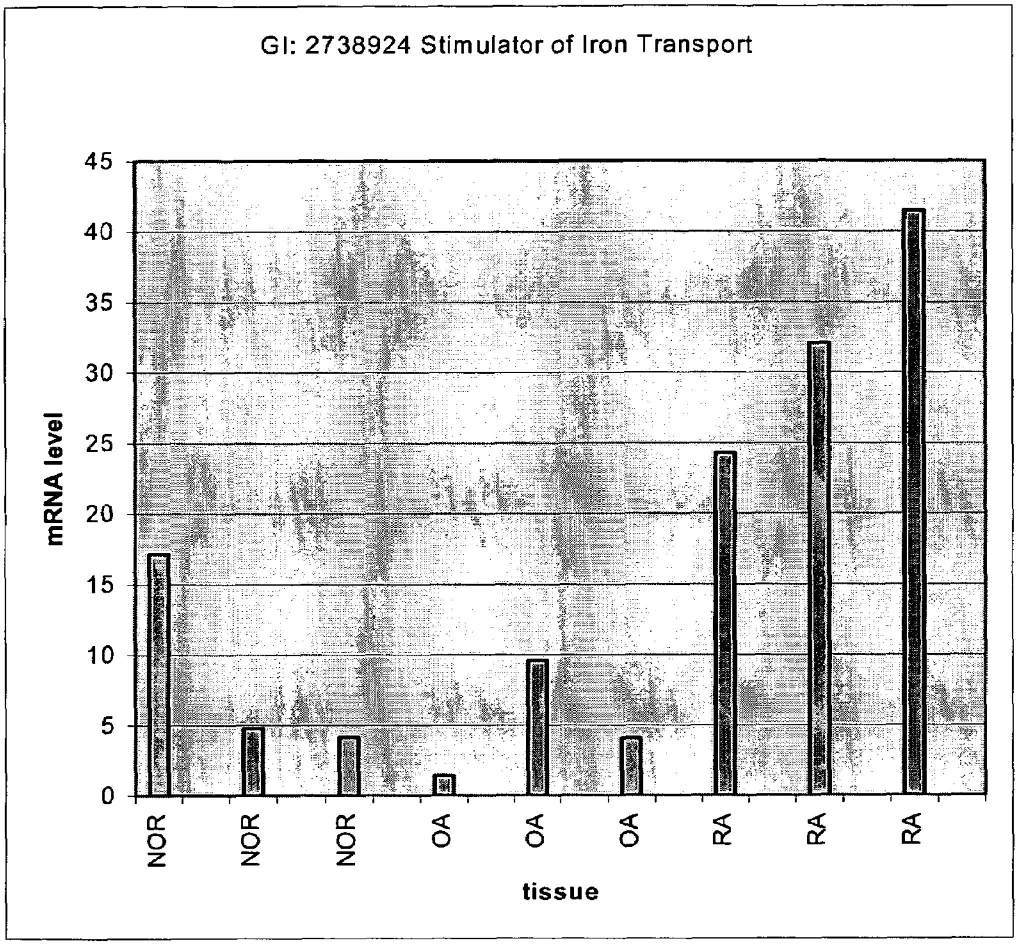

Using the materials and methods described hereinabove (Materials and Methods, Section A), increases in expression of Stimulator of Iron Transport were detected in the RA synovium. This increased expression is shown in the microarray data in FIG. 22. The polynucleotide sequence (SEQ ID NO:39) and amino acid sequence (SEQ ID NO:40) of Stimulator of Iron Transport are shown in FIGS. 23 and 24, respectively.

Stimulator of Iron Transport is a regulator of ferric and ferrous iron uptake (Yu et al., *J. Biol. Chem.* 273:21380-21385 (1998); Gutierrez, et al., *J. Cell Biol.* 139:895-905 (1997)).

3. Guanylate Binding Protein Isoform 1 Expression

Figure 25:
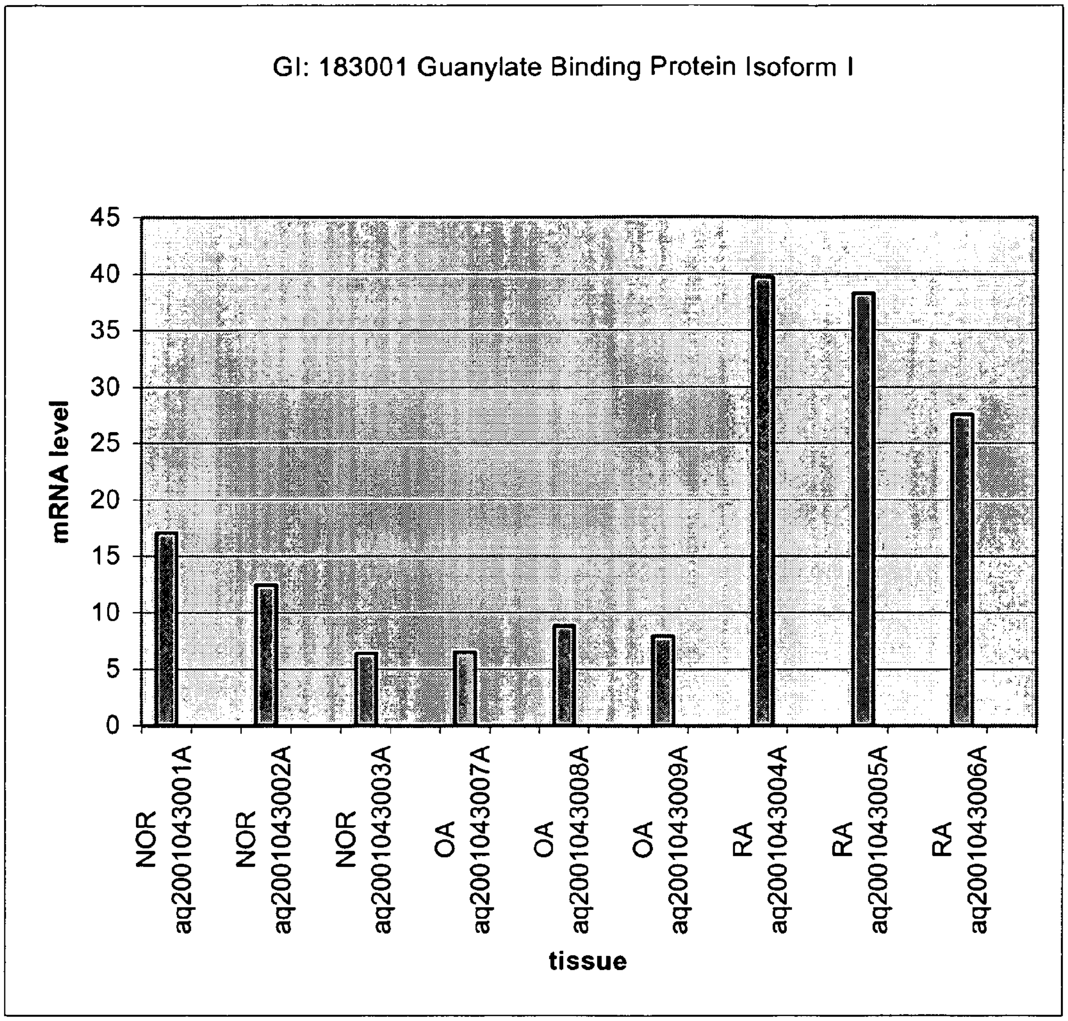

Using the materials and methods described hereinabove (Materials and Methods, Section A), increases in expression of Guanylate Binding Protein Isoform 1 (GBP-1) were detected in the RA synovium. This increased expression is shown in the microarray data in FIG. 25. The polynucleotide sequence (SEQ ID NO:41) and amino acid sequence (SEQ ID NO:42) of GBP-1 are shown in FIGS. 26 and 27 respectively.

Using the materials and methods described hereinabove (Materials and Methods, Section A), Real Time PCR was conducted to quantify the expression of GBP-1 in the RA synovium, the results of which are set forth in Table 7, below.

TABLE 7

Guanylate Binding Protein Isoform 1: Real Time PCR Results

| | Expression Level | T test |
|---|---|---|
| Normal | 1 | |
| OA | 1.00 | 0.985 |
| RA | 3.89 | 0.003 |

GBP-1 is an interferon-inducible protein that binds guanine nucleotides and possesses GTPase activity (Cheng, et al., *Mol. Cell. Biol.* 11:4717-4725 (1991)).

The regulation of GBP-1 was further characterized using the materials and methods described hereinabove (Materials and Methods, Section B), the results of which are set forth in Example 3 below.

4. ISGF-3 p91 (STAT1) Expression

Figure 28:
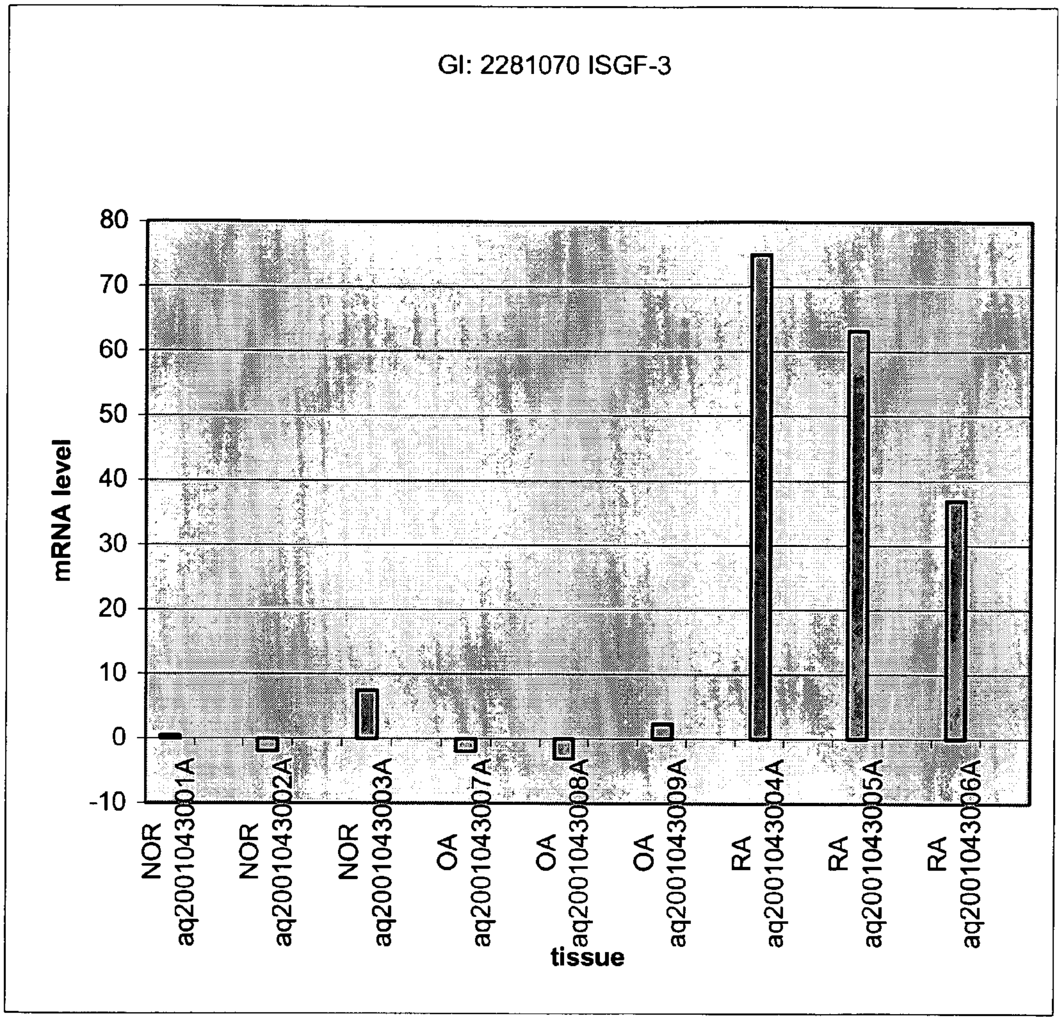

Using the materials and methods described hereinabove (Materials and Methods, Section A), increases in expression of ISGF-3 p91 (STAT1) were detected in the RA synovium. This increased expression is shown in the microarray data in FIG. 28. The polynucleotide sequence (SEQ ID NO:43) and amino acid sequence (SEQ ID NO:44) of ISGF-3 p91 (STAT1) are shown in FIGS. 29 and 30, respectively.

Using the materials and methods described hereinabove (Materials and Methods, Section A), Real Time PCR was conducted to quantify the expression of ISGF-3 p91 in the RA synovium, the results of which are set forth in Table 8, below.

TABLE 8

ISGF-3 p91: Real Time PCR Results

| | Expression Level | T test |
|---|---|---|
| Normal | 1 | |
| OA | 0.93 | 0.720 |
| RA | 3.91 | 0.002 |

ISGF-3 p91 (STAT1) is a transcription factor involved in interferon signaling pathways (Schindler, et al., *Proc. Nat. Acad. Sci.* 89:7836-7839 (1992)). Continuous activation of STAT1 has been seen in synovial fluid cells derived from RA but not osteoarthritis patients (Yokota, et al., *J. Rheumatol.* 28:1952-1959 (2001)).

5. Mad Protein Homolog-3 Expression

Figure 31:
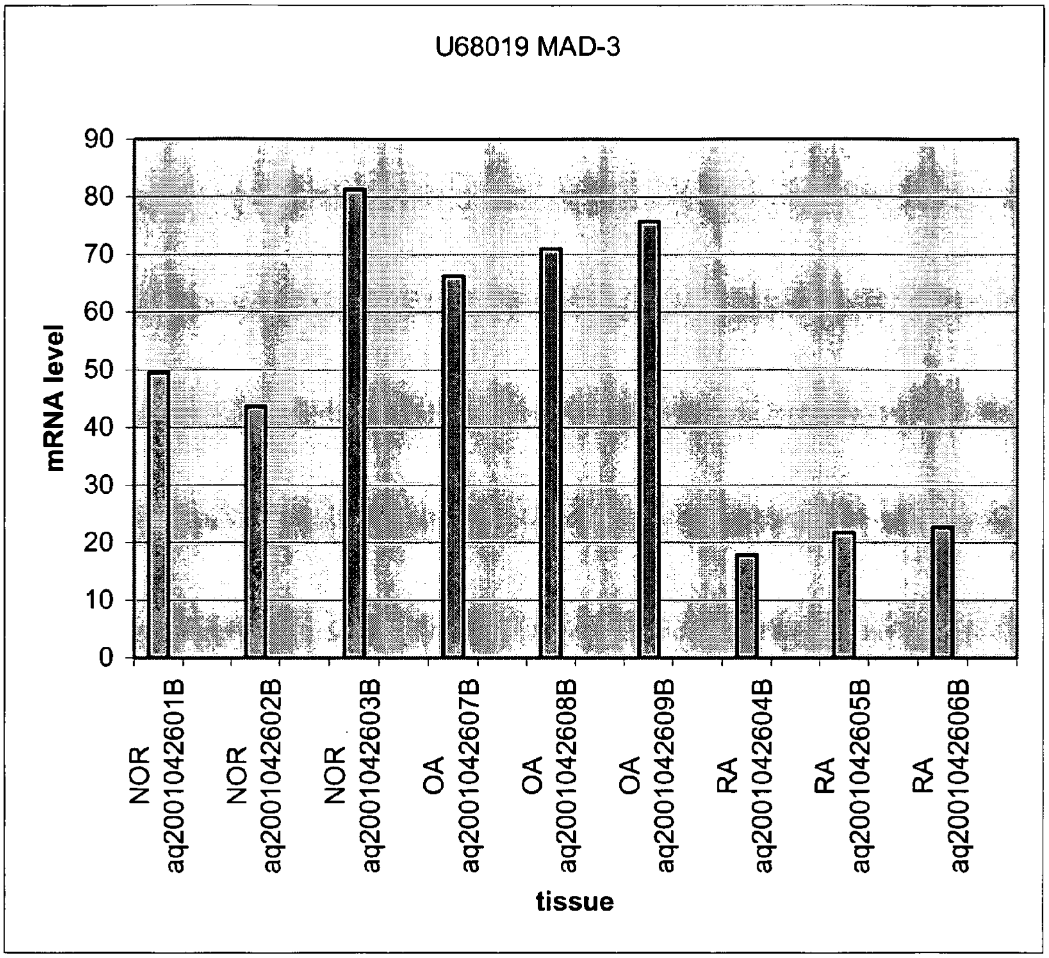

Using the materials and methods described hereinabove (Materials and Methods, Section A), decreases in expression of Mad Protein Homolog (MAD-3) were detected in the RA synovium. MAD-3 is also known as Mothers Against Decapentaplegic Homolog 3 (Smad-3). This decreased expression is shown in the microarray data in FIG. 31. The polynucleotide sequence (SEQ ID NO:45) and amino acid sequence (SEQ ID NO:46) of MAD-3 are shown in FIGS. 32 and 33, respectively.

Mad-3 is an intracellular mediator downstream of the TGF-β/activin receptors that appears to be important for monocyte chemotaxis in response to TGF-β (Zhang, et al., *Nature* 383:168-172 (1996); Ashcroft, et al., *Nature Cell Biol.* 1:260-266 (1999).

6. Human Transforming Growth Factor-Beta Type III Receptor Expression

Figure 34:
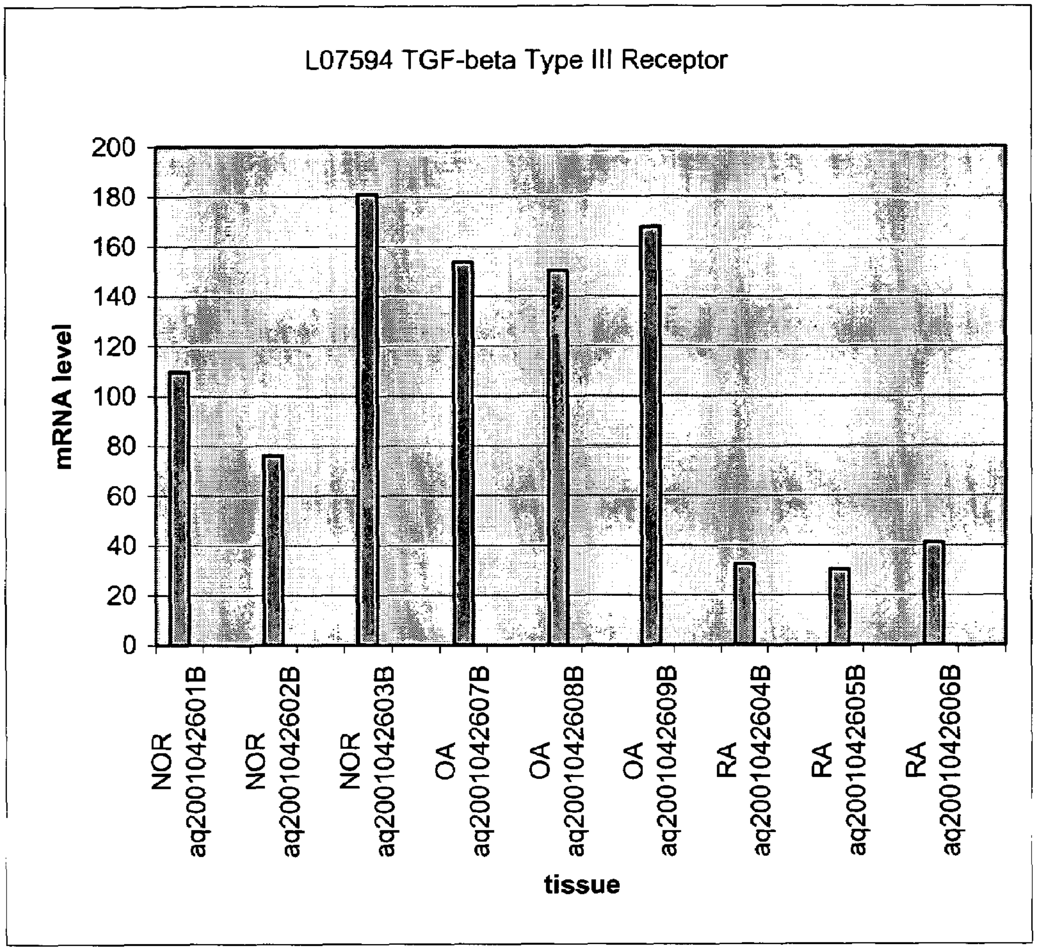

Using the materials and methods described hereinabove (Materials and Methods, Section A), decreases in expression of Human Transforming Growth Factor-Beta Type III Receptor (TGF-β type III receptor) were detected in the RA synovium. This decreased expression is shown in the microarray data in FIG. 34. The polynucleotide sequence (SEQ ID NO:47) and amino acid sequence (SEQ ID NO:48) of TGF-β type III receptor are shown in FIGS. 35 and 36, respectively.

7. Early B Cell Factor Expression

Figure 37:
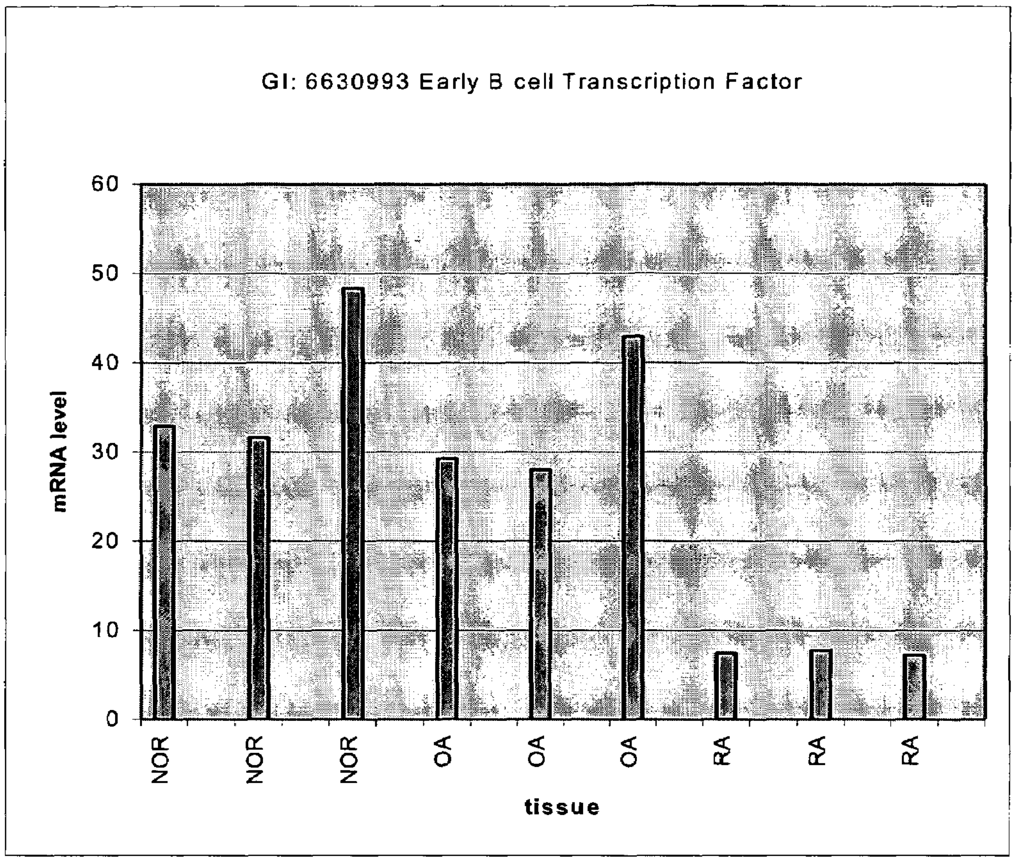

Using the materials and methods described hereinabove (Materials and Methods, Section A), decreases in expression of Early B Cell Factor (EBF) were detected in the RA synovium. This decreased expression is shown in the microarray data in FIG. 37. The polynucleotide sequence (SEQ ID NO:49) and amino acid sequence (SEQ ID NO:50) of EBF are shown in FIGS. 38 and 39, respectively.

Using the materials and methods described hereinabove (Materials and Methods, Section A), Real Time PCR was conducted to quantify the expression of EBF in the RA synovium, the results of which are set forth in Table 9, below.

TABLE 9

EBF: Real Time PCR Results

| | Expression Level | T test |
|---|---|---|
| Normal | 1 | 1 |
| OA | 0.72 | 0.66 |
| RA | 0.20 | 0.05 |

EBF is a transcription factor required for B cell differentiation (Gisler, et al., *Blood* 96:1457-1464 (2000)).

8. Duodenal Cytochrome b Expression

Figure 40:
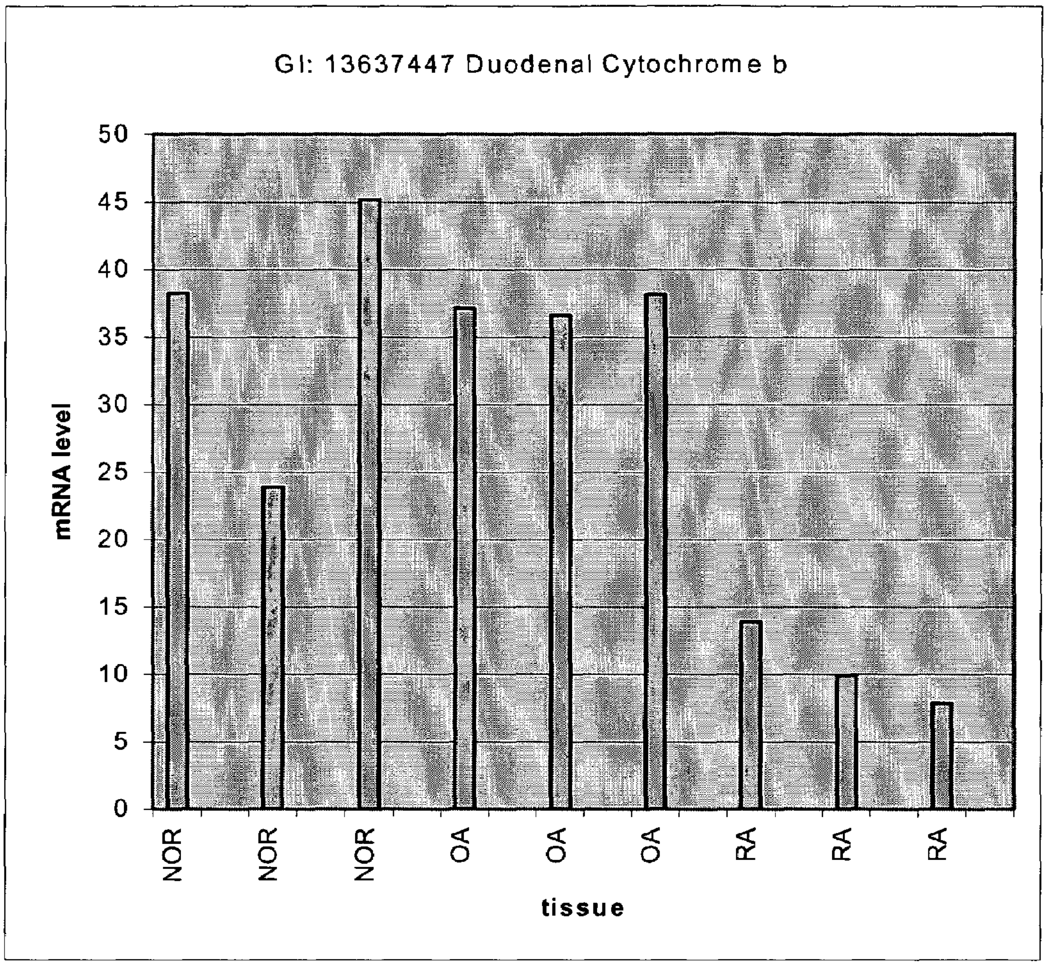

Using the materials and methods described hereinabove (Materials and Methods, Section A), decreases in expression of Duodenal Cytochrome b were detected in the RA synovium. This decreased expression is shown in the microarray data in FIG. 40. The polynucleotide sequence (SEQ ID NO:51) and amino acid sequence (SEQ ID NO:52) of Duodenal Cytochrome b are shown in FIGS. 41 and 42, respectively.

Duodenal cytochrome b is a protein localized to the duodenal mucosa possessing ferric reductase activity (McKie, et al., *Science* 291:1755-1759 (2001)).

9. Nuclear LIM Interactor-Interacting Factor Expression

Figure 43:
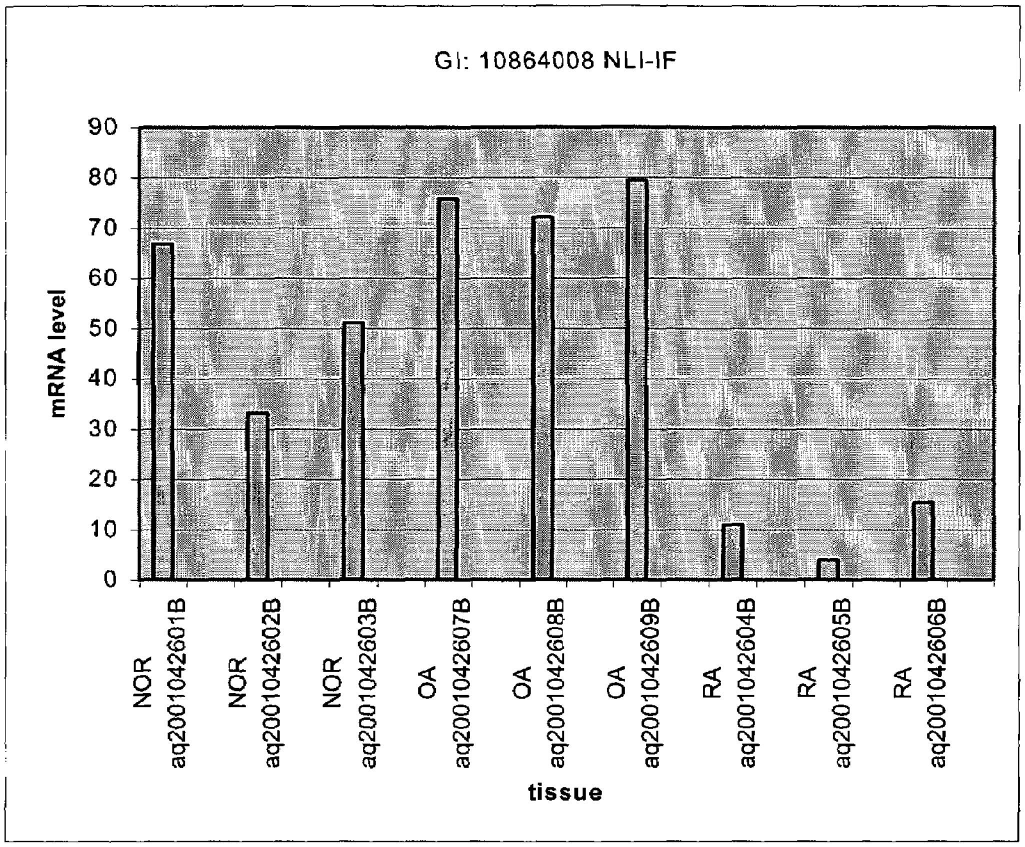

Using the materials and methods described hereinabove (Materials and Methods, Section A), decreases in expression of Nuclear LIM Interactor-Interacting Factor (NLI-IF) were detected in the RA synovium. This decreased expression is shown in the microarray data in FIG. 43. The polynucleotide sequence (SEQ ID NO:53) and amino acid sequence (SEQ ID NO:54) of NLI-IF are shown in FIGS. 44 and 45, respectively.

The NLI-IF amino acid sequence has homology to the nuclear Lim interactor interacting factor from Gallus gallus. It is one of a family of four related proteins of unknown function (Marquet, et al., *Mamm. Genome* 11:755-762 (2000)).

10. Deleted in Liver Cancer 1 Expression

Figure 46:
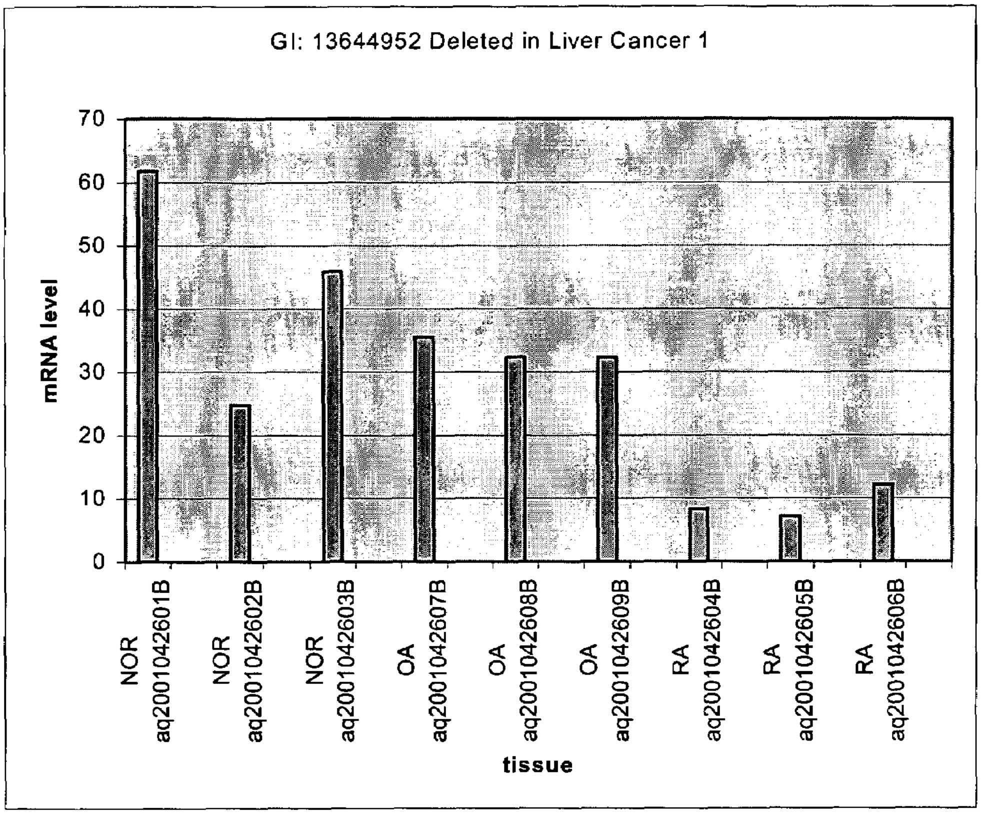

Using the materials and methods described hereinabove (Materials and Methods, Section A), decreases in expression of Deleted in Liver Cancer 1 (DLC1) were detected in the RA synovium. This decreased expression is shown in the microarray data in FIG. 46. The polynucleotide sequence (SEQ ID NO:55) and amino acid sequence (SEQ ID NO:56) of DLC1 are shown in FIGS. 47 and 48, respectively.

DLC1 is a candidate tumor suppressor gene possessing a high degree of sequence similarity to the rat p122 RhoGap gene (Yuan, et al., *Cancer Res.* 58:2196-2199 (1998); Ng, et al., *Cancer Res.* 60:6581-6584 (2000)).

11. GI: 12005907

Figure 49:
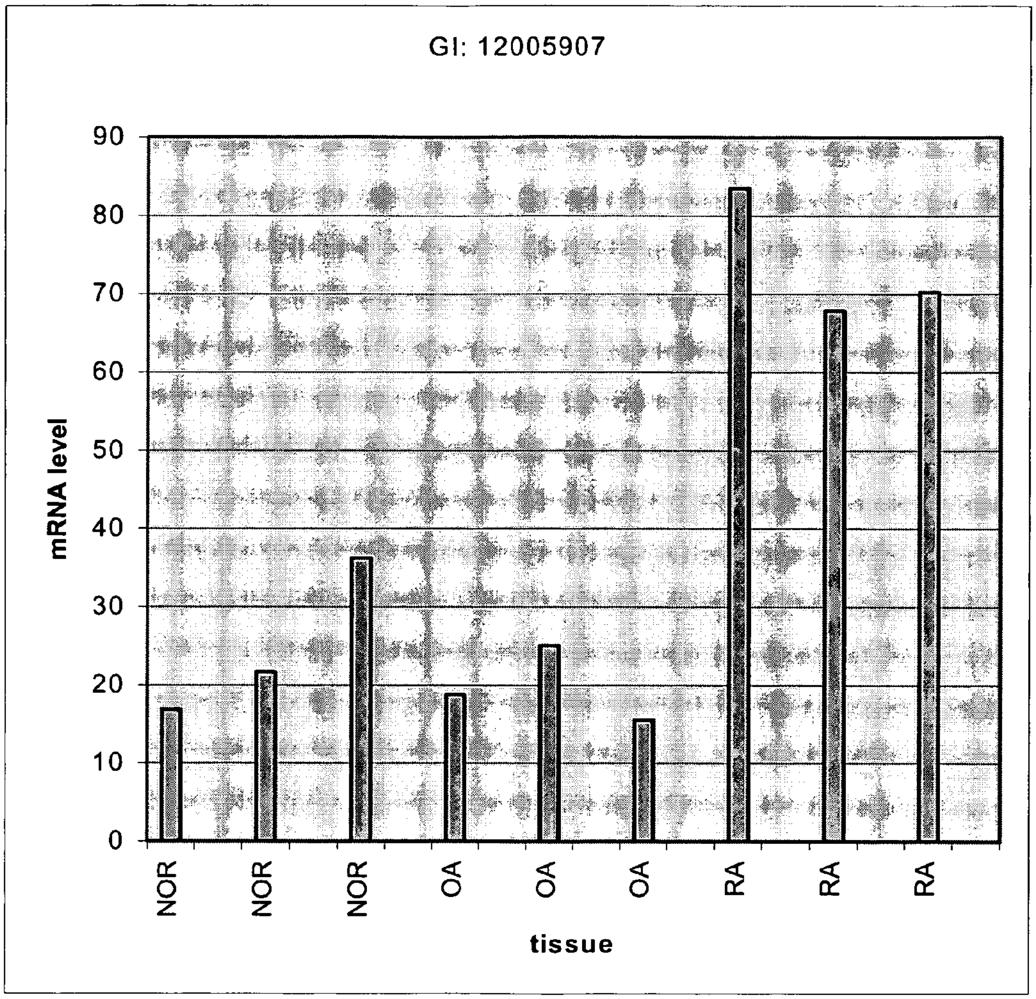

Using the materials and methods described hereinabove (Materials and Methods, Section A), increases in expression of the polynucleotide identified by Genbank Accession No. AF260335 (GI: 12005907) were detected in the RA synovium. This increased expression is shown in the microarray data in FIG. 49. The polynucleotide sequence (SEQ ID NO:57) and amino acid sequence (SEQ ID NO:58) are shown in FIGS. 50 and 51, respectively.

Further, Real Time PCR was conducted to quantify the expression of this polynucleotide in the RA synovium, the results of which are set forth in Table 10.

TABLE 10

GI: 12005907: Real Time PCR Results

| | Expression Level | T test |
|---|---|---|
| Normal | 1 | |
| OA | 1.44 | 0.34 |
| RA | 2.39 | 0.04 |

12. Apolipoprotein L Expression

Figure 52:
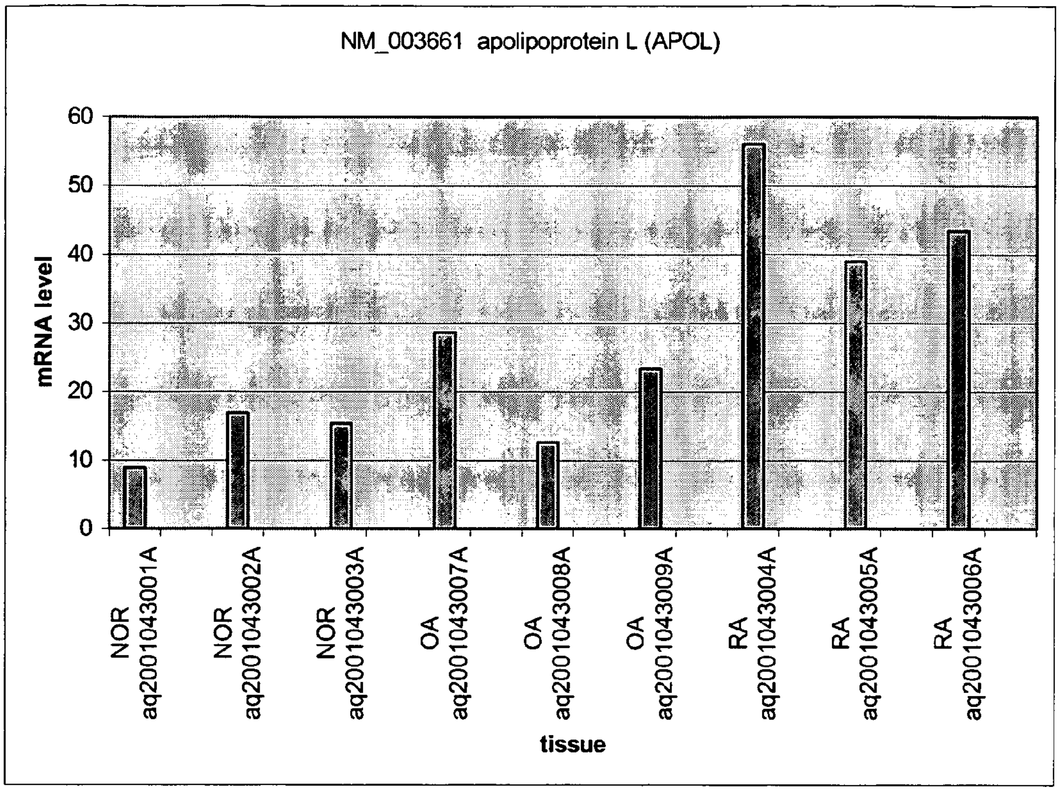

Using the materials and methods described hereinabove (Materials and Methods, Section A), increases in expression of Apolipoprotein L (APOL) (Genbank Accession No. NM_003661) were detected in the RA synovium. This increased expression is shown in the microarray data in FIG. 52. The polynucleotide sequence (SEQ ID NO:59) and amino acid sequence (SEQ ID NO:60) of APOL are shown in FIGS. 53 and 54, respectively.

Apolipoprotein L is a component of human plasma lipoproteins (Duchateau, et al., *J. Biol. Chem.* 272:25576-25582 (1997)).

13. Homo Sapiens Guanylate Binding Protein 5 Expression

Figure 55:
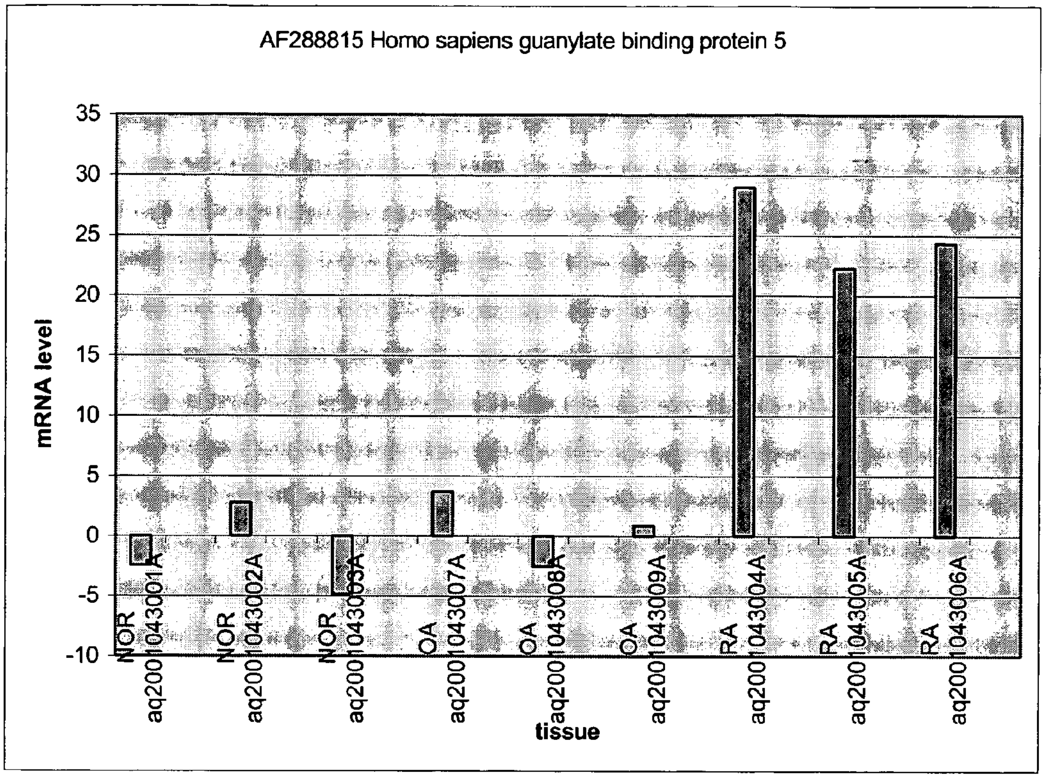

Using the materials and methods described hereinabove (Materials and Methods, Section A), increases in expression of Homo Sapiens Guanylate Binding Protein 5 (Genbank Accession No. AF288815) (GBP-5) were detected in the RA synovium. This increased expression is shown in the microarray data in FIG. 55. The polynucleotide sequence (SEQ ID NO:61) and amino acid sequence (SEQ ID NO:62) of Homo Sapiens GBP-5 are shown in FIGS. 56 and 57, respectively. GBP-5 is highly homologous to GBP-1 described above (SEQ ID NO: 42).

The regulation of GBP-5 was further characterized using the materials and methods described hereinabove (Materials and Methods, Section B), the results of which are set forth in Example 3 below.

14. Human Proteasome Activator hPA28 Subunit Beta Expression

Figure 58:
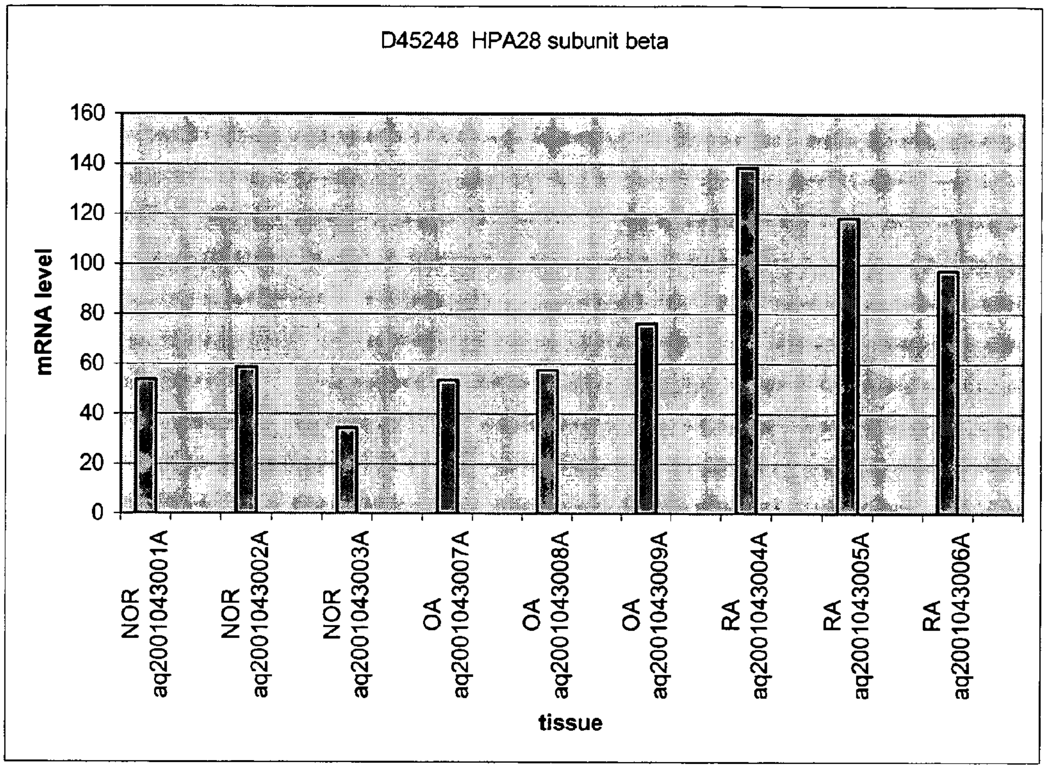

Using the materials and methods described hereinabove (Materials and Methods, Section A), increases in expression of HPA28 subunit beta (HPA28) (Genbank Accession No. D45248) were detected in the RA synovium. This increased expression is shown in the microarray data in FIG. 58. The polynucleotide sequence (SEQ ID NO:63) and amino acid sequence (SEQ ID NO:64) of HPA28 are shown in FIGS. 59 and 60, respectively.

HPA28 beta subunits associate with alpha subunits to form PA28, an activator of the 20S proteasome. Both subunits are coordinately regulated by interferon-γ (Ahn, et al., *FEBS Lett.* 366:37-42 (1995)).

15. Homo Sapiens FYN Binding Protein

Figure 61:
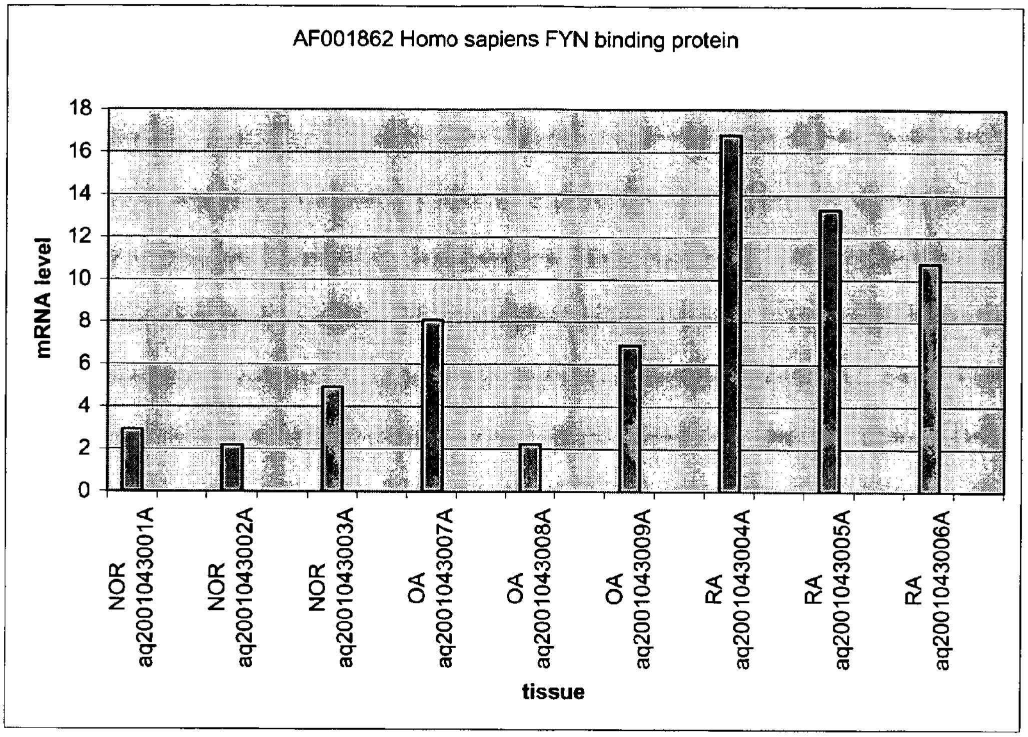

Using the materials and methods described hereinabove (Materials and Methods, Section A), increases in expression of Homo Sapiens FYN Binding Protein (Genbank Accession No. AF001862) were detected in the RA synovium. This increased expression is shown in the microarray data in FIG. 61. The polynucleotide sequence (SEQ ID NO:65) and amino acid sequence (SEQ ID NO:66) of Homo Sapiens FYN Binding Protein are shown in FIGS. 62 and 63, respectively.

FYN Binding Protein is a hematopoietic specific adapter protein that associates in a T cell receptor-inducible manner with another hematopoietic-specific adapter, SLP-76 (daSilva, et al., *Proc. Natl. Acad. Sci. USA* 94:7493-7498 (1997)). T cells from mice lacking FYN Binding Protein exhibit impaired proliferative responses and impaired integrin clustering following T cell receptor crosslinking (Peterson, et al., *Science* 293:2263-2265 (2001)).

16. VAMP5

Figure 64:
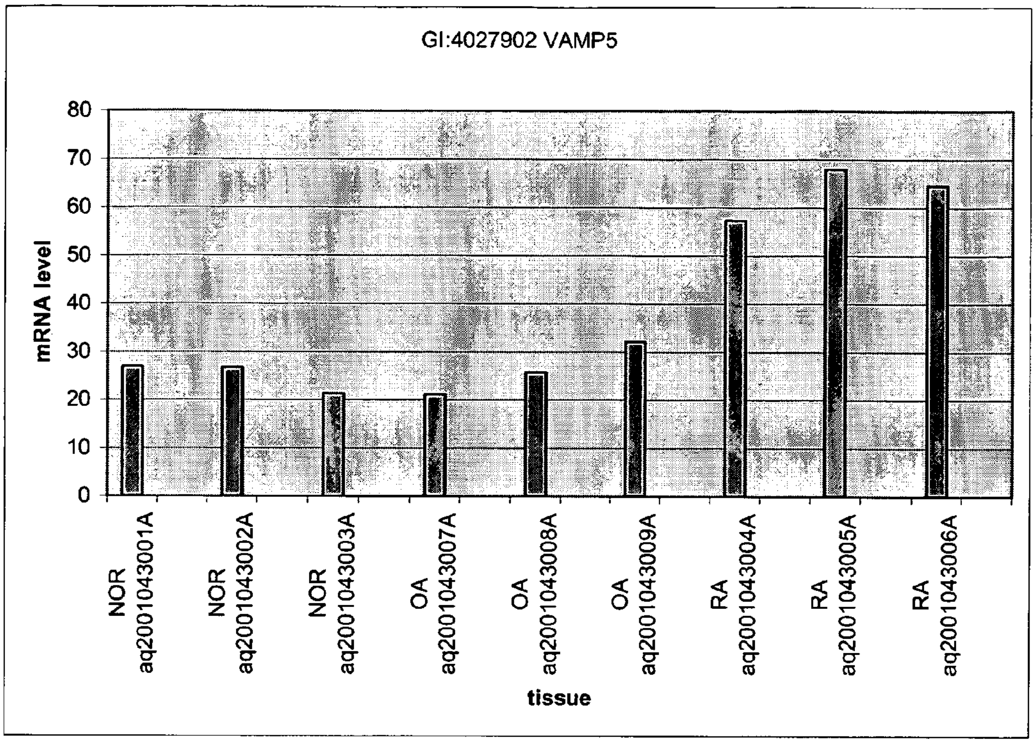

Using the materials and methods described hereinabove (Materials and Methods, Section A), increases in expression of VAMP5 (GI:4027902) were detected in the RA synovium. This increased expression is shown in the microarray data in FIG. 64. The polynucleotide sequence (SEQ ID NO:67) and amino acid sequence (SEQ ID NO:68) of VAMP5 are shown in FIGS. 65 and 66, respectively.

VAMP5 is a novel synaptobrevin protein that is preferentially expressed in skeletal muscle and heart. Its expression is increased during myogenesis and it localizes to the plasma membrane as well as intracellular perinuclear and peripheral vesicular structures of myotubes (Zeng, et al., *Mol. Biol. Cell* 9:2423-2437 (1998)).

17. GI: 2466183

Figure 67:
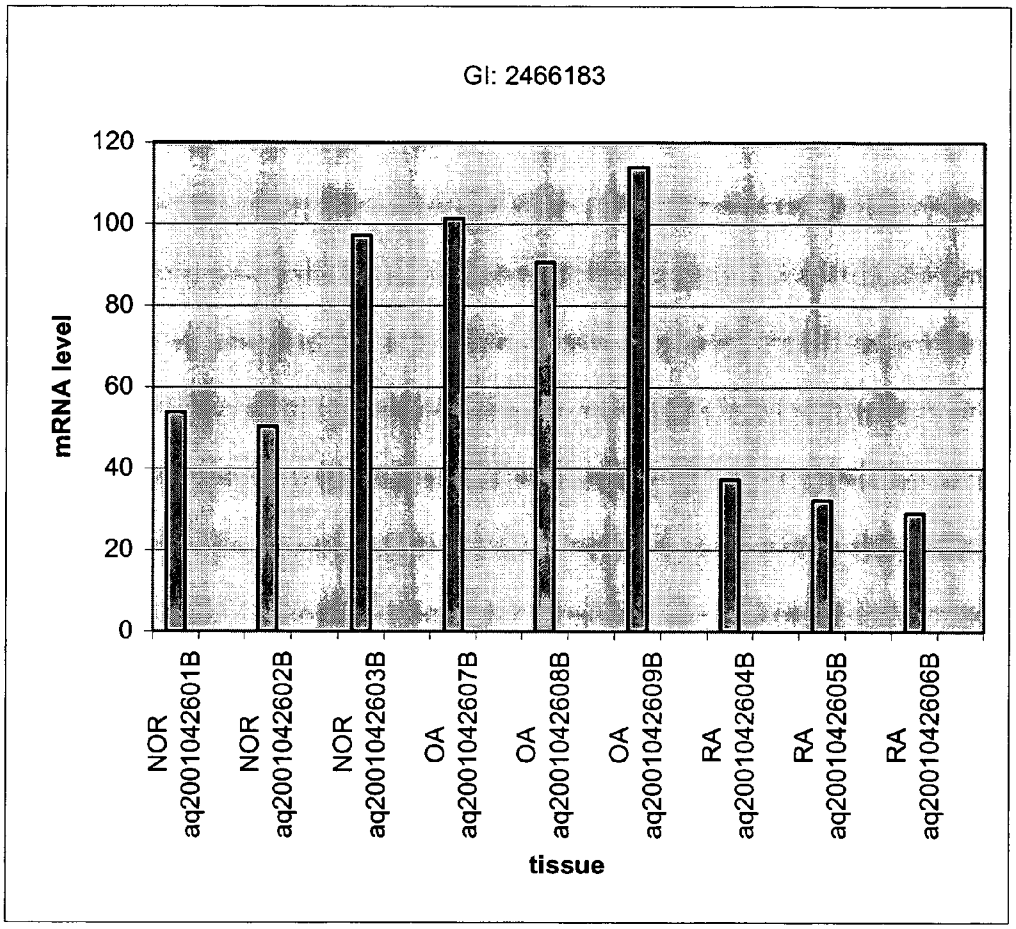

Using the materials and methods described hereinabove (Materials and Methods, Section A), decreases in expression of the polynucleotide identified by GI:2466183 were detected in the RA synovium. This decreased expression is shown in the microarray data in FIG. 67. The sequence of this polynucleotide is shown in FIG. 68 (SEQ ID NO:69).

18. GI: 22192831

Figure 69:
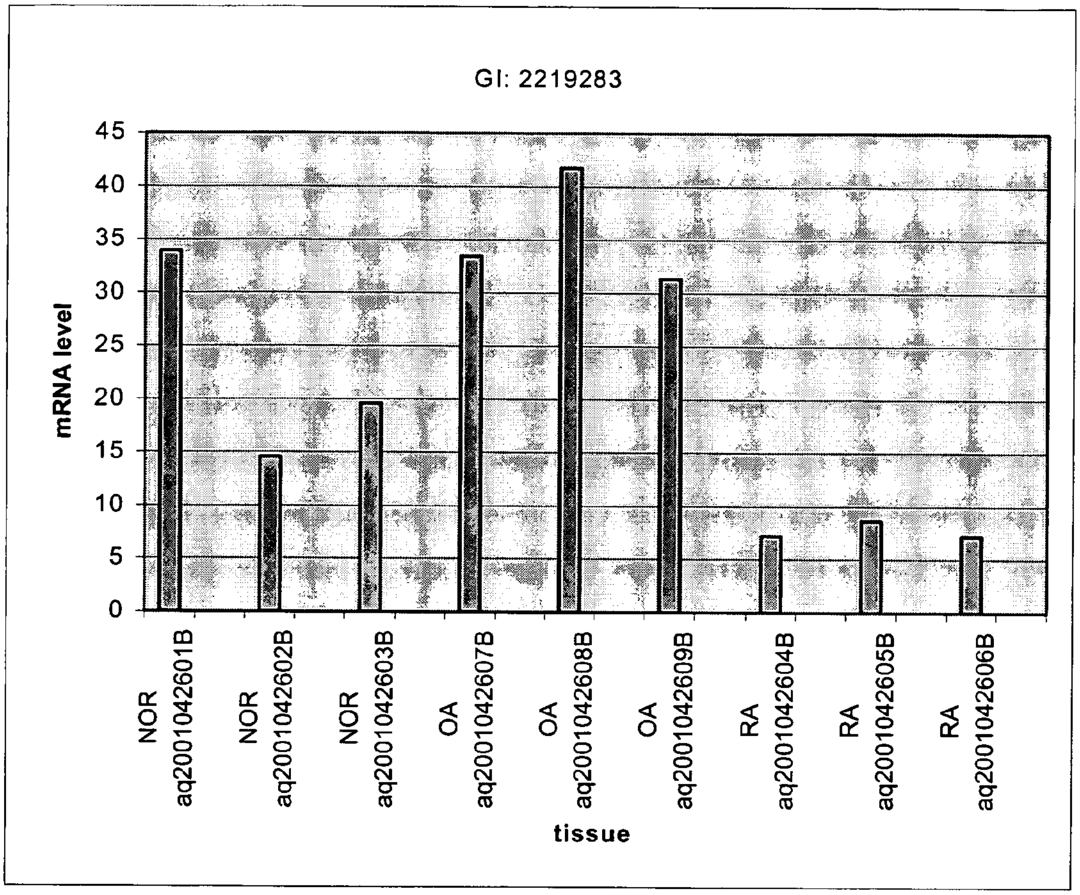

Using the materials and methods described hereinabove (Materials and Methods, Section A), decreases in expression of the polynucleotide identified by GI: 2219283 were detected in the RA synovium. This decreased expression is shown in the microarray data in FIG. 69. The sequence of this polynucleotide is shown in FIG. 70 (SEQ ID NO:70).

19. Hypothetical Protein FLJ20152 (GI: 9506660)

Figure 71:
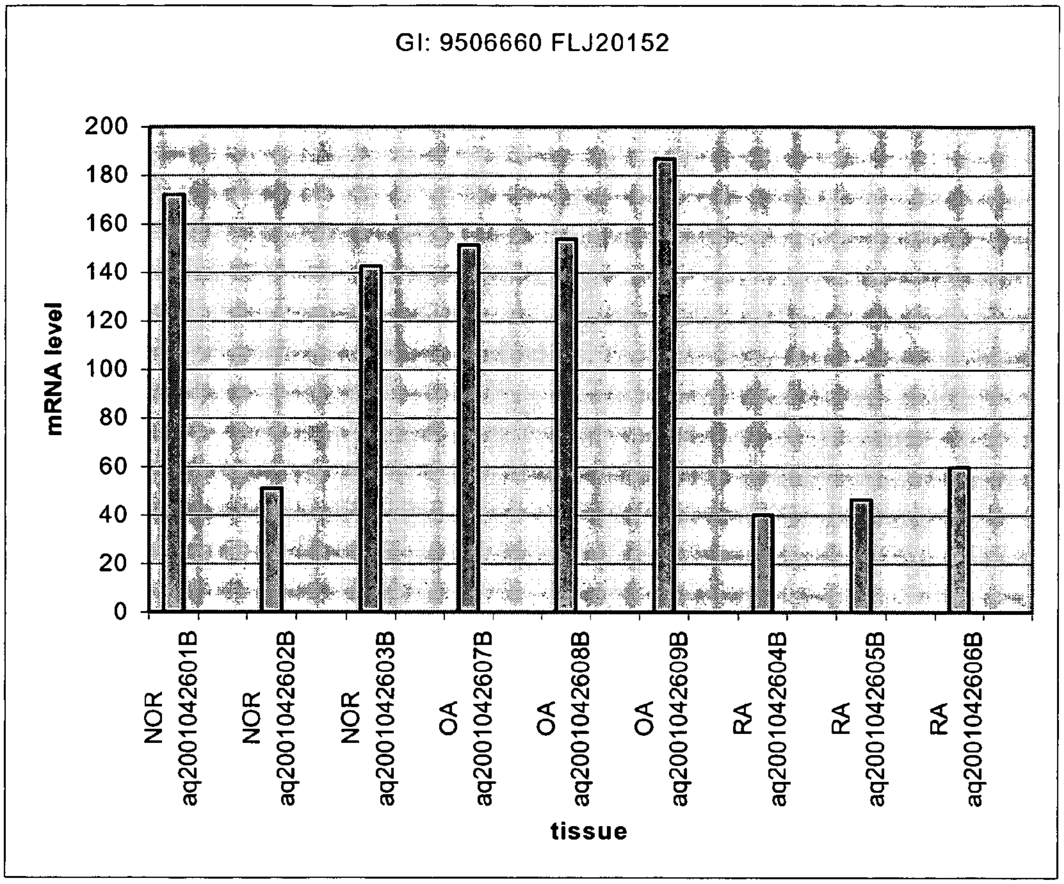

Using the materials and methods described hereinabove (Materials and Methods, Section A), decreases in expression of the Hypothetical Protein FLJ20152 identified by GI: 9506660 were detected in the RA synovium. This decreased expression is shown in the microarray data in FIG. 71. The polynucleotide sequence (SEQ ID NO:71) and amino acid sequence (SEQ ID NO:72) of Hypothetical Protein FLJ20152 are shown in FIGS. 72 and 73, respectively.

20. GI: 5876137

Figure 74:
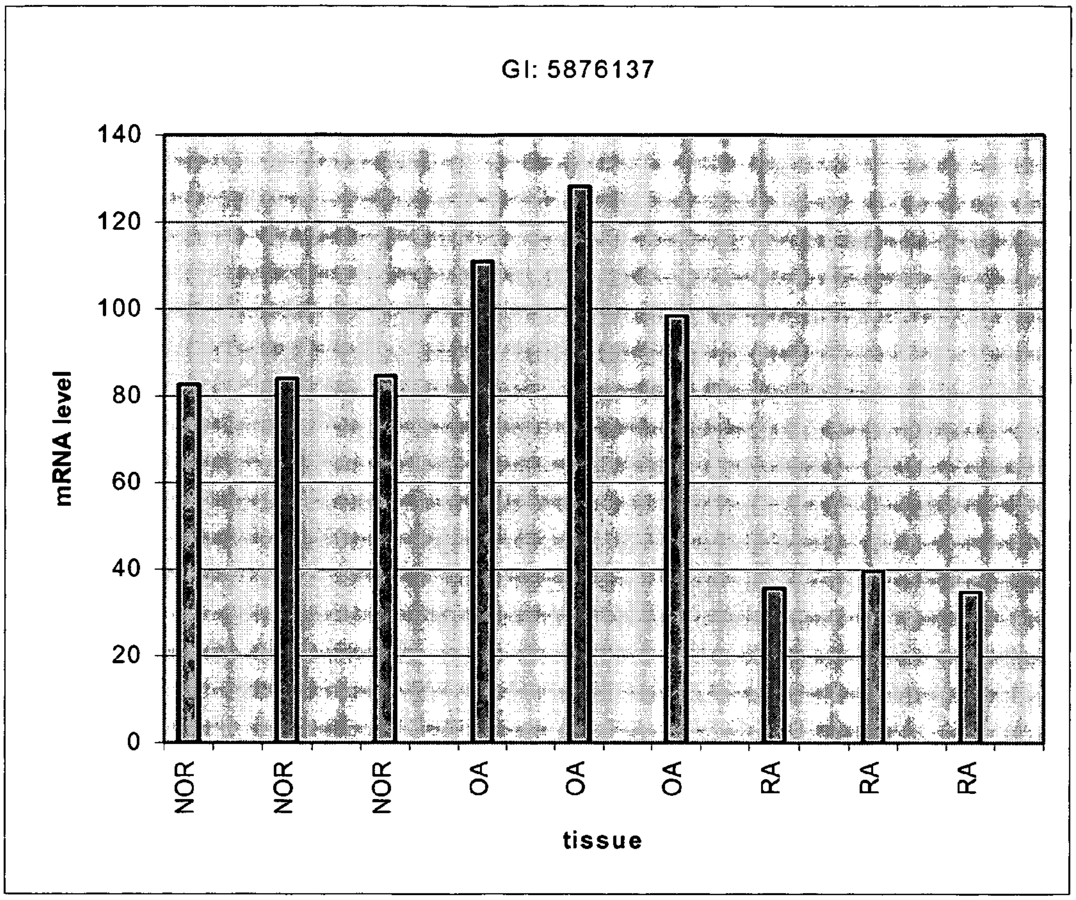

Using the materials and methods described hereinabove (Materials and Methods, Section A), decreases in expression of the polynucleotide identified by GI: 5876137 were detected in the RA synovium. This decreased expression is shown in the microarray data in FIG. 74. The sequence of this polynucleotide is shown in FIG. 75 (SEQ ID NO:73).

21. GI: 2185828

Figure 76:
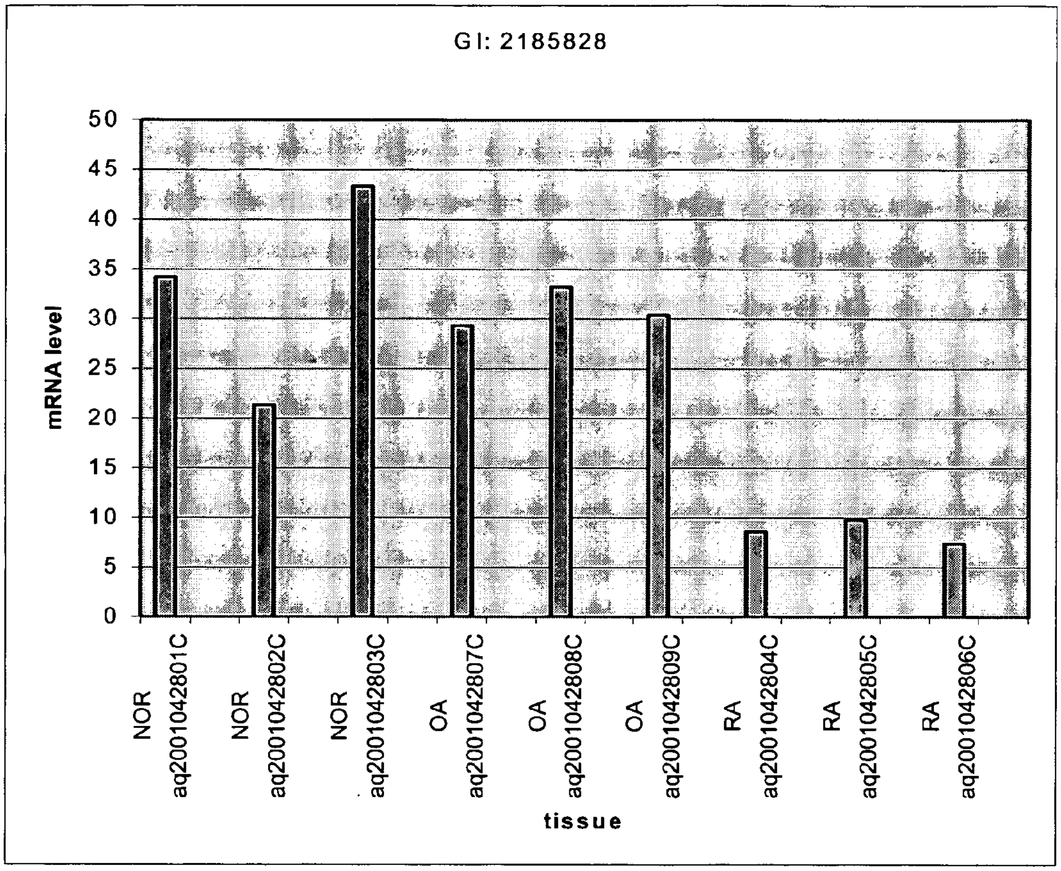

Using the materials and methods described hereinabove (Materials and Methods, Section A), decreases in expression of the polynucleotide identified by GI: 2185828 were detected in the RA synovium. This decreased expression is shown in the microarray data in FIG. 76. The polynucleotide sequence (SEQ ID NO:74) and amino acid sequence (SEQ ID NO:75) are shown in FIGS. 77 and 78, respectively.

Further, Real Time PCR was conducted to quantify the expression of this polynucleotide in the RA synovium, the results of which are set forth in Table 11.

TABLE 11

GI: 2185828 Real Time PCR Results

| | Expression Level | T test |
|---|---|---|
| Normal | 1 | |
| OA | 0.87 | 0.632 |
| RA | 0.21 | 0.014 |

22. Homo Sapiens Proteasome (Prosome, Macropain) Subunit, Beta Type, 9

Figure 79:
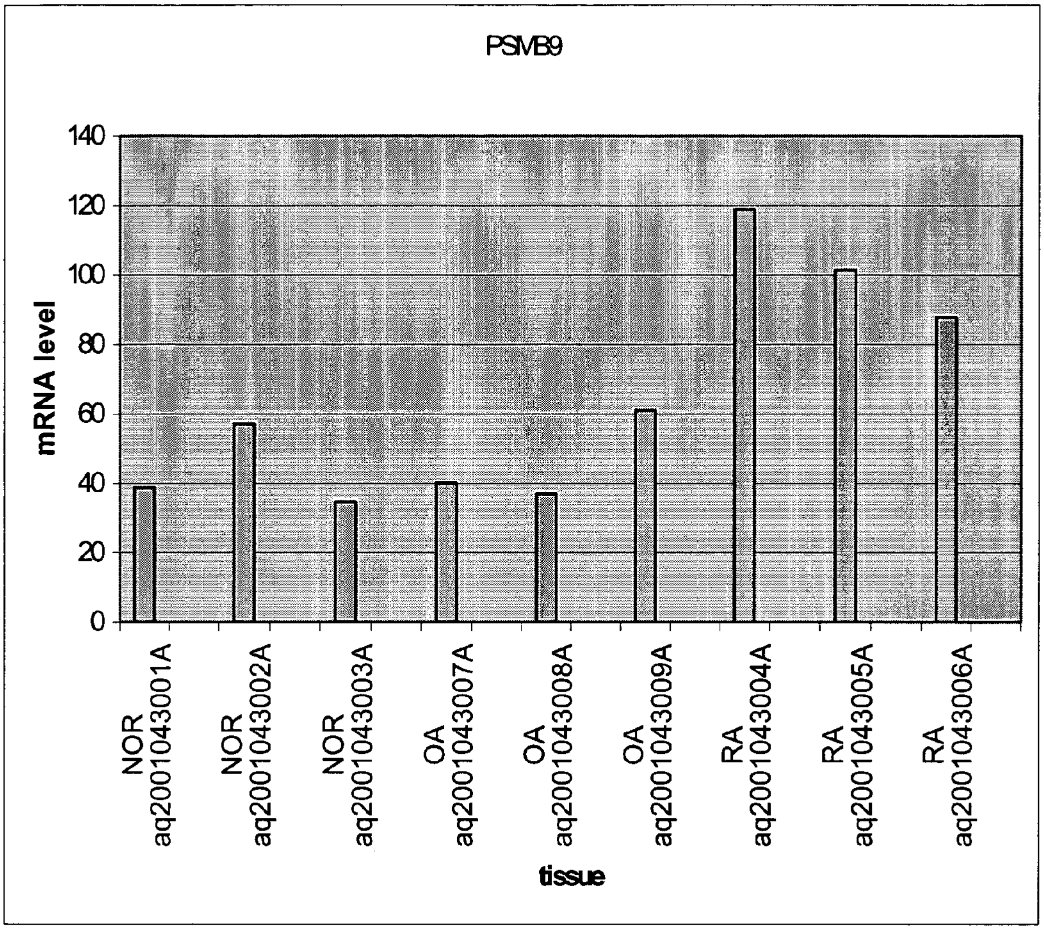

Using the materials and methods described hereinabove (Materials and Methods, Section A), increases in expression of the Homo sapiens proteasome (prosome, macropain) subunit, beta type, 9 (GI: 14754802) were detected in the RA synovium. This increased expression is shown in the microarray data in FIG. 79. The polynucleotide sequence (SEQ ID NO:76) and amino acid sequence (SEQ ID NO:77) of homo sapiens proteasome (prosome, macropain) subunit, beta type, 9 are shown in FIGS. 80 and 81, respectively.

The of homo sapiens proteasome (prosome, macropain) subunit, beta type, 9 is encoded by a gene within the major histocompatibility complex. This subunit replaces beta subunit PSMB6 following interferon gamma stimulation, thereby altering the proteasome specificity.

23. TYRO Protein Tyrosine Kinase Binding Protein (TYROBP); GI:4507754

Figure 82:
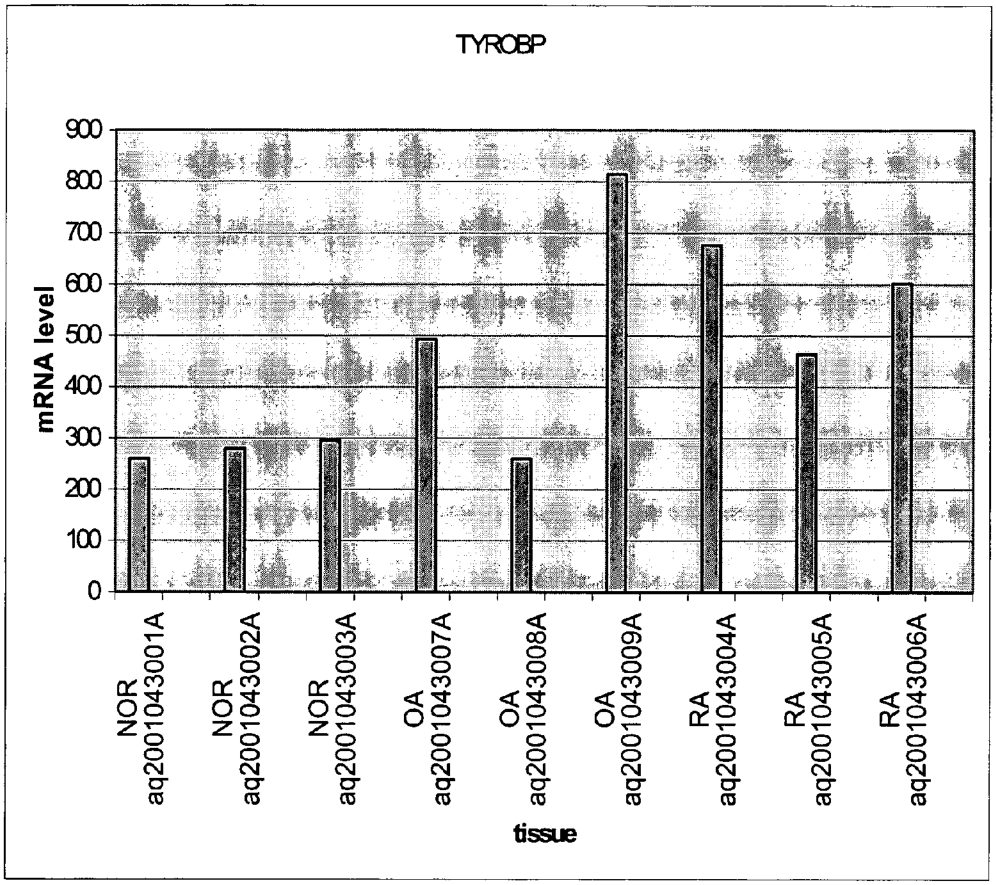

Using the materials and methods described hereinabove (Materials and Methods, Section A), increases in expression of the TYRO protein tyrosine kinase binding protein (TYROBP) (GI:4507754) were detected in the RA synovium. This increased expression is shown in the microarray data in FIG. 82. The polynucleotide sequence (SEQ ID NO:78) and amino acid sequence (SEQ ID NO:79) are shown in FIGS. 83 and 84, respectively.

TYRO protein tyrosine binding protein (TYROBP) is an ITAM-bearing transmembrane adaptor protein that associates non-covalently with receptors in natural killer and myeloid cells (Lanier, et al., *Nature* 391:703-707 (1998)). Mice deficient for TYROBP have normal lymphoid and myeloid development, however activating Ly49 receptors on NK cells are downregulated and nonfunctional. The TYROBP deficient mice are resistant to induction of experimental autoimmune encephalomyelitis and exhibit decreased interferon-γ production by antigen-primed CD4+ T cells due to inadequate T cell priming in vivo (Bakker, et al., *Immunity* 13:345-353 (2000)). Humans expressing loss of function mutations in TYROBP exhibit presenile dementia with bone cysts (Paloneva, et al., *Nat. Genet.* 25:357-361 (2000)).

24. Interleukin 15 Receptor, Alpha

Figure 85:
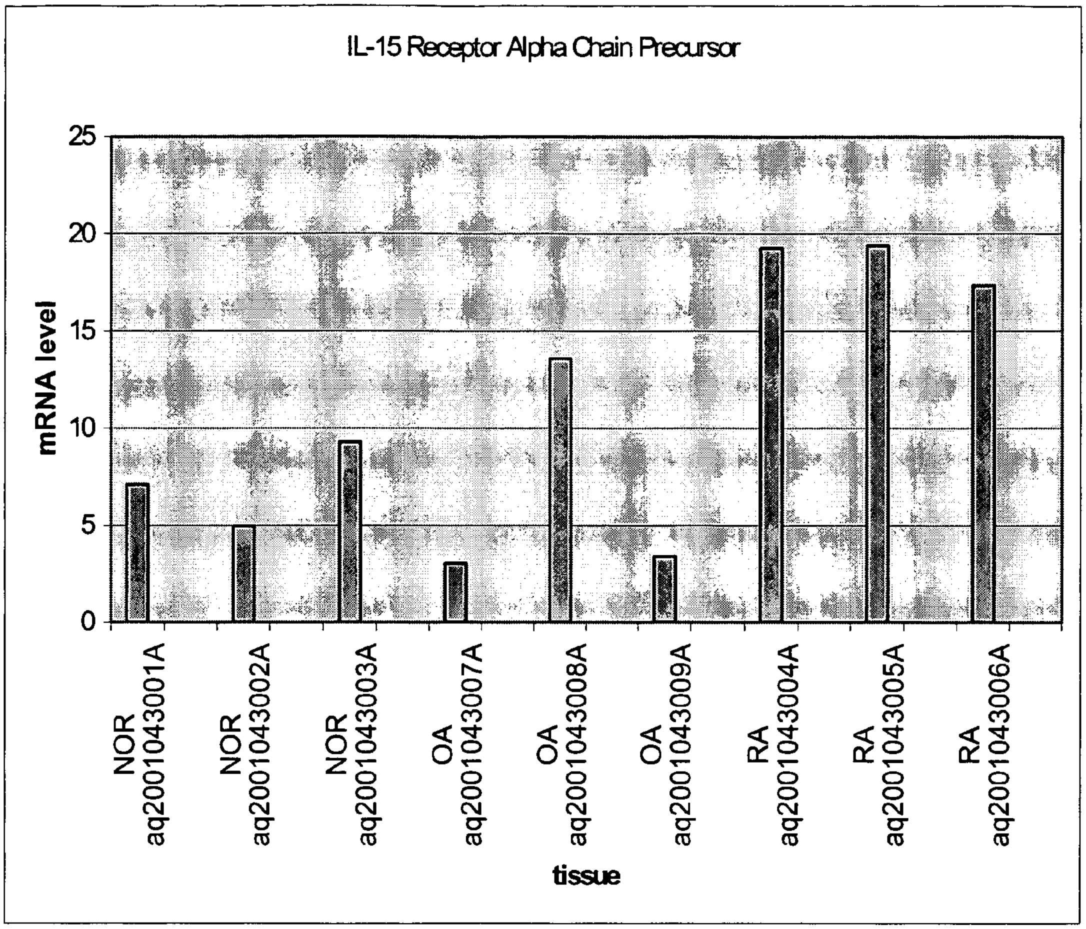
Figure 88A:
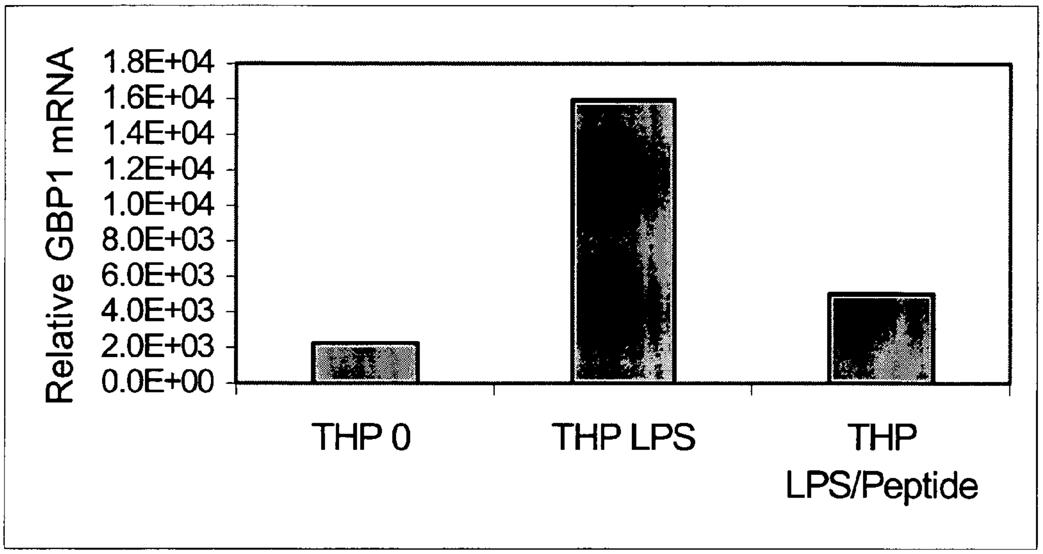
FIG. 88 shows the regulation of GBP-1 and GBP-5 expression by NFkB.
Figure 88B:
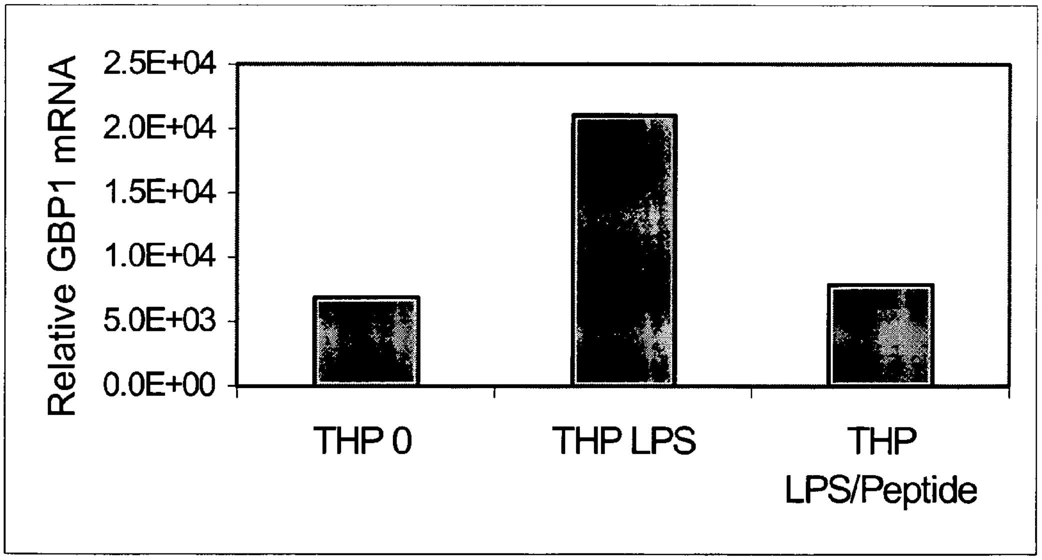
Figure 88C:
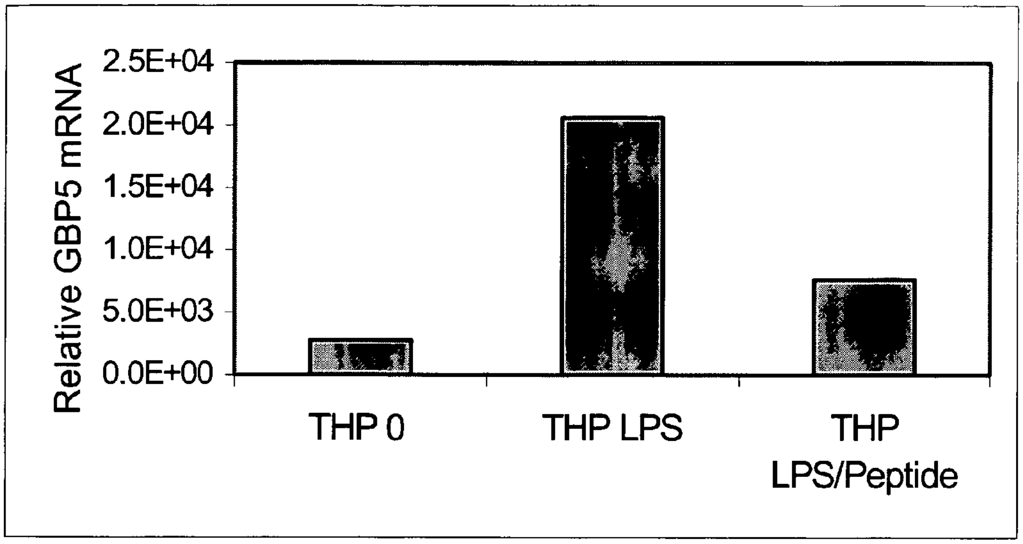
Figure 88D:
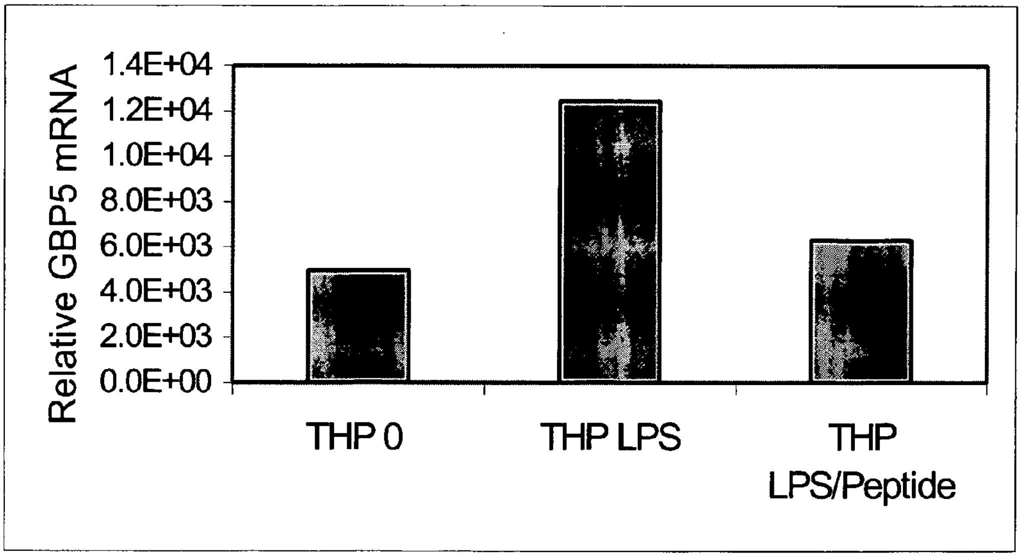

Using the materials and methods described hereinabove (Materials and Methods, Section A), increases in expression of Interleukin 15 Receptor, alpha were detected in the RA synovium. This increased expression is shown in the microarray data in FIG. 85. The polynucleotide sequence (SEQ ID NO:80) and amino acid sequence (SEQ ID NO:81) are shown in FIGS. 86 and 87, respectively.

IL-15 is a T cell growth factor that shares many functional similarities with IL-2. The IL-15 receptor consists of a high affinity binding alpha chain and the common IL-2 receptor beta and gamma chains (Anderson, et al., *J. Biol. Chem.* 270:29862-29869 (1995)). Elevated levels of IL-15 have been detected in the serum from systemic lupus erythematosus patients (Aringer, et al., *Rheumatology* 40:876-881 (2001)), in the synovial tissue of rheumatoid arthritis patients (Thurkow, et al., *J. Pathol.* 181:444-450 (1997)), and in synovial fluid from rheumatoid arthritis patients (McInnes, et al., *Nat. Med.* 2:175-182 (1996)). Administration of soluble IL-15 receptor alpha chain to mice prevented collagen-induced arthritis (Ruchatz, et al., *J. Immunol.* 160: 5654-5660 (1998)), suggesting that IL-15 plays a role in the development of rheumatoid arthritis. Upregulation of the IL-15 receptor alpha chain in rheumatoid arthritis has not been previously described.

EXAMPLE 3

Characterization of RA-Associated Genes GBP-1 and GBP5

As stated above, GBP-1 and GBP-5 were further characterized using the materials and methods set forth above (Materials and Methods, Section B).

GBP-1 has been identified as an interferon-inducible protein in human fibroblasts (Cheng et al., *J. Biol. Chem.* 258:7746-7750 (1983)). GBP-1 mRNA has been shown to be induced in endothelial cells in response to the pro-inflammatory stimuli, TNFα and IL-1α (Guenzi et al., *EMBO J.* 20:5568-5577 (2001)). This study also suggested that GBP-1 mediates the anti-proliferative effects of these cytokines.

As TNFα and IL-1α are known to activate the transcription factor NF-kB, it was determined whether NF-kB was required for induction of GBP-1 and GBP-5 in the human THP-1 monocyte line. THP-1 monocytes were stimulated with lipopolysaccharide (LPS), a known inducer of NF-kB, in the presence and absence of a selective peptide inhibitor of NF-kB nuclear translocation, which is set forth in Fujihara et al., *J. Immunol.* 165:1004-1012 (2000) and designated "BMS-205820".

Following a 2 hour stimulation, RNA was isolated from 2 sets of independently treated THPs, and real time PCR was performed using primers specific for either GBP-1 or GBP-5, as shown in FIG. 88. Treatment of THP-1 cells with LPS significantly increased steady-state mRNA levels of both GBP-1 (FIGS. 88A and 88B) and GBP-5 (FIGS. 88C and 88D). Expression of both genes was significantly inhibited by BMS-205820, suggesting that LPS-mediated induction of GBP-1 and GBP-5 expression is dependent on NF-kB activity.

Figure 89A:
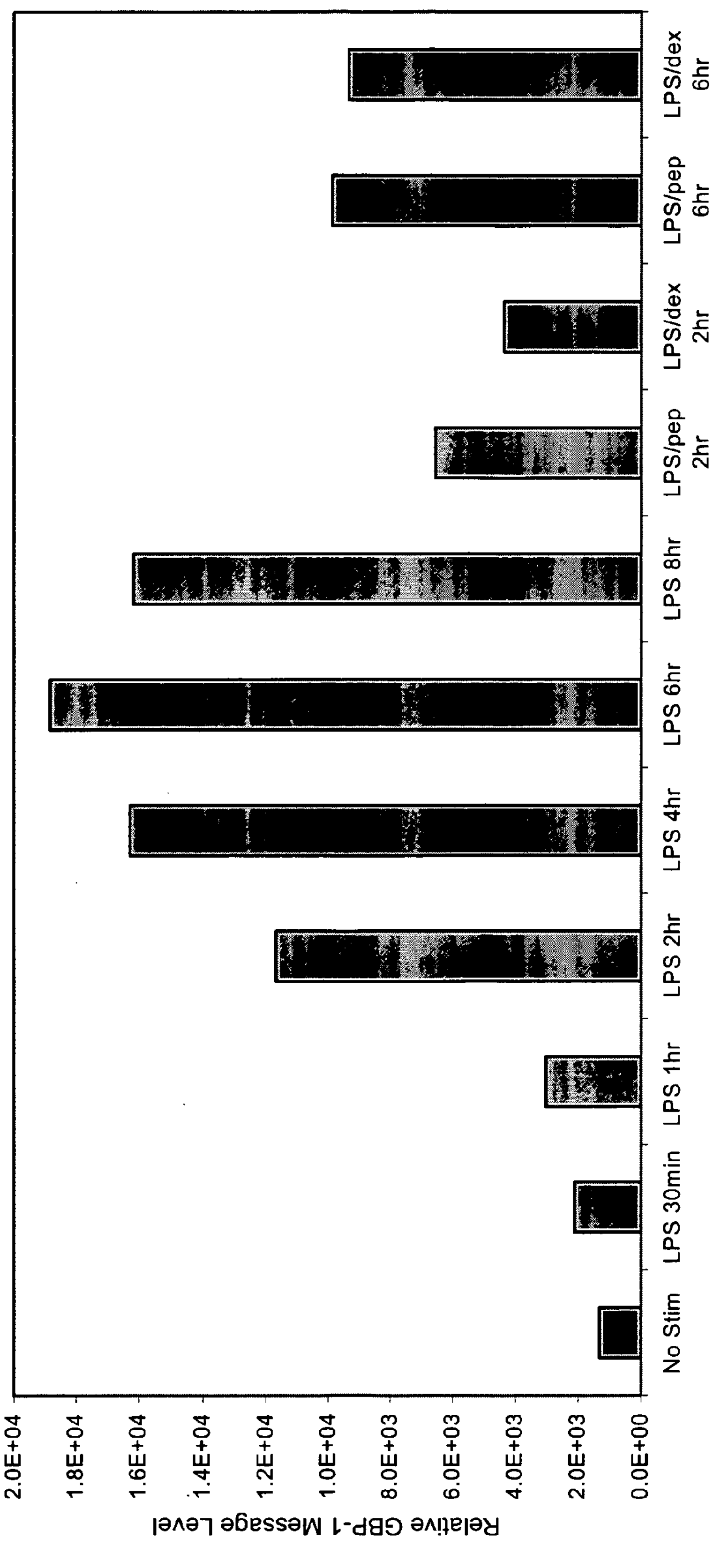
FIG. 89 shows the time course of GBP-1 and GBP-5 expression.
Figure 89B:
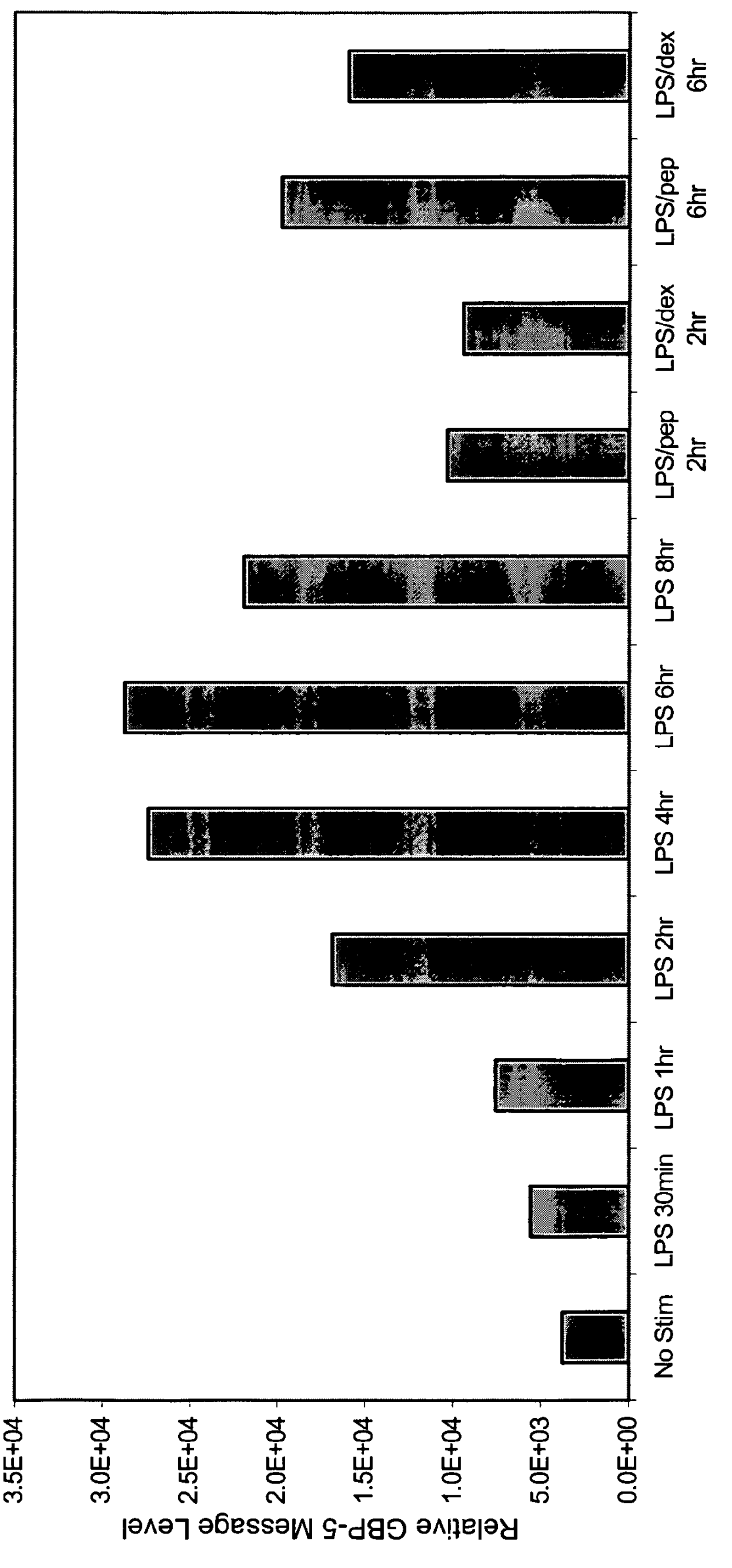

An extended time course was performed to further characterize GBP-1 and GBP-5 expression, as shown in FIG. 89. THP-1 cells were stimulated for 0.5, 1, 4, 6, and 8 hours with LPS. Some groups included either BMS-205820 or the steroid dexamethasone for 2 or 6 hours. Dexamethasone is also known to inhibit NF-KB activity (Scheinman et al., *Mol. Cell. Biol.* 15:943-953 (1995)). At each time point, mRNA was isolated and real time PCR was performed using primers specific for either GBP-1 FIG. 89A) or GBP-5 (FIG. 89B). Steady state mRNA levels for both GBP-1 and GBP-5 peaked at 6 hours post stimulation. Addition of either BMS-205820 or dexamethasone significantly inhibited mRNA induction of both genes at 2 and 6 hours. The ability of two different NF-kB inhibitors to block GBP-1 and GBP-5 expression further confirms that LPS-mediated induction of these genes is dependent on NF-kB activity.

Figure 90A:
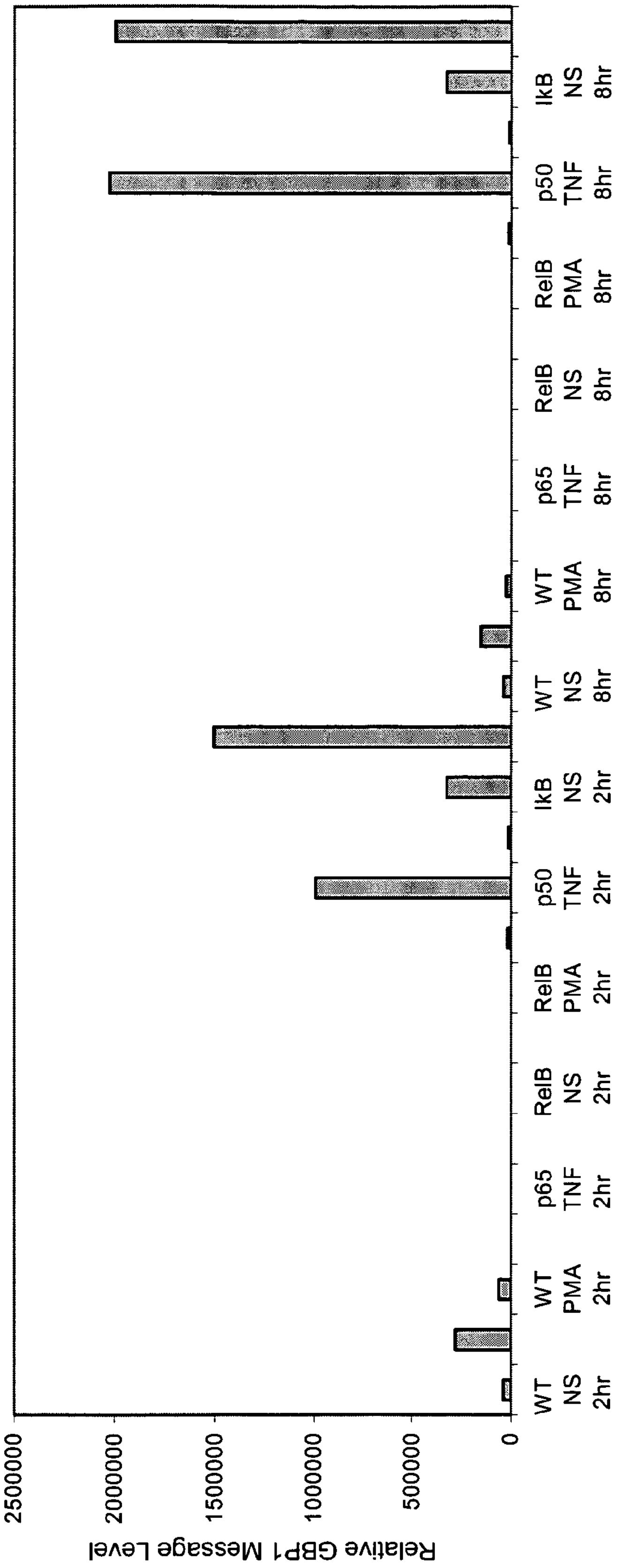
FIG. 90 shows GBP-1 and GBP-5 expression in mouse embryonic fibroblast lines derived from NFkB and IkBα germline knockouts.
Figure 90B:
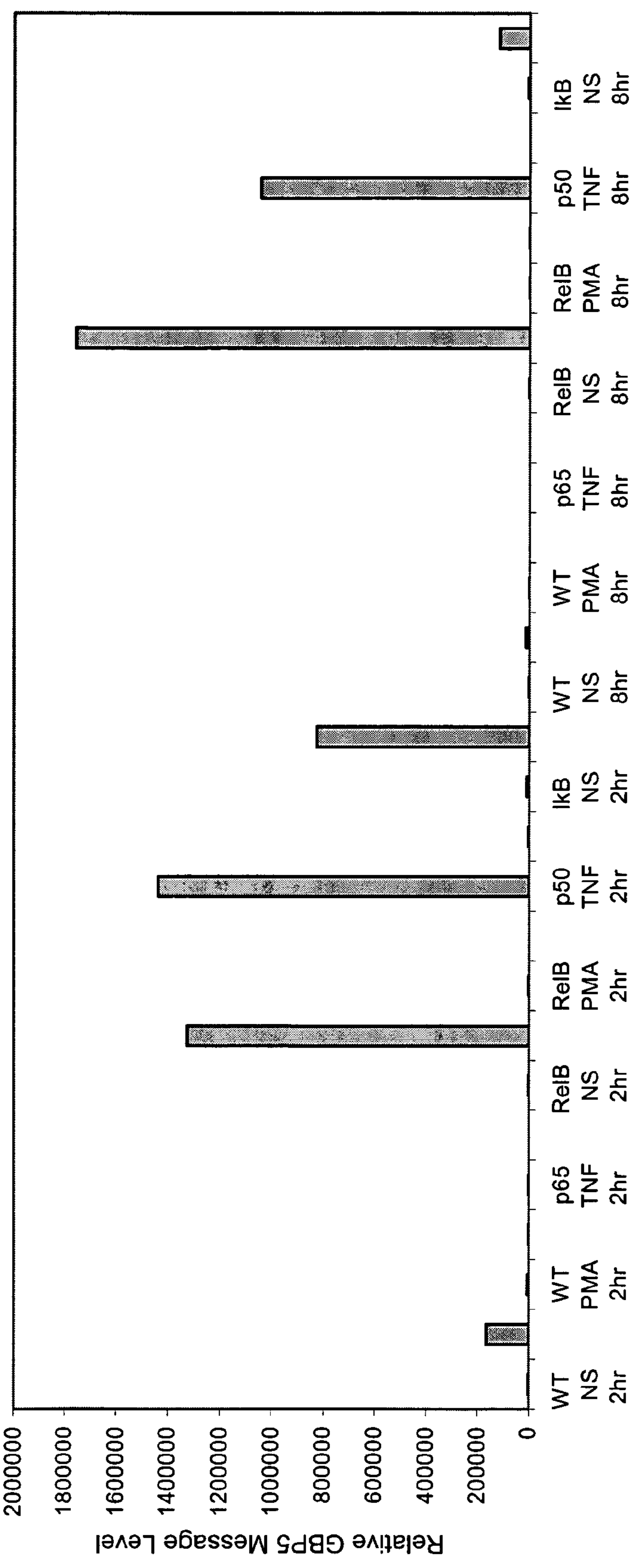

To further confirm that GBP-1 and GBP-5 are NF-kB target genes, expression in mouse embryonic fibroblasts derived from germline knockouts of members of the NF-kB family was examined (FIG. 90). Wild type 3T3 cells, embryonic fibroblasts derived from knockouts of p65, RelB, p50, and IkBα were stimulated for 2 or 8 hours with either TNFα or PMA. At each time point, mRNA was isolated and real time PCR was performed using primers specific for either mouse GBP-1 (FIG. 90A) or GBP-5 (FIG. 90B). Stimulation with TNF(α but not PMA induced increased steady-state levels of both GBP-1 and GBP-5 mRNA. Induction of GBP-1 mRNA was completely ablated in cells lacking either p65 or RelB. GBP-1 mRNA was superinduced in cells lacking either p50 or IkBα, suggesting that these proteins negatively regulate GBP-1 mRNA. IkBα is a known inhibitor of NF-kB activity (Baeuerle et al., *Science* 242:540-545 (1988)). Homodimers of p50 have also been shown to repress certain genes (Plaksin et al., *J. Exp. Med.* 177:1651-1662 (1993)).

Similar to GBP-1, induction of GBP-5 mRNA was completely ablated in cells lacking p65. In contrast to GBP-1, GBP-5 mRNA was superinduced in cells lacking RelB. Similar to GBP-1, GBP-5 mRNA was also superinduced in cells lacking either p50 or IkBα. These data suggest that p65 expression is required for the induction of both GBP-1 and GBP-5. Complexes containing RelB appear to differentially regulate GBP-1 and GBP-5 expression. Taken together, these data are consistent with NF-kB-dependent regulation of GBP-1 and GBP-5 expression.

Figure 91A:
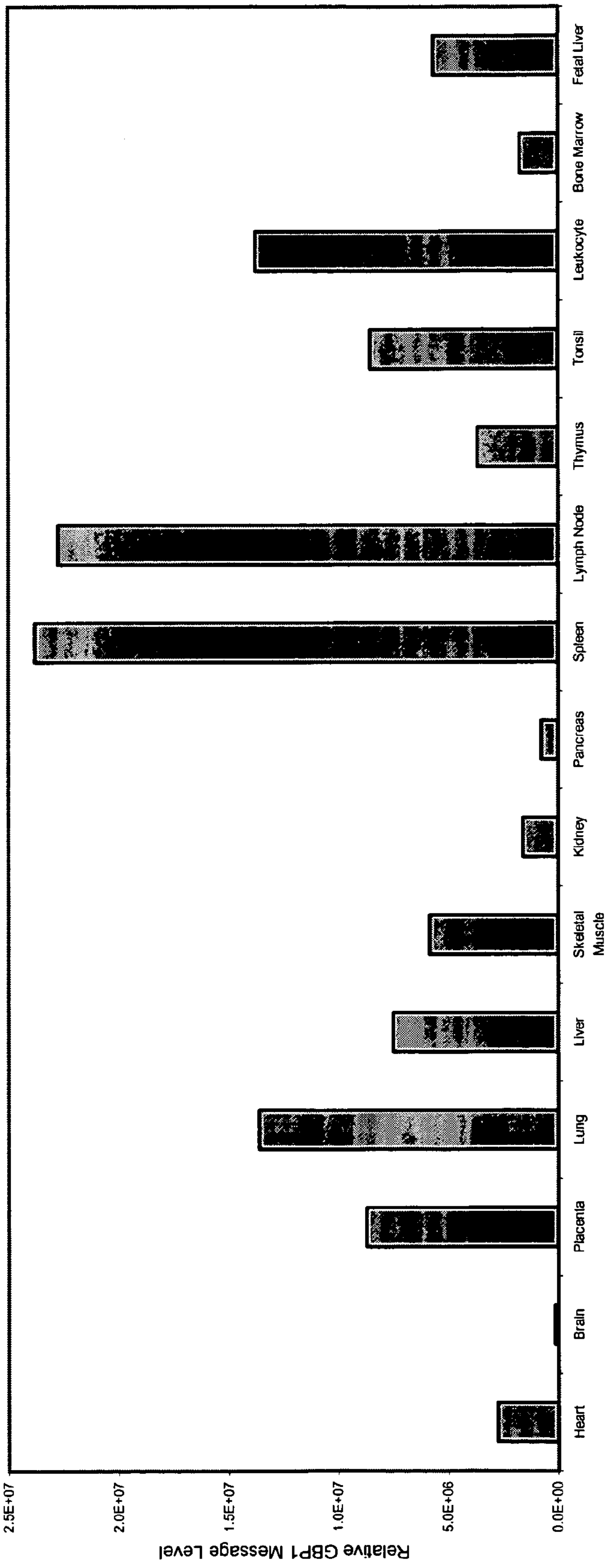
FIG. 91 shows tissue expression patterns of GBP-1 and GBP-5.
Figure 91B:
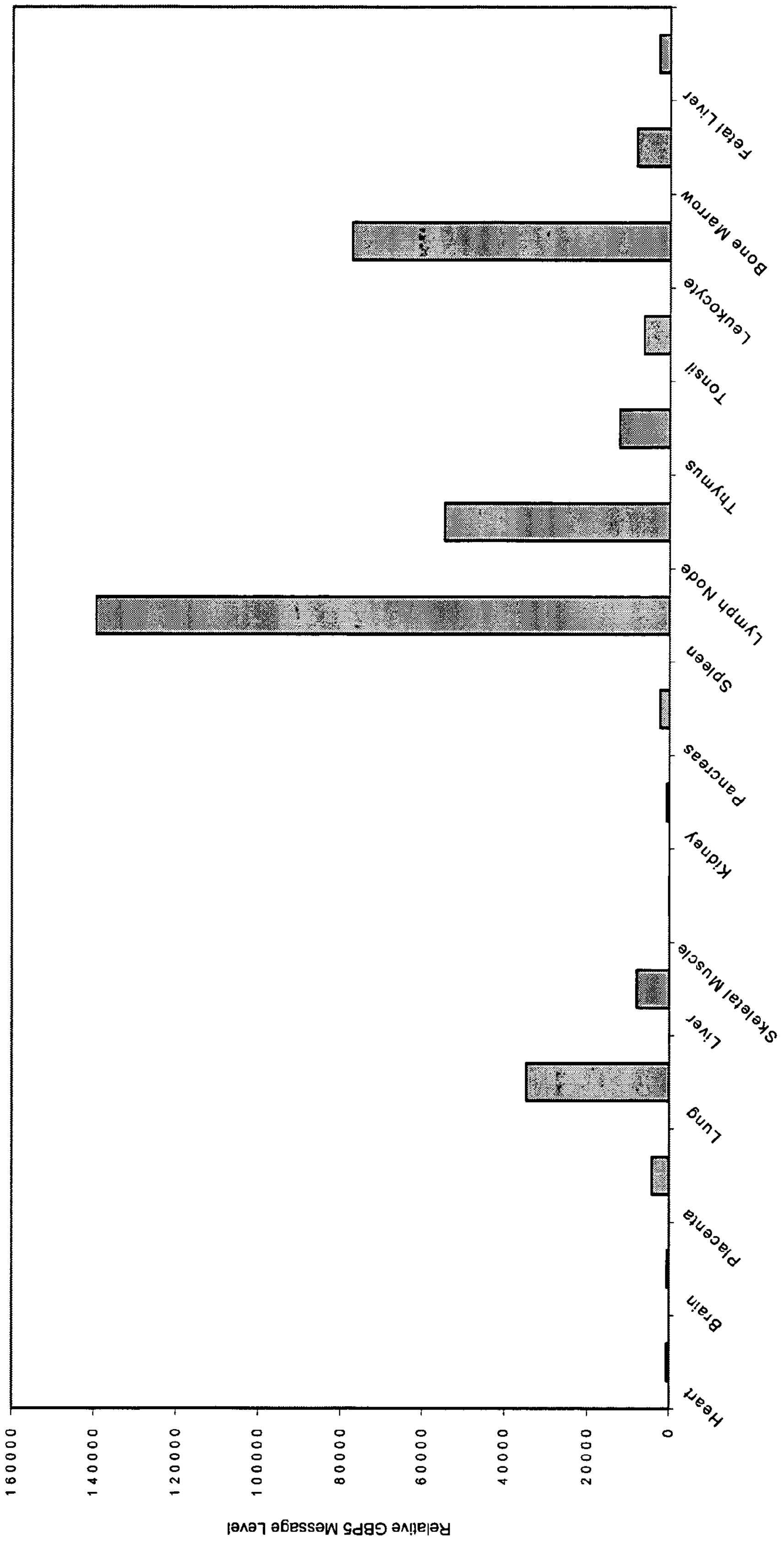

The tissue expression profiles of GBP-1 and GBP-5 were further characterized. Human tissue cDNA panels were analyzed by real time PCR with primers selective for GBP-1 (FIG. 91A) and GBP-5 (FIG. 91B). Both genes had very similar patterns of expression. The highest steady state mRNA levels were detected in hematopoietic tissues including spleen, peripheral blood leukocytes, and lymph nodes. Lower levels of expression were detected in lung, followed by liver, thymus, tonsil, bone marrow, placenta, fetal liver, tonsil, and pancreas.

Figure 92A:
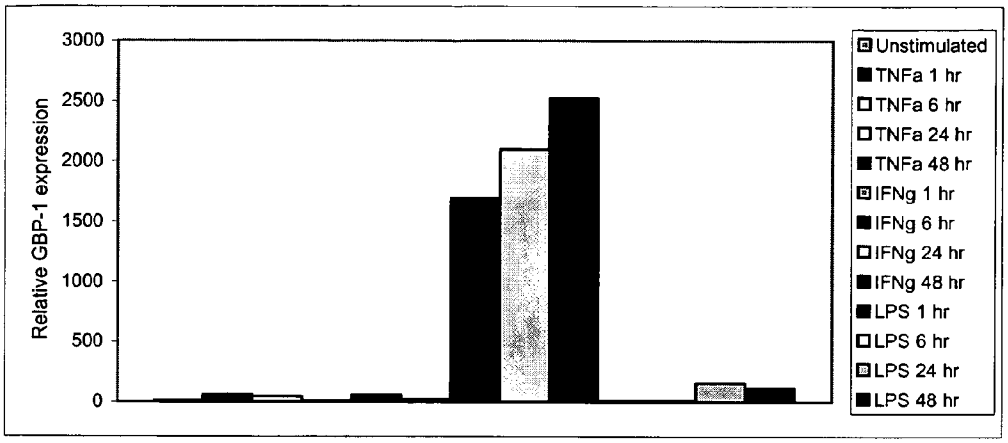
FIG. 92 shows expression of GBP-1 and GBP-5 in resting and stimulated THP-1 monocytes.
Figure 92B:
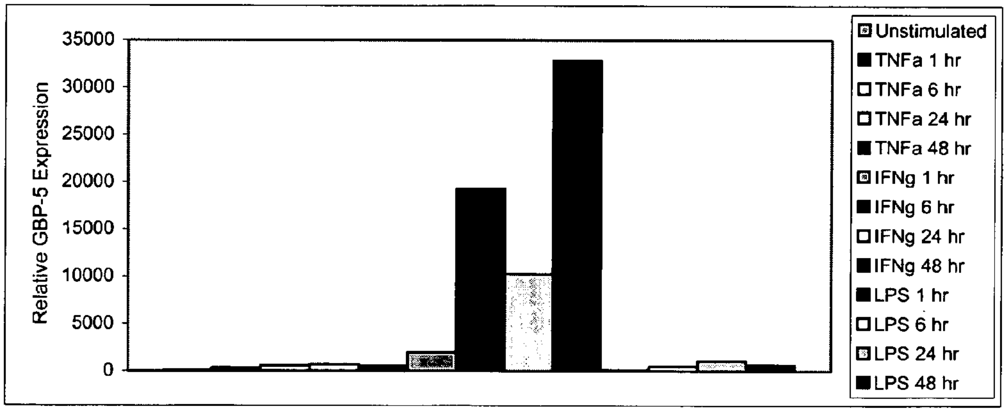

Based on the high expression detected in hematopoietic tissue, the expression of GBP-1 and GBP-5 in panels of resting and stimulated immune cells was examined. Consistent with the identification of GBP-1 as an interferon response gene (Cheng et al., *J. Biol. Chem.* 258:7746-7750 (1983)), steady state levels of GBP-1 and GBP-5 mRNA were strongly induced by interferon-γ treatment of THP-1 monocytes, as shown in FIGS. 92A and 92B. Much lower levels of expression were induced by TNFα and LPS.

Figure 93A:
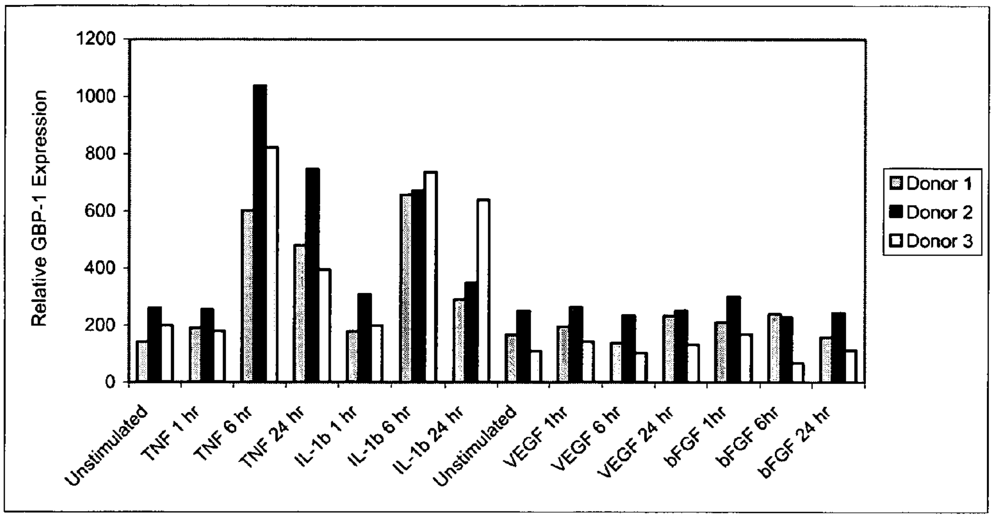
FIG. 93 shows expression of GBP-1 and GBP-5 in resting and stimulated human microvascular endothelial cells.
Figure 93B:
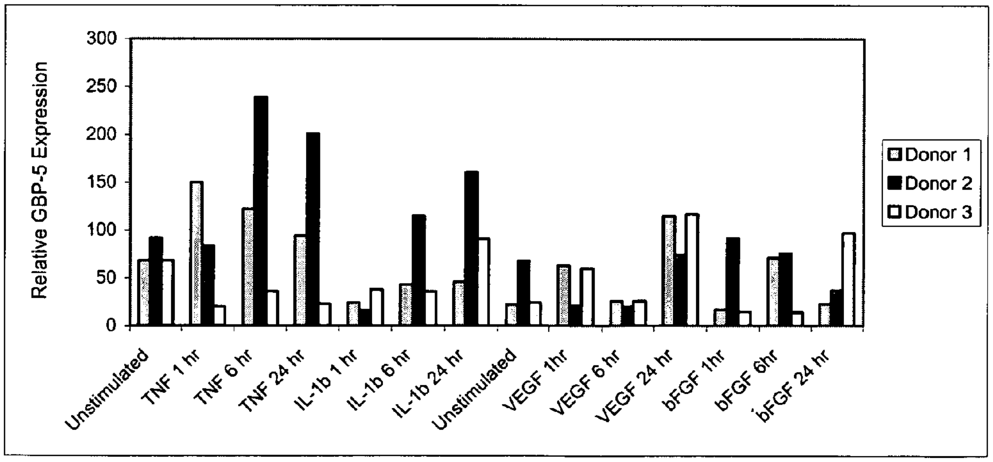

Consistent with published reports (Guenzi et al., *EMBO J.* 20:5568-5577 (2001)), GBP-1 expression was strongly induced by TNFα and IL-1β in human microvascular endothelial cells (FIG. 93A). No induction was seen in response to either VEGF or basic FGF. In contrast to GBP-1, induction of GBP-5 by TNFα and IL-1β was variable (FIG. 93B). Cells from two out of three donors upregulated GBP-5 mRNA in response to TNFα. Only one donor significantly induced GBP-5 mRNA in response to IL-1β.

Figure 94A:
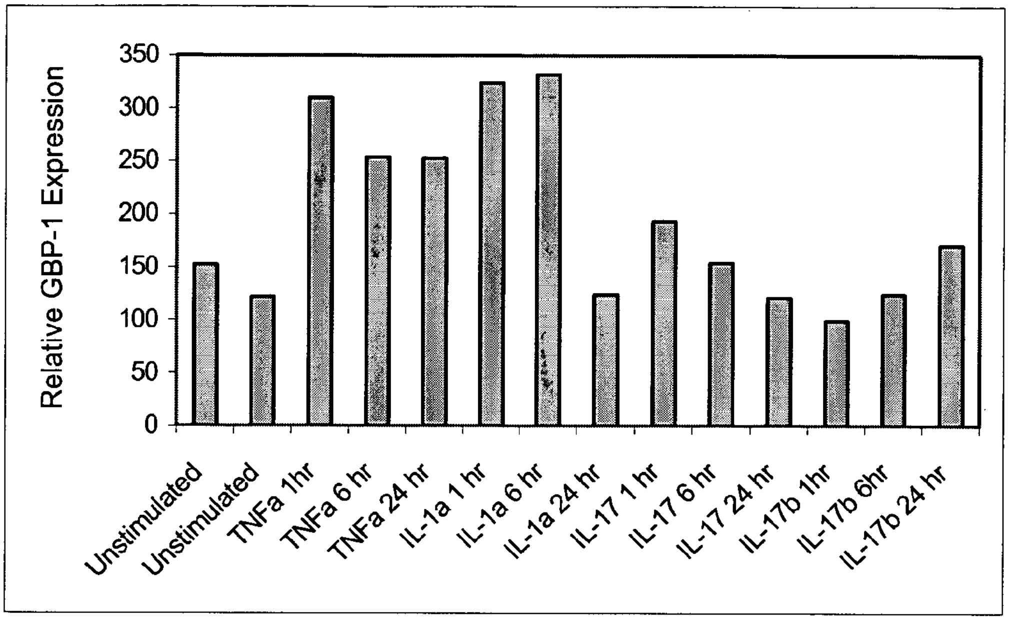
FIG. 94 shows expression of GBP-1 and GBP-5 in resting and stimulated fibroblasts derived from rheumatoid arthritis synovium.
Figure 94B:
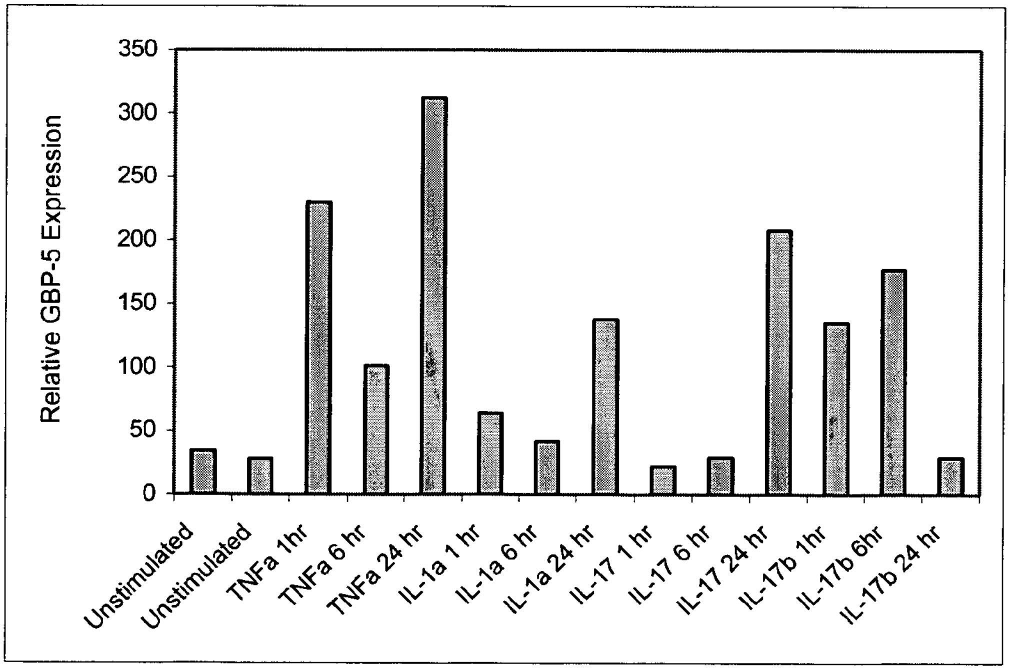

Synovial fibroblasts derived from rheumatoid arthritis patients were stimulated with either TNFα, IL-1α, IL-17, or IL-17b. GBP-1 mRNA was induced at 1 and 6 hours by stimulation with either TNFα or IL-1α, but not in response to either IL-17 or IL-17b (FIG. 94A). Low levels of GBP-5 expression were detected in synovial fibroblasts (FIG. 94B). Induction of GBP-5 in response to the different stimuli was variable and not sustained.

Figure 95A:
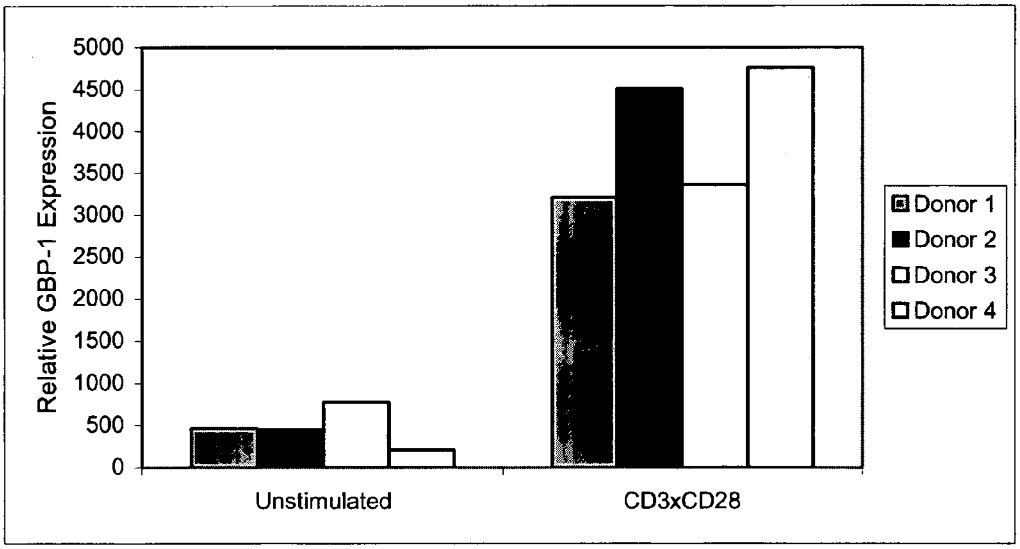
FIG. 95 shows expression of GBP-1 and GBP-5 in resting and stimulated peripheral blood T cells.
Figure 95B:
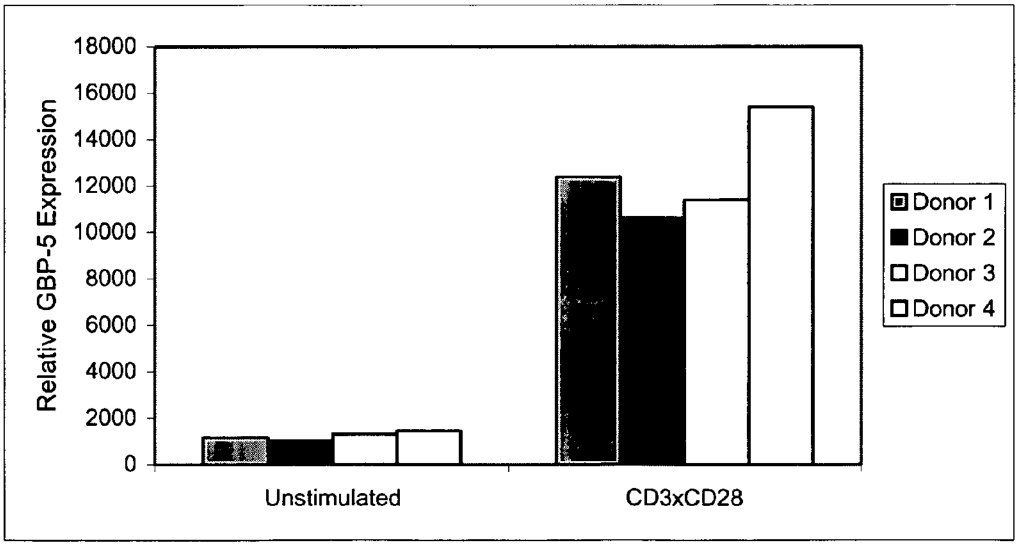

GBP-1 and GBP-5 had similar patterns of expression in T cells (FIG. 95). Peripheral blood T cells were isolated from 4 different donors and stimulated for 6 hours with antibodies to CD3 and CD28 as a mimic of antigen stimulation. Steady state levels of GBP-1 (FIG. 95A) and GBP-5 (FIG. 95B) mRNA were strongly induced by antigen receptor crosslinking.

The induction of GBP-1 and GBP-5 by pro-inflammatory stimuli including LPS, IL-1, TNFα, and antigen receptor crosslinking is consistent with NF-kB-dependent regulation of these genes. Overexpression of these genes in synovium from rheumatoid arthritis patients is also consistent with NF-kB-dependent regulation. NF-kB is activated in the inflamed synovium of rheumatoid arthritis patients (Marok et al., *Arthritis Rheum.* 39:583-591 (1996)) and animal models of arthritis (Miagkov et al., *Proc. Natl. Acad. Sci. USA* 95:13859-13864 (1998)). The regulation of GBP-1 and GBP-5 by NF-kB coupled with the involvement of NF-kB in the development of arthritis indicates that these genes play a role in disease pathology.

While the invention has been described in connection with specific embodiments therefore, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. All references cited herein are expressly incorporated in their entirety.

What is claimed is:

1. An assay for identifying a compound that modulates the expression of a protein associated with rheumatoid arthritis, comprising:

(1) providing a cell expressing said protein associated with rheumatoid arthritis, wherein the nucleic acid sequence encoding said protein associated with rheumatoid arthritis is the nucleic acid sequence comprising SEQ ID NO:37, (2) contacting said cell expressing said protein associated with rheumatoid arthritis with a test compound; and (3) determining whether said test compound modulates the expression of said protein associated with rheumatoid arthritis, wherein if the compound diminishes the expression of said protein, the test compound is an antagonist and if the compound enhances the expression of said protein, the test compound is an agonist to said protein.

2. The assay of claim 1, wherein said assay is a cell-based assay.

3. The assay of claim 1, wherein said assay is a ligand-binding assay.

4. The assay of claim 1, wherein said test compound is an antagonist of a protein associated with rheumatoid arthritis.

5. The assay of claim 1, wherein said test compound is an agonist of a protein associated with rheumatoid arthritis.

6. The assay of claim 1, wherein said test compound binds to said cell expressing said protein associated with rheumatoid arthritis.

* * * * *

SEQUENCE LISTING

<160> NUMBER OF SEQ ID NOS: 91

<210> SEQ ID NO 1
<211> LENGTH: 63
<212> TYPE: DNA
<213> ORGANISM: Artificial Sequence
<220> FEATURE:
<223> OTHER INFORMATION: Artificial Sequence equals primer

<400> SEQUENCE: 1
ggccagtgaa ttgtaatacg actcactata gggaggcggt tttttttttt tttttttttt 60
ttt 63

<210> SEQ ID NO 2
<211> LENGTH: 1316
<212> TYPE: DNA
<213> ORGANISM: homo sapiens

<400> SEQUENCE: 2
ggcacgaggc ctcctgagca gtcagcccgc gcgccggccg gctccgttat ggcgacccgc 60
agccctggcg tcgtgattag tgatgatgaa ccaggttatg accttgattt attttgcata 120
cctaatcatt atgctgagga tttggaaagg gtgtttattc ctcatggact aattatggac 180
aggactgaac gtcttgctcg agatgtgatg aaggagatgg gaggccatca cattgtagcc 240
ctctgtgtgc tcaagggggg ctataaattc tttgctgacc tgctggatta catcaaagca 300
ctgaatagaa atagtgatag atccattcct atgactgtag attttatcag actgaagagc 360
tattgtaatg accagtcaac aggggacata aaagtaattg gtggagatga tctctcaact 420
ttaactggaa agaatgtctt gattgtggaa gatataattg acactggcaa aacaatgcag 480
actttgcttt ccttggtcag gcagtataat ccaaagatgg tcaaggtcgc aagcttgctg 540
gtgaaaagga ccccacgaag tgttggatat aagccagact ttgttggatt tgaaattcca 600
gacaagtttg ttgtaggata tgcccttgac tataatgaat acttcaggga tttgaatcat 660
gtttgtgtca ttagtgaaac tggaaaagca aaatacaaag cctaagatga gagttcaagt 720
tgagtttgga aacatctgga gtcctattga catcgccagt aaaattatca atgttctagt 780
tctgtggcca tctgcttagt agagcttttt gcatgtatct tctaagaatt ttatctgttt 840
tgtactttag aaatgtcagt tgctgcattc ctaaactgtt tatttgcact atgagcctat 900
agactatcag ttccctttgg gcggattgtt gtttaacttg taaatgaaaa aattctctta 960
aaccacagca ctattgagtg aaacattgaa ctcatatctg taagaaataa agagaagata 1020
tattagtttt ttaattggta ttttaatttt tatatatgca ggaaagaata gaagtgattg 1080
aatattgtta attataccac cgtgtgttag aaaagtaaga agcagtcaat tttcacatca 1140
aagacagcat ctaagaagtt ttgttctgtc ctggaattat tttagtagtg tttcagtaat 1200
gttgactgta ttttccaact tgttcaaatt attaccagtg aatctttgtc agcagttccc 1260
ttttaaatgc aaatcaataa attcccaaaa atttaaaaaa aaaaaaaaaa aaaaaa 1316

<210> SEQ ID NO 3
<211> LENGTH: 20
<212> TYPE: DNA
<213> ORGANISM: Artificial Sequence
<220> FEATURE:
<223> OTHER INFORMATION: Artificial Sequence equals primer

<400> SEQUENCE: 3

-continued

```
ggtatactgc ctgaccaagg                                                   20


<210> SEQ ID NO 4
<211> LENGTH: 22
<212> TYPE: DNA
<213> ORGANISM: Artificial Sequence
<220> FEATURE:
<223> OTHER INFORMATION: Artificial Sequence equals primer.

<400> SEQUENCE: 4

cgagatgtga tgaaggagat gg                                                22


<210> SEQ ID NO 5
<211> LENGTH: 20
<212> TYPE: DNA
<213> ORGANISM: Artificial Sequence
<220> FEATURE:
<223> OTHER INFORMATION: Artificial Sequence equals primer.

<400> SEQUENCE: 5

ccccatggaa atcagacagt                                                   20


<210> SEQ ID NO 6
<211> LENGTH: 20
<212> TYPE: DNA
<213> ORGANISM: Artificial Sequence
<220> FEATURE:
<223> OTHER INFORMATION: Artificial Sequence equals primer.

<400> SEQUENCE: 6

ttgcttttcc gtatgttgtg                                                   20


<210> SEQ ID NO 7
<211> LENGTH: 18
<212> TYPE: DNA
<213> ORGANISM: Artificial Sequence
<220> FEATURE:
<223> OTHER INFORMATION: Artificial Sequence equals primer.

<400> SEQUENCE: 7

tgaagagcgt cctgggtc                                                     18


<210> SEQ ID NO 8
<211> LENGTH: 18
<212> TYPE: DNA
<213> ORGANISM: Artificial Sequence
<220> FEATURE:
<223> OTHER INFORMATION: Artificial Sequence equals primer.

<400> SEQUENCE: 8

cgtcgatggt cagcacag                                                     18


<210> SEQ ID NO 9
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 9

gcccatcagt gacagcaag                                                    19


<210> SEQ ID NO 10
<211> LENGTH: 19
<212> TYPE: DNA
```

-continued

<213> ORGANISM: Artificial Sequence
<220> FEATURE:
<223> OTHER INFORMATION: Artificial Sequence equals primer.

<400> SEQUENCE: 10
cccaggcaat gttgaggag 19

<210> SEQ ID NO 11
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 11
ccttcccctg tcattgttc 19

<210> SEQ ID NO 12
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 12
gacagtaacc ctgccacac 19

<210> SEQ ID NO 13
<211> LENGTH: 18
<212> TYPE: DNA
<213> ORGANISM: Artificial Sequence
<220> FEATURE:
<223> OTHER INFORMATION: Artificial Sequence equals primer.

<400> SEQUENCE: 13
ggcgactgat ggcgaatc 18

<210> SEQ ID NO 14
<211> LENGTH: 18
<212> TYPE: DNA
<213> ORGANISM: Artificial Sequence
<220> FEATURE:
<223> OTHER INFORMATION: Artificial Sequence equals primer.

<400> SEQUENCE: 14
caccgtggag cccagaga 18

<210> SEQ ID NO 15
<211> LENGTH: 20
<212> TYPE: DNA
<213> ORGANISM: Artificial Sequence
<220> FEATURE:
<223> OTHER INFORMATION: Artificial Sequence equals primer.

<400> SEQUENCE: 15
ggcgatgagg tcaatgtaga 20

<210> SEQ ID NO 16
<211> LENGTH: 20
<212> TYPE: DNA
<213> ORGANISM: Artificial Sequence
<220> FEATURE:
<223> OTHER INFORMATION: Artificial Sequence equals primer.

<400> SEQUENCE: 16
ctgtgtcctt caccccaaca 20

-continued

<210> SEQ ID NO 17
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 17
ggacaccaca aaggcagtga t 21

<210> SEQ ID NO 18
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 18
gcagatggag cacctcacag t 21

<210> SEQ ID NO 19
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 19
agctcagctg cttgtctgca t 21

<210> SEQ ID NO 20
<211> LENGTH: 20
<212> TYPE: DNA
<213> ORGANISM: Artificial Sequence
<220> FEATURE:
<223> OTHER INFORMATION: Artificial Sequence equals primer.

<400> SEQUENCE: 20
ttcaaagagc tggtgcgaaa 20

<210> SEQ ID NO 21
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 21
ggccagggca atgttatgc 19

<210> SEQ ID NO 22
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 22
acattctggc cctctgatcc t 21

<210> SEQ ID NO 23
<211> LENGTH: 19
<212> TYPE: DNA
<213> ORGANISM: Artificial Sequence
<220> FEATURE:

-continued

<223> OTHER INFORMATION: Artificial Sequence equals primer.

<400> SEQUENCE: 23
ccttcccctg tcattgttc 19

<210> SEQ ID NO 24
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 24
gacagtaacc ctgccacac 19

<210> SEQ ID NO 25
<211> LENGTH: 1371
<212> TYPE: DNA
<213> ORGANISM: homo sapiens

<400> SEQUENCE: 25
ctgcaggggg gggggggggc tgggacagtg aatcgacaat gccgtcttct gtctcgtggg 60
gcatcctcct gctggcaggc ctgtgctgcc tggtccctgt ctccctggct gaggatcccc 120
agggagatgc tgcccagaag acagatacat cccaccatga tcaggatcac ccaaccttca 180
acaagatcac ccccaacctg gctgagttcg ccttcagcct ataccgccag ctggcacacc 240
agtccaacag caccaatatc ttcttctccc cagtgagcat cgctacagcc tttgcaatgc 300
tctccctggg gaccaaggct gacactcacg atgaaatcct ggagggcctg aatttcaacc 360
tcacggagat tccggaggct cagatccatg aaggcttcca ggaactcctc cgtaccctca 420
accagccaga cagccagctc cagctgacca ccggcaatgg cctgttcctc agcgagggcc 480
tgaagctagt ggataagttt ttggaggatg ttaaaaagtt gtaccactca gaagccttca 540
ctgtcaactt cggggacacc gaagaggcca agaaacagat caacgattac gtggagaagg 600
gtactcaagg gaaaattgtg gatttggtca aggagcttga cagagacaca gtttttgctc 660
tggtgaatta catcttcttt aaaggcaaat gggagagacc ctttgaagtc aaggacaccg 720
aggaagagga cttccacgtg gaccaggtga ccaccgtgaa ggtgcctatg atgaagcgtt 780
taggcatgtt taacatccag cactgtaaga agctgtccag ctgggtgctg ctgatgaaat 840
acctgggcaa tgccaccgcc atcttcttcc tgcctgatga ggggaaacta cagcacctgg 900
aaaatgaact cacccacgat atcatcacca agttcctgga aaatgaagac agaaggtctg 960
ccagcttaca tttacccaaa ctgtccatta ctggaaccta tgatctgaag agcgtcctgg 1020
gtcaactggg catcactaag gtcttcagca atggggctga cctctccggg gtcacagagg 1080
aggcacccct gaagctctcc aaggccgtgc ataaggctgt gctgaccatc gacgagaaag 1140
ggactgaagc tgctggggcc atgtttttag aggccatacc catgtctatc ccccccgagg 1200
tcaagttcaa caaacccttt gtcttcttaa tgattgaaca aaataccaag tctcccctct 1260
tcatgggaaa agtggtgaat cccacccaaa aataactgcc tctcgctcct caacccctcc 1320
cctccatccc tggccccctc cctggatgac attaaagaag ggttgagctg g 1371

<210> SEQ ID NO 26
<211> LENGTH: 417
<212> TYPE: PRT
<213> ORGANISM: homo sapiens

<400> SEQUENCE: 26

-continued

```
Met Pro Ser Ser Val Ser Trp Gly Ile Leu Leu Ala Gly Leu Cys Cys
1               5                   10                  15

Leu Val Pro Val Ser Leu Ala Glu Asp Pro Gln Gly Asp Ala Ala Gln
            20                  25                  30

Lys Thr Asp Thr Ser His His Asp Gln Asp His Pro Thr Phe Asn Lys
        35                  40                  45

Ile Thr Pro Asn Leu Ala Glu Phe Ala Phe Ser Leu Tyr Arg Gln Leu
    50                  55                  60

Ala His Gln Ser Asn Ser Thr Asn Ile Phe Phe Ser Pro Val Ser Ile
65                  70                  75                  80

Ala Thr Ala Phe Ala Met Leu Ser Leu Gly Thr Lys Ala Asp Thr His
                85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
        115                 120                 125

Pro Asp Ser Gln Leu Gln Leu Thr Thr Gly Asn Gly Leu Phe Leu Ser
    130                 135                 140

Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Glu Lys Gly Thr Gln Gly Lys Ile
            180                 185                 190

Val Asp Leu Val Lys Glu Leu Asp Arg Asp Thr Val Phe Ala Leu Val
        195                 200                 205

Asn Tyr Ile Phe Phe Lys Gly Lys Trp Glu Arg Pro Phe Glu Val Lys
    210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
        275                 280                 285

Glu Leu Thr His Asp Ile Ile Thr Lys Phe Leu Glu Asn Glu Asp Arg
    290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
        355                 360                 365

Glu Ala Ala Gly Ala Met Phe Leu Glu Ala Ile Pro Met Ser Ile Pro
    370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
                405                 410                 415
```

-continued

```
Lys

<210> SEQ ID NO 27
<211> LENGTH: 858
<212> TYPE: DNA
<213> ORGANISM: Homo Sapiens

<400> SEQUENCE: 27

atggatgact ccacagaaag ggagcagtca cgccttactt cttgccttaa gaaaagagaa      60

gaaatgaaac tgaaggagtg tgtttccatc ctcccacgga aggaaagccc ctctgtccga     120

tcctccaaag acggaaagct gctggctgca accttgctgc tggcactgct gtcttgctgc     180

ctcacggtgg tgtctttcta ccaggtggcc gccctgcaag gggacctggc cagcctccgg     240

gcagagctgc agggccacca cgcggagaag ctgccagcag gagcaggagc ccccaaggcc     300

ggcttggagg aagctccagc tgtcaccgcg ggactgaaaa tctttgaacc accagctcca     360

ggagaaggca actccagtca gaacagcaga aataagcgtg ccgttcaggg tccagaagaa     420

acagtcactc aagactgctt gcaactgatt gcagacagtg aaacaccaac tatacaaaaa     480

ggatcttaca catttgttcc atggcttctc agctttaaaa ggggaagtgc cctagaagaa     540

aaagagaata aaatattggt caaagaaact ggttactttt ttatatatgg tcaggtttta     600

tatactgata agacctacgc catgggacat ctaattcaga ggaagaaggt ccatgtcttt     660

ggggatgaat tgagtctggt gactttgttt cgatgtattc aaaatatgcc tgaaacacta     720

cccaataatt cctgctattc agctggcatt gcaaaactgg aagaaggaga tgaactccaa     780

cttgcaatac caagagaaaa tgcacaaata tcactggatg gagatgtcac atttttttggt    840

gcattgaaac tgctgtga                                                   858

<210> SEQ ID NO 28
<211> LENGTH: 285
<212> TYPE: PRT
<213> ORGANISM: homo sapiens

<400> SEQUENCE: 28

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
```

-continued

```
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```

<210> SEQ ID NO 29
<211> LENGTH: 1128
<212> TYPE: DNA
<213> ORGANISM: homo sapiens

<400> SEQUENCE: 29

```
atgtggttct tgacaactct gctcctttgg gttccagttg atgggcaagt ggacaccaca      60

aaggcagtga tcactttgca gcctccatgg gtcagcgtgt tccaagagga aaccgtaacc     120

ttgcactgtg aggtgctcca tctgcctggg agcagctcta cacagtggtt tctcaatggc     180

acagccactc agacctcgac ccccagctac agaatcacct ctgccagtgt caatgacagt     240

ggtgaataca ggtgccagag aggtctctca gggcgaagtg accccataca gctggaaatc     300

cacagaggct ggctactact gcaggtctcc agcagagtct tcacggaagg agaacctctg     360

gccttgaggt gtcatgcgtg gaaggataag ctggtgtaca atgtgcttta ctatcgaaat     420

ggcaaagcct ttaagttttt ccactggaat tctaacctca ccattctgaa aaccaacata     480

agtcacaatg gcacctacca ttgctcaggc atgggaaagc atcgctacac atcagcagga     540

atatctgtca ctgtgaaaga gctatttcca gctccagtgc tgaatgcatc tgtgacatcc     600

ccactcctgg aggggaatct ggtcaccctg agctgtgaaa caaagttgct cttgcagagg     660

cctggtttgc agctttactt ctccttctac atgggcagca agaccctgcg aggcaggaac     720

acatcctctg aataccaaat actaactgct agaagagaag actctgggtt atactggtgc     780

gaggctgcca cagaggatgg aaatgtcctt aagcgcagcc ctgagttgga gcttcaagtg     840

cttggcctcc agttaccaac tcctgtctgg tttcatgtcc ttttctatct ggcagtggga     900

ataatgtttt tagtgaacac tgttctctgg gtgacaatac gtaaagaact gaaaagaaag     960

aaaaagtggg atttagaaat ctctttggat tctggtcatg agaagaaggt aatttccagc    1020

cttcaagaag acagacattt agaagaagag ctgaaatgtc aggaacaaaa agaagaacag    1080

ctgcaggaag ggtgcaccg gaaggagccc caggggccca cgtagcag                  1128
```

<210> SEQ ID NO 30
<211> LENGTH: 374
<212> TYPE: PRT
<213> ORGANISM: homo sapiens

<400> SEQUENCE: 30

```
Met Trp Phe Leu Thr Thr Leu Leu Leu Trp Val Pro Val Asp Gly Gln
1               5                   10                  15
```

-continued

```
Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370
```

<210> SEQ ID NO 31
<211> LENGTH: 586
<212> TYPE: DNA
<213> ORGANISM: homo sapiens

<400> SEQUENCE: 31

```
aaaacactct gtgtggctcc tcggctttga cagagtgcaa gacgatgact tgcaaaatgt     60
```

-continued

```
cgcagctgga acgcaacata gagaccatca tcaacacctt ccaccaatac tctgtgaagc    120

tggggcaccc agacaccctg aaccaggggg aattcaaaga gctggtgcga aaagatctgc    180

aaaattttct caagaaggag aataagaatg aaaaggtcat agaacacatc atggaggacc    240

tggacacaaa tgcagacaag cagctgagct tcgaggagtt catcatgctg atggcgaggc    300

taacctgggc ctcccacgag aagatgcacg agggtgacga gggccctggc caccaccata    360

agccaggcct cggggagggc accccctaag accacagtgg ccaagatcac agtggccacg    420

gccacggcca cagtcatggt ggccacggcc acagccacta atcaggaggc caggccaccc    480

tgcctctacc caaccagggc cccggggcct gttatgtcaa actgtcttgg ctgtggggct    540

aggggctggg gccaaataaa gtctcttcct ccaagtcagt gctctg                   586
```

<210> SEQ ID NO 32
<211> LENGTH: 114
<212> TYPE: PRT
<213> ORGANISM: homo sapiens

<400> SEQUENCE: 32

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```

<210> SEQ ID NO 33
<211> LENGTH: 1970
<212> TYPE: DNA
<213> ORGANISM: homo sapiens

<400> SEQUENCE: 33

```
atattggagc agcaagaggc tgggaagcca tcacttacct tgcactgaga aagaagacaa     60

aggccagtat gcacagcttt cctccactgc tgctgctgct gttctggggt gtggtgtctc    120

acagcttccc agcgactcta gaaacacaag agcaagatgt ggacttagtc cagaaatacc    180

tggaaaaata ctacaacctg aagaatgatg ggaggcaagt tgaaaagcgg agaaatagtg    240

gcccagtggt tgaaaaattg aagcaaatgc aggaattctt tgggctgaaa gtgactggga    300

aaccagatgc tgaaaccctg aaggtgatga agcagcccag atgtggagtg cctgatgtgg    360

ctcagtttgt cctcactgag ggaaaccctc gctgggagca aacacatctg aggtacagga    420

ttgaaaatta cacgccagat ttgccaagag cagatgtgga ccatgccatt gagaaagcct    480

tccaactctg gagtaatgtc acacctctga cattcaccaa ggtctctgag ggtcaagcag    540

acatcatgat atcttttgtc aggggagatc atcgggacaa ctctcctttt gatggacctg    600

gaggaaatct tgctcatgct tttcaaccag gcccaggtat tggaggggat gctcattttg    660
```

-continued

```
atgaagatga aaggtggacc aacaatttca gagagtacaa cttacatcgt gttgcggctc    720

atgaactcgg ccattctctt ggactctccc attctactga tatcggggct ttgatgtacc    780

ctagctacac cttcagtggt gatgttcagc tagctcagga tgacattgat ggcatccaag    840

ccatatatgg acgttcccaa aatcctgtcc agcccatcgg cccacaaacc ccaaaagcgt    900

gtgacagtaa gctaaccttt gatgctataa ctacgattcg gggagaagtg atgttcttta    960

aagacagatt ctacatgcgc acaaatccct tctacccgga agttgagctc aatttcattt   1020

ctgttttctg gccacaactg ccaaatgggc ttgaagctgc ttacgaattt gccgacagag   1080

atgaagtccg gtttttcaaa gggaataagt actgggctgt tcagggacag aatgtgctac   1140

acggataccc caaggacatc tacagctcct ttggcttccc tagaactgtg aagcatatcg   1200

atgctgctct ttctgaggaa aacactggaa aaacctactt ctttgttgct aacaaatact   1260

ggaggtatga tgaatataaa cgatctatgg atccaagtta tcccaaaatg atagcacatg   1320

actttcctgg aattggccac aaagttgatg cagttttcat gaaagatgga tttttctatt   1380

tctttcatgg aacaagacaa tacaaatttg atcctaaaac gaagagaatt ttgactctcc   1440

agaaagctaa tagctggttc aactgcagga aaaattgaac attactaatt tgaatggaaa   1500

acacatggtg tgagtccaaa gaaggtgttt tcctgaagaa ctgtctattt tctcagtcat   1560

ttttaacctc tagagtcact gatacacaga atataatctt atttatacct cagtttgcat   1620

attttttttac tatttagaat gtagcccttt ttgtactgat ataatttagt tccacaaatg   1680

gtgggtacaa aaagtcaagt ttgtggctta tggattcata taggccagag ttgcaaagat   1740

ctttttccaga gtatgcaact ctgacgttga tcccagagag cagcttcagt gacaaacata   1800

tcctttcaag acagaaagag acaggagaca tgagtctttg ccggaggaaa agcagctcaa   1860

gaacacatgt gcagtcactg gtgtcaccct agataggcaa gggataactc ttctaacaca   1920

aaataagtgt tttatgtttg gaataaagtc aaccttgttt ctactgtttt              1970
```

```
<210> SEQ ID NO 34
<211> LENGTH: 469
<212> TYPE: PRT
<213> ORGANISM: homo sapiens

<400> SEQUENCE: 34

Met His Ser Phe Pro Pro Leu Leu Leu Leu Leu Phe Trp Gly Val Val
1               5                   10                  15

Ser His Ser Phe Pro Ala Thr Leu Glu Thr Gln Glu Gln Asp Val Asp
            20                  25                  30

Leu Val Gln Lys Tyr Leu Glu Lys Tyr Tyr Asn Leu Lys Asn Asp Gly
        35                  40                  45

Arg Gln Val Glu Lys Arg Arg Asn Ser Gly Pro Val Val Glu Lys Leu
    50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
    130                 135                 140
```

-continued

Thr Pro Leu Thr Phe Thr Lys Val Ser Glu Gly Gln Ala Asp Ile Met
145 150 155 160

Ile Ser Phe Val Arg Gly Asp His Arg Asp Asn Ser Pro Phe Asp Gly
165 170 175

Pro Gly Gly Asn Leu Ala His Ala Phe Gln Pro Gly Pro Gly Ile Gly
180 185 190

Gly Asp Ala His Phe Asp Glu Asp Glu Arg Trp Thr Asn Asn Phe Arg
195 200 205

Glu Tyr Asn Leu His Arg Val Ala Ala His Glu Leu Gly His Ser Leu
210 215 220

Gly Leu Ser His Ser Thr Asp Ile Gly Ala Leu Met Tyr Pro Ser Tyr
225 230 235 240

Thr Phe Ser Gly Asp Val Gln Leu Ala Gln Asp Asp Ile Asp Gly Ile
245 250 255

Gln Ala Ile Tyr Gly Arg Ser Gln Asn Pro Val Gln Pro Ile Gly Pro
260 265 270

Gln Thr Pro Lys Ala Cys Asp Ser Lys Leu Thr Phe Asp Ala Ile Thr
275 280 285

Thr Ile Arg Gly Glu Val Met Phe Phe Lys Asp Arg Phe Tyr Met Arg
290 295 300

Thr Asn Pro Phe Tyr Pro Glu Val Glu Leu Asn Phe Ile Ser Val Phe
305 310 315 320

Trp Pro Gln Leu Pro Asn Gly Leu Glu Ala Ala Tyr Glu Phe Ala Asp
325 330 335

Arg Asp Glu Val Arg Phe Phe Lys Gly Asn Lys Tyr Trp Ala Val Gln
340 345 350

Gly Gln Asn Val Leu His Gly Tyr Pro Lys Asp Ile Tyr Ser Ser Phe
355 360 365

Gly Phe Pro Arg Thr Val Lys His Ile Asp Ala Ala Leu Ser Glu Glu
370 375 380

Asn Thr Gly Lys Thr Tyr Phe Phe Val Ala Asn Lys Tyr Trp Arg Tyr
385 390 395 400

Asp Glu Tyr Lys Arg Ser Met Asp Pro Gly Tyr Pro Lys Met Ile Ala
405 410 415

His Asp Phe Pro Gly Ile Gly His Lys Val Asp Ala Val Phe Met Lys
420 425 430

Asp Gly Phe Phe Tyr Phe Phe His Gly Thr Arg Gln Tyr Lys Phe Asp
435 440 445

Pro Lys Thr Lys Arg Ile Leu Thr Leu Gln Lys Ala Asn Ser Trp Phe
450 455 460

Asn Cys Arg Lys Asn
465

<210> SEQ ID NO 35
<211> LENGTH: 2995
<212> TYPE: DNA
<213> ORGANISM: homo sapiens

<400> SEQUENCE: 35
tcttcctcag catttcctgc caacccttt ctggtttctg tttcttcaac ctctttttgt 60
tttatggtcc cttttatggt attttctctt atttctagga aaacattaat gataggtttt 120
tgaacacttc ccctgagtag tctctgttgc aggttgcttt tttgtttgct ctgccctctg 180
tctttcatac tagaggcctt gctcaaatgt ctggtgacct tggcaatgtg ctaatattta 240

-continued

```
aaaaccaaga acaaaaaaat taattggtaa ccctgaacat gagtggagct tgtcaactgg    300
atttcacttt ttgatagtct ggcagagact ttttcttcag gaacttccag cgacaatatc    360
tttaaagctt ttttcttgag ccaatcagat tctctgagaa gttgcttcct atcttctgcc    420
cggaaagaaa aatcttgtct ggcagcattc tcgcagctag gtgatgacta aagcagggat    480
ttttaccatt cagtatggaa gcttttgttt aattcacctg tttttcacct gatttccatc    540
agtcccaagt tgatctctta cactctttct agagactaga ccttactctg ctgctgaaaa    600
gaaagaagag agagaattgg taaaagggtt ttgagactct acttcataaa caagctttaa    660
accagttctt atatctacag cctatcttta ccctcatttc cagaagtacc tggtgctgtc    720
aattcctgtg ctatttggag tttcaagata taaatcaggt tatttcttgg ttttctccat    780
ggatagctta ggatttagct ttctctgctc tgtaaagcta tccatcttac tttctaagct    840
ttcaaatttt tggtagggtt ttctctttcc ctatttggct ttgtatattg atgtcttttt    900
tattttttta ctgccattgg agagggtttt caggaaggag cagaggctaa tgcatgcgtg    960
tcacttacta tctttaactg caagttcaat tctaattaat atctattcca tttgcatcac   1020
aattgattca tgatctcaga tgactcacag agattttacc tacagctgtt atctaggctc   1080
ctttatctat ttttccttcc cggatattgt ttagattcca ttggcttaca tcgagtagag   1140
aacatcagcc atacggaacc tgctgtgagc cttcacttgt acagtccacc ttttgataca   1200
tgccatgcct ttgatcaaag aacaggacat aaaaacaaag tcacaatgac attccatagt   1260
aaatttggaa tcagaactcc aaatgtgagt ataatttctt ctaggtttaa atgctctgta   1320
ggttggcact gttacactgc atgtatgcaa agaatgagat gagtcttaat tcatggataa   1380
ggcccaatat atcttgattg ttttatttaa ctttagcgac tatcttttca atttattttt   1440
aaaaacttat tatgttagat ccaaacatta gttgagaaat ttcaaaatgt atgcttgttt   1500
ttaaagaaaa tgttttcatt tacttgggaa atgagagtga aaactattat ttgatataac   1560
tgttactgcc atggcttact atgcataggt ctaatttgct gggccaacag ggataagttg   1620
cataattaac ctttgtaaag gttattggct gatgatataa ctaaagcaaa ttgtctgttt   1680
tgtttgccaa tgttgcttat tcttagagtt gttatgccat ttataccaca aataagaata   1740
gactatacta acatgttcct ccttgagaaa caagcatttc ctaccaaaaa taaaaaggca   1800
accaacacta atatagcagg gcagtcttct acctctgaaa taagtttgtc atttagagga   1860
atagtcttta attatcagaa tatccagaaa tagacaatgt gtgaaaatgg agacccaagc   1920
aatccttgag tcttaatgaa agcgcagcct ctgagggaag ccagggcaga attttctcat   1980
tatcgctccg cttcatcttt atcttccaca ttccaaaccc taagagatat tcttattgcg   2040
ggaaaaacaa caaggctccc ttgcccttgc tgagttttca tacactgcta caaaagcaga   2100
actatttaga aggagttaaa atgtcttttg taaagtttct tacacagctt tctttttttc   2160
cctttttttac aggcaacttc gggctcgctg gagaacaact aaggggcacc aaagccctct   2220
gaggttttac tttaaggttc gctgtatgtt tgccttggac aaaaaggcta cctaccacgt   2280
gctatccagt aatatactta aataagccaa tacttagatc tactgtaagg cagatgctaa   2340
ttataaggca ttaagtaagc aaatagtgcc ctcagctact gcagaagaaa agtcccactg   2400
aggaaaagaa agtcttgtga tttttaaagg caagttttca agtgctctca tagttctatc   2460
ctctaattcc attaaatcca tactaggagc gtcagtgagg gttttcatag cttttggaaa   2520
tactttggtc tctgaactgt aattagcgca agaagtaaaa acagaaacgt caaacgtcaa   2580
```

-continued

```
atgtttgctt tgttacctgg aggactaaat gtagatgtct ttagtatact ttgtatgttc   2640

ttaaatattg gaagataatt ttgtgaatct gtagatttta ttttttcagt cttaccttac   2700

aaatttcttt tctatgaata atagaggaac tcacggcact ctgccacttg ttaatgaaag   2760

gaagtgcaga ggatttagaa aagtacatga tccccagacc acaacaaacc aaaacataaa   2820

ctcatgtctg tgtcccatgg tcatagtcaa agattttgta ctgctaaaat taccaaataa   2880

tttaaataaa gtggatttga acacaatttg aaggtgtctt tctgattaac atgatagaaa   2940

cttcacataa atcagtttct tagatctaga tatacaaaag cactgtgaca aatgg        2995


<210> SEQ ID NO 36
<211> LENGTH: 200
<212> TYPE: PRT
<213> ORGANISM: homo sapiens

<400> SEQUENCE: 36

Met Glu Gln Thr Glu Val Leu Lys Pro Arg Thr Leu Ala Asp Leu Ile
1               5                   10                  15

Arg Ile Leu His Gln Leu Phe Ala Gly Asp Glu Val Asn Val Glu Glu
            20                  25                  30

Val Gln Ala Ile Met Glu Ala Tyr Glu Ser Asp Pro Ile Glu Trp Ala
        35                  40                  45

Met Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asn Ser His Cys Phe Leu Lys
                85                  90                  95

Met Leu Gln Gly Asn Leu Lys Glu Thr Leu Phe Ala Trp Pro Asp Lys
            100                 105                 110

Lys Ser Asn Glu Met Val Lys Lys Ser Glu Arg Val Leu Arg Glu Asn
        115                 120                 125

Gln Cys Ala Tyr Ile Asn Asp Ser Ile Gly Leu His Arg Val Glu Asn
    130                 135                 140

Ile Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Thr Met Thr Phe His Ser Lys Phe Gly Ile Arg Thr Pro Asn Ala
            180                 185                 190

Thr Ser Gly Ser Leu Glu Asn Asn
        195                 200


<210> SEQ ID NO 37
<211> LENGTH: 1763
<212> TYPE: DNA
<213> ORGANISM: homo sapiens

<400> SEQUENCE: 37

gcactggact gagaaccttc accaaaaaaa tgtctgccca gagacagatg aggtccttca     60

gctccagtgc tgattggttc ttttccaaag gcccatctaa tcctaccacg cacggaaata    120

tccacaggtt tttattcttt ctgccagcta catcagatcc atcaggtccg agctgagttg    180

actaccacta cttttccctt tgtctcaatt atgtcttgga agaaggcttt gcggatcccc    240

ggaggccttc gggcaccaac tgtgaccttg atgctggcga tgctgagcac cccagtggct    300
```

-continued

```
gagggcagag accctcccga ggatttcgtg ctccagttta aggccatgtg ctacttcacc    360

aatgggacgg agcgcgtgcg ttatgtgacc agatacatct ataaccgaga ggaggacgtg    420

cgcttcgaca gcgacgtggg ggtgtatcgg gcggtgacgg cgcaggggcg gcctgacgcc    480

gagtactgga acagccagaa ggacatcctg gagaggaccc gagcggagtt ggacacggtg    540

tgcagacaca actacgaggt ggcgttccgc gggatcttgc agaggagagt ggagcccaca    600

gtgaccatct ccccatccag gacagaggcc ctcaaccacc acaacctgct ggtctgctcg    660

gtgacagatt tctatccagg ccagatcaaa gtccggtggt ttcggaatga ccaggaggag    720

acagctggcg ttgtgtccac ccccttatt aggaacggtg actggacctt ccagatcctg    780

gtgatgctgg aaatgactcc ccagcatgga gacgtctaca cctgccacgt ggagcacccc    840

agcctccaga gccccatcac cgtggagtgg cgggctcagt ctgaatctgc ccagaacaag    900

atgctgagtg gcattggagg cttcgtgctg gggctgatct tcctcgggct gggccttatc    960

atccgtcaaa ggagtcagaa aggacctcaa gggcctccac cagcagggct tctgcactga   1020

ctcctgagac tattttaact aggattggtt atcactcttc tgtgatgcct gcttgtgcct   1080

gcccagaatt cccagctgcc tgtgtcagct tgtcccccga gatcaaagtc ctacagtggc   1140

tgtcacgcag ccaccaggtc atctcctttc atccccaccc caaggcgctg gctgtgactc   1200

tgcttcctgc actgacccag agcctctgcc tgtgcacggc cagctgcgtc tactcaggtc   1260

ccaaggggtt tctgtttcta ttctctcctc agactgctca agagaagcac atgaaaaaca   1320

ttacctgact ttagagcttt tttacataat taaacatgat cctgagttaa aaaaaaaaaa   1380

ggaaatcgct gcagaatgaa ggaatatccc ttgaggtgac ccagccaacc tgtggccaga   1440

aggagggttg taccttgaaa agaccactga aagcattttg gggtgtcaag taagggtggg   1500

cagaggaggt agaaaatcaa ttcaattgtc gcatcattca tggttcttta atattgatgc   1560

tcagtgcatt ggccttagaa tatcccagcc tctcttctgg tttggtgagt gctgtgtaag   1620

taagcatggt agaattgttt ggagacatat atagtgatcc ttggtcactg gtgtttcaaa   1680

cattctggaa agtcacatcg atcaagaata ttttttattt ttaagaaagc ataaccagca   1740

ataaaaatac tatttttgag tct                                            1763


<210> SEQ ID NO 38
<211> LENGTH: 269
<212> TYPE: PRT
<213> ORGANISM: homo sapiens

<400> SEQUENCE: 38

Met Ser Trp Lys Lys Ala Leu Arg Ile Pro Gly Gly Leu Arg Ala Pro
1               5                   10                  15

Thr Val Thr Leu Met Leu Ala Met Leu Ser Thr Pro Val Ala Glu Gly
            20                  25                  30

Arg Asp Pro Pro Glu Asp Phe Val Leu Gln Phe Lys Ala Met Cys Tyr
        35                  40                  45

Phe Thr Asn Gly Thr Glu Arg Val Arg Tyr Val Thr Arg Tyr Ile Tyr
    50                  55                  60

Asn Arg Glu Glu Asp Val Arg Phe Asp Ser Asp Val Gly Val Tyr Arg
65                  70                  75                  80

Ala Val Thr Ala Gln Gly Arg Pro Asp Ala Glu Tyr Trp Asn Ser Gln
                85                  90                  95

Lys Asp Ile Leu Glu Arg Thr Arg Ala Glu Leu Asp Thr Val Cys Arg
            100                 105                 110
```

-continued

```
His Asn Tyr Glu Val Ala Phe Arg Gly Ile Leu Gln Arg Arg Val Glu
        115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Gly Gln Ile Lys
145                 150                 155                 160

Val Arg Trp Phe Arg Asn Asp Gln Glu Glu Thr Ala Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln His Gly Asp Val Tyr Thr Cys His Val Glu
        195                 200                 205

His Pro Ser Leu Gln Ser Pro Ile Thr Val Glu Trp Arg Ala Gln Ser
    210                 215                 220

Glu Ser Ala Gln Asn Lys Met Leu Ser Gly Ile Gly Gly Phe Val Leu
225                 230                 235                 240

Gly Leu Ile Phe Leu Gly Leu Gly Leu Ile Ile Arg Gln Arg Ser Gln
                245                 250                 255

Lys Gly Pro Gln Gly Pro Pro Pro Ala Gly Leu Leu His
            260                 265


<210> SEQ ID NO 39
<211> LENGTH: 1404
<212> TYPE: DNA
<213> ORGANISM: homo sapiens

<400> SEQUENCE: 39

gaattcggct gtcgcactta ctgttcaata gtatatactc tgtatttgaa aaatagatgt      60

atatattcta ggtgataaat taaaaatgaa agaatttaat cattggaaag tattaaatat     120

atattgctta tcttctccaa ggaagaggag ttctctcgta cccatccaaa ctgacctaat     180

tctcaagctg cttcatcttg cttgtactgt aggttcattt gcaatttgta gattatgctc     240

cttcaggatt ggcttttgta aatttctgtt agaagctggt ttctgcattt ttgatttttg     300

tgtatttgga tacattttca tattgtgcag agaaatccat gagttaaaaa attatttttc     360

cctgttttat ttctgcatga acctaagtca cattgaccca gtaattgata tatgtgtgat     420

tattgcaatt aagtataaga aggtagaata tatagtttta ttagacagat gcttcctgaa     480

atattatttt gtatgttttt actatatcct ttttgtgtat ctacagatac aacagacatg     540

caagagaatg gactcagaaa tatgcaatgt aaaaatcaaa aacattttca tatataacca     600

gagtactgta aaatctaggt tttttttcaa cattagcagt aaattgagca ctgtttacct     660

gtttcattgt accatgaaac catttgattt ttaccatttt aaatgtgtct caagcaagac     720

aaaacaaact tccaaaaata cccttaagac tgtgatgaga gcatttatca ttttgtatgc     780

attgagaaag acatttatta tggtttttaa gatacttgga catctgcatc ttcagcttac     840

aagatctaca atgcagctga aaaagcaacc aaattatttt ttgctgaaaa ctagatgttt     900

tttacatgag aaaatactgt atgtgtgtct aagatgtcag ttttataaat ctgtattcag     960

atttcatcct ttgttagctc actttataat ttgtattttt tttctgtata gaactaaata    1020

tattctattt acatgtatgt caactcatta ctttttttcct gtgaacagta ttgaaaaccc   1080

caaccggctg ataattaagt gaattaactg tgtctccctt gtcttaggat attctgtaga    1140

ttgattgcag atttcttaaa tctgaaatga ctttacactg taattctcag catactgatt    1200

atggagaaca cttgttttga attttgttat acttgactta actttattgc aatgtgaatt    1260
```

-continued

```
aattgactgc taagtaggaa gatgtgtaac ttttatttgt tgctattcac atttgaattt   1320

tttcctgtat aggcaatatt atattgacac cttttacaga tcttactgta gcaaaaacca   1380

tataaataaa atgctttttc tgct                                           1404


<210> SEQ ID NO 40
<211> LENGTH: 338
<212> TYPE: PRT
<213> ORGANISM: homo sapiens

<400> SEQUENCE: 40

Met Lys Glu Phe Asn His Trp Lys Val Leu Asn Ile Tyr Cys Leu Ser
1               5                   10                  15

Ser Pro Arg Lys Arg Ser Ser Leu Val Pro Ile Gln Thr Asp Leu Ile
            20                  25                  30

Leu Lys Leu Leu His Leu Ala Cys Thr Val Gly Ser Phe Ala Ile Cys
        35                  40                  45

Arg Leu Cys Ser Phe Arg Ile Gly Phe Cys Lys Phe Leu Leu Glu Ala
    50                  55                  60

Gly Phe Cys Ile Phe Asp Phe Cys Val Phe Gly Tyr Ile Phe Ile Leu
65                  70                  75                  80

Cys Arg Glu Ile His Glu Leu Lys Asn Tyr Phe Ser Leu Phe Tyr Phe
                85                  90                  95

Cys Met Asn Leu Ser His Ile Asp Pro Val Ile Asp Ile Cys Val Ile
            100                 105                 110

Ile Ala Ile Lys Tyr Lys Lys Val Glu Tyr Ile Val Leu Leu Asp Arg
        115                 120                 125

Cys Phe Leu Lys Tyr Tyr Phe Val Cys Phe Tyr Tyr Ile Leu Phe Val
    130                 135                 140

Tyr Leu Gln Ile Gln Gln Thr Cys Lys Arg Met Asp Ser Glu Ile Cys
145                 150                 155                 160

Asn Val Lys Ile Lys Asn Ile Phe Ile Tyr Asn Gln Ser Thr Val Lys
                165                 170                 175

Ser Arg Phe Phe Phe Asn Ile Ser Ser Lys Leu Ser Thr Val Tyr Leu
            180                 185                 190

Phe His Cys Thr Met Lys Pro Phe Asp Phe Tyr His Phe Lys Cys Val
        195                 200                 205

Ser Ser Lys Thr Lys Gln Thr Ser Lys Asn Thr Leu Lys Thr Val Met
    210                 215                 220

Arg Ala Phe Ile Ile Leu Tyr Ala Leu Arg Lys Thr Phe Ile Met Val
225                 230                 235                 240

Phe Lys Ile Leu Gly His Leu His Leu Gln Leu Thr Arg Ser Thr Met
                245                 250                 255

Gln Leu Lys Lys Gln Pro Asn Tyr Phe Leu Leu Lys Thr Arg Cys Phe
            260                 265                 270

Leu His Glu Lys Ile Leu Tyr Val Cys Leu Arg Cys Gln Phe Tyr Lys
        275                 280                 285

Ser Val Phe Arg Phe His Pro Leu Leu Ala His Phe Ile Ile Cys Ile
    290                 295                 300

Phe Phe Leu Tyr Arg Thr Lys Tyr Ile Leu Phe Thr Cys Met Ser Thr
305                 310                 315                 320

His Tyr Phe Phe Pro Val Asn Ser Ile Glu Asn Pro Asn Arg Leu Ile
                325                 330                 335

Ile Lys
```

-continued

<210> SEQ ID NO 41
<211> LENGTH: 2881
<212> TYPE: DNA
<213> ORGANISM: homo sapiens

<400> SEQUENCE: 41
acagaagtgc tagaagccag tgctcgtgaa ctaaggagaa aaagaacaga caagggaaca 60
gcctggacat ggcatcagag atccacatga caggcccaat gtgcctcatt gagaacacta 120
atgggcgact gatggcgaat ccagaagctc tgaagatcct ttctgccatt acacagccta 180
tggtggtggt ggcaattgtg ggcctctacc gcacaggcaa atcctacctg atgaacaagc 240
tggctggaaa gaaaaagggc ttctctctgg gctccacggt gcagtctcac actaaaggaa 300
tctggatgtg gtgtgtgccc caccccaaga agccaggcca catcctagtt ctgctggaca 360
ccgagggtct gggagatgta gagaagggtg acaaccagaa tgactcctgg atcttcgccc 420
tggccgtcct cctgagcagc accttcgtgt acaatagcat aggaaccatc aaccagcagg 480
ctatggacca actgtactat gtgacagagc tgacacatag aatccgatca aaatcctcac 540
ctgatgagaa tgagaatgag gttgaggatt cagctgactt tgtgagcttc ttcccagact 600
ttgtgtggac actgagagat ttctccctgg acttggaagc agatggacaa cccctcacac 660
cagatgagta cctgacatac tccctgaagc tgaagaaagg taccagtcaa aaagatgaaa 720
cttttaacct gcccagactc tgtatccgga aattcttccc aaagaaaaaa tgctttgtct 780
ttgatcggcc cgttcaccgc aggaagcttg cccagctcga gaaactacaa gatgaagagc 840
tggaccccga atttgtgcaa caagtagcag acttctgttc ctacatcttt agtaattcca 900
aaactaaaac tctttcagga ggcatccagg tcaacgggcc tcgtctagag agcctggtgc 960
tgacctacgt caatgccatc agcagtgggg atctgccgtg catggagaac gcagtcctgg 1020
ccttggccca gatagagaac tcagctgcag tgcaaaaggc tattgcccac tatgaacagc 1080
agatgggcca gaaggtgcag ctgcccacag aaagcctcca ggagctgctg gacctgcaca 1140
gggacagtga gagagaggcc attgaagtct tcatcaggag ttccttcaaa gatgtggacc 1200
atctatttca aaaggagtta gcggcccagc tagaaaaaaa gcgggatgac ttttgtaaac 1260
agaatcagga agcatcatca gatcgttgct caggtttact tcaggtcatt ttcagtcctc 1320
tagaagaaga agtgaaggcg ggaatttatt cgaaaccagg gggctatcgt ctctttgttc 1380
agaagctaca agacctgaag aaaaagtact atgaggaacc gaggaagggg atacaggctg 1440
aagagattct gcagacatac ttgaaatcca aggagtctat gactgatgca attctccaga 1500
cagaccagac tctcacagaa aaagaaaagg agattgaagt ggaacgtgtg aaagctgagt 1560
ctgcacaggc ttcagcaaaa atgttgcagg aaatgcaaag aaagaatgag cagatgatgg 1620
aacagaagga gaggagttat caggaacact tgaaacaact gactgagaag atggagaacg 1680
acagggtcca gttgctgaaa gagcaagaga ggaccctcgc tcttaaactt caggaacagg 1740
agcaactact aaaagaggga tttcaaaaag aaagcagaat aatgaaaaat gagatacagg 1800
atctccagac gaaaatgaga cgacgaaagg catgtaccat aagctaaaga ccagagcctt 1860
cctgtcaccc ctaaccaagg cataattgaa acaattttag aatttggaac aagcgtcact 1920
acatttgata ataattagat cttgcatcat aacaccaaaa gtttataaag gcatgtggta 1980
caatgatcaa aatcatgttt tttcttaaaa aaaaaaaaaa gactgtaaat tgtgcaacaa 2040
agatgcattt acctctgtat caactcagga aatctcataa gctggtacca ctcaggagaa 2100

-continued

```
gtttattctt ccagatgacc agcagtagac aaatggatac tgagcagagt cttaggtaaa   2160

agtcttggga aatatttggg cattggtctg gccaagtcta caatgtccca atatcaagga   2220

caaccaccct agcttcttag tgaagacaat gtacagttat ccattagatc aagactacac   2280

ggtctatgag caataatgtg atttctggac attgcccatg tataatcctc actgatgatt   2340

tcaagctaaa gcaaaccacc ttatacagag atctagaatc tctttatgtt ctccagagga   2400

aggtggaaga aaccatgggc aggagtagga attgagtgat aaacaattgg gctaatgaag   2460

aaaacttctc ttattgttca gttcatccag attataactt caatgggaca ctttagacca   2520

ttagacaatt gacactggat taaacaaatt cacataatgc caaatacaca atgtatttat   2580

agcaacgtat aatttgcaaa gatggacttt aaaagatgct gtgtaactaa actgaaataa   2640

ttcaattact tattatttag aatgttaaag cttatgatag tcttttctaa ttcttaacac   2700

tcatacttga aatctttccg agtttcccca gaagagaata tgggattttt tttgacattt   2760

ttgacccatt taataatgct cttgtgttta cctagtatat gtagactttg tcttatgtgt   2820

caaaagtcct aggaaagtgg ttgatgtttc ttatagcaat taaaaattat ttttgaactg   2880

a                                                                   2881
```

<210> SEQ ID NO 42
<211> LENGTH: 592
<212> TYPE: PRT
<213> ORGANISM: homo sapiens

<400> SEQUENCE: 42

```
Met Ala Ser Glu Ile His Met Thr Gly Pro Met Cys Leu Ile Glu Asn
1               5                   10                  15

Thr Asn Gly Arg Leu Met Ala Asn Pro Glu Ala Leu Lys Ile Leu Ser
            20                  25                  30

Ala Ile Thr Gln Pro Met Val Val Val Ala Ile Val Gly Leu Tyr Arg
        35                  40                  45

Thr Gly Lys Ser Tyr Leu Met Asn Lys Leu Ala Gly Lys Lys Lys Gly
    50                  55                  60

Phe Ser Leu Gly Ser Thr Val Gln Ser His Thr Lys Gly Ile Trp Met
65                  70                  75                  80

Trp Cys Val Pro His Pro Lys Lys Pro Gly His Ile Leu Val Leu Leu
                85                  90                  95

Asp Thr Glu Gly Leu Gly Asp Val Glu Lys Gly Asp Asn Gln Asn Asp
            100                 105                 110

Ser Trp Ile Phe Ala Leu Ala Val Leu Leu Ser Ser Thr Phe Val Tyr
        115                 120                 125

Asn Ser Ile Gly Thr Ile Asn Gln Gln Ala Met Asp Gln Leu Tyr Tyr
    130                 135                 140

Val Thr Glu Leu Thr His Arg Ile Arg Ser Lys Ser Ser Pro Asp Glu
145                 150                 155                 160

Asn Glu Asn Glu Val Glu Asp Ser Ala Asp Phe Val Ser Phe Phe Pro
                165                 170                 175

Asp Phe Val Trp Thr Leu Arg Asp Phe Ser Leu Asp Leu Glu Ala Asp
            180                 185                 190

Gly Gln Pro Leu Thr Pro Asp Glu Tyr Leu Thr Tyr Ser Leu Lys Leu
        195                 200                 205

Lys Lys Gly Thr Ser Gln Lys Asp Glu Thr Phe Asn Leu Pro Arg Leu
    210                 215                 220

Cys Ile Arg Lys Phe Phe Pro Lys Lys Lys Cys Phe Val Phe Asp Arg
```

-continued

```
225                 230                 235                 240

Pro Val His Arg Arg Lys Leu Ala Gln Leu Glu Lys Leu Gln Asp Glu
                245                 250                 255

Glu Leu Asp Pro Glu Phe Val Gln Gln Val Ala Asp Phe Cys Ser Tyr
            260                 265                 270

Ile Phe Ser Asn Ser Lys Thr Lys Thr Leu Ser Gly Gly Ile Gln Val
        275                 280                 285

Asn Gly Pro Arg Leu Glu Ser Leu Val Leu Thr Tyr Val Asn Ala Ile
    290                 295                 300

Ser Ser Gly Asp Leu Pro Cys Met Glu Asn Ala Val Leu Ala Leu Ala
305                 310                 315                 320

Gln Ile Glu Asn Ser Ala Ala Val Gln Lys Ala Ile Ala His Tyr Glu
                325                 330                 335

Gln Gln Met Gly Gln Lys Val Gln Leu Pro Thr Glu Ser Leu Gln Glu
            340                 345                 350

Leu Leu Asp Leu His Arg Asp Ser Glu Arg Glu Ala Ile Glu Val Phe
        355                 360                 365

Ile Arg Ser Ser Phe Lys Asp Val Asp His Leu Phe Gln Lys Glu Leu
    370                 375                 380

Ala Ala Gln Leu Glu Lys Lys Arg Asp Asp Phe Cys Lys Gln Asn Gln
385                 390                 395                 400

Glu Ala Ser Ser Asp Arg Cys Ser Gly Leu Leu Gln Val Ile Phe Ser
                405                 410                 415

Pro Leu Glu Glu Glu Val Lys Ala Gly Ile Tyr Ser Lys Pro Gly Gly
            420                 425                 430

Tyr Arg Leu Phe Val Gln Lys Leu Gln Asp Leu Lys Lys Lys Tyr Tyr
        435                 440                 445

Glu Glu Pro Arg Lys Gly Ile Gln Ala Glu Glu Ile Leu Gln Thr Tyr
    450                 455                 460

Leu Lys Ser Lys Glu Ser Met Thr Asp Ala Ile Leu Gln Thr Asp Gln
465                 470                 475                 480

Thr Leu Thr Glu Lys Glu Lys Glu Ile Glu Val Glu Arg Val Lys Ala
                485                 490                 495

Glu Ser Ala Gln Ala Ser Ala Lys Met Leu Gln Glu Met Gln Arg Lys
            500                 505                 510

Asn Glu Gln Met Met Glu Gln Lys Glu Arg Ser Tyr Gln Glu His Leu
        515                 520                 525

Lys Gln Leu Thr Glu Lys Met Glu Asn Asp Arg Val Gln Leu Leu Lys
    530                 535                 540

Glu Gln Glu Arg Thr Leu Ala Leu Lys Leu Gln Glu Gln Glu Gln Leu
545                 550                 555                 560

Leu Lys Glu Gly Phe Gln Lys Glu Ser Arg Ile Met Lys Asn Glu Ile
                565                 570                 575

Gln Asp Leu Gln Thr Lys Met Arg Arg Arg Lys Ala Cys Thr Ile Ser
            580                 585                 590


<210> SEQ ID NO 43
<211> LENGTH: 4003
<212> TYPE: DNA
<213> ORGANISM: homo sapiens

<400> SEQUENCE: 43

attaaacctc tcgccgagcc cctccgcaga ctctgcgccg gaaagtttca tttgctgtat     60

gccatcctcg agagctgtct aggttaacgt tcgcactctg tgtatataac ctcgacagtc    120
```

-continued

```
ttggcaccta acgtgctgtg cgtagctgct cctttggttg aatccccagg cccttgttgg    180
ggcacaaggt ggcaggatgt ctcagtggta cgaacttcag cagcttgact caaaattcct    240
ggagcaggtt caccagcttt atgatgacag ttttcccatg gaaatcagac agtacctggc    300
acagtggtta gaaaagcaag actgggagca cgctgccaat gatgtttcat ttgccaccat    360
ccgttttcat gacctcctgt cacagctgga tgatcaatat agtcgctttt ctttggagaa    420
taacttcttg ctacagcata acataaggaa aagcaagcgt aatcttcagg ataattttca    480
ggaagaccca atccagatgt ctatgatcat ttacagctgt ctgaaggaag aaaggaaaat    540
tctggaaaac gcccagagat ttaatcaggc tcagtcgggg aatattcaga gcacagtgat    600
gttagacaaa cagaaagagc ttgacagtaa agtcagaaat gtgaaggaca aggttatgtg    660
tatagagcat gaaatcaaga gcctggaaga tttacaagat gaatatgact tcaaatgcaa    720
aaccttgcag aacagagaac acgagaccaa tggtgtggca aagagtgatc agaaacaaga    780
acagctgtta ctcaagaaga tgtatttaat gcttgacaat aagagaaagg aagtagttca    840
caaaataata gagttgctga atgtcactga acttacccag aatgccctga ttaatgatga    900
actagtggag tggaagcgga gacagcagag cgcctgtatt ggggggccgc ccaatgcttg    960
cttggatcag ctgcagaact ggttcactat agttgcggag agtctgcagc aagttcggca   1020
gcagcttaaa aagttggagg aattggaaca gaaatacacc tacgaacatg accctatcac   1080
aaaaaacaaa caagtgttat gggaccgcac cttcagtctt ttccagcagc tcattcagag   1140
ctcgtttgtg gtggaaagac agccctgcat gccaacgcac cctcagaggc cgctggtctt   1200
gaagacaggg gtccagttca ctgtgaagtt gagactgttg gtgaaattgc aagagctgaa   1260
ttataatttg aaagtcaaag tcttatttga taaagatgtg aatgagagaa atacagtaaa   1320
aggatttagg aagttcaaca ttttgggcac gcacacaaaa gtgatgaaca tggaggagtc   1380
caccaatggc agtctggcgg ctgaatttcg gcacctgcaa ttgaaagaac agaaaaatgc   1440
tggcaccaga acgaatgagg gtcctctcat cgttactgaa gagcttcact cccttagttt   1500
tgaaacccaa ttgtgccagc ctggtttggt aattgacctc gagacgacct ctctgcccgt   1560
tgtggtgatc tccaacgtca gccagctccc gagcggttgg gcctccatcc tttggtacaa   1620
catgctggtg gcggaaccca ggaatctgtc cttcttcctg actccaccat gtgcacgatg   1680
ggctcagctt tcagaagtgc tgagttggca gttttcttct gtcaccaaaa gaggtctcaa   1740
tgtggaccag ctgaacatgt tgggagagaa gcttcttggt cctaacgcca gccccgatgg   1800
tctcattccg tggacgaggt tttgtaagga aaatataaat gataaaaatt ttcccttctg   1860
gctttggatt gaaagcatcc tagaactcat taaaaaacac ctgctccctc tctggaatga   1920
tgggtgcatc atgggcttca tcagcaagga gcgagagcgt gccctgttga aggaccagca   1980
gccggggacc ttcctgctgc ggttcagtga gagctcccgg gaaggggcca tcacattcac   2040
atgggtggag cggtcccaga acggaggcga acctgacttc catgcggttg aaccctacac   2100
gaagaaagaa ctttctgctg ttactttccc tgacatcatt cgcaattaca aagtcatggc   2160
tgctgagaat attcctgaga atcccctgaa gtatctgtat ccaaatattg acaaagacca   2220
tgcctttgga aagtattact ccaggccaaa ggaagcacca gagccaatgg aacttgatgg   2280
ccctaaagga actggatata tcaagactga gttgatttct gtgtctgaag ttcacccttc   2340
tagacttcag accacagaca acctgctccc catgtctcct gaggagtttg acgaggtgtc   2400
tcggatagtg ggctctgtag aattcgacag tatgatgaac acagtataga gcatgaattt   2460
```

-continued

```
ttttcatctt ctctggcgac agttttcctt ctcatctgtg attccctcct gctactctgt   2520

tccttcacat cctgtgtttc tagggaaatg aaagaaaggc cagcaaattc gctgcaacct   2580

gttgatagca agtgaatttt tctctaactc agaaacatca gttactctga agggcatcat   2640

gcatcttact gaaggtaaaa ttgaaaggca ttctctgaag agtgggtttc acaagtgaaa   2700

aacatccaga tacacccaaa gtatcaggac gagaatgagg gtcctttggg aaaggagaag   2760

ttaagcaaca tctagcaaat gttatgcata aagtcagtgc ccaactgtta taggttgttg   2820

gataaatcag tggttattta gggaactgct tgacgtagga acggtaaatt tctgtgggag   2880

aattcttaca tgttttcttt gctttaagtg taactggcag ttttccattg gtttacctgt   2940

gaaatagttc aaagccaagt ttatatacaa ttatatcagt cctctttcaa aggtagccat   3000

catggatctg gtagggggaa aatgtgtatt ttattacatc tttcacattg gctatttaaa   3060

gacaaagaca aattctgttt cttgagaaga gaatattagc tttactgttt gttatggctt   3120

aatgacacta gctaatatca atagaaggat gtacatttcc aaattcacaa gttgtgtttg   3180

atatccaaag ctgaatacat tctgctttca tcttggtcac atacaattat ttttacagtt   3240

ctcccaaggg agttaggcta ttcacaacca ctcattcaaa agttgaaatt aaccatagat   3300

gtagataaac tcagaaattt aattcatgtt tcttaaatgg gctactttgt cctttttgtt   3360

attagggtgg tatttagtct attagccaca aaattgggaa aggagtagaa aaagcagtaa   3420

ctgacaactt gaataataca ccagagataa tatgagaatc agatcatttc aaaactcatt   3480

tcctatgtaa ctgcattgag aactgcatat gtttcgctga tatatgtgtt tttcacattt   3540

gcgaatggtt ccattctctc tcctgtactt tttccagaca ctttttttgag tggatgatgt   3600

ttcgtgaagt atactgtatt tttacctttt tccttcctta tcactgacac aaaaagtaga   3660

ttaagagatg ggtttgacaa ggttcttccc ttttacatac tgctgtctat gtggctgtat   3720

cttgtttttc cactactgct accacaacta tattatcatg caaatgctgt attcttcttt   3780

ggtggagata aagatttctt gagttttgtt ttaaaattaa agctaaagta tctgtattgc   3840

attaaatata atatcgacac agtgctttcc gtggcactgc atacaatctg aggcctcctc   3900

tctcagtttt tatatagatg gcgagaacct aagtttcagt tgattttaca attgaaatga   3960

ctaaaaaaca aagaagacaa cattaaaaac aatattgttt cta                     4003
```

<210> SEQ ID NO 44
<211> LENGTH: 750
<212> TYPE: PRT
<213> ORGANISM: homo sapiens

<400> SEQUENCE: 44

```
Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
```

-continued

```
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525
```

-continued

Pro Asn Ala Ser Pro Asp Gly Leu Ile Pro Trp Thr Arg Phe Cys Lys
    530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750

<210> SEQ ID NO 45
<211> LENGTH: 2303
<212> TYPE: DNA
<213> ORGANISM: homo sapiens

<400> SEQUENCE: 45
cccggcgtcc cgtcgagccc agccccgccg ggggcgctcc tcgccgcccg cacgccctcc 60
ccagccatgt cgtccatcct gcctttcact cccccgatcg tgaagcgcct gctgggctgg 120
aagaagggcg agcagaacgg gcaggaggag aaatggtgcg agaaggcggt caagagcctg 180
gtcaagaaac tcaagaagac ggggcagctg gacgagctgg agaaggccat caccacgcag 240
aacgtcaaca ccaagtgcat caccatcccc aggtccctgg atggccggtt gcaggtgtcc 300
catcggaagg ggctccctca tgtcatctac tgccgcctgt ggcgatggcc agacctgcac 360
agccaccacg agctgcgggc catggagctg tgtgagttcg ccttcaatat gaagaaggac 420
gaggtctgcg tgaatcccta ccactaccag agagtagaga caccagttct acctcctgtg 480
ttggtgccac gccacacaga gatcccggcc gagttccccc cactggacga ctacagccat 540
tccatccccg aaaacactaa cttccccgca ggcatcgagc cccagagcaa tattccagag 600
accccacccc ctggctacct gagtgaagat ggagaaacca gtgaccacca gatgaaccac 660
agcatggacg caggttctcc aaacctatcc ccgaatccga tgtccccagc acataataac 720
ttggacctgc agccagttac ctactgcgag ccggccttct ggtgctccat ctcctactac 780
gagctgaacc agcgcgtcgg ggagacattc cacgcctcgc agccatccat gactgtggat 840

-continued

```
ggcttcaccg acccctccaa ttcggagcgc ttctgcctag ggctgctctc caatgtcaac    900

aggaatgcag cagtggagct gacacggaga cacatcggaa gaggcgtgcg gctctactac    960

atcggagggg aggtcttcgc agagtgcctc agtgacagcg ctatttttgt ccagtctccc   1020

aactgtaacc agcgctatgg ctggcacccg gccaccgtct gcaagatccc accaggatgc   1080

aacctgaaga tcttcaacaa ccaggagttc gctgccctcc tggcccagtc ggtcaaccag   1140

ggctttgagg ctgtctacca gttgacccga atgtgcacca tccgcatgag cttcgtcaaa   1200

ggctggggag cggagtacag gagacagact gtgaccagta ccccctgctg gattgagctg   1260

cacctgaatg ggcctttgca gtggcttgac aaggtcctca cccagatggg ctccccaagc   1320

atccgctgtt ccagtgtgtc ttagagacat caagtatggt aggggagggc aggcttgggg   1380

aaaatggcca tacaggaggt ggagaaaatt ggaactctac tcaacccatt gttgtcaagg   1440

aagaagaaat ctttctccct caactgaagg ggtgcaccca cctgttttct gaaacacacg   1500

agcaaaccca gaggtggatg ttatgaacag ctgtgtctgc caaacacatt taccctttgg   1560

ccccactttg aagggcaaga aatggcgtct gctctggtgg cttaagtgag cagaacaggt   1620

agtattacac caccggcacc ctccccccag actctttttt tgagtgacag ctttctggga   1680

tgtcacagtc caaccagaaa cgcccctctg tctaggactg cagtgtggag ttcaccttgg   1740

aagggcgttc taggtaggaa gagcccgcac gatgcagacc tcatgcccag ctctctgacg   1800

cttgtgacag tgcctcttcc agtgaacatt cccagcccag ccccgccccg ttgtgagctg   1860

gatagacttg ggatggggag ggagggagtt ttgtctgtct ccctcccctc tcagaacata   1920

ctgattggga ggtgcgtgtt cagcagaacc tgcacacagg acagcgggaa aaatcgatga   1980

gcgccacctc tttaaaaact cacttacgtt gtccttttc actttgaaaa gttggaagga    2040

ctgctgaggc ccagtgcata tgcaatgtat agtgtctatt atcacattaa tctcaaagag   2100

attcgaatga cggtaagtgt tctcatgaag caggaggccc ttgtcgtggg atggcatttg   2160

gtctcaggca gcaccacact gggtgcgtct ccagtcatct gtaagagctt gctccagatt   2220

ctgatgcata cggctatatt ggtttatgta gtcagttgca ttcattaaat caactttatc   2280

atatgctcaa aaaaaaaaaa aag                                           2303
```

<210> SEQ ID NO 46
<211> LENGTH: 425
<212> TYPE: PRT
<213> ORGANISM: homo sapiens

<400> SEQUENCE: 46

```
Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
            20                  25                  30

Lys Ala Val Lys Ser Leu Val Lys Lys Leu Lys Lys Thr Gly Gln Leu
        35                  40                  45

Asp Glu Leu Glu Lys Ala Ile Thr Thr Gln Asn Val Asn Thr Lys Cys
    50                  55                  60

Ile Thr Ile Pro Arg Ser Leu Asp Gly Arg Leu Gln Val Ser His Arg
65                  70                  75                  80

Lys Gly Leu Pro His Val Ile Tyr Cys Arg Leu Trp Arg Trp Pro Asp
                85                  90                  95

Leu His Ser His His Glu Leu Arg Ala Met Glu Leu Cys Glu Phe Ala
            100                 105                 110
```

-continued

```
Phe Asn Met Lys Lys Asp Glu Val Cys Val Asn Pro Tyr His Tyr Gln
        115                 120                 125

Arg Val Glu Thr Pro Val Leu Pro Pro Val Leu Val Pro Arg His Thr
    130                 135                 140

Glu Ile Pro Ala Glu Phe Pro Pro Leu Asp Asp Tyr Ser His Ser Ile
145                 150                 155                 160

Pro Glu Asn Thr Asn Phe Pro Ala Gly Ile Glu Pro Gln Ser Asn Ile
                165                 170                 175

Pro Glu Thr Pro Pro Pro Gly Tyr Leu Ser Glu Asp Gly Glu Thr Ser
            180                 185                 190

Asp His Gln Met Asn His Ser Met Asp Ala Gly Ser Pro Asn Leu Ser
        195                 200                 205

Pro Asn Pro Met Ser Pro Ala His Asn Asn Leu Asp Leu Gln Pro Val
    210                 215                 220

Thr Tyr Cys Glu Pro Ala Phe Trp Cys Ser Ile Ser Tyr Tyr Glu Leu
225                 230                 235                 240

Asn Gln Arg Val Gly Glu Thr Phe His Ala Ser Gln Pro Ser Met Thr
                245                 250                 255

Val Asp Gly Phe Thr Asp Pro Ser Asn Ser Glu Arg Phe Cys Leu Gly
            260                 265                 270

Leu Leu Ser Asn Val Asn Arg Asn Ala Ala Val Glu Leu Thr Arg Arg
        275                 280                 285

His Ile Gly Arg Gly Val Arg Leu Tyr Tyr Ile Gly Gly Glu Val Phe
    290                 295                 300

Ala Glu Cys Leu Ser Asp Ser Ala Ile Phe Val Gln Ser Pro Asn Cys
305                 310                 315                 320

Asn Gln Arg Tyr Gly Trp His Pro Ala Thr Val Cys Lys Ile Pro Pro
                325                 330                 335

Gly Cys Asn Leu Lys Ile Phe Asn Asn Gln Glu Phe Ala Ala Leu Leu
            340                 345                 350

Ala Gln Ser Val Asn Gln Gly Phe Glu Ala Val Tyr Gln Leu Thr Arg
        355                 360                 365

Met Cys Thr Ile Arg Met Ser Phe Val Lys Gly Trp Gly Ala Glu Tyr
    370                 375                 380

Arg Arg Gln Thr Val Thr Ser Thr Pro Cys Trp Ile Glu Leu His Leu
385                 390                 395                 400

Asn Gly Pro Leu Gln Trp Leu Asp Lys Val Leu Thr Gln Met Gly Ser
                405                 410                 415

Pro Ser Ile Arg Cys Ser Ser Val Ser
            420                 425
```

<210> SEQ ID NO 47
<211> LENGTH: 4208
<212> TYPE: DNA
<213> ORGANISM: homo sapiens

<400> SEQUENCE: 47

```
tctttaagat ttgtagctac taagaaagaa aggagctttt tttccttggg ccttcaaact      60

gaaagaaccg catgagcctg acggcgcatg gtcttaacat caggctgtgc aggaagaagc     120

tatctgcaga tggatgccag cacacacaag gaagcagagc tctggcaaca ttgagtcaaa     180

gcaaggacac aacatcagag ggacggcaga gaatccttgt gtgtagtctt tggtggcagt     240

ttgaaaattg caaggaggga ctttaagact acttctgatt tgcaaagatg gtctgtgctc     300

cgagcaggct aaagtgactg gacgagacgc actgttggag aaataaaaat gacttcccat     360
```

-continued

```
tatgtgattg ccatctttgc cctgatgagc ttctgtttag ccactgcagg tccagagcct    420
ggtgcactgt gtgaactgtc acctgtcagt gcctcccatc ctgtccaggc cttgatggag    480
agcttcactg ttttgtcagg ctgtgccagc agaggcacaa ctgggctgcc acaggaggtg    540
catgtcctga atctcgcact gcgccagggg cctggccagc tacagagaga ggtcacactt    600
cacctgaatc ccatctcctc agtccacatc caccacaagt ctgttgtgtt cctgctcaac    660
tccccacacc ccctggtgtg gcatctgaag acagagagac ttgccactgg ggtctccaga    720
ctgtttttgg tgtctgaggg ttctgtggtc cagttttcat cagcaaactt ctccttgaca    780
gcagaaacag aagaaaggaa cttcccccat ggaaatgaac atctgttaaa ttgggcccga    840
aaagagtatg gagcagttac ttcattcacc gaactcaaga tagcaagaaa catttatatt    900
aaagtggggg aagatcaagt gttccctcca aagtgcaaca tagggaagaa ttttctctca    960
ctcaattacc ttgctgagta ccttcaaccc aaagcagcag aagggtgtgt gatgtccagc   1020
cagccccaga atgaggaagt acacatcatc gagctaatca cccccaactc taacccctac   1080
agtgctttcc aggtggatat aacaattgat ataagacctt ctcaagagga tcttgaagtg   1140
gtcaaaaatc tcatcctgat cttgaagtgc aaaaagtctg tcaactgggt gatcaaatct   1200
tttgatgtta agggaagcct gaaaattatt gctcctaaca gtattggctt tggaaaagag   1260
agtgaaagat ctatgacaat gaccaaatca ataagagatg acattccttc aacccaaggg   1320
aatctggtga agtgggcttt ggacaatggc tatagtccaa taacttcata cacaatggct   1380
cctgtggcaa tagtatttca tcttcggctt gaaaataatg aggagatggg agatgaggaa   1440
gtccacacta ttcctcctga gctacggatc ctgctggacc ctggtgccct gcctgccctg   1500
cagaacccgc ccatccgggg aggggaaggc caaaatggag gccttccgtt tcctttccca   1560
gatatttcca ggagagtctg gaatgaagag ggagaagatg ggctccctcg gccaaaggac   1620
cctgtcattc ccagcataca actgtttcct ggtctcagag agccagaaga ggtgcaaggg   1680
agcgtggata ttgccctgtc tgtcaaatgt gacaatgaga agatgatcgt ggctgtagaa   1740
aaagattctt ttcaggccag tggctactcg gggatggacg tcaccctgtt ggatcctacc   1800
tgcaaggcca agatgaatgg cacacacttt gttttggagt ctcctctgaa tggctgcggt   1860
actcggcccc ggtggtcagc ccttgatggt gtggtctact ataactccat tgtgatacag   1920
gttccagccc ttggggacag tagtggttgg ccagatggtt atgaagatct ggagtcaggt   1980
gataatggat ttccgggaga tatggatgaa ggagatgctt ccctgttcac ccgacctgaa   2040
atcgtggtgt ttaattgcag ccttcagcag gtgaggaacc ccagcagctt ccaggaacag   2100
ccccacggaa acatcacctt caacatggag ctatacaaca ctgacctctt tttggtgccc   2160
tcccagggcg tcttctctgt gccagagaat ggacacgttt atgttgaggt atctgttact   2220
aaggctgaac aagaactggg atttgccatc caaacgtgct ttatctctcc atattcgaac   2280
cctgatagga tgtctcatta caccattatt gagaatattt gtcctaaaga tgaatctgtg   2340
aaattctaca gtcccaagag agtgcacttc cctatcccgc aagctgacat ggataagaag   2400
cgattcagct ttgtcttcaa gcctgtcttc aacacctcac tgctctttct acagtgtgag   2460
ctgacgctgt gtacgaagat ggagaagcac ccccagaagt tgcctaagtg tgtgcctcct   2520
gacgaagcct gcacctcgct ggacgcctcg ataatctggg ccatgatgca gaataagaag   2580
acgttcacca agccccttgc tgtgatccac catgaagcag aatctaaaga aaaaggtcca   2640
agcatgaagg aaccaaatcc aatttctcca ccaattttcc atggtctgga caccctaacc   2700
```

-continued

```
gtgatgggca ttgcgtttgc agcctttgtg atcggagcac tcctgacggg ggccttgtgg   2760

tacatctatt ctcacacagg ggagacagca ggaaggcagc aagtccccac ctccccgcca   2820

gcctcggaaa acagcagtgc tgcccacagc atcggcagca cgcagagcac gccttgctcc   2880

agcagcagca cggcctagcc caacccaggc ccaacccggc ccaacccagc ccagcccagc   2940

tcagctcagc tactccaagg gcaggaccaa tggctgagcc tcgtgtccag actcagaggg   3000

ctggattttg gttcccttgt aaagacagag tgaatttcag tataaagatc acccgttgta   3060

ttcaccccac acccagggct agtataaaca tgaccctggg cttctgtacc acactagaat   3120

tcatgtgaga aagctaaaat ggtggtcttc tccaccagcc cctcacaggc ttgggggttt   3180

tctatgtgaa acacatgcca gtttttaaaa tgctgctttg tccaggtgag aacatccata   3240

atttggggcc ctgagtttta cccagactca aggagttggt aaagggttaa tagccagata   3300

gtagaaccag tgaggagatg cggccaaaga ttctttatat ctgaaccaag atgtaaaaca   3360

agaaatgctt tgaggctttc taagcgatcc tcctgtctaa tttgcacctt tgtctggatg   3420

cactcttctg accttgctgc cacaacctgt ggggtctgat gtgtcccaag atgggtgctg   3480

ccctcaggga ctgcaccctg acaagtgtta aggcaacatt ccttgcttgt gccctgggcc   3540

aaaaccaatg ctgatgacct tatcagcttc ctgtttcttc ccatactgca tacaccactg   3600

caaaatgtct taatgcaaat tttgtatttc ttacaggcct acagaaattg aaaatgacca   3660

aaatcaggaa ccacagattt gtgcccattc ctaatatttt gttctgcaaa ttaatgtata   3720

atttgaggtg aaattcagtt ataaagtcaa ggacgaattt gcacagtgat atatttctat   3780

gtgtatgcaa gtacaagtat ataatatgtc acctggcaca ttcattttct cagttgaaga   3840

agagaaaatt tgaaaatgtc cttatgcttt tagagttgca acttaagtat atttggtagg   3900

gtgagtgttt ccactcaaaa tatgtcaact taaaaaaaaa taggcccttt cataaaaacc   3960

aaactgtagc aagatgcaaa tgcatggcaa atctgtcggt ctccagttgg ttatctgaat   4020

agtgtcacca attccaccaa gacagtgctg agattggaaa gggcactcat ttggattgcc   4080

ttacttctct tgccttaaat atatcccata tatttaatat gtcaaaaagg gcttgaggtg   4140

aatttcatta aatggaataa tatgatgcca ctttgcagct aaaataagct cagtgatacc   4200

tccttgtt                                                            4208


<210> SEQ ID NO 48
<211> LENGTH: 849
<212> TYPE: PRT
<213> ORGANISM: homo sapiens

<400> SEQUENCE: 48

Met Thr Ser His Tyr Val Ile Ala Ile Phe Ala Leu Met Ser Phe Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Ala Leu Arg Gln Gly Pro Gly Gln Leu Gln Arg
65                  70                  75                  80

Glu Val Thr Leu His Leu Asn Pro Ile Ser Ser Val His Ile His His
                85                  90                  95

Lys Ser Val Val Phe Leu Leu Asn Ser Pro His Pro Leu Val Trp His
```

-continued

```
            100                 105                 110

Leu Lys Thr Glu Arg Leu Ala Thr Gly Val Ser Arg Leu Phe Leu Val
        115                 120                 125

Ser Glu Gly Ser Val Val Gln Phe Ser Ser Ala Asn Phe Ser Leu Thr
    130                 135                 140

Ala Glu Thr Glu Glu Arg Asn Phe Pro His Gly Asn Glu His Leu Leu
145                 150                 155                 160

Asn Trp Ala Arg Lys Glu Tyr Gly Ala Val Thr Ser Phe Thr Glu Leu
                165                 170                 175

Lys Ile Ala Arg Asn Ile Tyr Ile Lys Val Gly Glu Asp Gln Val Phe
            180                 185                 190

Pro Pro Lys Cys Asn Ile Gly Lys Asn Phe Leu Ser Leu Asn Tyr Leu
        195                 200                 205

Ala Glu Tyr Leu Gln Pro Lys Ala Ala Glu Gly Cys Val Met Ser Ser
    210                 215                 220

Gln Pro Gln Asn Glu Glu Val His Ile Ile Glu Leu Ile Thr Pro Asn
225                 230                 235                 240

Ser Asn Pro Tyr Ser Ala Phe Gln Val Asp Ile Thr Ile Asp Ile Arg
                245                 250                 255

Pro Ser Gln Glu Asp Leu Glu Val Val Lys Asn Leu Ile Leu Ile Leu
            260                 265                 270

Lys Cys Lys Lys Ser Val Asn Trp Val Ile Lys Ser Phe Asp Val Lys
        275                 280                 285

Gly Ser Leu Lys Ile Ile Ala Pro Asn Ser Ile Gly Phe Gly Lys Glu
    290                 295                 300

Ser Glu Arg Ser Met Thr Met Thr Lys Ser Ile Arg Asp Asp Ile Pro
305                 310                 315                 320

Ser Thr Gln Gly Asn Leu Val Lys Trp Ala Leu Asp Asn Gly Tyr Ser
                325                 330                 335

Pro Ile Thr Ser Tyr Thr Met Ala Pro Val Ala Ile Val Phe His Leu
            340                 345                 350

Arg Leu Glu Asn Asn Glu Glu Met Gly Asp Glu Glu Val His Thr Ile
        355                 360                 365

Pro Pro Glu Leu Arg Ile Leu Leu Asp Pro Gly Ala Leu Pro Ala Leu
    370                 375                 380

Gln Asn Pro Pro Ile Arg Gly Gly Glu Gly Gln Asn Gly Gly Leu Pro
385                 390                 395                 400

Phe Pro Phe Pro Asp Ile Ser Arg Arg Val Trp Asn Glu Glu Gly Glu
                405                 410                 415

Asp Gly Leu Pro Arg Pro Lys Asp Pro Val Ile Pro Ser Ile Gln Leu
            420                 425                 430

Phe Pro Gly Leu Arg Glu Pro Glu Glu Val Gln Gly Ser Val Asp Ile
        435                 440                 445

Ala Leu Ser Val Lys Cys Asp Asn Glu Lys Met Ile Val Ala Val Glu
    450                 455                 460

Lys Asp Ser Phe Gln Ala Ser Gly Tyr Ser Gly Met Asp Val Thr Leu
465                 470                 475                 480

Leu Asp Pro Thr Cys Lys Ala Lys Met Asn Gly Thr His Phe Val Leu
                485                 490                 495

Glu Ser Pro Leu Asn Gly Cys Gly Thr Arg Pro Arg Trp Ser Ala Leu
            500                 505                 510

Asp Gly Val Val Tyr Tyr Asn Ser Ile Val Ile Gln Val Pro Ala Leu
        515                 520                 525
```

-continued

```
Gly Asp Ser Ser Gly Trp Pro Asp Gly Tyr Glu Asp Leu Glu Ser Gly
    530                 535                 540

Asp Asn Gly Phe Pro Gly Asp Met Asp Glu Gly Asp Ala Ser Leu Phe
545                 550                 555                 560

Thr Arg Pro Glu Ile Val Val Phe Asn Cys Ser Leu Gln Gln Val Arg
                565                 570                 575

Asn Pro Ser Ser Phe Gln Glu Gln Pro His Gly Asn Ile Thr Phe Asn
            580                 585                 590

Met Glu Leu Tyr Asn Thr Asp Leu Phe Leu Val Pro Ser Gln Gly Val
        595                 600                 605

Phe Ser Val Pro Glu Asn Gly His Val Tyr Val Glu Val Ser Val Thr
    610                 615                 620

Lys Ala Glu Gln Glu Leu Gly Phe Ala Ile Gln Thr Cys Phe Ile Ser
625                 630                 635                 640

Pro Tyr Ser Asn Pro Asp Arg Met Ser His Tyr Thr Ile Ile Glu Asn
                645                 650                 655

Ile Cys Pro Lys Asp Glu Ser Val Lys Phe Tyr Ser Pro Lys Arg Val
            660                 665                 670

His Phe Pro Ile Pro Gln Ala Asp Met Asp Lys Lys Arg Phe Ser Phe
        675                 680                 685

Val Phe Lys Pro Val Phe Asn Thr Ser Leu Leu Phe Leu Gln Cys Glu
    690                 695                 700

Leu Thr Leu Cys Thr Lys Met Glu Lys His Pro Gln Lys Leu Pro Lys
705                 710                 715                 720

Cys Val Pro Pro Asp Glu Ala Cys Thr Ser Leu Asp Ala Ser Ile Ile
                725                 730                 735

Trp Ala Met Met Gln Asn Lys Lys Thr Phe Thr Lys Pro Leu Ala Val
            740                 745                 750

Ile His His Glu Ala Glu Ser Lys Glu Lys Gly Pro Ser Met Lys Glu
        755                 760                 765

Pro Asn Pro Ile Ser Pro Pro Ile Phe His Gly Leu Asp Thr Leu Thr
    770                 775                 780

Val Met Gly Ile Ala Phe Ala Ala Phe Val Ile Gly Ala Leu Leu Thr
785                 790                 795                 800

Gly Ala Leu Trp Tyr Ile Tyr Ser His Thr Gly Glu Thr Ala Gly Arg
                805                 810                 815

Gln Gln Val Pro Thr Ser Pro Pro Ala Ser Glu Asn Ser Ser Ala Ala
            820                 825                 830

His Ser Ile Gly Ser Thr Gln Ser Thr Pro Cys Ser Ser Ser Ser Thr
        835                 840                 845

Ala


<210> SEQ ID NO 49
<211> LENGTH: 2181
<212> TYPE: DNA
<213> ORGANISM: homo sapiens

<400> SEQUENCE: 49

ggaaagcatc caacggagtg gaagcagcat gaaggaagag ccgctgggca gcggcatgaa      60

cgcggtgcgg acgtggatgc agggcgccgg ggtgctggac gccaacacgg cggcgcagag     120

cggggtgggt ctggcccggg ctcactttga gaagcagccg ccttccaatc tgcggaaatc     180

caacttcttc cacttcgtcc tggccctcta cgacagacag ggccagcccg tggagatcga     240
```

-continued

```
gaggacagcg tttgtggggt tcgtggagaa ggaaaaagaa gccaacagcg aaaagaccaa    300
taacggaatt cactaccgga ttcagcttct ctacagcaat gggataagga cggagcagga    360
tttctacgtg cgcctcattg actccatgac aaaacaagcc atagtgtatg aaggccaaga    420
caagagccca gaaatgtgcc gagtcttgct cacacatgag atcatgtgca gccgctgttg    480
tgacaagaaa agctgtggca accgaaatga gactccctca gatccagtga taattgacag    540
attcttcttg aaatttttcc tcaaatgtaa ccaaaattgc ctaaagaatg cgggaaaccc    600
acgtgacatg cggagattcc aggtcgtggt gtctacgaca gtcaatgtgg atggccatgt    660
cctggcagct cctgataaca tgtttgtcca taataattcc aagcatgggc ggagggctcg    720
gaggcttgac ccctcggaag gtacgccctc ttatctggaa catgctactc cctgtatcaa    780
agccatcagc ccgagtgaag gatggacgac cggaggtgcg actgtcatca tcatagggga    840
caatttcttt gatgggttac aggtcatatt cggtaccatg ctggtctgga gtgagttgac    900
aggtcctcat tccatccgtg tgcagacccc tcctcggcac atccctggtg ttgtggaagt    960
cacactgtcc tacaaatcta agcagttctg caaaggaaca ccaggcagat tcatttatac   1020
agcgcgcaac gaacccacca tcgattatgg tttccagagg ttacagaagg tcattcctcg   1080
gcaccctggt gaccctgagc gtttgccaaa ggaagtaata ctgaaaaggg ctgcggatct   1140
ggtagaagca ctgtatggga tgccacacaa caaccaggaa atcattctga agagagcggc   1200
cgacattgcc gaggccctgt acagtgtccc ccgcaaccac aaccaactcc cggcccttgc   1260
taacacctcg gtccacgcag ggatgatggg cgtgaattcg ttcagtggac aactggccgt   1320
gaatgtctcc gaggcatcac aagccaccaa tcagggtttc acccgcaact caagcagcgt   1380
atcaccacac gggtacgtgc cgagcaccac tccccagcag accaactata actccgtcac   1440
cacgagcatg aacggatacg gctctgccgc aatgtccaat ttgggtggct cccccacctt   1500
cctcaacggc tcagctgcca actcccccta tgccatagtg ccatccagcc ccaccatggc   1560
ctcctccaca agcctcccct ccaactgcag cagctcctcg ggcatcttct ccttctcacc   1620
agccaacatg gtctcagccg tgaaacagaa gagtgctttc gcaccagtcg tcagacccca   1680
gacctcccca cctcccacct gcaccagcac caacgggaac agcctgcaag cgatatctgg   1740
catgattgtt cctcctatgt gaaagaattg ccttgaagaa ttgtattaat gaagaggttg   1800
gattctgcta cagagagtaa tctgatacaa gtcccagagt ggaactttta actcaggcct   1860
ttataagagg aatcacacaa taactgcaga tttttaaaca aaatcaccga ccttgcaaat   1920
actgaaattg gaagaggaat ctgaaagtgc agggtgttgg ttaaagttgt acctcccaag   1980
tattttgggg atatatttat tctgtattga caaaagcaaa tccacttttt ctttttcttt   2040
ttttttttta agcttaattc tgcaatcatt tgacttttat ataccgtaat gctctataca   2100
agggacacta taaataagac tccatgtttt aatttatgtt tttaaagctg tgtaaaggaa   2160
gaatgaagtg gtgatattta c                                             2181
```

<210> SEQ ID NO 50
<211> LENGTH: 586
<212> TYPE: PRT
<213> ORGANISM: homo sapiens

<400> SEQUENCE: 50

```
Glu Ser Ile Gln Arg Ser Gly Ser Ser Met Lys Glu Glu Pro Leu Gly
1               5                   10                  15

Ser Gly Met Asn Ala Val Arg Thr Trp Met Gln Gly Ala Gly Val Leu
            20                  25                  30
```

-continued

```
Asp Ala Asn Thr Ala Ala Gln Ser Gly Val Gly Leu Ala Arg Ala His
        35                  40                  45

Phe Glu Lys Gln Pro Pro Ser Asn Leu Arg Lys Ser Asn Phe Phe His
    50                  55                  60

Phe Val Leu Ala Leu Tyr Asp Arg Gln Gly Gln Pro Val Glu Ile Glu
65                  70                  75                  80

Arg Thr Ala Phe Val Gly Phe Val Glu Lys Glu Lys Glu Ala Asn Ser
                85                  90                  95

Glu Lys Thr Asn Asn Gly Ile His Tyr Arg Ile Gln Leu Leu Tyr Ser
            100                 105                 110

Asn Gly Ile Arg Thr Glu Gln Asp Phe Tyr Val Arg Leu Ile Asp Ser
        115                 120                 125

Met Thr Lys Gln Ala Ile Val Tyr Glu Gly Gln Asp Lys Ser Pro Glu
    130                 135                 140

Met Cys Arg Val Leu Leu Thr His Glu Ile Met Cys Ser Arg Cys Cys
145                 150                 155                 160

Asp Lys Lys Ser Cys Gly Asn Arg Asn Glu Thr Pro Ser Asp Pro Val
                165                 170                 175

Ile Ile Asp Arg Phe Phe Leu Lys Phe Phe Leu Lys Cys Asn Gln Asn
            180                 185                 190

Cys Leu Lys Asn Ala Gly Asn Pro Arg Asp Met Arg Arg Phe Gln Val
        195                 200                 205

Val Val Ser Thr Thr Val Asn Val Asp Gly His Val Leu Ala Ala Pro
    210                 215                 220

Asp Asn Met Phe Val His Asn Asn Ser Lys His Gly Arg Arg Ala Arg
225                 230                 235                 240

Arg Leu Asp Pro Ser Glu Gly Thr Pro Ser Tyr Leu Glu His Ala Thr
                245                 250                 255

Pro Cys Ile Lys Ala Ile Ser Pro Ser Glu Gly Trp Thr Thr Gly Gly
            260                 265                 270

Ala Thr Val Ile Ile Ile Gly Asp Asn Phe Phe Asp Gly Leu Gln Val
        275                 280                 285

Ile Phe Gly Thr Met Leu Val Trp Ser Glu Leu Thr Gly Pro His Ser
    290                 295                 300

Ile Arg Val Gln Thr Pro Pro Arg His Ile Pro Gly Val Val Glu Val
305                 310                 315                 320

Thr Leu Ser Tyr Lys Ser Lys Gln Phe Cys Lys Gly Thr Pro Gly Arg
                325                 330                 335

Phe Ile Tyr Thr Ala Arg Asn Glu Pro Thr Ile Asp Tyr Gly Phe Gln
            340                 345                 350

Arg Leu Gln Lys Val Ile Pro Arg His Pro Gly Asp Pro Glu Arg Leu
        355                 360                 365

Pro Lys Glu Val Ile Leu Lys Arg Ala Ala Asp Leu Val Glu Ala Leu
    370                 375                 380

Tyr Gly Met Pro His Asn Asn Gln Glu Ile Ile Leu Lys Arg Ala Ala
385                 390                 395                 400

Asp Ile Ala Glu Ala Leu Tyr Ser Val Pro Arg Asn His Asn Gln Leu
                405                 410                 415

Pro Ala Leu Ala Asn Thr Ser Val His Ala Gly Met Met Gly Val Asn
            420                 425                 430

Ser Phe Ser Gly Gln Leu Ala Val Asn Val Ser Glu Ala Ser Gln Ala
        435                 440                 445
```

-continued

```
Thr Asn Gln Gly Phe Thr Arg Asn Ser Ser Ser Val Ser Pro His Gly
    450                 455                 460

Tyr Val Pro Ser Thr Thr Pro Gln Gln Thr Asn Tyr Asn Ser Val Thr
465                 470                 475                 480

Thr Ser Met Asn Gly Tyr Gly Ser Ala Ala Met Ser Asn Leu Gly Gly
                485                 490                 495

Ser Pro Thr Phe Leu Asn Gly Ser Ala Ala Asn Ser Pro Tyr Ala Ile
            500                 505                 510

Val Pro Ser Ser Pro Thr Met Ala Ser Ser Thr Ser Leu Pro Ser Asn
        515                 520                 525

Cys Ser Ser Ser Ser Gly Ile Phe Ser Phe Ser Pro Ala Asn Met Val
    530                 535                 540

Ser Ala Val Lys Gln Lys Ser Ala Phe Ala Pro Val Val Arg Pro Gln
545                 550                 555                 560

Thr Ser Pro Pro Pro Thr Cys Thr Ser Thr Asn Gly Asn Ser Leu Gln
                565                 570                 575

Ala Ile Ser Gly Met Ile Val Pro Pro Met
            580                 585
```

<210> SEQ ID NO 51
<211> LENGTH: 1129
<212> TYPE: DNA
<213> ORGANISM: homo sapiens

<400> SEQUENCE: 51

```
gtggccccg cggtgcggag tatggggcgc tgatggccat ggagggctac tggcgcttcc      60

tggcgctgct ggggtcggca ctgctcgtcg gcttcctgtc ggtgatcttc gccctcgtct    120

gggtcctcca ctaccgagag ggcttggct gggatgggag cgcactagag tttaactggc     180

acccagtgct catggtcacc ggcttcgtct tcatccaggg catcgccatc atcgtctaca    240

gactgccgtg gacctggaaa tgcagcaagc tcctgatgaa atccatccat gcagggttaa    300

atgcagttgc tgccattctt gcaattatct ctgtggtggc cgtgtttgag aaccacaatg    360

ttaacaatat agccaatatg tacagtctgc acagctgggt tggactgata gctgtcatat    420

gctatttgtt acagcttctt tcaggttttt cagtctttct gcttccatgg gctccgcttt    480

ctctccgagc atttctcatg cccatacatg tttattctgg aattgtcatc tttggaacag    540

tgattgcaac agcacttatg ggattgacag agaaactgat tttttccctg agagatcctg    600

catacagtac attcccgcca gaaggtgttt tcgtaaatac gcttggcctt ctgatcctgg    660

tgttcggggc cctcattttt tggatagtca ccagaccgca atggaaacgt cctaaggagc    720

caaattctac cattcttcat ccaaatggag gcactgaaca gggagcaaga ggttccatgc    780

cagcctactc tggcaacaac atggacaaat cagattcaga gttaaacagt gaagtagcag    840

caaggaaaag aaacttagct ctggatgagg ctgggcagag atctaccatg taaaatgttg    900

tagagataga gccatataac gtcacgtttc aaaactagct ctacagtttt gcttctccta    960

ttagccatat gataattggg ctatgtagta tcaatattta ctttaatcac aaaggatggt   1020

ttcttgaaat aatttgtatt gattgaggcc tatgaactga cctgaattgg aaaggatgtg   1080

attaatataa ataatagcag atataaatta aaaaaaaaaa aaaagaaaa               1129
```

<210> SEQ ID NO 52
<211> LENGTH: 286
<212> TYPE: PRT
<213> ORGANISM: homo sapiens -continued

<400> SEQUENCE: 52

```
Met Ala Met Glu Gly Tyr Trp Arg Phe Leu Ala Leu Leu Gly Ser Ala
1               5                   10                  15

Leu Leu Val Gly Phe Leu Ser Val Ile Phe Ala Leu Val Trp Val Leu
            20                  25                  30

His Tyr Arg Glu Gly Leu Gly Trp Asp Gly Ser Ala Leu Glu Phe Asn
        35                  40                  45

Trp His Pro Val Leu Met Val Thr Gly Phe Val Phe Ile Gln Gly Ile
    50                  55                  60

Ala Ile Ile Val Tyr Arg Leu Pro Trp Thr Trp Lys Cys Ser Lys Leu
65                  70                  75                  80

Leu Met Lys Ser Ile His Ala Gly Leu Asn Ala Val Ala Ala Ile Leu
                85                  90                  95

Ala Ile Ile Ser Val Val Ala Val Phe Glu Asn His Asn Val Asn Asn
            100                 105                 110

Ile Ala Asn Met Tyr Ser Leu His Ser Trp Val Gly Leu Ile Ala Val
        115                 120                 125

Ile Cys Tyr Leu Leu Gln Leu Leu Ser Gly Phe Ser Val Phe Leu Leu
    130                 135                 140

Pro Trp Ala Pro Leu Ser Leu Arg Ala Phe Leu Met Pro Ile His Val
145                 150                 155                 160

Tyr Ser Gly Ile Val Ile Phe Gly Thr Val Ile Ala Thr Ala Leu Met
                165                 170                 175

Gly Leu Thr Glu Lys Leu Ile Phe Ser Leu Arg Asp Pro Ala Tyr Ser
            180                 185                 190

Thr Phe Pro Pro Glu Gly Val Phe Val Asn Thr Leu Gly Leu Leu Ile
        195                 200                 205

Leu Val Phe Gly Ala Leu Ile Phe Trp Ile Val Thr Arg Pro Gln Trp
    210                 215                 220

Lys Arg Pro Lys Glu Pro Asn Ser Thr Ile Leu His Pro Asn Gly Gly
225                 230                 235                 240

Thr Glu Gln Gly Ala Arg Gly Ser Met Pro Ala Tyr Ser Gly Asn Asn
                245                 250                 255

Met Asp Lys Ser Asp Ser Glu Leu Asn Ser Glu Val Ala Ala Arg Lys
            260                 265                 270

Arg Asn Leu Ala Leu Asp Glu Ala Gly Gln Arg Ser Thr Met
        275                 280                 285
```

<210> SEQ ID NO 53
<211> LENGTH: 2655
<212> TYPE: DNA
<213> ORGANISM: homo sapiens

<400> SEQUENCE: 53

```
cgcctagccg cgccggtccc agaagtggcg aaagccgcag ccgagtccag gtcacgccga      60

agccgttgcc cttttaaggg ggagccttga aacggcgcct gggttccatg tttgcatccg     120

cctcgcggga aggaaactcc atgttgtaac aaagtttcct ccgcgccccc tccctccccc     180

tccccccctag aacctggctc ccctcccctc cggagctcgc ggggatccct ccctcccacc     240

cctcccctcc cccccgcgcc ccgattccgg ccccagccgg gggggaggcc gggcgcccgg     300

gccagagtcc ggccggagcg gagcgcgccc ggcccccatgg acagctcggc cgtcattact     360

cagatcagca aggaggaggc tcggggcccg ctgcggggca aaggtgacca gaagtcagca     420

gcttcccaga agccccgaag ccggggcatc ctccactcac tcttctgctg tgtctgccgg     480
```

-continued

```
gatgatgggg aggccctgcc tgctcacagc ggggcgcccc tgcttgtgga ggagaatgga    540
gccatcccta agcagacccc agtccaatac ctgctccctg aggccaaggc ccaggactca    600
gacaagatct gcgtggtcat cgacctggac gagaccctgg tgcacagctc cttcaagcca    660
gtgaacaacg cggacttcat catccctgtg gagattgatg gggtggtcca ccaggtctac    720
gtgttgaagc gtcctcacgt ggatgagttc ctgcagcgaa tgggcgagct ctttgaatgt    780
gtgctgttca ctgctagcct cgccaagtac gcagacccag tagctgacct gctggacaaa    840
tgggggggcct tccgggcccg gctgtttcga gagtcctgcg tcttccaccg gggggaactac    900
gtgaaggacc tgagccggtt gggtcgagac ctgcggcggg tgctcatcct ggacaattca    960
cctgcctcct atgtcttcca tccagacaat gctgtaccgg tggcctcgtg gtttgacaac   1020
atgagtgaca cagagctcca cgacctcctc cccttcttcg agcaactcag ccgtgtggac   1080
gacgtgtact cagtgctcag gcagccacgg ccagggagct agtgagggtg atggggccag   1140
gacctgcccc tgaccaatga tacccacacc tcctcccagg aagactgccc aggcctttgt   1200
taggaaaacc catgggccgc cgccacactc agtgccatgg ggaagcgggc gtctccccca   1260
ccagccccac caggcggtgt aggggcagca ggctgcactg aggaccgtga gctccaggcc   1320
ccgtgtcagt gccttcaaac ctcctcccct attctcaggg gacctggggg gccctgcctg   1380
ctgctccctt tttctgtctc tgtccatgct gccatgtttc tctgctgcca aattgggccc   1440
cttggcccct tccggttctg cttcctgggg gcagggttcc tgccttggac ccccagtctg   1500
ggaacggtgg acatcaagtg ccttgcatag agccccctct tccccgccca gctttcccag   1560
gggcacagct ctaggctggg aggggagaac cagcccctcc ccctgcccca cctcctccct   1620
tgggactgag agggccccta ccaacctttg cctctgcctt ggagggaggg gaggtctgtt   1680
accactgggg aaggcagcag gagtctgtcc ttcaggcccc acagtgcagc ttctccaggg   1740
ccgacagctg agggctgctc cctgcatcat ccaagcaatg acctcagact tctgccttaa   1800
ccagccccgg ggcttggctc ccccagctct gagcgtgggg gcataggcag gacccccctt   1860
gtggtgccat ataaatatgt acatgtgtat atagattttt aggggaagga gagagggaag   1920
ggtcagggta gagacacccc tcccttgccc ctttcctggg cccagaagtt ggggggaggg   1980
agggaaagga tttttacatt ttttaaactg ctattttctg aatggaacaa gctgggccaa   2040
ggggcccagg ccctgtcctc tgtccctcac accccctttgc tccgttcatt cattcaaaaa   2100
aacatttctt gagcaccttc tgtgcccagc atatgctagg cccaccagct aagtgtgtgt   2160
gggggggtctc tacgccagct catcagtgcc tccttgccca tccttcaccg gtgcctttgg   2220
gggatctgta ggaggtggga ccttctgtgg ggtttgggga tctccaggaa gcccgaccaa   2280
gctgtcccct tcccctgtgc caacccatct cctacagccc cctgcctgat cccctgctgg   2340
ctgggggcag ctcccaggat atcctgcctt ccaactgttt ctgaagcccc tcctcctaac   2400
atggcgattc cggaggtcaa ggccttgggc tctccccagg gtctaacggt taaggggacc   2460
cacataccag tgccaagggg gatgtcaagt ggtgatgtcg ttgtgctccc ctcccccaga   2520
gcgggtgggc ggggggtgaa tatggttggc ctgcatcagg tggccttccc atttaagtgc   2580
cttctctgtg actgagagcc ctagtgtgat gagaactaaa gagaaagcca gacccctaaa   2640
aaaaaaaaaa aaaaa                                                    2655
```

<210> SEQ ID NO 54
<211> LENGTH: 261
<212> TYPE: PRT

-continued

<213> ORGANISM: homo sapiens

<400> SEQUENCE: 54

```
Met Asp Ser Ser Ala Val Ile Thr Gln Ile Ser Lys Glu Glu Ala Arg
1               5                   10                  15

Gly Pro Leu Arg Gly Lys Gly Asp Gln Lys Ser Ala Ala Ser Gln Lys
            20                  25                  30

Pro Arg Ser Arg Gly Ile Leu His Ser Leu Phe Cys Cys Val Cys Arg
        35                  40                  45

Asp Asp Gly Glu Ala Leu Pro Ala His Ser Gly Ala Pro Leu Leu Val
    50                  55                  60

Glu Glu Asn Gly Ala Ile Pro Lys Gln Thr Pro Val Gln Tyr Leu Leu
65                  70                  75                  80

Pro Glu Ala Lys Ala Gln Asp Ser Asp Lys Ile Cys Val Val Ile Asp
                85                  90                  95

Leu Asp Glu Thr Leu Val His Ser Ser Phe Lys Pro Val Asn Asn Ala
            100                 105                 110

Asp Phe Ile Ile Pro Val Glu Ile Asp Gly Val Val His Gln Val Tyr
        115                 120                 125

Val Leu Lys Arg Pro His Val Asp Glu Phe Leu Gln Arg Met Gly Glu
    130                 135                 140

Leu Phe Glu Cys Val Leu Phe Thr Ala Ser Leu Ala Lys Tyr Ala Asp
145                 150                 155                 160

Pro Val Ala Asp Leu Leu Asp Lys Trp Gly Ala Phe Arg Ala Arg Leu
                165                 170                 175

Phe Arg Glu Ser Cys Val Phe His Arg Gly Asn Tyr Val Lys Asp Leu
            180                 185                 190

Ser Arg Leu Gly Arg Asp Leu Arg Arg Val Leu Ile Leu Asp Asn Ser
        195                 200                 205

Pro Ala Ser Tyr Val Phe His Pro Asp Asn Ala Val Pro Val Ala Ser
    210                 215                 220

Trp Phe Asp Asn Met Ser Asp Thr Glu Leu His Asp Leu Leu Pro Phe
225                 230                 235                 240

Phe Glu Gln Leu Ser Arg Val Asp Asp Val Tyr Ser Val Leu Arg Gln
                245                 250                 255

Pro Arg Pro Gly Ser
            260
```

<210> SEQ ID NO 55
<211> LENGTH: 3804
<212> TYPE: DNA
<213> ORGANISM: homo sapiens

<400> SEQUENCE: 55

```
gcccgagcga gggcgcttcg ctcccagcca ggacatggcc gcacctctcc gcatcaggag     60

cgccggctca cggacttctc gcccaactcc ctgagcgctc cctcgtttcg atctttagaa    120

aaccccgctt tctttctggg gccgtgacga ggggcaggga gcggcgagca aggatgcgtt    180

gaggaccgcg agggcgcgcg tctcgggtgc cgccgtgggt cccgacgcgg aagccgagcc    240

gcctccgcct gcctcgactt ccccacagcg cttccgccgc cgcctgccgt gcttgtatgt    300

gcagaaagaa gccggacacc atgatcctaa cacaaattga agccaaggaa gcttgtgatt    360

ggctacgggc aactggtttc cccccagtatg cacagcttta tgaagatttc ctgttcccca    420

tcgatatttc cttggtcaag agagagcatg attttttgga cagagatgcc attgaggctc    480
```

-continued

```
tataggcgtc taaatacttt aaacaaatgt gcggtgatga agctagaaat tagtcctcat    540
cggaaacgag tgacgattca gacgaggatg agccttgtgc catcagtggc aaatggactt    600
tccaaaggga cagcaagagg tggtcccggc ttgaagagtt tgatgtcttt tctccaaaac    660
aagacctggt ccctgggtcc ccagacgact cccacccgaa ggacggcccc agccccggag    720
gcacgctgat ggacctcagc gagcgccagg aggtgtcttc cgtccgcagc ctcagcagca    780
ctggcagcct ccccagccac gcgcccccca gcgaggatgc tgccaccccc cggactaact    840
ccgtcatcag cgtttgctcc tccagcaact tggcaggcaa tgacgactct ttcggcagcc    900
tgccctctcc caaggaactg tccagcttca gcttcagcat gaaaggccac gaaaaaactg    960
ccaagtccaa gacgcgcagt ctgctgaaac ggatggagag cctgaagctc aagagctccc   1020
atcacagcaa gcacaaagcg ccctcaaagc tggggttgat catcagcggg cccatcttgc   1080
aagaggggat ggatgaggag aagctgaagc agctcaactg cgtggagatc tccgccctca   1140
atggcaaccg catcaacgtc cccatggtac gaaagaggag cgtttccaac tccacgcaga   1200
ccagcagcag cagcagccag tcggagacca gcagcgcggt cagcacgccc agccctgtta   1260
cgaggacccg gagcctcagt gcgtgcaaca agcgggtggg catgtactta gagggcttcg   1320
atcctttcaa tcagtcaaca tttaacaacg tgatggagca gaactttaag aaccgcgaga   1380
gctacccaga ggacacggtg ttctacatcc ctgaagatca caagcctggc actttcccca   1440
aagctctcac caatggcagt ttctccccct cggggaataa cggctctgtg aactggagga   1500
cgggaagctt ccacggccct ggccacatca gcctcaggag ggaaaacagt agcgacagcc   1560
ccaaggaact gaagagacgc aattcttcca gctccatgag cagccgcctg agcatctacg   1620
acaacgtgcc gggctccatc ctctactcca gttcagggga cctggcggat ctggagaacg   1680
aggacatctt ccccgagctg gacgacatcc tctaccacgt gaaggggatg cagcggatag   1740
tcaatcagtg gtcggagaag ttttctgatg agggagattc ggactcagcc ctggactcgg   1800
tctctccctg cccgtcctct ccaaaacaga tacacctgga tgtggacaac gaccgaacca   1860
cacccagcga cctggacagc acaggcaact ccctgaatga accggaagag ccctccgaga   1920
tcccggaaag aagggattct ggggttgggg cttccctaac caggtccaac aggcaccgac   1980
tgagatggca cagtttccag agctcacatc ggccaagcct caactctgta tcactacaga   2040
ttaactgcca gtctgtggcc cagatgaacc tgctgcagaa atactcactc ctaaagctaa   2100
cggccctgct ggagaaatac acaccttcta acaagcatgg ttttagctgg gccgtgccca   2160
agttcatgaa gaggatcaag gttccagact acaaggaccg gagtgtgttt ggggtcccac   2220
tgacggtcaa cgtgcagcgc acaggacaac cgttgcctca gagcatccag caggccatgc   2280
gatacctccg gaaccattgt ttggatcagg ttgggctctt cagaaaatcg gggggtcaagt   2340
cccggattca ggctctgcgc cagatgaatg aaggtgccat agactgtgtc aactacgaag   2400
gacagtctgc ttatgacgtg gcagacatgc tgaagcagta ttttcgagat cttcctgagc   2460
cactaatgac gaacaaactc tcagaaacct ttctacagat ctaccaatat gtgcccaagg   2520
accagcgact gcaggccatc aaggctgcca tcatgctgct gcctgacgag aaccgggagg   2580
ttctgcagac cctgctttat ttcctgagcg atgtcacagc agccgtaaaa gaaaaccaga   2640
tgaccccaac caacctggcc gtgtgcttag cgccttccct cttccatctc aacaccctga   2700
agagagagaa ttcctctccc aggggtaatg caaagaaaac aaagtttggg caaaccagat   2760
cagaaagatt tgaatgaaaa cctagctgcc actcaagggc tggcccatat gatcgccgag   2820
tgcaagaagc ttttccaggt tcccgaggaa atgagccgat gtcgtaattc ctataccgaa   2880
```

-continued

```
caagagctga agcccctcac tctggaagca ctcgggcacc tgggtaatga tgactcagct   2940

gactaccaac acttcctcca ggactgtgtg gatggcctgt ttaaagaagt caaagagaag   3000

tttaaaggct gggtcagcta ctccacttcg gagcaggctg agctgtccta taagaaggtg   3060

agcgaaggac cccctctgag gctttggagg tcagtcattg aagtccctgc tgtgccagag   3120

gaaatcttaa agcgcctact taaagaacag cacctctggg atgtagacct gttggattca   3180

aaagtgatcg aaattctgga cagccaaact gaaatttacc agtatgtcca aaacagtatg   3240

gcacctcatc ctgctcgaga ctacgttgtt ttaagaacct ggaggactaa tttacccaaa   3300

ggagcctgtg cccttttact aacctctgtg gatcacgatc gcgcacctgt ggtgggtgtg   3360

agggttaatg tgctcttgtc caggtatttg attgaaccct gtgggccagg aaaatccaaa   3420

ctcacctaca tgtgcagagt tgacttaagg ggccacatgc cagaatggta cacaaaatct   3480

tttggacatt tgtgtgcagc tgaagttgta aagatccggg attccttcag taaccagaac   3540

actgaaacca aagacaccaa atctaggtga tcactgaagc aacgcaaccg cttccaccac   3600

catggtgttt gtttctagaa cttttgccag tccttgaaga atgggttctg tgtctaatcc   3660

tgaaacaaag aaaactacaa gctggagtgt aggaattgac tatagcaatt tgatacattt   3720

ttaaagctgc ttcctgtttg ttgagggtct gtattcatag accttgactg gaatatgtaa   3780

gactgtgcaa aaaaaaaaaa aaaa                                          3804
```

<210> SEQ ID NO 56
<211> LENGTH: 1091
<212> TYPE: PRT
<213> ORGANISM: homo sapiens

<400> SEQUENCE: 56

```
Met Cys Arg Lys Lys Pro Asp Thr Met Ile Leu Thr Gln Ile Glu Ala
1               5                   10                  15

Lys Glu Ala Cys Asp Trp Leu Arg Ala Thr Gly Phe Pro Gln Tyr Ala
            20                  25                  30

Gln Leu Tyr Glu Asp Phe Leu Phe Pro Ile Asp Ile Ser Leu Val Lys
        35                  40                  45

Arg Glu His Asp Phe Leu Asp Arg Asp Ala Ile Glu Ala Leu Cys Arg
    50                  55                  60

Arg Leu Asn Thr Leu Asn Lys Cys Ala Val Met Lys Leu Glu Ile Ser
65                  70                  75                  80

Pro His Arg Lys Arg Ser Asp Asp Ser Asp Glu Asp Glu Pro Cys Ala
                85                  90                  95

Ile Ser Gly Lys Trp Thr Phe Gln Arg Asp Ser Lys Arg Trp Ser Arg
            100                 105                 110

Leu Glu Glu Phe Asp Val Phe Ser Pro Lys Gln Asp Leu Val Pro Gly
        115                 120                 125

Ser Pro Asp Asp Ser His Pro Lys Asp Gly Pro Ser Pro Gly Gly Thr
    130                 135                 140

Leu Met Asp Leu Ser Glu Arg Gln Glu Val Ser Ser Val Arg Ser Leu
145                 150                 155                 160

Ser Ser Thr Gly Ser Leu Pro Ser His Ala Pro Pro Ser Glu Asp Ala
                165                 170                 175

Ala Thr Pro Arg Thr Asn Ser Val Ile Ser Val Cys Ser Ser Ser Asn
            180                 185                 190

Leu Ala Gly Asn Asp Asp Ser Phe Gly Ser Leu Pro Ser Pro Lys Glu
        195                 200                 205
```

-continued

```
Leu Ser Ser Phe Ser Phe Ser Met Lys Gly His Glu Lys Thr Ala Lys
    210                 215                 220

Ser Lys Thr Arg Ser Leu Leu Lys Arg Met Glu Ser Leu Lys Leu Lys
225                 230                 235                 240

Ser Ser His His Ser Lys His Lys Ala Pro Ser Lys Leu Gly Leu Ile
                245                 250                 255

Ile Ser Gly Pro Ile Leu Gln Glu Gly Met Asp Glu Glu Lys Leu Lys
            260                 265                 270

Gln Leu Ser Cys Val Glu Ile Ser Ala Leu Asn Gly Asn Arg Ile Asn
        275                 280                 285

Val Pro Met Val Arg Lys Arg Ser Val Ser Asn Ser Thr Gln Thr Ser
    290                 295                 300

Ser Ser Ser Ser Gln Ser Glu Thr Ser Ser Ala Val Ser Thr Pro Ser
305                 310                 315                 320

Pro Val Thr Arg Thr Arg Ser Leu Ser Ala Cys Asn Lys Arg Val Gly
                325                 330                 335

Met Tyr Leu Glu Gly Phe Asp Pro Phe Asn Gln Ser Thr Phe Asn Asn
            340                 345                 350

Val Val Glu Gln Asn Phe Lys Asn Arg Glu Ser Tyr Pro Glu Asp Thr
        355                 360                 365

Val Phe Tyr Ile Pro Glu Asp His Lys Pro Gly Thr Phe Pro Lys Ala
    370                 375                 380

Leu Thr Asn Gly Ser Phe Ser Pro Ser Gly Asn Asn Gly Ser Val Asn
385                 390                 395                 400

Trp Arg Thr Gly Ser Phe His Gly Pro Gly His Ile Ser Leu Arg Arg
                405                 410                 415

Glu Asn Ser Ser Asp Ser Pro Lys Glu Leu Lys Arg Arg Asn Ser Ser
            420                 425                 430

Ser Ser Met Ser Ser Arg Leu Ser Ile Tyr Asp Asn Val Pro Gly Ser
        435                 440                 445

Ile Leu Tyr Ser Ser Ser Gly Asp Leu Ala Asp Leu Glu Asn Glu Asp
    450                 455                 460

Ile Phe Pro Glu Leu Asp Asp Ile Leu Tyr His Val Lys Gly Met Gln
465                 470                 475                 480

Arg Ile Val Asn Gln Trp Ser Glu Lys Phe Ser Asp Glu Gly Asp Ser
                485                 490                 495

Asp Ser Ala Leu Asp Ser Val Ser Pro Cys Pro Ser Ser Pro Lys Gln
            500                 505                 510

Ile His Leu Asp Val Asp Asn Asp Arg Thr Thr Pro Ser Asp Leu Asp
        515                 520                 525

Ser Thr Gly Asn Ser Leu Asn Glu Pro Glu Glu Pro Ser Glu Ile Pro
    530                 535                 540

Glu Arg Arg Asp Ser Gly Val Gly Ala Ser Leu Thr Arg Ser Asn Arg
545                 550                 555                 560

His Arg Leu Arg Trp His Ser Phe Gln Ser Ser His Arg Pro Ser Leu
                565                 570                 575

Asn Ser Val Ser Leu Gln Ile Asn Cys Gln Ser Val Ala Gln Met Asn
            580                 585                 590

Leu Leu Gln Lys Tyr Ser Leu Leu Lys Leu Thr Ala Leu Leu Glu Lys
        595                 600                 605

Tyr Thr Pro Ser Asn Lys His Gly Phe Ser Trp Ala Val Pro Lys Phe
    610                 615                 620
```

-continued

```
Met Lys Arg Ile Lys Val Pro Asp Tyr Lys Asp Arg Ser Val Phe Gly
625                 630                 635                 640

Val Pro Leu Thr Val Asn Val Gln Arg Thr Gly Gln Pro Leu Pro Gln
                645                 650                 655

Ser Ile Gln Gln Ala Met Arg Tyr Leu Arg Asn His Cys Leu Asp Gln
            660                 665                 670

Val Gly Leu Phe Lys Lys Ser Gly Val Lys Ser Arg Ile Gln Ala Leu
        675                 680                 685

Arg Gln Met Asn Glu Gly Ala Ile Asp Cys Val Asn Tyr Glu Gly Gln
    690                 695                 700

Ser Ala Tyr Asp Val Ala Asp Met Leu Lys Gln Tyr Phe Arg Asp Leu
705                 710                 715                 720

Pro Glu Pro Leu Met Thr Asn Lys Leu Ser Glu Thr Phe Leu Gln Ile
                725                 730                 735

Tyr Gln Tyr Val Pro Lys Asp Gln Arg Leu Gln Ala Ile Lys Ala Ala
            740                 745                 750

Ile Met Leu Leu Pro Asp Glu Asn Arg Val Val Leu Gln Thr Leu Leu
        755                 760                 765

Tyr Phe Leu Cys Asp Val Thr Ala Ala Val Lys Glu Asn Gln Met Thr
    770                 775                 780

Pro Thr Asn Leu Ala Val Cys Leu Ala Pro Ser Leu Phe His Leu Asn
785                 790                 795                 800

Thr Leu Lys Arg Glu Asn Ser Ser Pro Arg Val Met Gln Arg Lys Gln
                805                 810                 815

Ser Leu Gly Lys Pro Asp Gln Lys Asp Leu Asn Glu Asn Leu Ala Ala
            820                 825                 830

Thr Gln Gly Leu Ala His Met Ile Ala Glu Cys Lys Lys Leu Phe Gln
        835                 840                 845

Val Pro Glu Glu Met Ser Arg Cys Arg Asn Ser Tyr Thr Glu Gln Glu
    850                 855                 860

Leu Lys Pro Leu Thr Leu Glu Ala Leu Gly His Leu Gly Asn Asp Asp
865                 870                 875                 880

Ser Ala Asp Tyr Gln His Phe Leu Gln Asp Cys Val Asp Gly Leu Phe
                885                 890                 895

Lys Glu Val Lys Glu Lys Phe Lys Gly Trp Val Ser Tyr Ser Thr Ser
            900                 905                 910

Glu Gln Ala Glu Leu Ser Tyr Lys Lys Val Ser Glu Gly Pro Arg Leu
        915                 920                 925

Arg Leu Trp Arg Ser Val Ile Glu Val Pro Ala Val Pro Glu Glu Ile
    930                 935                 940

Leu Lys Arg Leu Leu Lys Glu Gln His Leu Trp Asp Val Asp Leu Leu
945                 950                 955                 960

Asp Ser Lys Val Ile Glu Ile Leu Asp Ser Gln Thr Glu Ile Tyr Gln
                965                 970                 975

Tyr Val Gln Asn Ser Met Ala Pro His Pro Ala Arg Asp Tyr Val Val
            980                 985                 990

Leu Arg Thr Trp Arg Thr Asn Leu  Pro Lys Gly Ala Cys  Ala Leu Leu
        995                 1000                1005

Leu Thr  Ser Val Asp His Asp  Arg Ala Pro Val Val  Gly Val Arg
    1010                1015                1020

Val Asn  Val Leu Leu Ser Arg  Tyr Leu Ile Glu Pro  Cys Gly Pro
    1025                1030                1035

Gly Lys  Ser Lys Leu Thr Tyr  Met Cys Arg Val Asp  Leu Arg Gly
```

-continued

```
    1040                1045                1050

His Met  Pro Glu Trp Tyr Thr  Lys Ser Phe Gly His  Leu Cys Ala
    1055                1060                1065

Ala Glu  Val Val Lys Ile Arg  Asp Ser Phe Ser Asn  Gln Asn Thr
    1070                1075                1080

Glu Thr  Lys Asp Thr Lys Ser  Arg
    1085                1090


<210> SEQ ID NO 57
<211> LENGTH: 2501
<212> TYPE: DNA
<213> ORGANISM: homo sapiens

<400> SEQUENCE: 57

ctggccccga gcagctgaag cctggggtca gcaggcgctg cgggcgcagc tccggtgcaa     60

gcgaggacac gacacatgca gtggcttctg gactgcgcga tgactggacg caagtaactt    120

ctaggtctgc agacaagagg aagagaagat gaaggaagac tgtctgccga gttctcacgt    180

gcccatcagt gacagcaagt ccattcagaa gtcggagctc ttaggcctgc tgaaaaccta    240

caactgctac catgagggca agagcttcca gctgagacac cgtgaggaag aagggactct    300

gatcatcgag gggctcctca acattgcctg gggctgaggg cggcccatcc ggctgcagat    360

gcaggatgac cgggagcagg tgcacctccc ctccacctca tggatgccca gacggcctag    420

ctgccctcta aaggagccat cgccccagaa cgggaacatc acagcccagg ggccaagcat    480

tcagccagtg cacaaggctg agagttccac agacagctcg ggcccctgg aggaggcaga     540

ggaggccccc cagctgatgc ggaccaagag cgacgccagt tgcatgagcc agaggaggcc    600

caagtgccgc gcccccggtg aggcccagcg catccggcga caccggttct ctatcaacgg    660

ccacttctac aatcataaga cctccgtgtt tactccagcc tatggatccg tgaccaatgt    720

gagggtcaac agcaccatga caaccctgca ggtgctcacc ctgctgctga acaaatttag    780

ggtggaagat ggccccagtg agttcgcact ctacatcgtt cacgagtctg gggagcggac    840

aaaattaaaa gactgcgagt acccgctgat ttccagaatc ctgcatgggc catgtgagaa    900

gatcgccagg atcttcctga tggaagctga cttgggcgtg gaagtccccc atgaagtcgc    960

tcagtacatt aagtttgaaa tgccggtgct ggacagtttt gttgaaaaat taaaagaaga   1020

ggaagaaaga gaaataatca aactgaccat gaagttccaa gccctgcgtc tgacgatgct   1080

gcagcgcctg gagcagctgg tggaggccaa gtaactggcc aacacctgcc tcttccaaag   1140

tccccagcag tggcaggtgt acactgagcc ctggttgctg gccccggccg gtcacattga   1200

ctgatggcca ccgcctgacg aatcgagtgc ctgtgtgtct acctctctga agcctgagca   1260

ccatgattcc cacagccagc tcttggctcc aagatgagca cccacaggaa gccgacccag   1320

gcctgagggg ccaggaactt gctgggtcag atctgtgtgg ccagccctgt ccacaccatg   1380

cctctcctgc actggagagc agtgctggcc cagcccctgc ggcttaggct tcatctgctt   1440

gcacattgcc tgtcccagag cccctgtggg tccacaagcc cctgtcctct tccttcatat   1500

gagattcttg tctgccctca tatcacgctg ccccacagga atgctgctgg gaaaagcagg   1560

gcctgccagc aggtatgaga tctagcctgc tttcagccat caccttgcca cagtgtcccc   1620

ggcttctaag cctccaatat caccctgtga gcctcgcaca gctcagcccc aacacagagg   1680

tgagaccagg aataaggcca caagtatctc actttctcgc agggaatcaa tcttagcttc   1740

agcagagaga cttaaagcga ttctgacaag gagctgctgc aagaaacgcg gtcattcaat   1800
```

-continued

```
cgcattgagg agggtccaca tggcattgag agggtgctgc ccgctcaatg cccagcagca   1860

gctctggaag gcagtgctca gccccatcac cactgtcccg tggatgcctg tgtacctctt   1920

gccttttctg ggcttgcgtt tctctcctct agtgggtggg gatgactttc aatgactttc   1980

aatacttccc ctgaaggaag aatgataagg agaaatgtct gttttgagga aagggctttg   2040

aattccccag atactgaaca atttgtgttt gtgactgatg gagaatttca ggaatgaatg   2100

agaaagcctt tgcgaaacta tgcaacagtt tacatcagtc atgtgaagta tttgtctaaa   2160

acagagcaaa ctgaagacca aattattctc ctgttgaggt ccgtggatgg cagatttaaa   2220

gggaagaacc acaaaggctt gcaaagatag gagaggctcc atctctaatg catgtagaag   2280

ctccttacgg gtgcccatca agagcatagc ttggaagcca ccatgctgtg cggaactgcg   2340

tcagggcaaa tgtcacagca ggatttcccc aacccagctc catcatcaca gacacagaga   2400

gctgcagggg aggcctgccc actgttttgt cgactctgcc ctcctctggc agcatagatc   2460

cttaggtgct caataaaggt gtgctgtatt gaactgaaga a                       2501
```

```
<210> SEQ ID NO 58
<211> LENGTH: 321
<212> TYPE: PRT
<213> ORGANISM: homo sapiens

<400> SEQUENCE: 58

Met Lys Glu Asp Cys Leu Pro Ser Ser His Val Pro Ile Ser Asp Ser
1               5                   10                  15

Lys Ser Ile Gln Lys Ser Glu Leu Leu Gly Leu Leu Lys Thr Tyr Asn
            20                  25                  30

Cys Tyr His Glu Gly Lys Ser Phe Gln Leu Arg His Arg Glu Glu Glu
        35                  40                  45

Gly Thr Leu Ile Ile Glu Gly Leu Leu Asn Ile Ala Trp Gly Leu Arg
    50                  55                  60

Arg Pro Ile Arg Leu Gln Met Gln Asp Asp Arg Glu Gln Val His Leu
65                  70                  75                  80

Pro Ser Thr Ser Trp Met Pro Arg Arg Pro Ser Cys Pro Leu Lys Glu
                85                  90                  95

Pro Ser Pro Gln Asn Gly Asn Ile Thr Ala Lys Gly Pro Ser Ile Gln
            100                 105                 110

Pro Val His Lys Ala Glu Ser Ser Thr Asp Ser Ser Gly Pro Leu Glu
        115                 120                 125

Glu Ala Glu Glu Ala Pro Gln Leu Met Arg Thr Lys Ser Asp Ala Ser
    130                 135                 140

Cys Met Ser Gln Arg Arg Pro Lys Cys Arg Ala Pro Gly Glu Ala Gln
145                 150                 155                 160

Arg Ile Arg Arg His Arg Phe Ser Ile Asn Gly His Phe Tyr Asn His
                165                 170                 175

Lys Thr Ser Val Phe Thr Pro Ala Tyr Gly Ser Val Thr Asn Val Arg
            180                 185                 190

Val Asn Ser Thr Met Thr Thr Leu Gln Val Leu Thr Leu Leu Leu Asn
        195                 200                 205

Lys Phe Arg Val Glu Asp Gly Pro Ser Glu Phe Ala Leu Tyr Ile Val
    210                 215                 220

His Glu Ser Gly Glu Arg Thr Lys Leu Lys Asp Cys Glu Tyr Pro Leu
225                 230                 235                 240

Ile Ser Arg Ile Leu His Gly Pro Cys Glu Lys Ile Ala Arg Ile Phe
                245                 250                 255
```

-continued

```
Leu Met Glu Ala Asp Leu Gly Val Glu Val Pro His Glu Val Ala Gln
            260                 265                 270

Tyr Ile Lys Phe Glu Met Pro Val Leu Asp Ser Phe Val Glu Lys Leu
        275                 280                 285

Lys Glu Glu Glu Glu Arg Glu Ile Ile Lys Leu Thr Met Lys Phe Gln
    290                 295                 300

Ala Leu Arg Leu Thr Met Leu Gln Arg Leu Glu Gln Leu Val Glu Ala
305                 310                 315                 320

Lys


<210> SEQ ID NO 59
<211> LENGTH: 1152
<212> TYPE: DNA
<213> ORGANISM: homo sapiens

<400> SEQUENCE: 59

atgagtgcac ttttccttgg tgtgggagtg agggcagagg aagctggagc gagggtgcaa     60

caaaacgttc caagtgggac agatactgga gatcctcaaa gtaagcccct cggtgactgg    120

gctgctggca ccatggaccc agagagcagt atctttattg aggatgccat taagtatttc    180

aaggaaaaag tgagcacaca gaatctgcta ctcctgctga ctgataatga ggcctggaac    240

ggattcgtgg ctgctgctga actgcccagg aatgaggcag atgagctccg taaagctctg    300

gacaaccttg caagacaaat gatcatgaaa gacaaaaact ggcacgataa aggccagcag    360

tacagaaact ggtttctgaa agagtttcct cggttgaaaa gtgagcttga ggataacata    420

agaaggctcc gtgcccttgc agatggggtt cagaaggtcc acaaaggcac caccatcgcc    480

aatgtggtgt ctggctctct cagcatttcc tctggcatcc tgaccctcgt cggcatgggt    540

ctggcaccct tcacagaggg aggcagcctt gtactcttgg aacctgggat ggagttggga    600

atcacagccg ctttgaccgg gattaccagc agtaccatgg actacggaaa gaagtggtgg    660

acacaagccc aagcccacga cctggtcatc aaaagccttg acaaattgaa ggaggtgagg    720

gagtttttgg gtgagaacat atccaacttt ctttccttag ctggcaatac ttaccaactc    780

acacgaggca ttgggaagga catccgtgcc ctcagacgag ccagagccaa tcttcagtca    840

gtaccgcatg cctcagcctc acgcccccgg gtcactgagc caatctcagc tgaaagcggt    900

gaacaggtgg agagggttaa tgaacccagc atcctggaaa tgagcagagg agtcaagctc    960

acggatgtgg cccctgtaag cttctttctt gtgctggatg tagtctacct cgtgtacgaa   1020

tcaaagcact tacatgaggg ggcaaagtca gagacagctg aggagctgaa gaaggtggct   1080

caggagctgg aggagaagct aaacattctc aacaataatt ataagattct gcaggcggac   1140

caagaactgt ga                                                        1152


<210> SEQ ID NO 60
<211> LENGTH: 383
<212> TYPE: PRT
<213> ORGANISM: homo sapiens

<400> SEQUENCE: 60

Met Ser Ala Leu Phe Leu Gly Val Gly Val Arg Ala Glu Glu Ala Gly
1               5                   10                  15

Ala Arg Val Gln Gln Asn Val Pro Ser Gly Thr Asp Thr Gly Asp Pro
            20                  25                  30

Gln Ser Lys Pro Leu Gly Asp Trp Ala Ala Gly Thr Met Asp Pro Glu
        35                  40                  45
```

-continued

```
Ser Ser Ile Phe Ile Glu Asp Ala Ile Lys Tyr Phe Lys Glu Lys Val
    50                  55                  60

Ser Thr Gln Asn Leu Leu Leu Leu Leu Thr Asp Asn Glu Ala Trp Asn
65                  70                  75                  80

Gly Phe Val Ala Ala Ala Glu Leu Pro Arg Asn Glu Ala Asp Glu Leu
                85                  90                  95

Arg Lys Ala Leu Asp Asn Leu Ala Arg Gln Met Ile Met Lys Asp Lys
            100                 105                 110

Asn Trp His Asp Lys Gly Gln Gln Tyr Arg Asn Trp Phe Leu Lys Glu
        115                 120                 125

Phe Pro Arg Leu Lys Ser Glu Leu Glu Asp Asn Ile Arg Arg Leu Arg
    130                 135                 140

Ala Leu Ala Asp Gly Val Gln Lys Val His Lys Gly Thr Thr Ile Ala
145                 150                 155                 160

Asn Val Val Ser Gly Ser Leu Ser Ile Ser Ser Gly Ile Leu Thr Leu
                165                 170                 175

Val Gly Met Gly Leu Ala Pro Phe Thr Glu Gly Gly Ser Leu Val Leu
            180                 185                 190

Leu Glu Pro Gly Met Glu Leu Gly Ile Thr Ala Ala Leu Thr Gly Ile
        195                 200                 205

Thr Ser Ser Thr Met Asp Tyr Gly Lys Lys Trp Trp Thr Gln Ala Gln
    210                 215                 220

Ala His Asp Leu Val Ile Lys Ser Leu Asp Lys Leu Lys Glu Val Arg
225                 230                 235                 240

Glu Phe Leu Gly Glu Asn Ile Ser Asn Phe Leu Ser Leu Ala Gly Asn
                245                 250                 255

Thr Tyr Gln Leu Thr Arg Gly Ile Gly Lys Asp Ile Arg Ala Leu Arg
            260                 265                 270

Arg Ala Arg Ala Asn Leu Gln Ser Val Pro His Ala Ser Ala Ser Arg
        275                 280                 285

Pro Arg Val Thr Glu Pro Ile Ser Ala Glu Ser Gly Glu Gln Val Glu
    290                 295                 300

Arg Val Asn Glu Pro Ser Ile Leu Glu Met Ser Arg Gly Val Lys Leu
305                 310                 315                 320

Thr Asp Val Ala Pro Val Ser Phe Phe Leu Val Leu Asp Val Val Tyr
                325                 330                 335

Leu Val Tyr Glu Ser Lys His Leu His Glu Gly Ala Lys Ser Glu Thr
            340                 345                 350

Ala Glu Glu Leu Lys Lys Val Ala Gln Glu Leu Glu Glu Lys Leu Asn
        355                 360                 365

Ile Leu Asn Asn Asn Tyr Lys Ile Leu Gln Ala Asp Gln Glu Leu
    370                 375                 380
```

<210> SEQ ID NO 61
<211> LENGTH: 1761
<212> TYPE: DNA
<213> ORGANISM: homo sapiens

<400> SEQUENCE: 61

```
atggctttag agatccacat gtcagacccc atgtgcctca tcgagaactt taatgagcag     60

ctgaaggtta atcaggaagc tttggagatc ctgtctgcca ttacgcaacc tgtagttgtg    120

gtagcgattg tgggcctcta tcgcactggc aaatcctacc tgatgaacaa gctggctggg    180

aagaacaagg gcttctctgt tgcatctacg gtgcagtctc acaccaaggg aatttggata    240
```

-continued

```
tggtgtgtgc ctcatcccaa ctggccaaat cacacattag ttctgcttga caccgagggc    300

ctgggagatg tagagaaggc tgacaacaag aatgatatcc agatctttgc actggcactc    360

ttactgagca gcacctttgt gtacaatact gtgaacaaaa ttgatcaggg tgctatcgac    420

ctactgcaca atgtgacaga actgacagat ctgctcaagg caagaaactc acccgacctt    480

gacagggttg aagatcctgc tgactctgcg agcttcttcc cagacttagt gtggactctg    540

agagatttct gcttaggcct ggaaatagat gggcaacttg tcacaccaga tgaatacctg    600

gagaattccc taaggccaaa gcaaggtagt gatcaaagag ttcaaaattt caatttgcct    660

cgtctgtgta tacagaagtt ctttccaaaa aagaaatgct ttatctttga cttacctgct    720

caccaaaaaa agcttgccca acttgaaaca ctgcctgatg atgagctaga gcctgaattt    780

gtgcaacaag tgacagaatt ctgttcctac atctttagcc attctatgac caagactctt    840

ccaggtggca tcatggtcaa tggatctcgt ctaaagaacc tggtgctgac ctatgtcaat    900

gccatcagca gtggggatct gccttgcata gagaatgcag tcctggcctt ggctcagaga    960

gagaactcag ctgcagtgca aaaggccatt gcccactatg accagcaaat gggccagaaa   1020

gtgcagctgc ccatggaaac cctccaggag ctgctggacc tgcacaggac cagtgagagg   1080

gaggccattg aagtcttcat gaaaaactct ttcaaggatg tagaccaaag tttccagaaa   1140

gaattggaga ctctactaga tgcaaaacag aatgacattt gtaaacggaa cctggaagca   1200

tcctcggatt attgctcggc tttacttaag gatatttttg gtcctctaga agaagcagtg   1260

aagcagggaa tttattctaa gccaggaggc cataatctct tcattcagaa aacagaagaa   1320

ctgaaggcaa agtactatcg ggagcctcgg aaaggaatac aggctgaaga agttctgcag   1380

aaatatttaa agtccaagga gtctgtgagt catgcaatat tacagactga ccaggctctc   1440

acagagacgg aaaaaaagaa gaaagaggca caagtgaaag cagaagctga aaaggctgaa   1500

gcgcaaaggt tggcggcgat tcaaaggcag aacgagcaaa tgatgcagga gagggagaga   1560

ctccatcagg aacaagtgag acaaatggag atagccaaac aaaattggct ggcagagcaa   1620

cagaaaatgc aggaacaaca gatgcaggaa caggctgcac agctcagcac aacattccaa   1680

gctcaaaata gaagccttct cagtgagctc cagcacgccc agaggactgt taataacgat   1740

gatccatgtg ttttactcta a                                             1761
```

<210> SEQ ID NO 62
<211> LENGTH: 586
<212> TYPE: PRT
<213> ORGANISM: homo sapiens

<400> SEQUENCE: 62

```
Met Ala Leu Glu Ile His Met Ser Asp Pro Met Cys Leu Ile Glu Asn
1               5                   10                  15

Phe Asn Glu Gln Leu Lys Val Asn Gln Glu Ala Leu Glu Ile Leu Ser
            20                  25                  30

Ala Ile Thr Gln Pro Val Val Val Val Ala Ile Val Gly Leu Tyr Arg
        35                  40                  45

Thr Gly Lys Ser Tyr Leu Met Asn Lys Leu Ala Gly Lys Asn Lys Gly
    50                  55                  60

Phe Ser Val Ala Ser Thr Val Gln Ser His Thr Lys Gly Ile Trp Ile
65                  70                  75                  80

Trp Cys Val Pro His Pro Asn Trp Pro Asn His Thr Leu Val Leu Leu
                85                  90                  95
```

-continued

```
Asp Thr Glu Gly Leu Gly Asp Val Glu Lys Ala Asp Asn Lys Asn Asp
            100                 105                 110

Ile Gln Ile Phe Ala Leu Ala Leu Leu Leu Ser Ser Thr Phe Val Tyr
        115                 120                 125

Asn Thr Val Asn Lys Ile Asp Gln Gly Ala Ile Asp Leu Leu His Asn
    130                 135                 140

Val Thr Glu Leu Thr Asp Leu Leu Lys Ala Arg Asn Ser Pro Asp Leu
145                 150                 155                 160

Asp Arg Val Glu Asp Pro Ala Asp Ser Ala Ser Phe Phe Pro Asp Leu
                165                 170                 175

Val Trp Thr Leu Arg Asp Phe Cys Leu Gly Leu Glu Ile Asp Gly Gln
            180                 185                 190

Leu Val Thr Pro Asp Glu Tyr Leu Glu Asn Ser Leu Arg Pro Lys Gln
        195                 200                 205

Gly Ser Asp Gln Arg Val Gln Asn Phe Asn Leu Pro Arg Leu Cys Ile
    210                 215                 220

Gln Lys Phe Phe Pro Lys Lys Lys Cys Phe Ile Phe Asp Leu Pro Ala
225                 230                 235                 240

His Gln Lys Lys Leu Ala Gln Leu Glu Thr Leu Pro Asp Asp Glu Leu
                245                 250                 255

Glu Pro Glu Phe Val Gln Gln Val Thr Glu Phe Cys Ser Tyr Ile Phe
            260                 265                 270

Ser His Ser Met Thr Lys Thr Leu Pro Gly Gly Ile Met Val Asn Gly
        275                 280                 285

Ser Arg Leu Lys Asn Leu Val Leu Thr Tyr Val Asn Ala Ile Ser Ser
    290                 295                 300

Gly Asp Leu Pro Cys Ile Glu Asn Ala Val Leu Ala Leu Ala Gln Arg
305                 310                 315                 320

Glu Asn Ser Ala Ala Val Gln Lys Ala Ile Ala His Tyr Asp Gln Gln
                325                 330                 335

Met Gly Gln Lys Val Gln Leu Pro Met Glu Thr Leu Gln Glu Leu Leu
            340                 345                 350

Asp Leu His Arg Thr Ser Glu Arg Glu Ala Ile Glu Val Phe Met Lys
        355                 360                 365

Asn Ser Phe Lys Asp Val Asp Gln Ser Phe Gln Lys Glu Leu Glu Thr
    370                 375                 380

Leu Leu Asp Ala Lys Gln Asn Asp Ile Cys Lys Arg Asn Leu Glu Ala
385                 390                 395                 400

Ser Ser Asp Tyr Cys Ser Ala Leu Leu Lys Asp Ile Phe Gly Pro Leu
                405                 410                 415

Glu Glu Ala Val Lys Gln Gly Ile Tyr Ser Lys Pro Gly Gly His Asn
            420                 425                 430

Leu Phe Ile Gln Lys Thr Glu Glu Leu Lys Ala Lys Tyr Tyr Arg Glu
        435                 440                 445

Pro Arg Lys Gly Ile Gln Ala Glu Glu Val Leu Gln Lys Tyr Leu Lys
    450                 455                 460

Ser Lys Glu Ser Val Ser His Ala Ile Leu Gln Thr Asp Gln Ala Leu
465                 470                 475                 480

Thr Glu Thr Glu Lys Lys Lys Lys Glu Ala Gln Val Lys Ala Glu Ala
                485                 490                 495

Glu Lys Ala Glu Ala Gln Arg Leu Ala Ala Ile Gln Arg Gln Asn Glu
            500                 505                 510

Gln Met Met Gln Glu Arg Glu Arg Leu His Gln Glu Gln Val Arg Gln
```

-continued

```
        515                 520                 525

Met Glu Ile Ala Lys Gln Asn Trp Leu Ala Glu Gln Gln Lys Met Gln
    530                 535                 540

Glu Gln Gln Met Gln Glu Gln Ala Ala Gln Leu Ser Thr Thr Phe Gln
545                 550                 555                 560

Ala Gln Asn Arg Ser Leu Leu Ser Glu Leu Gln His Ala Gln Arg Thr
                565                 570                 575

Val Asn Asn Asp Asp Pro Cys Val Leu Leu
            580                 585


<210> SEQ ID NO 63
<211> LENGTH: 828
<212> TYPE: DNA
<213> ORGANISM: homo sapiens

<400> SEQUENCE: 63

gggggagtga aagcgaaagc ccgggcgact agccgggaga ccagagatct agcgactgaa      60

gcagcatggc caagccgtgt ggggtgcgcc tgagcgggga agcccgcaaa caggtggagg     120

tcttcaggca gaatcttttc caggaggctg aggaattcct ctacagattc ttgccacaga     180

aaatcatata cctgaatcag ctcttgcaag aggactccct caatgtggct gacttgactt     240

ccctccgggc cccactggac atccccatcc cagaccctcc acccaaggat gatgagatgg     300

aaacagataa gcaggagaag aaagaagtcc ctaagtgtgg atttctccct gggaatgaga     360

aagtcctgtc cctgcttgcc ctggttaagc cagaagtctg gactctcaaa gagaaatgca     420

ttctggtgat tacatggatc caacacctga tccccaagat tgaagatgga aatgattttg     480

gggtagcaat ccaggagaag gtgctggaga gggtgaatgc cgtcaagacc aaagtggaag     540

ctttccagac aaccatttcc aagtacttct cagaacgtgg ggatgctgtg gccaaggcct     600

ccaaggagac tcatgtaatg gattaccggg ccttggtgca tgagcgagat gaggcagcct     660

atggggagct cagggccatg gtgctggacc tgagggcctt ctatgctgag ctttatcata     720

tcatcagcag caacctggag aaaattgtca ccccaaaggg tgaagaaaag ccatctatgt     780

actgaacccg ggactagaag gaaaataaat gatctatatg ttgtgtgg                  828


<210> SEQ ID NO 64
<211> LENGTH: 239
<212> TYPE: PRT
<213> ORGANISM: homo sapiens

<400> SEQUENCE: 64

Met Ala Lys Pro Cys Gly Val Arg Leu Ser Gly Glu Ala Arg Lys Gln
1               5                   10                  15

Val Glu Val Phe Arg Gln Asn Leu Phe Gln Glu Ala Glu Glu Phe Leu
            20                  25                  30

Tyr Arg Phe Leu Pro Gln Lys Ile Ile Tyr Leu Asn Gln Leu Leu Gln
        35                  40                  45

Glu Asp Ser Leu Asn Val Ala Asp Leu Thr Ser Leu Arg Ala Pro Leu
    50                  55                  60

Asp Ile Pro Ile Pro Asp Pro Pro Pro Lys Asp Asp Glu Met Glu Thr
65                  70                  75                  80

Asp Lys Gln Glu Lys Lys Glu Val Pro Lys Cys Gly Phe Leu Pro Gly
                85                  90                  95

Asn Glu Lys Val Leu Ser Leu Leu Ala Leu Val Lys Pro Glu Val Trp
            100                 105                 110
```

-continued

```
Thr Leu Lys Glu Lys Cys Ile Leu Val Ile Thr Trp Ile Gln His Leu
        115                 120                 125

Ile Pro Lys Ile Glu Asp Gly Asn Asp Phe Gly Val Ala Ile Gln Glu
    130                 135                 140

Lys Val Leu Glu Arg Val Asn Ala Val Lys Thr Lys Val Glu Ala Phe
145                 150                 155                 160

Gln Thr Thr Ile Ser Lys Tyr Phe Ser Glu Arg Gly Asp Ala Val Ala
                165                 170                 175

Lys Ala Ser Lys Glu Thr His Val Met Asp Tyr Arg Ala Leu Val His
            180                 185                 190

Glu Arg Asp Glu Ala Ala Tyr Gly Glu Leu Arg Ala Met Val Leu Asp
        195                 200                 205

Leu Arg Ala Phe Tyr Ala Glu Leu Tyr His Ile Ile Ser Ser Asn Leu
    210                 215                 220

Glu Lys Ile Val Thr Pro Lys Gly Glu Glu Lys Pro Ser Met Tyr
225                 230                 235
```

<210> SEQ ID NO 65
<211> LENGTH: 2578
<212> TYPE: DNA
<213> ORGANISM: homo sapiens

<400> SEQUENCE: 65

```
cttttgtctc tcagctattt tttgttccct atgtttgtag gatggaaagg cagatgtaaa     60

gtccctcatg gcgaaatata acacgggggg caacccgaca gaggatgtct cagtcaatag    120

ccgacccttc agagtcacag ggccaaactc atcttcagga atacaagcaa gaaagaactt    180

attcaacaac caaggaaatg ccagccctcc tgcaggaccc agcaatgtac ctaagtttgg    240

gtccccaaag ccacctgtgg cagtcaaacc ttcttctgag gaaaagcctg acaaggaacc    300

caagcccccg tttctaaagc ccactggagc aggccaaaga ttcggaacac cagccagctt    360

gaccaccaga gaccccgagg cgaaagtggg atttctgaaa cctgtaggcc ccaagcccat    420

caacttgccc aaagaagatt ccaaacctac atttccctgg cctcctggaa acaagccatc    480

tcttcacagt gtaaaccaag accatgactt aaagccacta ggcccgaaat ctgggcctac    540

tcctccaacc tcagaaaatg aacagaagca agcgtttccc aaattgactg gggttaaagg    600

gaaatttatg tcagcatcac aagatcttga acccaagccc ctcttcccca aacccgcctt    660

tggccagaag ccgcccctaa gtaccgagaa ctcccatgaa gacgaaagcc ccatgaagaa    720

tgtgtcttca tcaaaagggt ccccagctcc cctgggagtc aggtccaaaa gcggcccttt    780

aaaaccagca agggaagact cagaaaataa agaccatgca ggggagattt caagtttgcc    840

ctttcctgga gtggttttga aacctgctgc gagcagggga ggcccaggtg tctccaaaaa    900

tggtgaagaa aaaaaggaag ataggaagat agatgctgct aagaacacct tccagagcaa    960

aataaatcag gaagagttgg cctcagggac tcctcctgcc aggttcccta aggccccttc   1020

taagctgaca gtgggggggc catggggcca aagtcaggaa aaggaaaagg gagacaagaa   1080

ttcagccacc ccgaaacaga agccattgcc tcccttgttt accttgggtc cacctccacc   1140

aaaacccaac agaccaccaa atgttgacct gacgaaattc cacaaaacct cttctggaaa   1200

cagtactagc aaaggccaga cgtcttactc aacaacttcc ctgccaccac ctccaccatc   1260

ccatccggcc agccaaccac cattgccagc atctcaccca tcacaaccac cagtcccaag   1320

cctacctccc agaaacatta aacctccgtt tgacctaaaa agccctgtca atgaagacaa   1380

tcaagatggt gtcacgcact ctgatggtgc tggaaatcta gatgaggaac aagacagtga   1440
```

-continued

```
aggagaaaca tatgaagaca tagaagcatc caaagaaaga gagaagaaaa gggaaaagga   1500
agaaaagaag aggttagagc tggagaaaaa ggaacagaaa gagaaagaaa agaaagaaca   1560
agaaataaag aagaaattta aactaacagg ccctattcaa gtcatccatc ttgcaaaagc   1620
ttgttgtgat gtcaaaggag gaaagaatga actgagcttc aagcaaggag agcaaattga   1680
aatcatccgc atcacagaca acccagaagg aaaatggttg ggcagaacag caaggggttc   1740
atatggctat attaaaacaa ctgctgtaga gattgactat gattctttga aactgaaaaa   1800
agactctctt ggtgcccctt caagacctat tgaagatgac caagaagtat atgatgatgt   1860
tgcagagcag gatgatatta gcagccacag tcagagtgga agtggaggga tattccctcc   1920
accaccagat gatgacattt atgatgggat tgaagaggaa gatgctgatg atggtttccc   1980
tgctcctcct aaacaattgg acatgggaga tgaagtttac gatgatgtgg atacctctga   2040
tttccctgtt tcatcagcag agatgagtca aggaactaat tttggaaaag ctaagacaga   2100
agaaaaggac cttaagaagc taaaaaagca ggaaaaagaa gaaaaagact tcaggaaaaa   2160
atttaaatat gatggtgaaa ttagagtcct atattcaact aaagttacaa cttccataac   2220
ttctaaaaag tggggaacca gagatctaca ggtaaaacct ggtgaatctc tagaagttat   2280
acaaaccaca gatgacacaa aagttctctg cagaaatgaa gaagggaaat atggttatgt   2340
ccttcggagt tacctagcgg acaatgatgg agagatctat gatgatattg ctgatggctg   2400
catctatgac aatgactagc actcaacttt ggtcattctg ctgtgttcat taggtgccaa   2460
tgtgaagtct ggattttaat tggcatgtta ttgggtatca agaaaattaa tgcacaaaac   2520
cacttattat catttgttat gaaatcccaa ttatctttac aaagtgttta aagtttga     2578
```

<210> SEQ ID NO 66
<211> LENGTH: 783
<212> TYPE: PRT
<213> ORGANISM: homo sapiens

<400> SEQUENCE: 66

```
Met Ala Lys Tyr Asn Thr Gly Gly Asn Pro Thr Glu Asp Val Ser Val
1               5                   10                  15

Asn Ser Arg Pro Phe Arg Val Thr Gly Pro Asn Ser Ser Ser Gly Ile
            20                  25                  30

Gln Ala Arg Lys Asn Leu Phe Asn Asn Gln Gly Asn Ala Ser Pro Pro
        35                  40                  45

Ala Gly Pro Ser Asn Val Pro Lys Phe Gly Ser Pro Lys Pro Pro Val
    50                  55                  60

Ala Val Lys Pro Ser Ser Glu Glu Lys Pro Asp Lys Glu Pro Lys Pro
65                  70                  75                  80

Pro Phe Leu Lys Pro Thr Gly Ala Gly Gln Arg Phe Gly Thr Pro Ala
                85                  90                  95

Ser Leu Thr Thr Arg Asp Pro Glu Ala Lys Val Gly Phe Leu Lys Pro
            100                 105                 110

Val Gly Pro Lys Pro Ile Asn Leu Pro Lys Glu Asp Ser Lys Pro Thr
        115                 120                 125

Phe Pro Trp Pro Pro Gly Asn Lys Pro Ser Leu His Ser Val Asn Gln
    130                 135                 140

Asp His Asp Leu Lys Pro Leu Gly Pro Lys Ser Gly Pro Thr Pro Pro
145                 150                 155                 160

Thr Ser Glu Asn Glu Gln Lys Gln Ala Phe Pro Lys Leu Thr Gly Val
                165                 170                 175
```

-continued

```
Lys Gly Lys Phe Met Ser Ala Ser Gln Asp Leu Glu Pro Lys Pro Leu
            180                 185                 190

Phe Pro Lys Pro Ala Phe Gly Gln Lys Pro Pro Leu Ser Thr Glu Asn
        195                 200                 205

Ser His Glu Asp Glu Ser Pro Met Lys Asn Val Ser Ser Ser Lys Gly
    210                 215                 220

Ser Pro Ala Pro Leu Gly Val Arg Ser Lys Ser Gly Pro Leu Lys Pro
225                 230                 235                 240

Ala Arg Glu Asp Ser Glu Asn Lys Asp His Ala Gly Glu Ile Ser Ser
                245                 250                 255

Leu Pro Phe Pro Gly Val Val Leu Lys Pro Ala Ala Ser Arg Gly Gly
            260                 265                 270

Pro Gly Val Ser Lys Asn Gly Glu Glu Lys Lys Glu Asp Arg Lys Ile
        275                 280                 285

Asp Ala Ala Lys Asn Thr Phe Gln Ser Lys Ile Asn Gln Glu Glu Leu
    290                 295                 300

Ala Ser Gly Thr Pro Pro Ala Arg Phe Pro Lys Ala Pro Ser Lys Leu
305                 310                 315                 320

Thr Val Gly Gly Pro Trp Gly Gln Ser Gln Glu Lys Glu Lys Gly Asp
                325                 330                 335

Lys Asn Ser Ala Thr Pro Lys Gln Lys Pro Leu Pro Pro Leu Phe Thr
            340                 345                 350

Leu Gly Pro Pro Pro Pro Lys Pro Asn Arg Pro Pro Asn Val Asp Leu
        355                 360                 365

Thr Lys Phe His Lys Thr Ser Ser Gly Asn Ser Thr Ser Lys Gly Gln
    370                 375                 380

Thr Ser Tyr Ser Thr Thr Ser Leu Pro Pro Pro Pro Pro Ser His Pro
385                 390                 395                 400

Ala Ser Gln Pro Pro Leu Pro Ala Ser His Pro Ser Gln Pro Pro Val
                405                 410                 415

Pro Ser Leu Pro Pro Arg Asn Ile Lys Pro Pro Phe Asp Leu Lys Ser
            420                 425                 430

Pro Val Asn Glu Asp Asn Gln Asp Gly Val Thr His Ser Asp Gly Ala
        435                 440                 445

Gly Asn Leu Asp Glu Glu Gln Asp Ser Glu Gly Glu Thr Tyr Glu Asp
    450                 455                 460

Ile Glu Ala Ser Lys Glu Arg Glu Lys Lys Arg Glu Lys Glu Glu Lys
465                 470                 475                 480

Lys Arg Leu Glu Leu Glu Lys Lys Glu Gln Lys Glu Lys Glu Lys Lys
                485                 490                 495

Glu Gln Glu Ile Lys Lys Lys Phe Lys Leu Thr Gly Pro Ile Gln Val
            500                 505                 510

Ile His Leu Ala Lys Ala Cys Cys Asp Val Lys Gly Gly Lys Asn Glu
        515                 520                 525

Leu Ser Phe Lys Gln Gly Glu Gln Ile Glu Ile Ile Arg Ile Thr Asp
    530                 535                 540

Asn Pro Glu Gly Lys Trp Leu Gly Arg Thr Ala Arg Gly Ser Tyr Gly
545                 550                 555                 560

Tyr Ile Lys Thr Thr Ala Val Glu Ile Asp Tyr Asp Ser Leu Lys Leu
                565                 570                 575

Lys Lys Asp Ser Leu Gly Ala Pro Ser Arg Pro Ile Glu Asp Asp Gln
            580                 585                 590
```

-continued

```
Glu Val Tyr Asp Asp Val Ala Glu Gln Asp Asp Ile Ser Ser His Ser
        595                 600                 605

Gln Ser Gly Ser Gly Gly Ile Phe Pro Pro Pro Pro Asp Asp Asp Ile
    610                 615                 620

Tyr Asp Gly Ile Glu Glu Glu Asp Ala Asp Asp Gly Phe Pro Ala Pro
625                 630                 635                 640

Pro Lys Gln Leu Asp Met Gly Asp Glu Val Tyr Asp Asp Val Asp Thr
                645                 650                 655

Ser Asp Phe Pro Val Ser Ser Ala Glu Met Ser Gln Gly Thr Asn Phe
            660                 665                 670

Gly Lys Ala Lys Thr Glu Glu Lys Asp Leu Lys Lys Leu Lys Lys Gln
        675                 680                 685

Glu Lys Glu Glu Lys Asp Phe Arg Lys Lys Phe Lys Tyr Asp Gly Glu
    690                 695                 700

Ile Arg Val Leu Tyr Ser Thr Lys Val Thr Thr Ser Ile Thr Ser Lys
705                 710                 715                 720

Lys Trp Gly Thr Arg Asp Leu Gln Val Lys Pro Gly Glu Ser Leu Glu
                725                 730                 735

Val Ile Gln Thr Thr Asp Asp Thr Lys Val Leu Cys Arg Asn Glu Glu
            740                 745                 750

Gly Lys Tyr Gly Tyr Val Leu Arg Ser Tyr Leu Ala Asp Asn Asp Gly
        755                 760                 765

Glu Ile Tyr Asp Asp Ile Ala Asp Gly Cys Ile Tyr Asp Asn Asp
    770                 775                 780
```

<210> SEQ ID NO 67
<211> LENGTH: 618
<212> TYPE: DNA
<213> ORGANISM: homo sapiens

<400> SEQUENCE: 67

```
gcggccgctc cgcaggcaga gaagccggga gcgtttgagg cggcggcggc acgagcgatg      60

gcaggaatag agttggagcg gtgccagcag caggcgaacg aggtgacgga aattatgcgt     120

aacaacttcg gcaaggtcct ggagcgtggt gtgaagctgg ccgaactgca gcagcgttca     180

gaccaactcc tggatatgag ctcaaccttc aacaagacta cacagaacct ggcccagaag     240

aagtgctggg agaacatccg ttaccggatc tgcgtggggc tggtggtggt tggtgtcctg     300

ctcatcatcc tgattgtgct gctggtcgtc tttctccctc agagcagtga cagcagtagt     360

gccccacgga cccaggatgc aggcattgcc tcagggcctg ggaactgacc cagctggtcc     420

tgaaggagaa gcccaatggc tgcactggcc gattctggtc tccaaggacc ttggtgtttg     480

ctctccctga cccagcccag tgagtgccaa agggcagccc caacatgtgc acccctgcat     540

tcccgtcatg cacagacttg cccttgagca ggccgctgta ctggccagct gggcaacccc     600

cctggagctc ataaaaat                                                   618
```

<210> SEQ ID NO 68
<211> LENGTH: 116
<212> TYPE: PRT
<213> ORGANISM: homo sapiens

<400> SEQUENCE: 68

```
Met Ala Gly Ile Glu Leu Glu Arg Cys Gln Gln Gln Ala Asn Glu Val
1               5                   10                  15

Thr Glu Ile Met Arg Asn Asn Phe Gly Lys Val Leu Glu Arg Gly Val
            20                  25                  30
```

-continued

```
Lys Leu Ala Glu Leu Gln Gln Arg Ser Asp Gln Leu Leu Asp Met Ser
        35                  40                  45

Ser Thr Phe Asn Lys Thr Thr Gln Asn Leu Ala Gln Lys Lys Cys Trp
    50                  55                  60

Glu Asn Ile Arg Tyr Arg Ile Cys Val Gly Leu Val Val Val Gly Val
65                  70                  75                  80

Leu Leu Ile Ile Leu Ile Val Leu Leu Val Val Phe Leu Pro Gln Ser
                85                  90                  95

Ser Asp Ser Ser Ser Ala Pro Arg Thr Gln Asp Ala Gly Ile Ala Ser
            100                 105                 110

Gly Pro Gly Asn
        115
```

<210> SEQ ID NO 69
<211> LENGTH: 1316
<212> TYPE: DNA
<213> ORGANISM: homo sapiens

<400> SEQUENCE: 69

```
gggtttgggg tagaagggag ggagggggca ggacagtgtg gaatctctag ggtgtatggg     60
taggtagggg gcacagttag ttctaagtgg gcttttatgc taaaagcctc tggggatatc    120
tgttttgaaa ataaagatag gtgtcccctc cttgctgtca tctagcccag acactctgct    180
tgctctctgg ctgtctgctc cctgggaagg ctttaggagg accacccagg acaggatgac    240
catgctgcca tctgctctgg agctgggtct cagtgcagag ggacagtgac tgtggatggt    300
tgcagtctct ggtgggaggt gaggatagaa gtgataaaga gctaagagga gcttctggga    360
gccttggagg aggtcagtct tgcagtggtg aagccaggac ataggagatg gagcagggct    420
gtgagaggag gagattctga ggaggatgca ggggaaatct tgtctgttaa tgaaatagga    480
gtggggtggg gtttggggtg gggtggtcat tgccgtttga gctgctgatt ttcatgagtc    540
gccttcaaaa ctctcgtgta gggttgacaa tgtggggggg tgggggatcc agcttattct    600
tttattttca agtccattct tggggctggt ggggaggcag gagaataccc ctccctaagc    660
ccttagtgtg tgccgagctt gctttgtgat gttggcaggg gaggggagac ctgggtggtg    720
actgagttcc ctttatcaaa cccttcagtg ggcacaaaat tgagtgcttg attttaggtt    780
ttattttttt atgaatgtcc aaatctgtgt ttccccctgc cctcccagac tgtgtggcca    840
gttgaaagtg tctggtttgt gttcatctct ccctcatttc tggagcaggg cctgagaccc    900
tgccacatct cctatgctct gcatccacgc ctcttttgga cattaaaggt tgattgatgc    960
acctctgcac tgtttgggtc tctttgggga tgaggggttg gcatggtggc agtggtgcca   1020
cacagtgggt gagggtggag agtctccagg gtggaataga atggggactg aagggaagac   1080
cagccactag atactgattg gcctgtagca gcacttattt gtgcctaggc ttatgcccct   1140
taagtagagg aaaactaacc agcagcactc acccttaagg gctcctgggt tctgccttcc   1200
ttggtggtga tggccaggtg aatcatattt tgtgtctttg ggatagtaac tgctaccttc   1260
ccagctgccg tcatggacct gcctgagctt tgctgcttca acttttgccc aaagct       1316
```

<210> SEQ ID NO 70
<211> LENGTH: 3517
<212> TYPE: DNA
<213> ORGANISM: homo sapiens

<400> SEQUENCE: 70

-continued

```
ccgtaaagcg gtggagaatc tcaagcatgt gcatttaatt gaggaatagc agaagggcta     60
aagcaaccaa gaaaagaagt gtgggtattt ttgttaagta aaacagccca agtgcttctg    120
gaggtgggtt tctaccaaga tagaggaaaa gggctgaatt ccctctaagt gggacagccg    180
agctcaggat gtgcttccca gcttcactgg ttaatttgac ctgaacctat ttaaagatcc    240
cttctgcccc tgaagaccta tccgcactca aattctaaca tgaagaaatc tactcgaatg    300
catcctttac tttgaatgag ctctattcgg ttgcatgtta tatgtgattt ccttcctccc    360
aactgtttcc actgagcgca cccagtctcc cctagtcttc ctctgtgggt gtgatttttg    420
tgatttttac aaacaaaacc cttgaagttc ttggcagatg tgtttgtttc tgtttgcatg    480
tactgcagat accccaggac aagcgggggga ttcatttttc agccattcag ttgtttcctc    540
aataatccgc agcaaagtga aaatattctt agcactcaga ctgtacttag agtgttttct    600
cagtccagtc tgtacagtct gtaggcagaa ggcctcagaa gaaagtcatg gccactcagt    660
gcccactgtg ggctttgtaa gtcctggctc tcccgtcaag gttacccaga ggtaaaagct    720
tcctgggagt ggggccaggt gtgtttggca ctccagatag aaggcaaaat gctcagattc    780
gggcctgtgc acttgtatgc aacctgtcgg tcgataccta gcatttattt ttccctgaca    840
atgaacgacc tttccctcac ccaccctaag ctcaaagagt ttagcaaaat tctcttttaa    900
ataaacagaa tgccagtaag aggttgaccc ctaccatgga acttctggga tgctaaatac    960
ttcctcatga acaaaataag ttccttatta taagttcctt atactagcag cttcacctaa   1020
agaattttct ctccagcaat attgacttca ctggggaaaa gccaagagtg tgtggtgagt   1080
gatttgttct cactcgacct ggctaggact ggctaggagc tgttttttgt acatgaggga   1140
atttgggctt tcctcagtta tctgaatgtt ttacccaagt gccttcctgc tattgtagca   1200
aagtagctca gcttccttgt ccacagggtg aaaaaggact aatgcatttt ccatcagttt   1260
tctaactatg ttagcaaaaa cggcctcctg gtagctcaac ctcctgtacg cgtgtgtgtg   1320
tgtaatacac acacaaataa acccctctgt ttttctaaga catcttagct ggatattata   1380
ggaagcactt tcataaacaa ctgtaacaaa tcgcaaagga aagagaaaca aaagcattag   1440
atttgagaca taaacaggca agagaaagtg tattaggaac tgacagctat caaggaagtt   1500
ttgtcagtta caaatgctag gaggaaattt tgccaagaag gatggctcat gaaatatttc   1560
cagtacggga agaggcaata agatcctcta agagaatgag aaagtagggg tgtctaaatg   1620
gtaaagatgg gtgtgttgca cgtgtgttag aaggatctca gttgagtgaa ggtttgcact   1680
gctacatcta agttaatgta aatatgtagc actctgacag gtctaccgtg ttgctgaatg   1740
tagtatattt ccaaagtttg caagtcttcc tgtattgtac aaagatgctg ctgcttgata   1800
atatgtatag caatccagat tagtatgtta ttaaatttta ttttcttacc tgtattttta   1860
tgctttttac ctgtcctcaa aatattacac ccctgttgga attagattta tatttataaa   1920
tggtcagaaa tctttttaag tgtctctttt tacacatagg ttgatttttt tttcttaaga   1980
gaaatgatgt attcttgaaa catttgttac tcattccagg aaacaaaaac ccatataata   2040
aaacccccac tcagagcctg ttagtcacct ctctagaaga tggcatctca ggagaaggaa   2100
tggctttgtg gaagaaggaa tcaccttttt cttgctcaag aattatgctg acttcagccc   2160
tgagcctgga tctggtcact gagaatcatc aagtgtctag atcctccccc caaaataact   2220
aatttagtag gtgattttga ttttaaaaaa ttgacaccaa aaccctgcct gcattgtaat   2280
ggaattcgaa aagaattcat gttcacagaa ctcaacgttc aggctaatat ttacagaagg   2340
gaccaaatct aaatcctggt agataactcc tgtatgcttt atccaaagga cacccacagt   2400
```

-continued

```
tttccagcat agatataacc aaggatgaat tgattccttc aaagaactgg gaggcacgga   2460
tattgcattt tttgtttaca tccagtagcc aagacgcctc agtgagccag tcttgggcag   2520
aggctgtcac atttaggcag attggaagtt ggtatgttct aattctcact ctggactaca   2580
gtgaggctga atttatcatg tcaaaaaaaa aaaaaaaaaa agacctttcc aagtgctttc   2640
tattgctcag aattgaaaga atgttttcat ttcaagttta caagaggcat ggatggagtt   2700
gtgacgttct tgacaagctg ggctaacctt tcccgaactt gtttcccgga ggcaaggtgc   2760
tcggtgaccc agcgcatctt aaccttgggt ctcctaggct cgaggctagg gcattacgtt   2820
tcgtggaacc aaagcagcca attgcatagc aagtattttc ctgcattcca attaaatgct   2880
taagaaaaag cagcatccta taaaattgtg atcataaaca tccatttccc tcagcttttg   2940
tgagtgcctt gacttacagc caacatcact gtttaactca gtctgtttaa aaacaaactt   3000
ttctggtggt tgataacaga gagttgctcc ctgagccatc agggtcctgg gagctggaag   3060
tgaaagggtt attaacattc tacctttatg cagctgttgg ctgaccagaa taaactccct   3120
gctgagttca agctttgaat ggaatggatg caaatgatgt tgtttccatt agagcaggtg   3180
ctcacagcat tctgattggc ctgagcagac cgaggctatg gctgttggga caagcttagc   3240
atcctggaca tcttgtcaaa gaacctcact cacccctctg gcctctacag ccctcagagg   3300
agagaaaacc aattctccaa caaacaggtc tctccaacat ggtggtgctg gcaggcttag   3360
gtttagaaaa tcctgactgt taaaggcgtt tgaatacatc acattcctat gcaaatgttt   3420
ttaatctcca gtttaatgta gtttattttt cctatatgta aagtattttt atacggcttg   3480
tatcatgata gtttagcaat aaaacagttg gaagcaa                            3517
```

<210> SEQ ID NO 71
<211> LENGTH: 3720
<212> TYPE: DNA
<213> ORGANISM: homo sapiens

<400> SEQUENCE: 71

```
acaccttctc acaggactgg agagagaatg cggggcagct gggcagggct cacttccagc     60
cgcctgtcac agtactggga gtaagaggtg acctatttat ttttagaagg gggcagtgat    120
aataacccag ctcctagctt cattcaaggg aggcaggcgc tttggaagtt tgtaaacacc    180
aactttctga gtaagggagg agcacttttt ttccaaaaag gaaagaacgt ctctactggg    240
tttttttcct cctgatattc agcattagag tagaaaagaa actattgttt ggccacatta    300
gccgtggtta gcaggtgctg cagcctttgc cactgttatt atttttaaag ggcagaaatg    360
cctgaaggtg aagactttgg accaggcaaa agctgggaag ttatcaattc caaaccagat    420
gaaagaccca ggctcagcca ctgtattgca gaatcatgga tgaatttcag catatttctt    480
caagaaatgt ctctttttaa acagcagagc cctggcaagt tttgtctcct ggtctgtagt    540
gtgtgcacat tttttacgat cttgggaagt tacattcctg ggttatact cagctatcta     600
ctgttactgt gtgcattttt gtgtccattg tttaaatgta atgatattgg acaaaaaatt    660
tacagcaaaa ttaagtcagt tctgctgaaa ctggattttg gaattggaga atatattaat    720
cagaagaaac gtgagagatc tgaagcagac aaagaaaaaa gtcacaaaga tgacagtgaa    780
ttagactttt cagctctttg tcctaagatt agcctcacgg ttgctgccaa agagttatct    840
gtgtctgaca cagacgtctc agaggtatcc tggactgata atgggacctt caacctttca    900
gaaggataca ctccacagac agacacttct gatgatcttg accgacccag tgaggaagtt    960
```

-continued

```
ttctctagag atctttcaga ttttccatct ctagaaaatg gcatgggaac aaatgatgaa   1020
gatgaattaa gccttggttt gcccactgag ctcaagagaa agaaggaaca gttggacagt   1080
ggtcacagac caagcaaaga gacgcaatca gcagctggtc tcacccttcc tctgaacagt   1140
gaccaaacct ttcacctgat gagcaacctg gctggggatg ttatcacagc tgcagtgact   1200
gcagctatca aagaccagtt agagggtgtg cagcaagcac tttctcaggc tgccccccatc   1260
ccagaagagg acacagacac tgaagaaggt gatgactttg aactacttga ccagtcagag   1320
ctggatcaaa ttgagagtga attgggactt acacaagacc aggaagcaga agcacagcaa   1380
aataagaagt cttcaggttt cctttcaaat ctgctgggag gccattaatc taggaatcag   1440
cttgcaacag agcacaaaaa acaccaaaaa aatttcaaac aagaaaaaaa aaaaaaaaag   1500
gaaaagaaaa aaattgaact gtaagcttta atgattactt tagatttgtt ttattttccc   1560
tcctgcagtg aattaattgg atatatatca gctgacactg atagattgat atttctgatc   1620
gttatttttg tgtcataagc atggaaatga actttataca caccactgtg ttgtcagaga   1680
taaatattag ggttgtttt taaagcaaaa agaaaaaaac aaaaaccaaa ctattaaaat   1740
cctcctataa atattctttt tctttacagt ttttcaagca tgcaaaacag tttattgtaa   1800
cttactgaaa aatattaaca attaattgtg aatacatgct gttaccagct tccttattcc   1860
taatacctgg aaaatttttt tttcaacgga tagattttga tgtaaaaaag accgaaatta   1920
tcaaggtatc ttagttgaag gacttgggaa atactatcaa aattaatttc ttaggaaaaa   1980
atttaaaagt atatttaagt actctggata gactgaaacg tttccatgtt atttctgcag   2040
ttgtagactt aggcttattt gtaaagaagc atgctccatt gactgccatc tctagtcttg   2100
cagtgggtgg tattaaccca tagaaagcaa gcagttgtgt atcacataga caatggttat   2160
gatgtaaaca gattcagttg ttttgttgtt cattcgtcat atgtttgtga tagggatgtt   2220
gggagcacag ctctattctg cctgctcaga cttaagttag acccttatct tttatattat   2280
gtcatgaaaa aagtctccta aaattgtgaa actagttctt gatgagtgat gtgatcatca   2340
gcaataaaga tataataact ctgttttctt agcctgtata gaggagagga acttgcttgg   2400
ctttaaaata tatttatttg ccatttaagt ataaatatga aatctgtttc ttattgggaa   2460
gatagaatat atatattttc ctttaaactt tttaaggtca cttttaaata accaaatttg   2520
atttatggtt tttaacaaag gactaaagag ctgaaaccaa cctagttttg tttttgtgat   2580
ataaacttta agtgtcgagg gaccatgcca gcaactacca aaaatctctt aaatcttcag   2640
gtacagctgg cattttggca gatgcataga gacatctgag accctcagaa aggaaggata   2700
atccaagaat ataggaaatc tgtgttctct tcctttcatt ttatccctta tatttctaaa   2760
gactaattat aagtaatctg acattttaat gtagctactc ttatttattt tttctttctg   2820
aggtattaaa atatctggac tgagttttgc caaatgttaa agggagaaga gttactgaag   2880
actttgaaca cttgcttttt gtgattgctt atgtcattag tgcctcatga ctgtgtttga   2940
tgtcctttat tgatacaaag tgagcctgtg ccttcattat cttgcccatt ttaatacaaa   3000
tggaaacctg gtgtttgaaa atctctgaac tgtgtgggtt ttggaggaat atacctgaat   3060
tttattcaat aacagtttct ggacaggaag aaaaatacag ttacatattt ataaaatagt   3120
cgttatcagt atttttttat gtgtatgttt ctttctttaa aacaatattc ttggatataa   3180
agtagaaaag tttaaaggtc atttccattt cttcactaag gagaaaaaaa gttaaataat   3240
ccaagtaatt aaagaatata agtcactaga tgaccttaca ggaagacgaa ctcaagggct   3300
gataatctgt ggtggtatga acaataaatc tagaataaaa tgttaataac tacaaattaa   3360
```

-continued aaggggtgtg aggatgggag gaagttggta gggtagaaaa atgtgctatt accactattg 3420
aggagacatg ccagctctct agggacagca gcattataac tatgtatgaa ttttaatatt 3480
atttgtatat gactgtatga ctacaaattt acacaataca ataatgggac tttctcacaa 3540
ctattaattc aaacaaacac aaggatgttg aaggttcttg tttgtgtata tgtgtgtttt 3600
ggtggtgggg ggtcactgtt tctggtttta aaagatgaag gagcagatac atttcatatg 3660
attgatccag tgtagtagag gactacatgt cctttactat gagaatataa atagcaatat 3720

<210> SEQ ID NO 72
<211> LENGTH: 356
<212> TYPE: PRT
<213> ORGANISM: homo sapiens

<400> SEQUENCE: 72

```
Met Pro Glu Gly Glu Asp Phe Gly Pro Gly Lys Ser Trp Glu Val Ile
1               5                   10                  15

Asn Ser Lys Pro Asp Glu Arg Pro Arg Leu Ser His Cys Ile Ala Glu
            20                  25                  30

Ser Trp Met Asn Phe Ser Ile Phe Leu Gln Glu Met Ser Leu Phe Lys
        35                  40                  45

Gln Gln Ser Pro Gly Lys Phe Cys Leu Leu Val Cys Ser Val Cys Thr
    50                  55                  60

Phe Phe Thr Ile Leu Gly Ser Tyr Ile Pro Gly Val Ile Leu Ser Tyr
65                  70                  75                  80

Leu Leu Leu Leu Cys Ala Phe Leu Cys Pro Leu Phe Lys Cys Asn Asp
                85                  90                  95

Ile Gly Gln Lys Ile Tyr Ser Lys Ile Lys Ser Val Leu Leu Lys Leu
            100                 105                 110

Asp Phe Gly Ile Gly Glu Tyr Ile Asn Gln Lys Lys Arg Glu Arg Ser
        115                 120                 125

Glu Ala Asp Lys Glu Lys Ser His Lys Asp Asp Ser Glu Leu Asp Phe
    130                 135                 140

Ser Ala Leu Cys Pro Lys Ile Ser Leu Thr Val Ala Ala Lys Glu Leu
145                 150                 155                 160

Ser Val Ser Asp Thr Asp Val Ser Glu Val Ser Trp Thr Asp Asn Gly
                165                 170                 175

Thr Phe Asn Leu Ser Glu Gly Tyr Thr Pro Gln Thr Asp Thr Ser Asp
            180                 185                 190

Asp Leu Asp Arg Pro Ser Glu Glu Val Phe Ser Arg Asp Leu Ser Asp
        195                 200                 205

Phe Pro Ser Leu Glu Asn Gly Met Gly Thr Asn Asp Glu Asp Glu Leu
    210                 215                 220

Ser Leu Gly Leu Pro Thr Glu Leu Lys Arg Lys Lys Glu Gln Leu Asp
225                 230                 235                 240

Ser Gly His Arg Pro Ser Lys Glu Thr Gln Ser Ala Ala Gly Leu Thr
                245                 250                 255

Leu Pro Leu Asn Ser Asp Gln Thr Phe His Leu Met Ser Asn Leu Ala
            260                 265                 270

Gly Asp Val Ile Thr Ala Ala Val Thr Ala Ala Ile Lys Asp Gln Leu
        275                 280                 285

Glu Gly Val Gln Gln Ala Leu Ser Gln Ala Ala Pro Ile Pro Glu Glu
    290                 295                 300

Asp Thr Asp Thr Glu Glu Gly Asp Asp Phe Glu Leu Leu Asp Gln Ser
```

-continued 305 310 315 320

Glu Leu Asp Gln Ile Glu Ser Glu Leu Gly Leu Thr Gln Asp Gln Glu
325 330 335

Ala Glu Ala Gln Gln Asn Lys Lys Ser Ser Gly Phe Leu Ser Asn Leu
340 345 350

Leu Gly Gly His
355

<210> SEQ ID NO 73
<211> LENGTH: 4052
<212> TYPE: DNA
<213> ORGANISM: homo sapiens

<400> SEQUENCE: 73
gtaagtattt aaatacaatt atttttttct ctcaatggta tagcatattc ctatgcttga 60
gaagtatagg tctactgaaa aaccattgta aatggacgtt acaggtatgc tgtatttttg 120
aaggtatttt gttgtattaa gtttgatgaa gctaaaatta gggaactctg aacagatttg 180
caggaaaaaa tgttttaaag gctttaaaac attagggagg cagtctaggg tgataacgaa 240
caggggttaa gtattaaata cacgaagtta catttttgtt catgtttcat tgtccagaaa 300
gcagcaggaa actattcagt tgtgatcaag caggaaaaaa gaaacaccaa cagttgccag 360
tgtttttgct ttttagctta aaagcatagt gaagatgctt gaggaagact ttgctacctg 420
gggtgtgtag acagacagac tgagagctat cagcatttga aggcccagcc cttgactctg 480
agacacattt gaatttttc tttcccatca aatggcatta acaagattgg gcaaagatga 540
gtccctcaaa tttctgtgtt ttttgtttgt ttgtttgttt gttttttctt tgggaactga 600
agtcagaggc acgaacacta actcttagca tttttctgta gactttttct tctggccctt 660
gtccctgcca gcaaaacgcc ccttttctga tcattcgtgc gcagagggcc tcccagtaat 720
gccacgctct ccatgctaga gagccttctc tttcctctga ggtttgaact gatgttctgt 780
gtcttcacac cctggcatga cagttacgtg tggtcagccc gctccccagg cccgtccctg 840
ccgccgccag gtgtgggctc taggcaggcc gacaaggtta cacctcccag agcttgtgat 900
cttcattttc tgacagtcaa agtgtgaagg aacccagact tccccgagcc acggtgttca 960
gtcagcccac aggaatatgc aagacccatc tccaaaagtt tgtctttgat tttttccaag 1020
cccttagccc cataagcttt gaatcctgta gttacagtgg cataaaggac tgacaaaacc 1080
tggataagga aaaacctttt ttttctatga atttttttttg tttttaggg gaaagggatt 1140 ctaagaatgt catttaatgt actttgcatc atgtctctag aaatatcttt gtccatagtg 1200
gtggtggagt ctctctctct ctctctcttt ttgtttgctt ctgttttctt tcttgtcttc 1260
attctttctt ttctttttta tttctggtag caggcctcca tagaacaaat ctaaaacaca 1320
accaccatag taatgtaagg agagcttcag tggcacctca aaacccaccc ttcgagatct 1380
gtccaaagac agtctcagaa agctgcactg cccaccggct cagctttcat tcaaaaaggc 1440
ttccaaggcc aattctgtct tgaagtcaat gcatgtattt actgtttgac agtaaacccg 1500
ctctgccttc tccacgtcca aggctgtgca ttcgtctaat tagcgtcgtg tatgttttcc 1560
ttttattttt tccaataaaa aagcagtggg atgaaaattg ctttgatata tagcaggtaa 1620
cattgaagct attccatagc acttaactgt agtgaatact gtgtcaccaa ttttgaaatc 1680
aatttaatgt ttaatgcaaa tccattacat ggtgctatta taggctgaca aaatgattta 1740
cacaaatgtg acaacttggg ctcaattcac tctgctttcc aacagtgtaa atgcatagca 1800

-continued

```
gtgtttatct gcatgagaac tatgcactaa tctatctgaa gaaaaaaact atatcaactt   1860
tggtatctac tttccgttta cttcaatcct tgcctttttg gtcattgtta taatgccagc   1920
tttaggacag aaagaattat aagaaaacca gcataatacc tgatatatta aaatgtagtg   1980
cctgtgaaat ctgtattata ttgctcttct gaagtaagat ttttctacac cggtagcctt   2040
cgctgtctgt cagtcaggac cttctggtat aggtgatgta aaataaccgt acaatattaa   2100
tgcatgcgat tccataatgc ttagtgaact gtatgaatat tactcaaagt tatgttagtc   2160
ttttttttccg acttggttct tgtcagctag gtttaaaggt atttcactga gaacgcaaat   2220
tctgtctttt cttgatttcg gctgttttca gtattttgga ggtatacatt tacttaaatt   2280
cagtattact cgtgttttgt ttttgttttt gtttttttgtt ttctttttcc taggggacaa   2340
gcatgggtgt ttgatttcag aaatcagtac ctggcgagat ttttgtctca aaacgactat   2400
ttgaatttca agaactgtgc tgcgaagaca ctctgagaac atttgcaagt caggggcatt   2460
ttccttgacc cttgactgat gctatgcgga gactgataca ttttcttaat ggacaatgtt   2520
caagccaggt acccatgctt gatctgtctt cacaccagac ctcctcatat taaaaggaaa   2580
aataagaaaa aaaatgtaag aaatcacatg gctatttagt ttcatgcaca gttgcaatat   2640
tttcttcaaa aataaaactc tgtacaaact ttgggcccga ttcataagaa aaagaagttt   2700
gctattaaca cgggattttt ttaatatact ttttttggtc taaatttgaa attacttgct   2760
tcccaaatta aataaatttc atctcatttt tttccctaaa ccagcaccca tctgcctttt   2820
attccccaaa gagttacctt tcccagatta gggggatggt atgtggggag cagatagcgg   2880
aaatgcttag aaagataagg gggaccaccc acagctggtc gtgagaacag ggagacagtg   2940
tgtgggggtg ggacctcatc tgtgtgcctg gtatcctgag ttttacatgt agatgcattc   3000
gcctatttga ttcagaaaaa taaactttcc caaaatgtgt ctgaaccaca agagcataca   3060
gtggaagtgc tacctctaat ctaaccagag caccttcatg gtggaagaca cccaccaggt   3120
catacaatgt gaacttttgt atctctgcag tggtttcaag gacaaatagt gtccaatgta   3180
ttgggccatt tttcctgctg tttttatact caacttctca aaatgaaaaa agcttttatt   3240
tttcctttga cttatttgtg ttgttcttat tttttaaatt tttatttttt gataatagtc   3300
tgtaagttag cctttttggg tttttttttt ttttttttgg cttttttttt tgtttgtttt   3360
tttttctttt gacattgcaa ccgaaggtca taaggccgct agctccgctg ggacagaggc   3420
ttgagagaac taacggctcg gtgccttctc cctggtctca gaccatcgtc tctgcactgc   3480
gaaggcattt ggtagcctcg ccactgagat actaactaga cctagactag gagctttatc   3540
aggttctagg aggtccttta ggaagactct caaaggcaaa tccctgatcc cccgccccac   3600
ccttagccct gccctctcac cagagcaaaa ttcactgggg acttttccca ccacacatgg   3660
aaatctgtcc actcggaata cctctgtttt ccatttcaaa ttgtaggggg aggggatgga   3720
acacttccag tgatggtaag agatctgtta tgaaacgaaa cacccccgt gttaataact   3780
tggtctgaaa tctgttttta tgagccgggc cccctgtgcc tctagtatac ttgtattgac   3840
tctcatagtt accctttttag ttttactgtg ttctgtgaaa atttgtaatt ggttgagaat   3900
cactgtgggc gtccattctt attcaactaa atctccacag gttttttgag ctggtgtgga   3960
ttagtttaac tcttgtattc aaccattagt gctaccacct tctcacatta caatacaatt   3020
actggaagca agtactgcat ttcctatgca ac                                 4052
```

```
<210> SEQ ID NO 74
<211> LENGTH: 2572
```

-continued

<212> TYPE: DNA
<213> ORGANISM: homo sapiens

<400> SEQUENCE: 74
ccgctttctc cgcgcggtgc ctgcagggct cccagcgagt ggcagcttgg gaggggccgc 60
ccgggcggtc agactggcac ctgagcggcc accgcgtccc ggccaggcgg gcagaccgac 120
cccctcctca cctcgcgcgc ggctgacgca ggcagggcgc ccggcccctc ctggggacca 180
tcaggtgccg gctgggggct gtaggcaccg gacggaagca ggcggtgtga ggaccgacga 240
cgcgggcatg gcgggggcgg cctgcgagcc ggtggccagg ccgagcctga cctccatctc 300
gtctggggag cttcgcagcc tgtggacctg cgactgcgag ctggccctgc tgccgctggc 360
tcagctgctg cgcctgcagc ccggtgcctt ccagctgagc ggcgaccagc tcgtggtggc 420
caggcccggg gagccggcgg cggcgcgggg gggcttcaac gtcttcggtg acggcctcgt 480
gcgcctcgac gggcagctct accgcctcag cagctacatc aagaggtatg tggaactgac 540
caactactgt gattataaag actacaggga aactatattg agcaaaccaa tgttgttctt 600
tattaatgta cagaccaaaa aagacacctc aaaagaaagg acgtacgcgt ttcttgtaaa 660
cacgaggcac cccaagataa gaagacagat agagcaaggg atggacatgg tcatctcctc 720
agtgattgga gaaagttacc ggcttcagtc aatgcaatgt tcctctctct ttcagtttga 780
ttttcaagag gcagtgaaga atttcttccc cccaggaaat gaagtggtta atggagaaaa 840
tttaagcttt gcatatgaat tcaaagctga tgcattattt gatttcttct attggtttgg 900
gctcagtaat tccgttgtaa aagtaaatgg aaaagttctg aatttgtcaa gtacaagtcc 960
agaaaagaag gagacgatta agttatttct ggaaaaaatg agtgagcctt taatccgaag 1020
gagcagtttc tctgaccgaa agttcagtgt aacttccaga ggttcaatag atgatgtttt 1080
taactgcaat ctgtcaccca gatcatctct gacagagcct cttttggcag aattaccatt 1140
tccaagtgtt ctggaatctg aagagacacc caaccaattt atctgattga actgaacatt 1200
gtagcagttg ctcccgcact ccaggcctgt gctagactat aggctggggg gagggtagga 1260
ggtgggaggc agatacttcc acctgcgtgt caatctccgg ctcctccatg gcttctatgg 1320
aggactcctc tcttctgctt ctgtggatgt gatgccctgg caggcccagg gcagctgatt 1380
cccctaaaac ttatgattac caggatggaa aggccttggt cccatggcac tgggtggggc 1440
tgggggatat tctctacttt gaacacttct ccaaagaggc agaagggcca cagagttctg 1500
ccaccctgaa catttttctc agttccctgg gagtttttgt ggcagccttt gtgggagtgg 1560
tctgactggc tgttgaccta gcatgcttca taaatcaggg tttggccctc tgcttggagc 1620
atccaacccc ttgaactcaa acctgtcgag caaggggtta agagttctgt tctcttgcca 1680
acctggctgg gcaaaagcct gtgccatctt tcactgggag gcaaatatgt ttttcatcct 1740
gccatatgac acctatgaga aacgttcaca gtgaggagta gccaggttgc taggacagta 1800
accctgccac acactgcctg aaatcggaac tcccttggcc tccctcttaa ctaagtgacc 1860
catgtagaag gaagccagga gatatggtac cgaacaatga caggggaagg gtattggaca 1920
cggcagcgtc ctccttattg aaaacacatt atgtcagttg ggaattttaa ataagctttt 1980
agcaaaccta acactaaaag caaaatagaa gaaagctata ccattaccat aatacatttt 2040
tcatctcatg gctacaatgg aattcttgaa aaggaaaaaa aaatcctatc tacatataaa 2100
aacctgcatg aatgaatcac tacatatgct tataatgagg aagagttatg ggtcctgagt 2160
gtaatttttt atcctttctt aaaaagtttc tgtattatgc attttgataa cactactgat 2220

-continued

```
gatccttcca cttatatttg aaatgttatg taccacattt gcacaattaa aacttttctt   2280

agcattcaac ctagaattga ttaaatttat gactgaggct tcatgtgagc tttccattgt   2340

ggtttgtggg tgttgtattt gccttgtaac ttactgaatt acaataagaa ttgtgggttt   2400

tcatagccac tttctcaaga agcgcctttt gaagaacaag gctatgaagt atttgaagaa   2460

aggaaataaa atttgatact gatctttcag aaaagagaag gggaatgcta cttaataaca   2520

gaagatgtta aacatttatt attacactca ataaaaaatg aagagtatta ac           2572
```

<210> SEQ ID NO 75
<211> LENGTH: 312
<212> TYPE: PRT
<213> ORGANISM: homo sapiens

<400> SEQUENCE: 75

```
Met Ala Gly Ala Ala Cys Glu Pro Val Ala Arg Pro Ser Leu Thr Ser
1               5                   10                  15

Ile Ser Ser Gly Glu Leu Arg Ser Leu Trp Thr Cys Asp Cys Glu Leu
            20                  25                  30

Ala Leu Leu Pro Leu Ala Gln Leu Leu Arg Leu Gln Pro Gly Ala Phe
        35                  40                  45

Gln Leu Ser Gly Asp Gln Leu Val Val Ala Arg Pro Gly Glu Pro Ala
    50                  55                  60

Ala Ala Arg Gly Gly Phe Asn Val Phe Gly Asp Gly Leu Val Arg Leu
65                  70                  75                  80

Asp Gly Gln Leu Tyr Arg Leu Ser Ser Tyr Ile Lys Arg Tyr Val Glu
                85                  90                  95

Leu Thr Asn Tyr Cys Asp Tyr Lys Asp Tyr Arg Glu Thr Ile Leu Ser
            100                 105                 110

Lys Pro Met Leu Phe Phe Ile Asn Val Gln Thr Lys Lys Asp Thr Ser
        115                 120                 125

Lys Glu Arg Thr Tyr Ala Phe Leu Val Asn Thr Arg His Pro Lys Ile
    130                 135                 140

Arg Arg Gln Ile Glu Gln Gly Met Asp Met Val Ile Ser Ser Val Ile
145                 150                 155                 160

Gly Glu Ser Tyr Arg Leu Gln Ser Met Gln Cys Ser Ser Leu Phe Gln
                165                 170                 175

Phe Asp Phe Gln Glu Ala Val Lys Asn Phe Phe Pro Pro Gly Asn Glu
            180                 185                 190

Val Val Asn Gly Glu Asn Leu Ser Phe Ala Tyr Glu Phe Lys Ala Asp
        195                 200                 205

Ala Leu Phe Asp Phe Phe Tyr Trp Phe Gly Leu Ser Asn Ser Val Val
    210                 215                 220

Lys Val Asn Gly Lys Val Leu Asn Leu Ser Ser Thr Ser Pro Glu Lys
225                 230                 235                 240

Lys Glu Thr Ile Lys Leu Phe Leu Glu Lys Met Ser Glu Pro Leu Ile
                245                 250                 255

Arg Arg Ser Ser Phe Ser Asp Arg Lys Phe Ser Val Thr Ser Arg Gly
            260                 265                 270

Ser Ile Asp Asp Val Phe Asn Cys Asn Leu Ser Pro Arg Ser Ser Leu
        275                 280                 285

Thr Glu Pro Leu Leu Ala Glu Leu Pro Phe Pro Ser Val Leu Glu Ser
    290                 295                 300

Glu Glu Thr Pro Asn Gln Phe Ile
305                 310
```

-continued

<210> SEQ ID NO 76
<211> LENGTH: 1010
<212> TYPE: DNA
<213> ORGANISM: homo sapiens

<400> SEQUENCE: 76

```
caggcggcga ggagagcggt gccttgcagg gatgctgcgg gcgggagcac caaccgggga      60

cttaccccgg gcgggagaag tccacaccgg gaccaccatc atggcagtgg agtttgacgg     120

gggcattgtg atgggttctg attcccgagt gtctgcaggc gaggcggtgg tgaaccgagt     180

gtttgacaag ctgtccccgc tgcacgagcg catctactgt gcactctctg gttcagctgc     240

tgatgcccaa gccgtggccg acatggccgc ctaccagctg gagctccatg ggatagaact     300

ggaggaacct ccacttgttt tggctgctgc aaatgtggtg agaaatatca gctataaata     360

tcgagaggac ttgtctgcac atctcatggt agctggctgg gaccaacgtg aaggaggtca     420

ggtatatgga accctgggag gaatgctgac tcgacagcct tttgccattg gtggctccgg     480

cagcaccttt atctatggtt atgtggatgc agcatataag ccaggcatgt ctcccgagga     540

gtgcaggcgc ttcaccacag acgctattgc tctggccatg agccgggatg gctcaagcgg     600

gggtgtcatc tacctggtca ctattacagc tgccggtgtg gaccatcgag tcatcttggg     660

caatgaactg ccaaaattct atgatgagtg aaccttcccc agacttctct ttcttatttt     720

gtaataaact ctctaggacc aaaacctggt atggtcattg ggaaatgagt gctcagggag     780

atggagctta ggggaggtgg gtgcttccct cctagatgtc agcatacact ctttcttctt     840

ttgtcccagg tctaaaacat ctttcctaga gaaaacaaaa gggactaaac tagaaatata     900

aagagcccta tacatgacag gtgatcacgt actgaatgat tttgaagtag tacaaacaat     960

aaaaattctc attccgcatc atcatgcggt ccatgatgat gaggccgcaa               1010
```

<210> SEQ ID NO 77
<211> LENGTH: 219
<212> TYPE: PRT
<213> ORGANISM: homo sapiens

<400> SEQUENCE: 77

```
Met Leu Arg Ala Gly Ala Pro Thr Gly Asp Leu Pro Arg Ala Gly Glu
1               5                   10                  15

Val His Thr Gly Thr Thr Ile Met Ala Val Glu Phe Asp Gly Gly Val
            20                  25                  30

Val Met Gly Ser Asp Ser Arg Val Ser Ala Gly Glu Ala Val Val Asn
        35                  40                  45

Arg Val Phe Asp Lys Leu Ser Pro Leu His Glu His Ile Tyr Cys Ala
    50                  55                  60

Leu Ser Gly Ser Ala Ala Asp Ala Gln Ala Val Ala Asp Met Ala Ala
65                  70                  75                  80

Tyr Gln Leu Glu Leu His Gly Ile Glu Leu Glu Glu Pro Pro Leu Val
                85                  90                  95

Leu Ala Ala Ala Asn Val Val Arg Asn Ile Ser Tyr Lys Tyr Arg Glu
            100                 105                 110

Asp Leu Ser Ala His Leu Met Val Ala Gly Trp Asp Gln Arg Glu Gly
        115                 120                 125

Gly Gln Val Tyr Gly Thr Leu Gly Gly Met Leu Thr Arg Gln Pro Phe
    130                 135                 140

Ala Ile Gly Gly Ser Gly Ser Thr Phe Ile Tyr Gly Tyr Val Asp Ala
```

-continued

```
145                 150                 155                 160

Ala Tyr Lys Pro Gly Met Ser Pro Glu Glu Cys Arg Arg Phe Thr Thr
                165                 170                 175

Asp Ala Ile Ala Leu Ala Met Ser Arg Asp Gly Ser Ser Gly Gly Val
            180                 185                 190

Ile Tyr Leu Val Thr Ile Thr Ala Ala Gly Val Asp His Arg Val Ile
        195                 200                 205

Leu Gly Asn Glu Leu Pro Lys Phe Tyr Asp Glu
    210                 215


<210> SEQ ID NO 78
<211> LENGTH: 604
<212> TYPE: DNA
<213> ORGANISM: homo sapiens

<400> SEQUENCE: 78

ccacgcgtcc gcgctgcgcc acatcccacc ggcccttaca ctgtggtgtc cagcagcatc      60

cggcttcatg gggggacttg aaccctgcag caggctcctg ctcctgcctc tcctgctggc     120

tgtaagtggt ctccgtcctg tccaggccca ggcccagagc gattgcagtt gctctacggt     180

gagcccgggc gtgctggcag ggatcgtgat gggagacctg gtgctgacag tgctcattgc     240

cctggccgtg tacttcctgg gccggctggt ccctcggggg cgaggggctg cggaggcagc     300

gacccggaaa cagcgtatca ctgagaccga gtcgccttat caggagctcc agggtcagag     360

gtcggatgtc tacagcgacc tcaacacaca gaggccgtat tacaaatgag cccgaatcat     420

gacagtcagc aacatgatac ctggatccag ccattcctga agcccaccct gcacctcatt     480

ccaactccta ccgcgataca gacccacaga gtgccatccc tgagagacca gaccgctccc     540

caatactctc ctaaaataaa catgaagcac aaaaaaaaaa aaaaaaaaaa aaaaaaaaaa     600

aaaa                                                                  604


<210> SEQ ID NO 79
<211> LENGTH: 113
<212> TYPE: PRT
<213> ORGANISM: homo sapiens

<400> SEQUENCE: 79

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys


<210> SEQ ID NO 80
<211> LENGTH: 1610
<212> TYPE: DNA
```

-continued

<213> ORGANISM: homo sapiens

<400> SEQUENCE: 80
cccagagcag cgctcgccac ctccccccgg cctgggcagc gctcgcccgg ggagtccagc 60
ggtgtcctgt ggagctgccg ccatggcccc gcggcgggcg cgcggctgcc ggaccctcgg 120
tctcccggcg ctgctactgc tgctgctgct ccggccgccg gcgacgcggg gcatcacgtg 180
ccctcccccc atgtccgtgg aacacgcaga catctgggtc aagagctaca gcttgtactc 240
cagggagcgg tacatttgta actctggttt caagcgtaaa gccggcacgt ccagcctgac 300
ggagtgcgtg ttgaacaagg ccacgaatgt cgcccactgg acaaccccca gtctcaaatg 360
cattagagac cctgccctgg ttcaccaaag gccagcgcca ccctccacag taacgacggc 420
aggggtgacc ccacagccag agagcctctc cccttctgga aaagagcccg cagcttcatc 480
tcccagctca aacaacacag cggccacaac agcagctatt gtcccgggct cccagctgat 540
gccttcaaaa tcaccttcca caggaaccac agagataagc agtcatgagt cctcccacgg 600
caccccctct cagacaacag ccaagaactg ggaactcaca gcatccgcct cccaccagcc 660
gccaggtgtg tatccacagg gccacagcga caccactgtg gctatctcca cgtccactgt 720
cctgctgtgt gggctgagcg ctgtgtctct cctggcatgc tacctcaagt caaggcaaac 780
tcccccgctg gccagcgttg aaatggaagc catggaggct ctgccggtga cttgggggac 840
cagcagcaga gatgaagact tggaaaactg ctctcaccac ctatgaaact cggggaaacc 900
agcccagcta agtccggagt gaaggagcct ctctgcttta gctaaagacg actgagaaga 960
ggtgcaagga agcgggctcc aggagcaagc tcaccaggcc tctcagaagt cccagcagga 1020
tctcacggac tgccgggtcg gcgcctcctg cgcgagggag caggttctcc gcattcccat 1080
gggcaccacc tgcctgcctg tcgtgccttg gacccaggcc ccagcttccc aggagagacc 1140
aaaggcttct gagcaggatt tttatttcat tacagtgtga gctgcctgga atacatgtgg 1200
taatgaaata aaaaccctgc cccgaatctt ccgtccctca tcctaacttg cagttcacag 1260
agaaaagtga catacccaaa gctctctgtc aattacaagg cttctcctgg cgtgggagac 1320
gtctacaggg aagacaccag cgtttgggct tctaaccacc ctgtctccag ctgctctgca 1380
cacatggaca gggacctggg aaaggtggga gagatgctga gcccagcgaa tcctctccat 1440
tgaaggattc aggaagaaga aaactcaact cagtgccatt ttacgaatat atgcgtttat 1500
atttatactt ccttgtctat tatatctata cattatatat tatttgtatt ttgacattgt 1560
accttgtata aacaaaataa aacatctatt ttcaatattt ttaaaatgca 1610

<210> SEQ ID NO 81
<211> LENGTH: 267
<212> TYPE: PRT
<213> ORGANISM: homo sapiens

<400> SEQUENCE: 81

Met Ala Pro Arg Arg Ala Arg Gly Cys Arg Thr Leu Gly Leu Pro Ala
1 5 10 15

Leu Leu Leu Leu Leu Leu Leu Arg Pro Pro Ala Thr Arg Gly Ile Thr
20 25 30

Cys Pro Pro Pro Met Ser Val Glu His Ala Asp Ile Trp Val Lys Ser
35 40 45

Tyr Ser Leu Tyr Ser Arg Glu Arg Tyr Ile Cys Asn Ser Gly Phe Lys
50 55 60

Arg Lys Ala Gly Thr Ser Ser Leu Thr Glu Cys Val Leu Asn Lys Ala

-continued

```
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265


<210> SEQ ID NO 82
<211> LENGTH: 24
<212> TYPE: DNA
<213> ORGANISM: Artificial Sequence
<220> FEATURE:
<223> OTHER INFORMATION: Artificial Sequence equals primer.

<400> SEQUENCE: 82

ggaacaggaa agacttctca agca                                            24


<210> SEQ ID NO 83
<211> LENGTH: 23
<212> TYPE: DNA
<213> ORGANISM: Artificial Sequence
<220> FEATURE:
<223> OTHER INFORMATION: Artificial Sequence equals primer.

<400> SEQUENCE: 83

cttgacgtag ttgcaagctc tca                                             23


<210> SEQ ID NO 84
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 84

gctgaagcaa ggtagcgatg a                                               21


<210> SEQ ID NO 85
<211> LENGTH: 20
<212> TYPE: DNA
<213> ORGANISM: Artificial Sequence
```

-continued

<220> FEATURE:
<223> OTHER INFORMATION: Artificial Sequence equals primer.

<400> SEQUENCE: 85
cctcgttgct gagtgttgga 20

<210> SEQ ID NO 86
<211> LENGTH: 28
<212> TYPE: DNA
<213> ORGANISM: Artificial Sequence
<220> FEATURE:
<223> OTHER INFORMATION: Artificial Sequence equals primer.

<400> SEQUENCE: 86
tcagactgaa gagctactgt aatgatca 28

<210> SEQ ID NO 87
<211> LENGTH: 26
<212> TYPE: DNA
<213> ORGANISM: Artificial Sequence
<220> FEATURE:
<223> OTHER INFORMATION: Artificial Sequence equals primer.

<400> SEQUENCE: 87
caacaatcaa gacattcttt ccagtt 26

<210> SEQ ID NO 88
<211> LENGTH: 22
<212> TYPE: DNA
<213> ORGANISM: Artificial Sequence
<220> FEATURE:
<223> OTHER INFORMATION: Artificial Sequence equals primer.

<400> SEQUENCE: 88
tgctttcact tgtgcctctt tc 22

<210> SEQ ID NO 89
<211> LENGTH: 21
<212> TYPE: DNA
<213> ORGANISM: Artificial Sequence
<220> FEATURE:
<223> OTHER INFORMATION: Artificial Sequence equals primer.

<400> SEQUENCE: 89
caggctctca cagagacgga a 21

<210> SEQ ID NO 90
<211> LENGTH: 17
<212> TYPE: DNA
<213> ORGANISM: Artificial Sequence
<220> FEATURE:
<223> OTHER INFORMATION: Artificial Sequence equals primer.

<400> SEQUENCE: 90
agccgagcca catcgct 17

<210> SEQ ID NO 91
<211> LENGTH: 19
<212> TYPE: DNA
<213> ORGANISM: Artificial Sequence
<220> FEATURE:
<223> OTHER INFORMATION: Artificial Sequence equals primer.

<400> SEQUENCE: 91
gtgaccaggc gcccaatac 19